(12) United States Patent
Subramanian et al.

(10) Patent No.: US 11,986,391 B2
(45) Date of Patent: May 21, 2024

(54) PERCUTANEOUS DELIVERY SYSTEMS FOR ANCHORING AN IMPLANT IN A CARDIAC VALVE ANNULUS

(71) Applicant: Heart Repair Technologies, Inc., San Jose, CA (US)

(72) Inventors: Valavanur A. Subramanian, New York, NY (US); Michael L. Reo, Redwood City, CA (US); Gary Hulme, San Jose, CA (US); Thomas Afzal, Menlo Park, CA (US); Jeffrey Christian, Morgan Hill, CA (US); Maurice Buchbinder, La Jolla, CA (US)

(73) Assignee: Heart Repair Technologies, Inc., San Jose, CA (US)

( * ) Notice: Subject to any disclaimer, the term of this patent is extended or adjusted under 35 U.S.C. 154(b) by 431 days.

(21) Appl. No.: 17/222,233

(22) Filed: Apr. 5, 2021

(65) Prior Publication Data

US 2021/0290391 A1    Sep. 23, 2021

Related U.S. Application Data

(63) Continuation of application No. 15/851,557, filed on Dec. 21, 2017, now Pat. No. 11,033,391.
(Continued)

(51) Int. Cl.
*A61F 2/24* (2006.01)
*A61B 17/00* (2006.01)
(Continued)

(52) U.S. Cl.
CPC ........ *A61F 2/2466* (2013.01); *A61B 17/0401* (2013.01); *A61B 18/1492* (2013.01);
(Continued)

(58) Field of Classification Search
CPC .... A61F 2/2418; A61F 2/2427; A61F 2/2445; A61F 2/2454; A61F 2/2457; A61F 2/246;
(Continued)

(56) References Cited

U.S. PATENT DOCUMENTS

| 3,789,851 A | 2/1974 | LeVeen |
| 4,056,854 A | 11/1977 | Boretos et al. |

(Continued)

FOREIGN PATENT DOCUMENTS

| AU | 2016339984 | 4/2018 |
| DE | 29618925 | 1/1997 |

(Continued)

OTHER PUBLICATIONS

Final Office Action for U.S. Appl. No. 16/665,786 dated Aug. 31, 2021, in 21 pages.
(Continued)

*Primary Examiner* — Robert A Lynch
(74) *Attorney, Agent, or Firm* — Knobbe, Martens, Olson & Bear, LLP

(57) ABSTRACT

Mitral valve prolapse and mitral regurgitation can be treating by implanting in the mitral annulus a transvalvular intraannular band. The band has a first end, a first anchoring portion located proximate the first end, a second end, a second anchoring portion located proximate the second end, and a central portion. The central portion is positioned so that it extends transversely across a coaptive edge formed by the closure of the mitral valve leaflets. The band may be implanted via translumenal access or via thoracotomy.

20 Claims, 113 Drawing Sheets

Related U.S. Application Data

(60) Provisional application No. 62/549,215, filed on Aug. 23, 2017, provisional application No. 62/491,750, filed on Apr. 28, 2017, provisional application No. 62/437,898, filed on Dec. 22, 2016.

(51) Int. Cl.
| | |
|---|---|
| *A61B 17/04* | (2006.01) |
| *A61B 17/06* | (2006.01) |
| *A61B 17/064* | (2006.01) |
| *A61B 18/00* | (2006.01) |
| *A61B 18/14* | (2006.01) |
| *A61M 25/00* | (2006.01) |

(52) U.S. Cl.
CPC .......... *A61F 2/2445* (2013.01); *A61F 2/2454* (2013.01); *A61F 2/2457* (2013.01); *A61F 2/246* (2013.01); *A61B 2017/00243* (2013.01); *A61B 2017/00247* (2013.01); *A61B 2017/003* (2013.01); *A61B 2017/00783* (2013.01); *A61B 2017/00986* (2013.01); *A61B 2017/0406* (2013.01); *A61B 2017/0409* (2013.01); *A61B 2017/0417* (2013.01); *A61B 2017/0419* (2013.01); *A61B 2017/0464* (2013.01); *A61B 17/0469* (2013.01); *A61B 17/0482* (2013.01); *A61B 2017/06052* (2013.01); *A61B 2017/0647* (2013.01); *A61B 2017/0649* (2013.01); *A61B 2018/00369* (2013.01); *A61B 2018/00577* (2013.01); *A61B 2018/00589* (2013.01); *A61B 2018/00607* (2013.01); *A61F 2220/0008* (2013.01); *A61F 2230/0006* (2013.01); *A61F 2230/0008* (2013.01); *A61F 2230/001* (2013.01); *A61F 2230/0013* (2013.01); *A61F 2230/0023* (2013.01); *A61F 2230/0036* (2013.01); *A61F 2230/0039* (2013.01); *A61F 2230/005* (2013.01); *A61M 25/0026* (2013.01); *A61M 2025/0095* (2013.01)

(58) Field of Classification Search
CPC .. A61F 2/2466; A61F 2/2487; A61B 17/0401; A61B 18/1492
See application file for complete search history.

(56) References Cited

U.S. PATENT DOCUMENTS

| | | | |
|---|---|---|---|
| 4,270,143 A | 5/1981 | Morris | |
| 5,181,513 A | 1/1993 | Touboul et al. | |
| 5,291,889 A | 3/1994 | Kenet et al. | |
| 5,360,444 A | 11/1994 | Kusuhara | |
| 5,381,791 A | 1/1995 | Qian | |
| 5,398,691 A | 3/1995 | Martin et al. | |
| 5,400,771 A | 3/1995 | Pirak et al. | |
| 5,434,617 A | 7/1995 | Bianchi | |
| 5,572,999 A | 11/1996 | Funda et al. | |
| 5,593,424 A | 1/1997 | Northrup, III | |
| 5,631,970 A | 5/1997 | Hsu | |
| 5,631,981 A | 5/1997 | Rao | |
| 5,638,819 A | 6/1997 | Manwaring et al. | |
| 5,690,108 A | 11/1997 | Chakeres | |
| 5,765,561 A | 6/1998 | Chen et al. | |
| 5,792,155 A * | 8/1998 | Van Cleef ........ | A61B 17/12109 606/198 |
| 5,906,578 A | 5/1999 | Rajan et al. | |
| 5,961,440 A | 10/1999 | Schweich, Jr. et al. | |
| 6,001,127 A | 12/1999 | Schoon et al. | |
| 6,019,791 A | 2/2000 | Wood | |
| 6,045,497 A | 4/2000 | Schweich, Jr. et al. | |
| 6,050,936 A | 4/2000 | Schweich, Jr. et al. | |
| 6,332,893 B1 | 12/2001 | Mortier et al. | |
| 6,416,522 B1 | 7/2002 | Strecker | |
| 6,419,695 B1 | 7/2002 | Gabbay | |
| 6,626,899 B2 | 9/2003 | Houser et al. | |
| 6,723,038 B1 | 4/2004 | Schroeder et al. | |
| 6,726,717 B2 | 4/2004 | Alfieri et al. | |
| 6,752,813 B2 | 6/2004 | Goldfarb et al. | |
| 6,764,510 B2 | 7/2004 | Vidlund et al. | |
| 6,797,002 B2 | 9/2004 | Spence et al. | |
| 6,805,710 B2 | 10/2004 | Bolling et al. | |
| 6,869,444 B2 | 3/2005 | Gabbay | |
| 6,913,608 B2 | 7/2005 | Liddicoat et al. | |
| 7,070,618 B2 | 7/2006 | Streeter | |
| 7,077,862 B2 | 7/2006 | Vidlund et al. | |
| 7,087,064 B1 | 8/2006 | Hyde | |
| 7,101,395 B2 | 9/2006 | Tremulis et al. | |
| 7,125,421 B2 | 10/2006 | Tremulis et al. | |
| 7,160,322 B2 | 1/2007 | Gabbay | |
| 7,291,168 B2 | 11/2007 | Macoviak et al. | |
| 7,381,220 B2 | 6/2008 | Macoviak et al. | |
| 7,455,690 B2 | 11/2008 | Cartledge | |
| 7,527,646 B2 | 5/2009 | Rahdert et al. | |
| 7,691,144 B2 | 4/2010 | Chang et al. | |
| 7,704,277 B2 | 4/2010 | Zakay et al. | |
| 8,262,725 B2 | 9/2012 | Subramanian | |
| 8,333,777 B2 | 12/2012 | Schaller et al. | |
| 8,348,963 B2 | 1/2013 | Wilson | |
| 8,382,829 B1 | 2/2013 | Call et al. | |
| 8,480,732 B2 | 7/2013 | Subramanian | |
| 8,845,717 B2 | 9/2014 | Khairkhahan et al. | |
| 8,956,406 B2 | 2/2015 | Subramanian et al. | |
| 8,961,597 B2 | 2/2015 | Subramanian et al. | |
| 9,168,137 B2 | 10/2015 | Subramanian et al. | |
| 9,180,005 B1 | 11/2015 | Lashinski et al. | |
| 9,468,526 B2 | 10/2016 | Subramanian et al. | |
| 9,554,903 B2 | 1/2017 | Rowe et al. | |
| 9,585,753 B2 | 3/2017 | Subramanian et al. | |
| 9,615,925 B2 | 4/2017 | Subramanian et al. | |
| 9,968,451 B2 | 5/2018 | Marquez et al. | |
| 10,143,553 B2 | 12/2018 | Alon et al. | |
| 10,219,903 B2 | 3/2019 | Subramanian et al. | |
| 10,238,488 B2 | 3/2019 | Subramanian et al. | |
| 10,456,259 B2 | 10/2019 | Subramanian et al. | |
| 11,013,599 B2 | 5/2021 | Subramanian et al. | |
| 11,033,391 B2 | 6/2021 | Subramanian et al. | |
| 11,083,579 B2 | 8/2021 | Subramanian et al. | |
| 2002/0065554 A1 | 5/2002 | Streeter | |
| 2003/0033009 A1 | 2/2003 | Gabbay | |
| 2003/0083742 A1 | 5/2003 | Spence et al. | |
| 2003/0093148 A1 | 5/2003 | Bolling et al. | |
| 2003/0120340 A1 | 6/2003 | Liska et al. | |
| 2003/0199974 A1 | 10/2003 | Lee et al. | |
| 2003/0233022 A1 | 12/2003 | Vidlund et al. | |
| 2004/0088047 A1 | 5/2004 | Spence et al. | |
| 2004/0106989 A1 | 6/2004 | Wilson et al. | |
| 2004/0127981 A1 | 7/2004 | Rahdert et al. | |
| 2004/0127982 A1 | 7/2004 | Machold et al. | |
| 2004/0138745 A1 | 7/2004 | Macoviak et al. | |
| 2004/0148021 A1 | 7/2004 | Cartledge et al. | |
| 2004/0152947 A1 | 8/2004 | Schroeder et al. | |
| 2004/0162610 A1 | 8/2004 | Liska et al. | |
| 2004/0225300 A1 | 11/2004 | Goldfarb et al. | |
| 2004/0260393 A1 | 12/2004 | Rahdert et al. | |
| 2005/0004665 A1 | 1/2005 | Aklog et al. | |
| 2005/0004666 A1 | 1/2005 | Alfieri et al. | |
| 2005/0004668 A1 | 1/2005 | Aklog et al. | |
| 2005/0038505 A1 | 2/2005 | Shulze et al. | |
| 2005/0038508 A1 | 2/2005 | Gabbay | |
| 2005/0070999 A1 | 3/2005 | Spence | |
| 2005/0075723 A1 | 4/2005 | Schroeder et al. | |
| 2005/0107871 A1 | 5/2005 | Realyvasquez et al. | |
| 2005/0010287 A1 | 6/2005 | Macoviak et al. | |
| 2005/0143811 A1 | 6/2005 | Realyvasquez | |
| 2005/0216039 A1 | 9/2005 | Lederman | |
| 2005/0256568 A1 | 11/2005 | Lim et al. | |
| 2005/0267572 A1 | 12/2005 | Schoon et al. | |
| 2005/0267573 A9 | 12/2005 | Macoviak et al. | |
| 2005/0288776 A1 | 12/2005 | Shaoulian et al. | |
| 2006/0004443 A1 | 1/2006 | Liddicoat et al. | |
| 2006/0020336 A1 | 1/2006 | Liddicoat | |

(56) References Cited

U.S. PATENT DOCUMENTS

| | | |
|---|---|---|
| 2006/0058871 A1 | 3/2006 | Zakay et al. |
| 2006/0069430 A9 | 3/2006 | Rahdert et al. |
| 2006/0106456 A9 | 5/2006 | Machold et al. |
| 2006/0135967 A1 | 6/2006 | Realyvasquez |
| 2006/0149368 A1 | 7/2006 | Spence |
| 2006/0161040 A1 | 7/2006 | McCarthy et al. |
| 2006/0195012 A1 | 8/2006 | Mortier et al. |
| 2006/0229708 A1 | 10/2006 | Powell et al. |
| 2006/0247492 A1 | 11/2006 | Streeter |
| 2006/0287661 A1 | 12/2006 | Bolduc et al. |
| 2007/0015957 A1 | 1/2007 | Li |
| 2007/0118151 A1 | 5/2007 | Davidson |
| 2007/0213810 A1 | 9/2007 | Newhauser |
| 2007/0250161 A1 | 10/2007 | Dolan |
| 2008/0243245 A1 | 10/2008 | Thambar et al. |
| 2008/0306586 A1 | 12/2008 | Cartledge et al. |
| 2009/0163934 A1 | 6/2009 | Raschdorf et al. |
| 2009/0177277 A1 | 7/2009 | Milo |
| 2009/0228099 A1 | 9/2009 | Rahdert et al. |
| 2009/0264995 A1 | 10/2009 | Subramanian |
| 2009/0276055 A1 | 11/2009 | Harris et al. |
| 2009/0292353 A1 | 11/2009 | Yoganathan et al. |
| 2010/0076550 A1 | 3/2010 | Subramanian |
| 2010/0121435 A1 | 5/2010 | Subramanian et al. |
| 2010/0121437 A1 | 5/2010 | Subramanian et al. |
| 2010/0131057 A1 | 5/2010 | Subramanian et al. |
| 2010/0262233 A1 | 10/2010 | He |
| 2011/0082538 A1 | 4/2011 | Dahlgren et al. |
| 2012/0101489 A1 | 4/2012 | Bloom et al. |
| 2012/0209375 A1* | 8/2012 | Madrid ............. A61M 25/1011 604/95.04 |
| 2013/0090724 A1 | 4/2013 | Subramanian et al. |
| 2013/0103140 A1 | 4/2013 | Subramanian et al. |
| 2013/0103142 A1 | 4/2013 | Subramanian et al. |
| 2013/0226289 A1 | 8/2013 | Shaolian et al. |
| 2013/0331930 A1 | 12/2013 | Rowe et al. |
| 2014/0039607 A1 | 2/2014 | Kovach |
| 2014/0039615 A1 | 2/2014 | Padala et al. |
| 2014/0275757 A1 | 9/2014 | Goodwin et al. |
| 2014/0343601 A1 | 11/2014 | Abbott et al. |
| 2015/0223793 A1 | 8/2015 | Goldfarb et al. |
| 2015/0223935 A1 | 8/2015 | Subramanian et al. |
| 2015/0257884 A1 | 9/2015 | Subramanian et al. |
| 2015/0366556 A1 | 12/2015 | Khairkhahan et al. |
| 2016/0045314 A1 | 2/2016 | Keren et al. |
| 2016/0143735 A1* | 5/2016 | Subramanian ........ A61F 2/2457 623/2.36 |
| 2016/0324636 A1 | 11/2016 | Rourke et al. |
| 2017/0100245 A1 | 4/2017 | Subramanian et al. |
| 2017/0105839 A1 | 4/2017 | Subramanian et al. |
| 2017/0172741 A1 | 6/2017 | Subramanian et al. |
| 2017/0224477 A1 | 8/2017 | Seguin |
| 2017/0354500 A1 | 12/2017 | Martinez et al. |
| 2018/0055638 A1 | 3/2018 | Subramanian et al. |
| 2018/0126119 A1 | 5/2018 | McNiven et al. |
| 2018/0214270 A1 | 8/2018 | Subramanian et al. |
| 2018/0256153 A1 | 9/2018 | Stone et al. |
| 2018/0318083 A1 | 11/2018 | Bolling et al. |
| 2019/0282361 A1 | 9/2019 | Subramanian et al. |
| 2019/0298521 A1 | 10/2019 | Rafiee et al. |
| 2019/0298522 A1 | 10/2019 | Subramanian et al. |
| 2020/0030096 A1 | 1/2020 | Zeitani |
| 2020/0188109 A1 | 6/2020 | Fatemi Far et al. |
| 2020/0253733 A1 | 8/2020 | Subramanian et al. |
| 2020/0276017 A1 | 9/2020 | Subramanian et al. |
| 2021/0290388 A1 | 9/2021 | Subramanian et al. |
| 2021/0290391 A1 | 9/2021 | Subramanian et al. |
| 2021/0386546 A1 | 12/2021 | Subramanian et al. |
| 2022/0151783 A1 | 5/2022 | Subramanian et al. |
| 2022/0273432 A1 | 9/2022 | Subramanian et al. |

FOREIGN PATENT DOCUMENTS

| | | |
|---|---|---|
| EP | 1 059 893 | 9/2005 |
| GB | 2 254 254 | 7/1992 |
| JP | 05-184611 | 7/1993 |
| JP | 2008-523886 | 7/2008 |
| WO | WO 1998/18411 | 5/1998 |
| WO | WO 2000/60995 | 10/2000 |
| WO | WO 2006/052687 | 5/2006 |
| WO | WO 2006/065212 | 6/2006 |
| WO | WO 2007/029252 | 3/2007 |
| WO | WO 2009/129189 | 10/2009 |
| WO | WO 2011/047168 | 4/2011 |
| WO | WO 2011/086401 | 7/2011 |
| WO | WO 2017/066480 | 4/2017 |
| WO | WO 2018/119304 | 6/2018 |
| WO | WO 2019/241777 | 12/2019 |

OTHER PUBLICATIONS

Non-Final Office Action for U.S. Appl. No. 16/786,580 dated Mar. 28, 2022, in 31 pages.
International Search Report for PCT/US2022/070534 dated May 19, 2022, in 9 pages.
Extended European Search Report for Application No. EP 20756481.6 dated Oct. 11, 2022 in 6 pages.
Final Office Action for U.S. Appl. No. 16/786,580 dated Sep. 19, 2022, in 10 pages.
U.S. Appl. No. 16/655,786, filed Oct. 17, 2019, Subramanian et al.
U.S. Appl. No. 16/655,780, filed Feb. 20, 2020, Subramanian et al.
Final Office Action for U.S. Appl. No. 12/104,011, dated Nov. 15, 2010, in 9 pages.
Final Office Action for U.S. Appl. No. 12/104,011 dated Mar. 30, 2012, in 8 pages.
Non-Final Office Action for U.S. Appl. No. 12/104,011 dated Jul. 12, 2011, in 9 pages.
Non-Final Office Action for U.S. Appl. No. 12/104,011 dated Feb. 23, 2010, in 12 pages.
Non-Final Office Action for U.S. Appl. No. 12/104,011 dated Feb. 3, 2011, in 9 pages.
Notice of Allowance for U.S. Appl. No. 12/104,011 dated Jun. 25, 2012, in 7 pages.
Australian 1st Office Action for App. No. 2009/236358, dated Nov. 26, 2013, in 4 pages.
Australian Notice of Acceptance for Application No. 2009/236358, dated Aug. 17, 2015 in 5 pages.
Australian 1st Office Action for App. No. 2015/261696, dated Feb. 10, 2017, in 5 pages.
Australian 1st Office Action for App. No. 2018200859, dated Sep. 21, 2018, in 3 pages.
Canadian 1st Office Action for Application No. 2,721,450, dated Feb. 1, 2016, in 4 pages.
Canadian Notice of Allowance for Application No. 2,721,450, dated Oct. 27, 2016, in 4 pages.
Canadian Notice of Abandonment for Application No. 2,965,632, dated Oct. 30, 2017, in 1 page.
Non-Final Office Action for U.S. Appl. No. 12/579,330 dated Jul. 13, 2012, in 13 pages.
Non-Final Office Action for U.S. Appl. No. 12/579,331 dated Jun. 26, 2012, in 14 pages.
Non-Final Office Action for U.S. Appl. No. 12/579,364 dated Jul. 18, 2012, in 18 pages.
Non-Final Office Action for U.S. Appl. No. 12/626,272 dated Apr. 29, 2010, in 10 pages.
Non-Final Office Action for U.S. Appl. No. 12/626,272 dated Jan. 6, 2012, in 8 pages.
Final Office Action for U.S. Appl. No. 12/626,272 dated Jan. 24, 2011, in 9 pages.
Notice of Allowance for U.S. Appl. No. 12/626,272 dated May 13, 2013, in 6 pages.
Extended European Search Report for Application No. EP 09732605 dated Jul. 31, 2013, in 6 pages.

(56) References Cited

OTHER PUBLICATIONS

EPO Communcaiton for Application No. EP 09732605 dated May 9, 2014, in 4 pages.
EPO Communcaiton for Application No. EP 09732605 dated Aug. 13, 2015, in 4 pages.
EPO Communcaiton for Application No. EP 09732605 dated Aug. 22, 2016, in 4 pages.
Japanese First Office Action for Application No. 2011/505117 dated May 28, 2013, in 4 pages.
Japanese Office Action for Application No. 2011-505117 dated Nov. 26, 2013, in 3 pages.
Japanese Notice of Allowance for Application No. 2011/505117 dated May 26, 2014, in 3 pages.
International Search Report for PCT/US2009/040386 dated Jun. 4, 2009, in 7 pages.
Australian 1st Office Action for Application No. 2010/306762 dated Jan. 9, 2014, in 6 pages.
Australian Notice of Acceptance for Application No. 2010/306762 dated Sep. 29, 2015, in 3 pages.
Canadian 1st Office Action for Application No. 2,777,067 dated Sep. 1, 2016, in 4 pages.
Canadian 2nd Office Action for Application No. 2,777,067 dated May 17, 2017, in 4 pages.
Canadian Notice of Abandonment for Application No. 2,777,067, dated Nov. 17, 2017, in 1 page.
Office Action for Application No. 10824103.5 dated Nov. 12, 2018, in 4 pages.
Notice of Allowance for U.S. Appl. No. 13/650,998 dated Oct. 10, 2014, in 7 pages.
Non-Final Office Action for U.S. Appl. No. 14/628,114 dated Oct. 7, 2015, in 13 pages.
Notice of Allowance for U.S. Appl. No. 13/650,998 dated Jun. 15, 2016, in 5 pages.
Non-Final Office Action for U.S. Appl. No. 15/295,204 dated Apr. 20, 2018, in 13 pages.
Notice of Allowance for U.S. Appl. No. 15/295,204 dated Nov. 6, 2018, in 6 pages.
Extended European Search Report for Application No. 10824103.5 dated Sep. 16, 2013, in 9 pages.
EPO Communication for Application No. EP 10824103 dated Jan. 12, 2017, in 4 pages.
Japanese First Office Action for Application No. 2012-534360 dated Aug. 25, 2014, in 3 pages.
Japanese Notice of Allowance for Application No. 2012-534360 dated Jun. 1, 2015, in 3 pages.
International Search Report and Written Opinion for PCT/US2010/052695 dated Dec. 6, 2010, in 18 pages.
Non-Final Office Action for U.S. Appl. No. 13/630,197 dated Sep. 12, 2013, in 12 pages.
Notice of Allowance for U.S. Appl. No. 13/630,197 dated Oct. 10, 2014, in 5 pages.
Non-Final Office Action for U.S. Appl. No. 14/622,611 dated Nov. 6, 2015, in 9 pages.
Final Office Action for U.S. Appl. No. 14/622,611 dated Jun. 3, 2016, in 6 pages.
Notice of Allowance for U.S. Appl. No. 14/622,611 dated Nov. 9, 2016, in 5 pages.
Non-Final Office Action for U.S. Appl. No. 15/482,650 dated Mar. 27, 2018, in 15 pages.
Notice of Allowance for U.S. Appl. No. 15/482,650 dated Oct. 24, 2018, in 8 pages.
Non-Final Office Action for U.S. Appl. No. 13/653,783 dated Oct. 24, 2014, in 11 pages.
Notice of Allowance for U.S. Appl. No. 13/653,783 dated Aug. 14, 2015, in 5 pages.
Non-Final Office Action for U.S. Appl. No. 14/919,525 dated Apr. 4, 2016, in 5 pages.
Notice of Allowance for U.S. Appl. No. 14/919,525 dated Oct. 17, 2016, in 5 pages.
Non-Final Office Action for U.S. Appl. No. 15/450,971 dated Oct. 20, 2017, in 4 pages.
Final Office Action for U.S. Appl. No. 15/450,971 dated Oct. 5, 2018, in 18 pages.
International Search Report and Written Opinion for PCT/US2016/056900 dated Jan. 12, 2017, in 7 pages.
International Search Report and Written Opinion for PCT/US2017/068011 dated Mar. 29, 2018, in 11 pages.
EPO Communication for Application No. EP 09732605 dated Jan. 15, 2019, in 4 pages.
Canadian 3nd Office Action for Application No. 2,777,067 dated Feb. 11, 2019, in 4 pages.
Non-Final Office Action for U.S. Appl. No. 15/293,111 dated Apr. 25, 2018, in 26 pages.
Notice of Allowance for U.S. Appl. No. 15/293,111 dated Oct. 11, 2018, in 7 pages.
Extended European Search Report for Application No. EP 16856213.0 dated Apr. 9, 2019 in 8 pages.
Non-Final Office Action for U.S. Appl. No. 15/450,971 dated Jul. 18, 2019, in 11 pages.
EPO Communcaiton for Application No. EP 09732605 dated Sep. 3, 2019, in 44 pages.
Australian Notice of Acceptance for App. No. 2018200859, dated Sep. 9, 2019, in 4 pages.
Non-Final Office Action for U.S. Appl. No. 15/851,577 dated Dec. 9, 2019, in 26 pages.
Non-Final Office Action for U.S. Appl. No. 16/290,195 dated Nov. 18, 2019, in 15 pages.
Notice of Acceptance for Application No. 2,965,632, dated Sep. 25, 2019, in 1 page.
Final Office Action for U.S. Appl. No. 15/450,971 dated Apr. 9, 2020 in 11 pages.
International Search Report and Written Opinion for PCT/US2020/017526 dated May 21, 2020, in 7 pages.
Non-Final Office Action for U.S. Appl. No. 16/361,694 dated Jun. 25, 2020, in 16 pages.
Non-Final Office Action for U.S. Appl. No. 16/290,195 dated Aug. 18, 2020, in 6 pages.
Office Action for Application No. 10824103.5 dated Mar. 15, 2021, in 4 pages.
Notice of Allowance for U.S. Appl. No. 16/361,694 dated Jan. 27, 2021, in 10 pages.
Notice of Allowance for U.S. Appl. No. 16/290,195 dated Mar. 30, 2021, in 10 pages.
Notice of Allowance for U.S. Appl. No. 15/851,577 dated Jan. 11, 2021, in 10 pages.
Notice of Allowance for U.S. Appl. No. 15/851,577 dated Sep. 8, 2020, in 10 pages.
Notice of Allowance for U.S. Appl. No. 15/851,577 dated May 18, 2020, in 8 pages.
Extended European Search Report for Application No. EP 17883051.9 dated Mar. 1, 2021, in 11 pages.
Non-Final Office Action for U.S. Appl. No. 16/665,786 dated May 14, 2021, in 25 pages.
Medical Carbon Research Institute, LLC, "Summary of Safety and Effectiveness Data On-X Prosthetic Heart Valve, Models ONXM and ONXMC," Mar. 6, 2002; 16 pages.

* cited by examiner

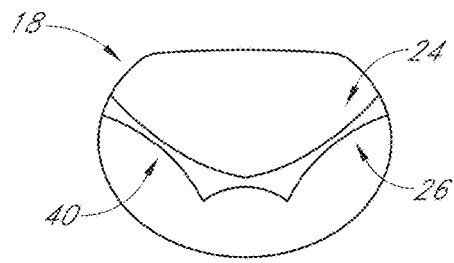 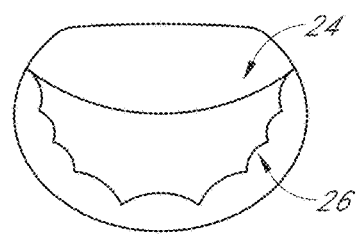
FIG. 3　　　　FIG. 4
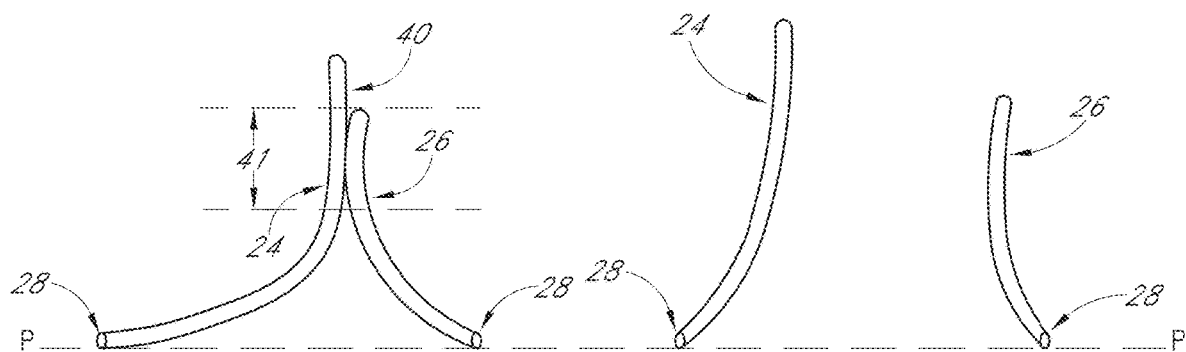
FIG. 5　　　　FIG. 6

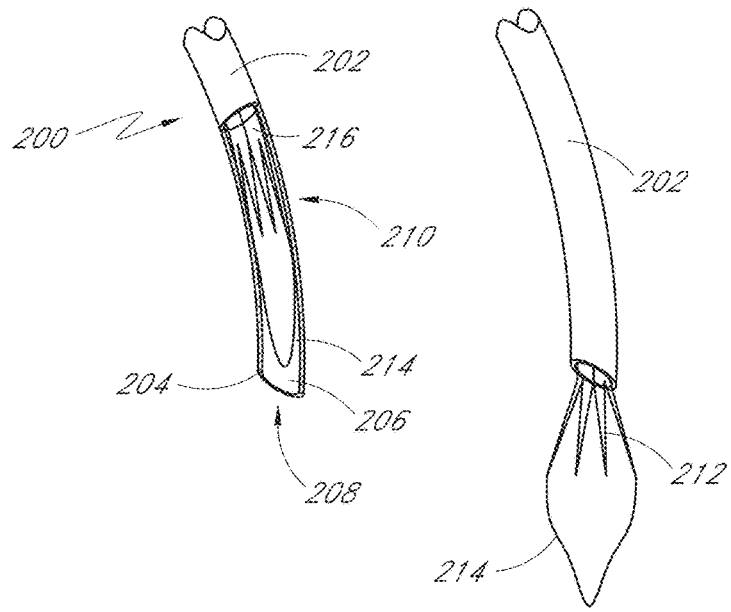
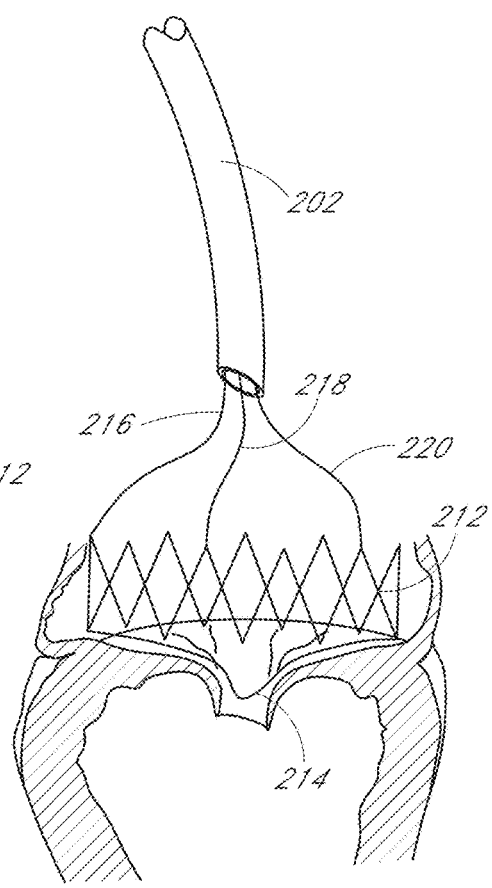
FIG. 43A  FIG. 43B  FIG. 43C
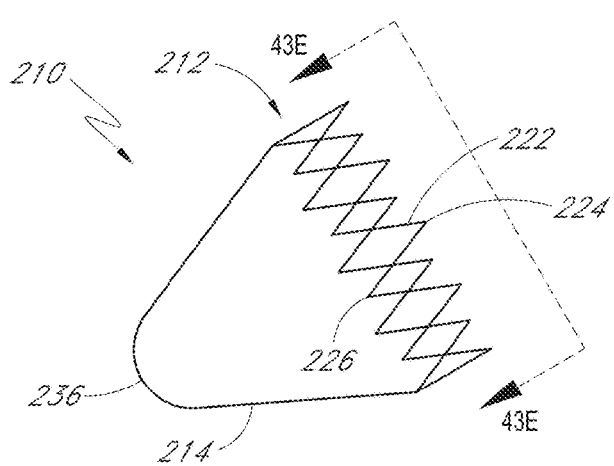
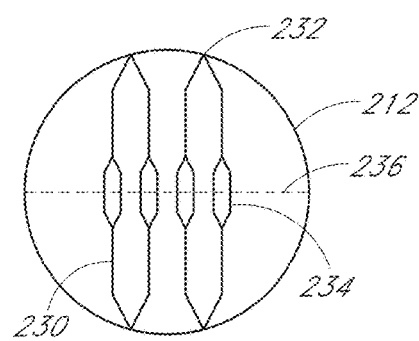
FIG. 43D  FIG. 43E

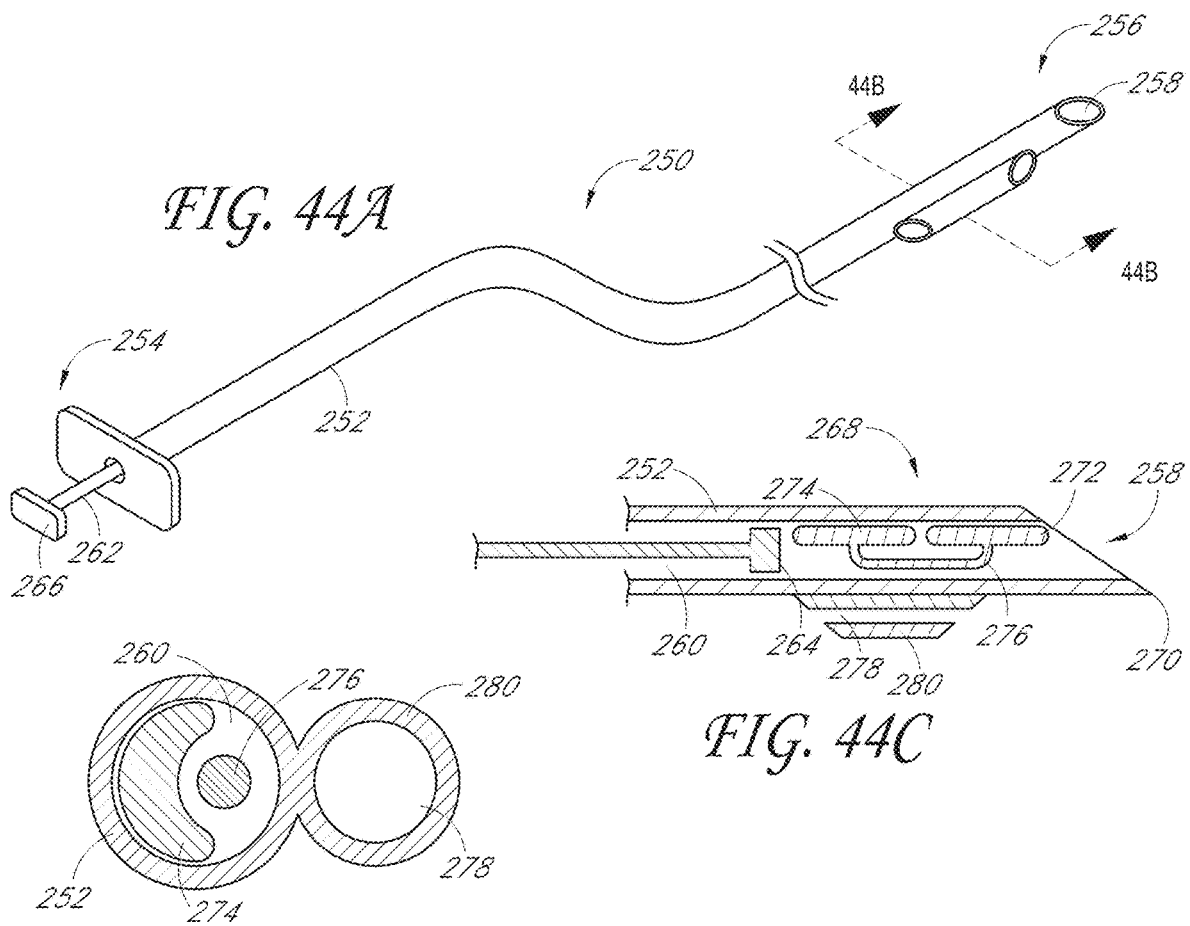
FIG. 44A
FIG. 44C
FIG. 44B
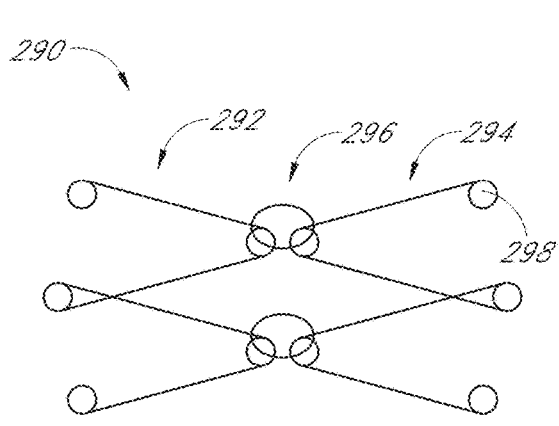
FIG. 45A
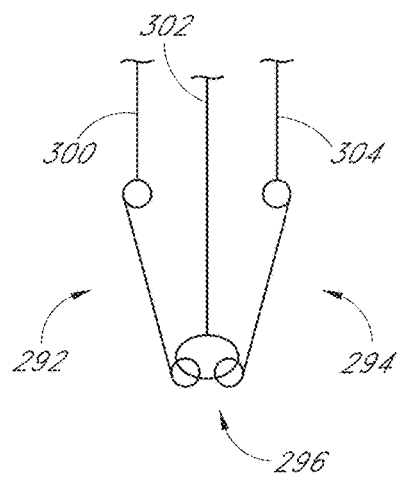
FIG. 45B

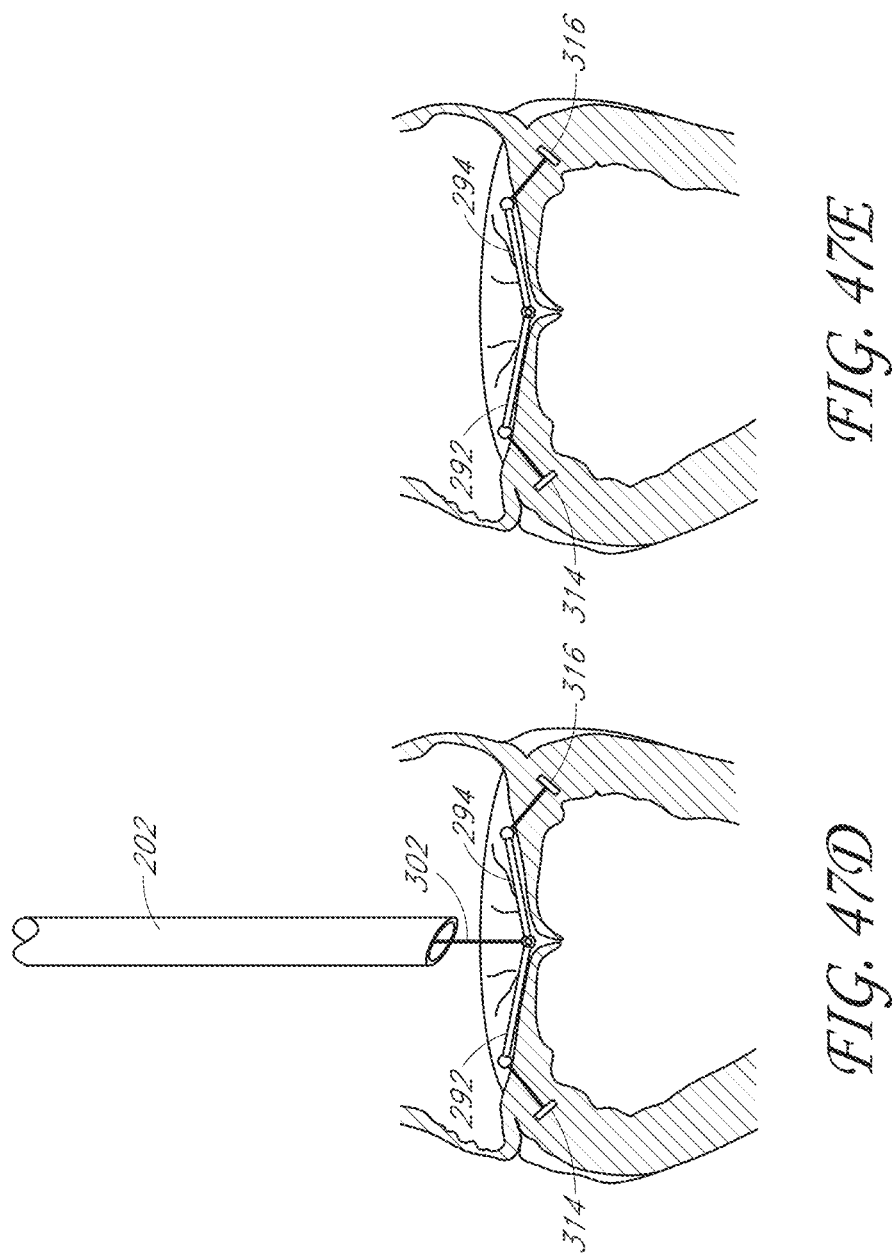

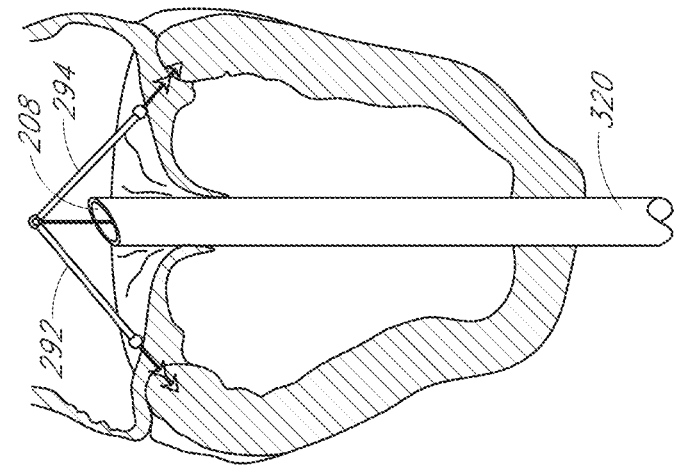
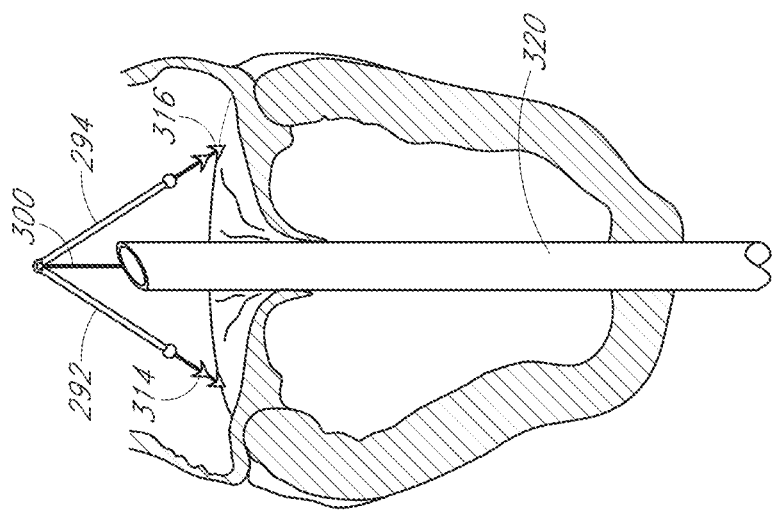

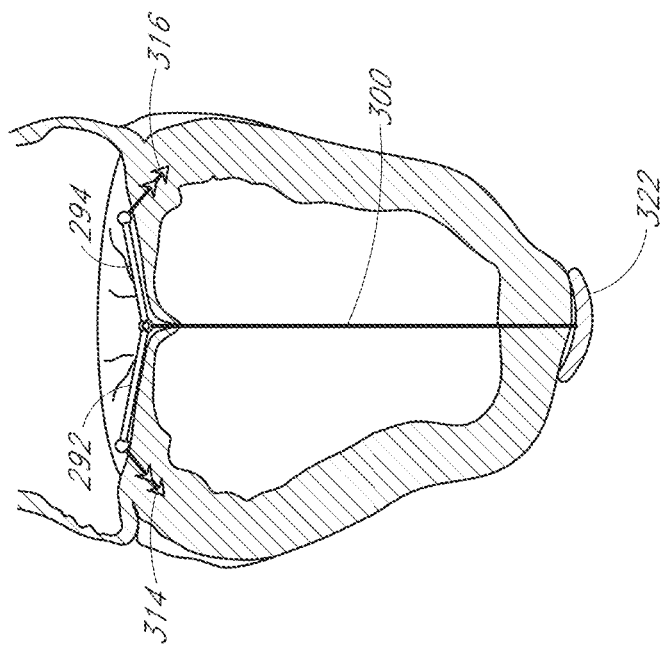
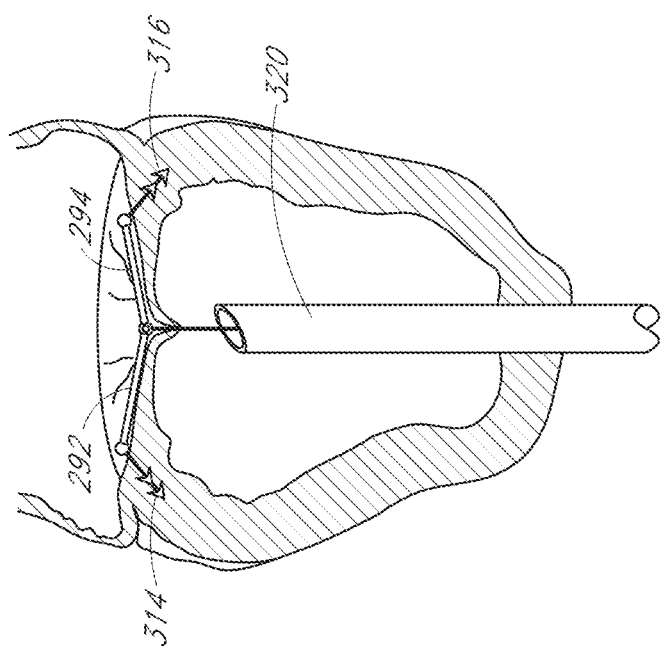

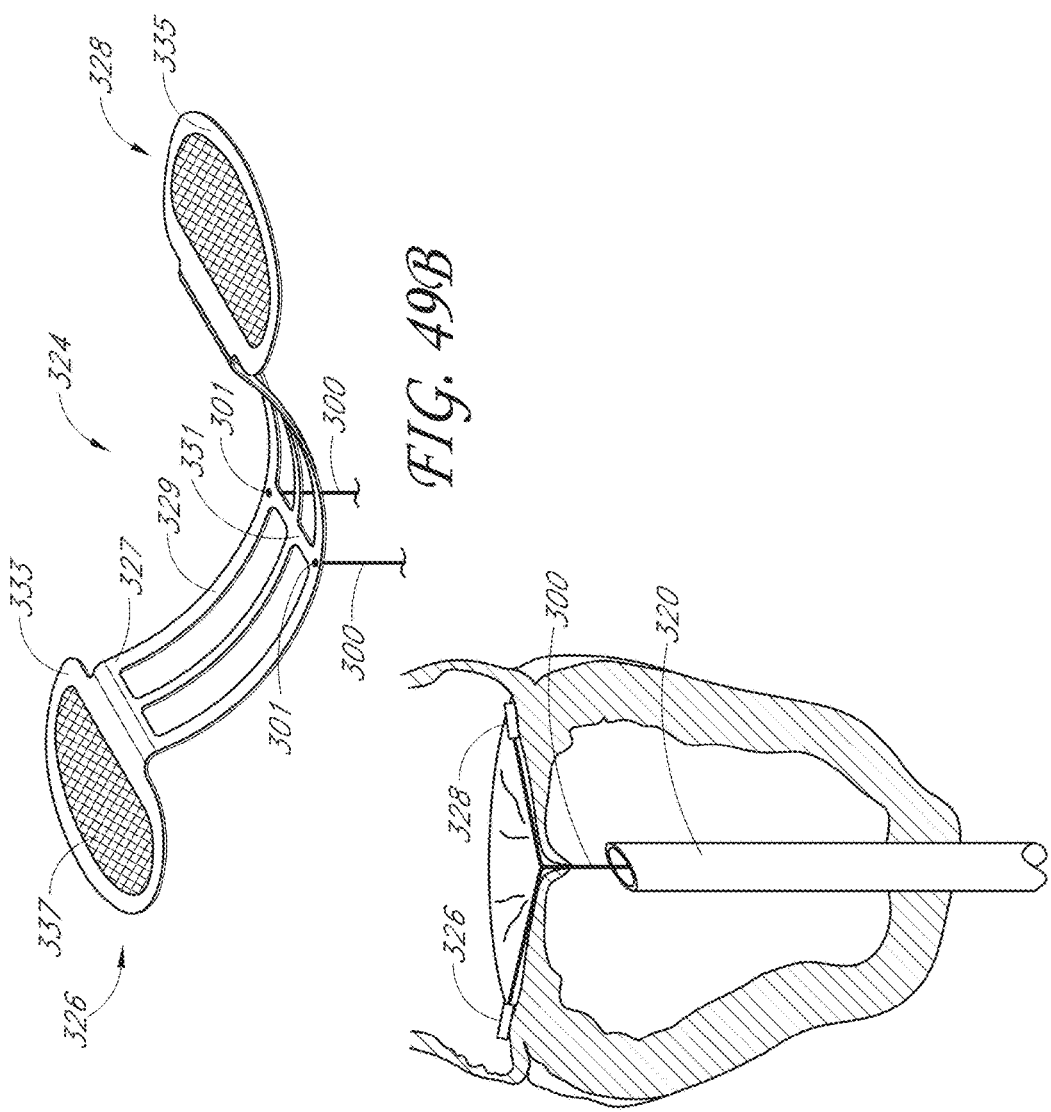
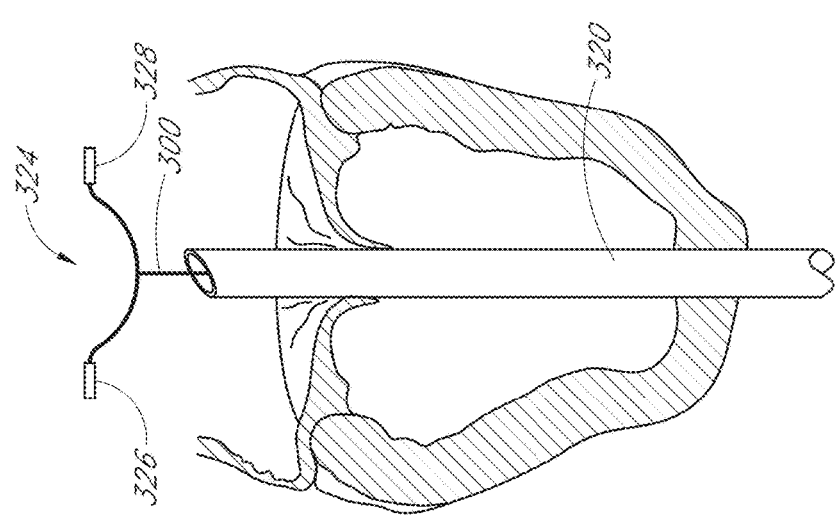
FIG. 49B
FIG. 49C
FIG. 49A

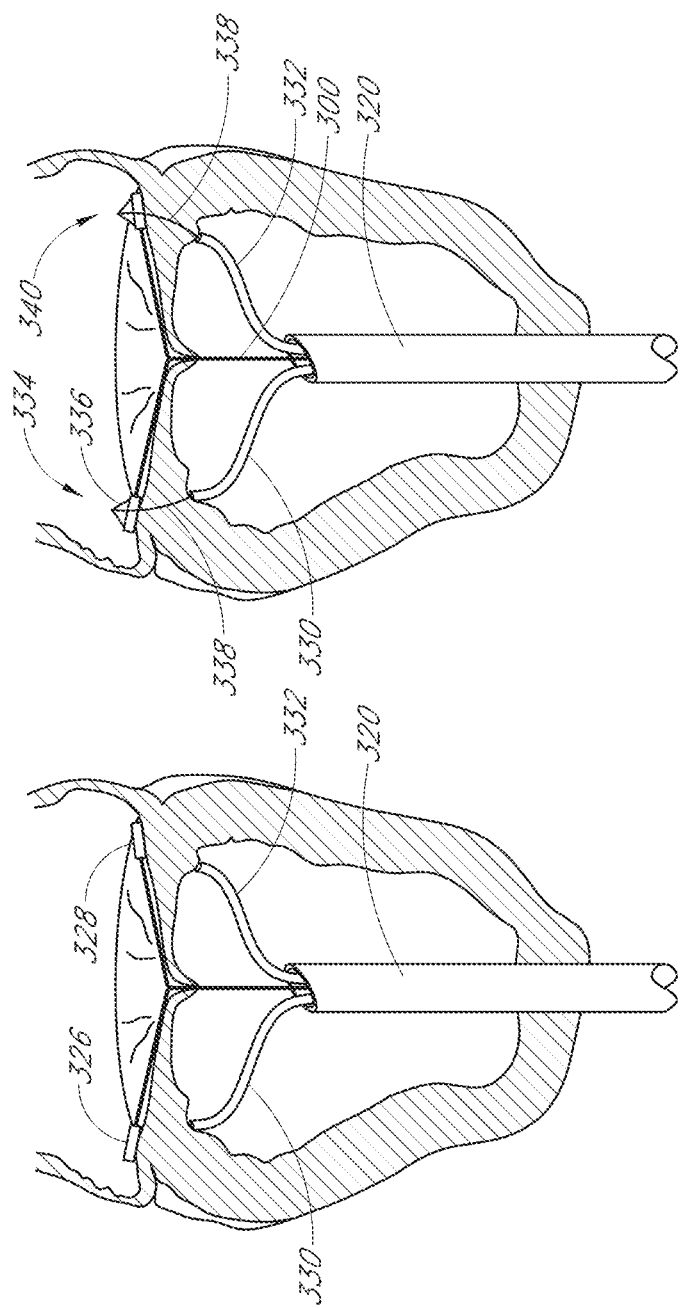

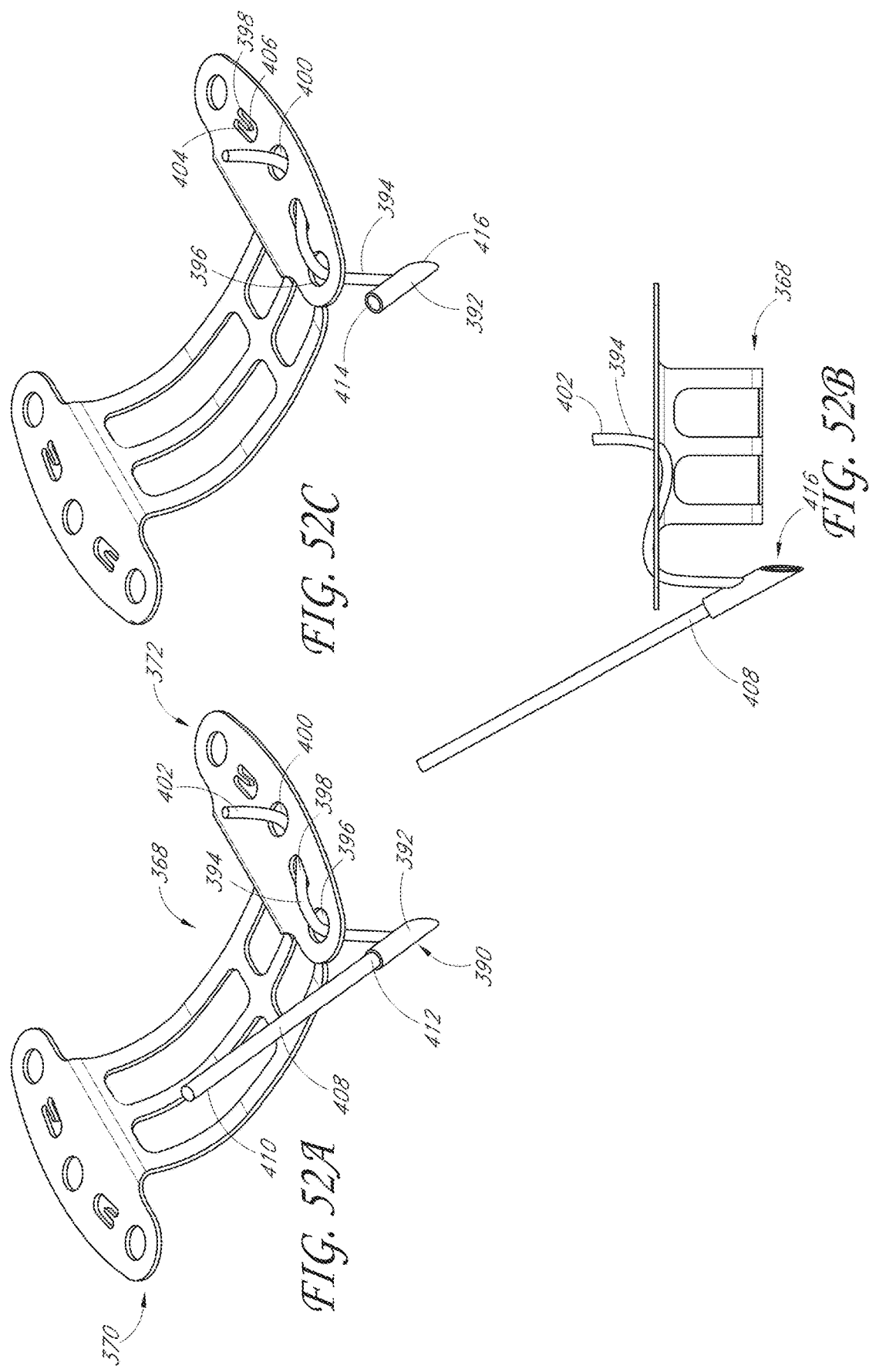

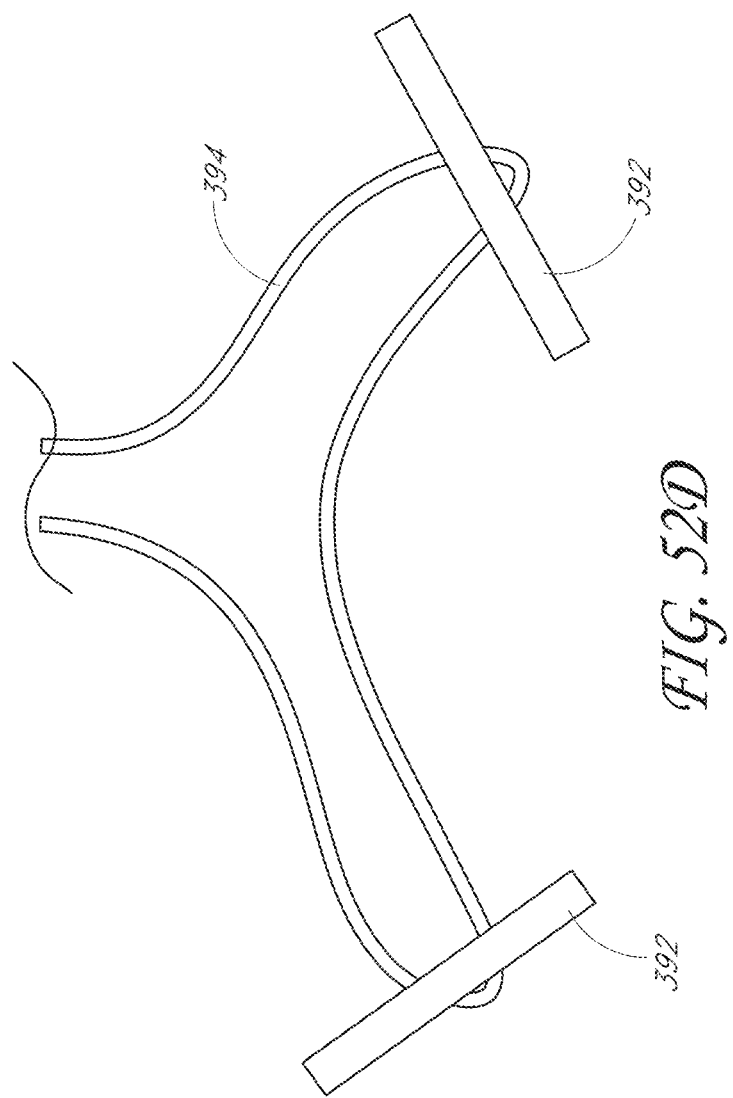

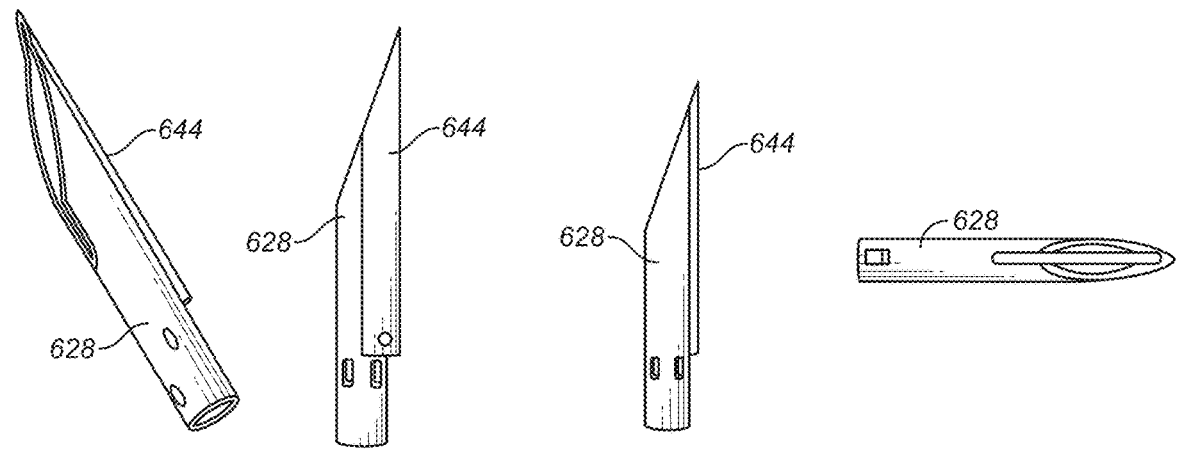
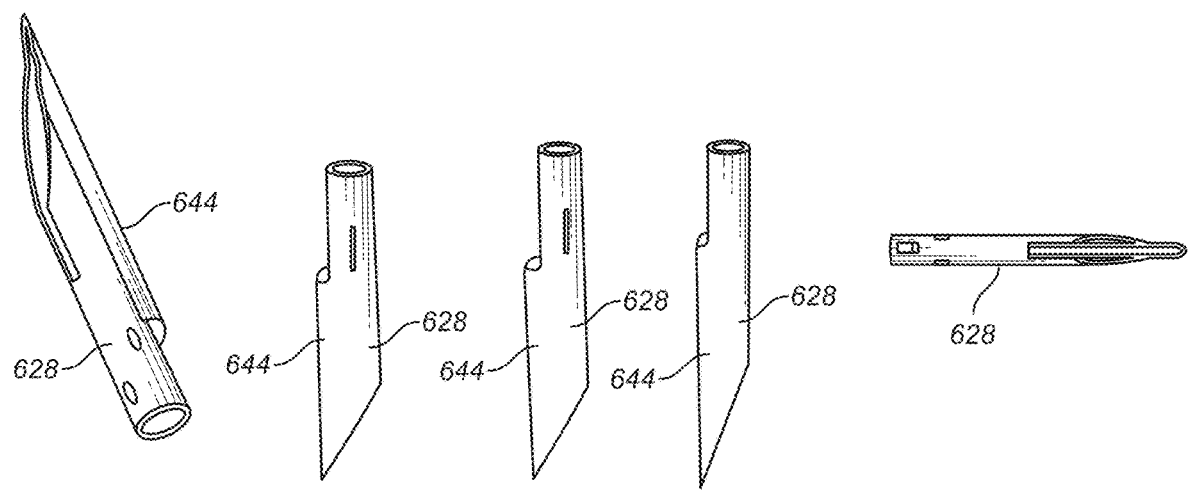
FIG. 63C

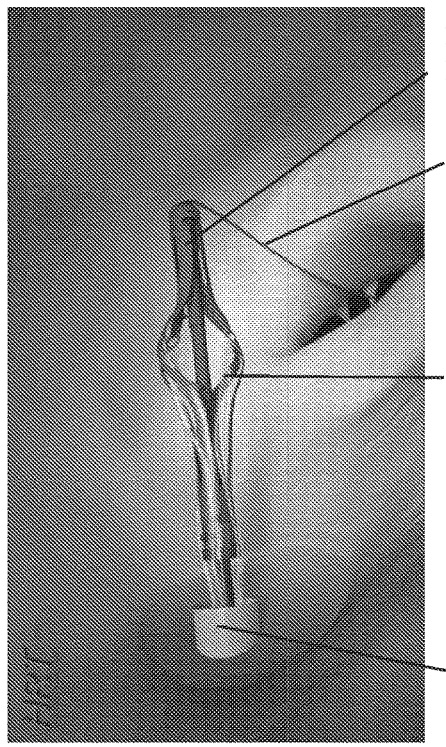
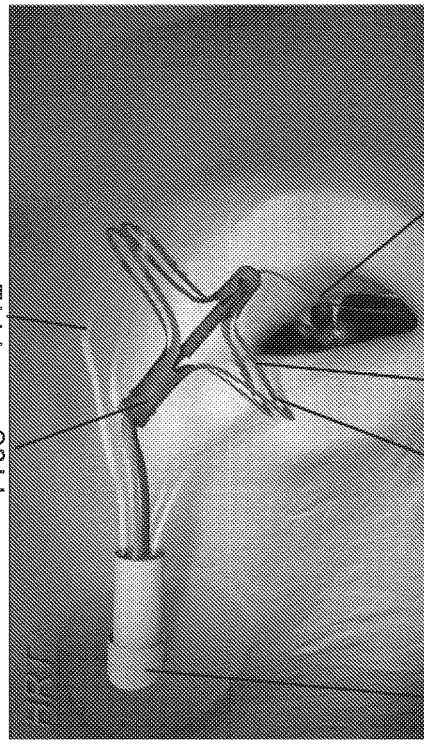
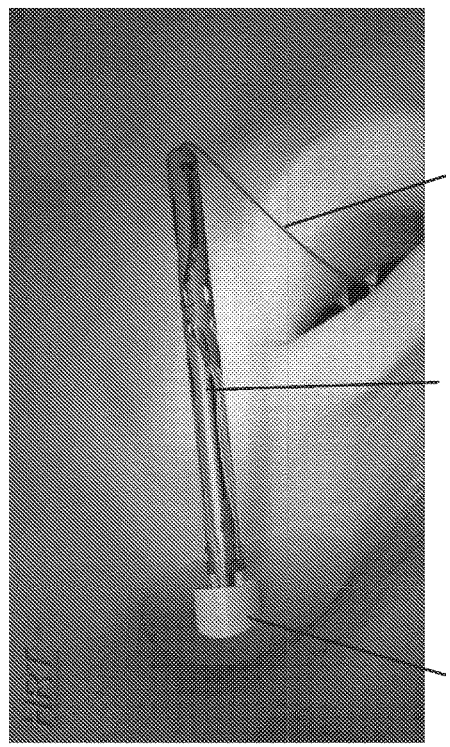
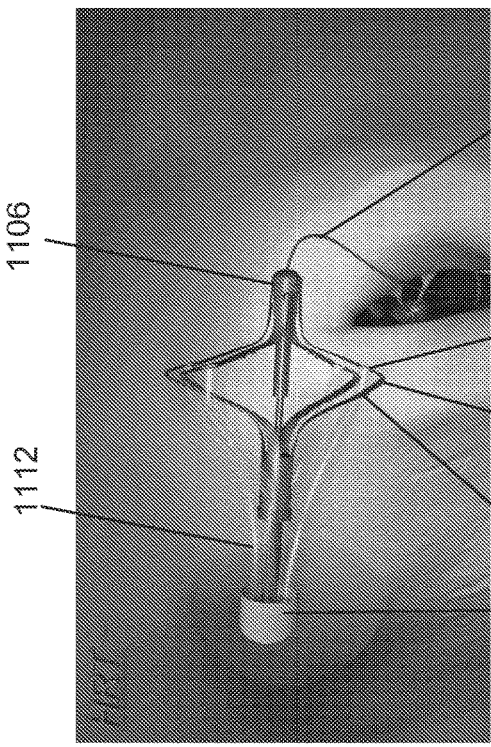
FIG. 113A
FIG. 113B
FIG. 113C
FIG. 113D

PERCUTANEOUS DELIVERY SYSTEMS FOR ANCHORING AN IMPLANT IN A CARDIAC VALVE ANNULUS

CROSS-REFERENCE TO RELATED APPLICATIONS

This application is a continuation of U.S. application Ser. No. 15/851,557 filed on Dec. 21, 2017, which claims the benefit under 35 U.S.C. § 119(e) as a nonprovisional application of U.S. Prov. App. No. 62/437,898 filed on Dec. 22, 2016, U.S. Prov. App. No. 62/491,750 filed Apr. 28, 2017, and U.S. Prov. App. No. 62/549,215 filed Aug. 23, 2017. The disclosure of each of the aforementioned priority applications is hereby incorporated by reference herein in their entireties. This application is also related to U.S. application Ser. No. 15/293,111, filed Oct. 13, 2016, which in turn claims the benefit under 35 U.S.C. § 119(e) as a nonprovisional application of U.S. Prov. App. No. 62/241,687 filed on Oct. 14, 2015. This application is also related to U.S. patent application Ser. No. 14/628,114 filed on Feb. 20, 2015, which is in turn a continuation of U.S. patent application Ser. No. 13/650,998 filed Oct. 12, 2012, now issued as U.S. Pat. No. 8,961,597 on Feb. 24, 2015, which is a continuation of U.S. patent application Ser. No. 12/579,330 filed Oct. 14, 2009, now abandoned, which is a continuation-in-part of U.S. patent application Ser. No. 12/104,011 filed Apr. 16, 2008, and issued as U.S. Pat. No. 8,262,725 on Sep. 11, 2012. This application is related to U.S. Prov. App. No. 62/437,898 filed Dec. 22, 2016 and U.S. Prov. App. No. 62/491,750 filed Apr. 28, 2017. The disclosure of each of the aforementioned applications is hereby incorporated by reference herein in their entireties.

BACKGROUND

Field of the Invention

Embodiments of the present invention relate generally to treatment of mitral or tricuspid valve prolapse and mitral regurgitation, and more specifically, relate to the use of a transvalvular intraannular band to treat mitral valve prolapse and mitral regurgitation.

Description of the Related Art

The heart is a double (left and right side), self-adjusting muscular pump, the parts of which work in unison to propel blood to all parts of the body. The right side of the heart receives poorly oxygenated ("venous") blood from the body from the superior vena cava and inferior vena cava and pumps it through the pulmonary artery to the lungs for oxygenation. The left side receives well-oxygenated ("arterial") blood from the lungs through the pulmonary veins and pumps it into the aorta for distribution to the body.

The heart has four chambers, two on each side—the right and left atria, and the right and left ventricles. The atria are the blood-receiving chambers, which pump blood into the ventricles. A wall composed of membranous and muscular parts, called the interatrial septum, separates the right and left atria. The ventricles are the blood-discharging chambers. A wall composed of membranous and muscular parts, called the interventricular septum, separates the right and left ventricles.

The synchronous pumping actions of the left and right sides of the heart constitute the cardiac cycle. The cycle begins with a period of ventricular relaxation, called ventricular diastole. The cycle ends with a period of ventricular contraction, called ventricular systole.

The heart has four valves that ensure that blood does not flow in the wrong direction during the cardiac cycle; that is, to ensure that the blood does not back flow from the ventricles into the corresponding atria, or back flow from the arteries into the corresponding ventricles. The valve between the left atrium and the left ventricle is the mitral valve. The valve between the right atrium and the right ventricle is the tricuspid valve. The pulmonary valve is at the opening of the pulmonary artery. The aortic valve is at the opening of the aorta.

Various disease processes can impair the proper functioning of one or more of these valves. These include degenerative processes (e.g., Barlow's Disease, fibroelastic deficiency), inflammatory processes (e.g., Rheumatic Heart Disease) and infectious processes (e.g., endocarditis). In addition, damage to the ventricle from prior heart attacks (i.e., myocardial infarction secondary to coronary artery disease) or other heart diseases (e.g., cardiomyopathy) can distort the valve's geometry causing it to dysfunction.

The mitral valve is comprised of an anterior leaflet and a posterior leaflet. The bases of the leaflets are fixed to a circumferential partly fibrous structure, the annulus, preventing dehiscence of the valve. A subvalvular apparatus of chordae and papillary muscles prevents the valve from prolapsing into the left atrium. Mitral valve disease can be expressed as a complex variety of pathological lesions of either valve or subvalvular structures, but can also be related to the functional status of the valve. Functionally the mitral valve disease can be categorized into two anomalies, increased leaflet motion i.e. leaflet prolapse leading to regurgitation, or diminished leaflet motion i.e. restricted leaflet motion leading to obstruction and/or regurgitation of blood flow.

Leaflet prolapse is defined as when a portion of the leaflet overrides the plane of the orifice during ventricular contraction. The mitral regurgitation can also develop secondary to alteration in the annular ventricular apparatus and altered ventricular geometry, followed by incomplete leaflet coaptation. In ischemic heart failure this can be attributed to papillary or lateral wall muscle dysfunction, and in non-ischemic heart failure it can be ascribed to annular dilation and chordal tethering, all as a result of dysfunctional remodeling.

The predominant cause of dysfunction of the mitral valve is regurgitation which produces an ineffective cardiac pump function resulting in several deleterious conditions such as ventricular and atrial enlargement, pulmonary hypertension and heart-failure and ultimately death.

The main objective for the surgical correction is to restore normal function and not necessarily anatomical correction. This is accomplished by replacing the valve or by reconstructing the valve. Both of the procedures require the use of cardiopulmonary bypass and is a major surgical operation carrying a non-negligible early morbidity and mortality risk, and a postoperative rehabilitation for months with substantial postoperative pain. Historically, the surgical approach to patients with functional mitral regurgitation was mitral valve replacement, however with certain adverse consequences such as thromboembolic complications, the need for anticoagulation, insufficient durability of the valve, loss of ventricular function and geometry.

Reconstruction of the mitral valve is therefore the preferred treatment for the correction of mitral valve regurgitation and typically consists of a quadrangular resection of the posterior valve (valvuloplasty) in combination with a reduction of the mitral valve annulus (annuloplasty) by the means of suturing a ring onto the annulus. These procedures are surgically demanding and require a bloodless and well-exposed operating field for an optimal surgical result. The technique has virtually not been changed for more than three decades.

More recently, prolapse of the valve has been repaired by anchoring the free edge of the prolapsing leaflet to the corresponding free edge of the opposing leaflet and thereby restoring apposition but not necessarily coaptation. In this procedure a ring annuloplasty is also required to attain complete coaptation.

This method commonly referred to as an edge-to-edge or "Alfieri" repair also has certain drawbacks such as the creation of a double orifice valve and thereby reducing the effective orifice area. Several less invasive approaches related to the edge-to-edge technique has been suggested, for repairing mitral valve regurgitation by placing a clip through a catheter to suture the valve edges. However, it still remains to conduct an annuloplasty procedure, which has not yet been resolved by a catheter technique and therefore is to be performed by conventional surgery, which makes the method impractical.

Notwithstanding the presence of a variety of presently available surgical techniques and promising catheter based procedures for the future, there remains a need for a simple but effective device and corresponding surgical, minimally invasive or transvascular procedure to reduce mitral valve regurgitation.

SUMMARY OF THE INVENTION

Further features and advantages of the present invention will become apparent to those of skill in the art in view of the detailed description of preferred embodiments which follows, when considered together with the attached drawings and claims.

Some embodiments of this invention are directed to a transvalvular intraannular band to treat mitral valve prolapse and mitral regurgitation. The terminology "transvalvular" as used herein encompasses "across", "over", or "through" the valve surfaces by any means, and "intraannular" provides an axial spatial reference to within the native valve annulus or an annular band that serves to function within the valve annulus. Axial with respect to the valve axis means along the axis of the valve and can describe position relative to the atrium, "supra", or relative to the ventricle, "infra". Specifically, it creates an axis through which a plane is pierced by the aforementioned axis, and encompasses an embodiment that is intraannular to address coaptation at the valvular plane or series of valvular planes created during each cardiac cycle, but does not obviate other salient features of the invention that may be clearly infraannular or supraannular during the cardiac cycle. Further, the terminology in the following descriptions may use "transannular band" or "band" and it means to include all features that may be infraannular, intraannular, or suprannular without or with stating each axially descriptive term. As well "offset" refers to directionally displaced from a frame of reference.

In some embodiments, disclosed herein is a method of delivering a transvalvular intraannular implant. The method includes the steps of providing a delivery catheter, the delivery catheter comprising an elongate body; a movable outer sheath; and a transvalvular intraannular implant having a longitudinal axis and comprising a valve leaflet support portion and an anchoring portion, the valve leaflet support portion at least partially longitudinally offset from the anchoring portion; percutaneously delivering the delivery catheter to the vicinity of a heart valve annulus; transforming the implant from a first radially reduced configuration to a second radially enlarged configuration; and positioning the implant in its second radially enlarged configuration within the heart valve annulus such that the implant is oriented in the valve annulus such that the longitudinal axis of the implant is oriented substantially transversely to a coaptive edge of a heart valve positioned within the valve annulus. The heart valve annulus can be, for example, a mitral, aortic, tricuspid, or pulmonary valve annulus. In some embodiments, transforming the implant from the first radially reduced configuration to the second radially enlarged configuration comprises retracting or pushing forward the movable outer sheath of the delivery catheter, exposing the implant. The delivery catheter can further include a self-expandable support structure, such as a ring or stent for example, operably connected to the transvalvular implant. Percutaneously delivering the delivery catheter to the vicinity of the valve annulus can include one or more of approaching the valve annulus from a supraannular location, infraannular location, cardiac septum, such as the intra-atrial or intra-ventricular septum, a vascular cut-down, or a thoracoscopic procedure. The anchoring portion of the implant can be secured to tissue of the valve annulus, such as passing a tissue anchor through the anchoring portion of the implant and tissue of the valve annulus. In some embodiments, providing a delivery catheter includes providing a control wire operably attached to the implant, and positioning the implant includes applying tension to the control wire to move the implant. The control wire can be detached from the implant after being properly positioned, in some embodiments.

Also disclosed herein is a transvalvular intraannular delivery system. The system includes a percutaneous delivery catheter comprising an elongate body; a movable outer sheath; and a transvalvular intraannular implant having a longitudinal axis and comprising a valve leaflet support portion and an anchoring portion, the valve leaflet support portion at least partially longitudinally offset from the anchoring portion, wherein the transvalvular implant is configured to be transformable from a first radially reduced configuration to a second radially enlarged configuration; wherein the transvalvular implant is configured to be housed within the percutaneous delivery catheter in its first radially reduced configuration, wherein the transvalvular implant is configured to be positioned in its second radially enlarged configuration within a heart valve annulus such that the implant is oriented in the valve annulus such that the longitudinal axis of the implant is oriented substantially transversely to a coaptive edge of a heart valve positioned within the valve annulus. The system can also include a control wire operably attached to the implant for positioning the implant within the heart valve annulus. In some embodiments, the system also includes at least one tissue anchor for attaching the implant to tissue of the valve annulus. In some embodiments, the system also includes a self-expandable support structure operably connected to the transvalvular implant, for securing the implant to tissue of the valve annulus. Also disclosed herein is a transvalvular intraannular band that can include an elongate body having a first end, a first anchoring portion located proximate the first end, a second end, a second anchoring portion located proximate the second end, and a central portion connected to the first end and the second end. In some embodiments, the central portion has a convex arcuate shape and can include a plurality of crossing struts encapsulated by a thermoplastic material, the crossing struts intersecting at an intersection zone, the central portion displaced transversely from the intraannular plane which includes the mitral valve annulus and is transverse to the direction of blood flow when the band is attached to the annulus. The central portion can extend generally along a second plane which is perpendicular to the intraannular plane, the second plane including the first end and the second end; wherein the first end and the second end are configured to be attached to the mitral valve annulus within the intraannular plane and the central portion is configured to be convex in the direction of the ventricle to support the mitral valve leaflets at a point displaced toward the ventricle from the intraannular plane. The first end and the second end can reside on a generally septal-lateral axis transverse to the coaptive edges of the mitral valve leaflets when the band is attached to the mitral valve annulus. In some embodiments, the band does, or does not, comprise an annuloplasty ring, stent-valve, or replacement valve leaflets.

In some embodiments, disclosed herein is a system for delivering and anchoring an implant to a valve annulus. The system can include an anchor catheter configured to deliver a subannular anchor to a valve annulus of a heart of a patient. The anchor catheter can include a portion configured to create a hole in the valve annulus through which the anchor catheter delivers the subannular anchor. In some embodiments, the subannular anchor comprises a first configuration in which the subannular anchor has a low profile to be delivered through the hole and a second configuration in which the subannular anchor is expanded. In some embodiments, the subannular anchor comprises a suture. The system can include a transvalvular band configured to be delivered by sliding the transvalvular band along the suture toward the valve annulus. In some embodiments, the transvalvular band includes a first anchoring portion and wherein the suture is configured to extend through the first anchoring portion.

In some embodiments, the system can include a locking clip configured to be delivered by sliding the locking clip along the suture toward the valve annulus. In some embodiments, the anchor catheter is configured to deliver a plurality of subannular anchors. In some embodiments, the anchor catheter is configured to deliver four subannular anchors. In some embodiments, the anchor catheter is configured to deliver two subannular anchors on each leaflet. In some embodiments, the subannular anchor has a star configuration in which a plurality of prongs fold outward. In some embodiments, the subannular anchor compresses with tension, wherein the anchor catheter applies tension to compress the subannular anchor in the first configuration. In some embodiments, the transvalvular band comprises the first anchoring portion and a second anchoring portion, and a central portion therebetween. In some embodiments, the central portion comprises a convex arcuate shape and comprises a plurality of crossing struts encapsulated by a material. In some embodiments, the transvalvular band comprises the first anchoring portion and a second anchoring portion, and a central portion therebetween, wherein each anchoring portion is configured to accept sutures connected to subannular anchors therethrough. In some embodiments, the system can include a trimming catheter, wherein the trimming catheter is configured to slide along the suture after the transvalvular band is delivered and trims the excess suture. In some embodiments, the system can include a catheter configured to allow transseptal access. In some embodiments, at least one catheter is steerable. In some embodiments, the system can include a means for suture management. In some embodiments, the anchor catheter further comprises a lumen for each suture. In some embodiments, the anchor catheter comprises four lumens, each lumen configured to receive a suture connected to a subannular anchor. In some embodiments, the anchor catheter comprises a sleeve for each suture. In some embodiments, the system can include four sleeves, each sleeve configured to receive a suture connected to a subannular anchor. In some embodiments, the anchor catheter is configured to apply energy to create the hole.

Also disclosed herein is a method for delivering and anchoring an implant to a valve annulus of a valve. The method can include percutaneously creating a hole in the valve annulus to deliver a subannular anchor. The method can include delivering a subannular anchor through the hole in the valve annulus in a low profile configuration and expanding the subannular anchor on the ventricular side of the annulus. In some embodiments, the subannular anchor comprises a suture extending to the upstream side of the annulus relative to a direction of blood flow. The method can include delivering a transvalvular band to the valve annulus by sliding the transvalvular band along the suture toward the valve annulus.

In some embodiments, the method can include delivering a locking clip by sliding the locking clip along the suture toward the valve annulus. In some embodiments, the locking clip slides freely along the suture in a first direction, but resists movement in a second direction, opposite the first direction. In some embodiments, the method can include delivering a plurality of subannular anchors. In some embodiments, the method can include delivering four subannular anchors. In some embodiments, the method can include delivering two subannular anchors on the posterior annulus and two subannular anchors on the anterior annulus. In some embodiments, the subannular anchor is reversible. In some embodiments, the method can include applying tension to compress the subannular anchor. In some embodiments, creating the hole in the valve annulus comprises applying energy to the valve annulus. In some embodiments, creating the hole in the valve annulus comprises mechanically puncturing the valve annulus. In some embodiments, the valve is a mitral valve. In some embodiments, the method can include creating a second hole in the valve annulus to deliver a second subannular anchor, and delivering the second subannular anchor through the second hole in the valve annulus, wherein the first hole and the second hole are spaced apart.

In some embodiments, disclosed herein is a method of using a subannular anchor to percutaneously anchor an implant in a valve annulus. The method can include providing a subannular anchor. In some embodiments, the subannular anchor comprises a first configuration in which the subannular anchor has a low profile and a second configuration in which the subannular anchor is expanded. In some embodiments, the subannular anchor comprises a suture. The method can include threading the suture of the subannular anchor through an anchoring portion of a transvalvular band.

In some embodiments, the method can include providing an anchor catheter configured to deliver the subannular anchor. In some embodiments, the anchor catheter is configured to apply energy to tissue. In some embodiments, the method can include providing a delivery catheter configured to deliver the transvalvular band to the valve annulus. In some embodiments, the method can include threading the suture through the delivery catheter after threading the suture through the anchoring portion of the transvalvular band. In some embodiments, the method can include compressing the transvalvular band after threading the suture through the anchoring portion of the transvalvular band. In some embodiments, the method can include threading the suture of the subannular anchor through a locking clip. In some embodiments, the method can include threading the suture through the delivery catheter after threading the suture the locking clip. In some embodiments, the method can include threading the suture through a locking clip after threading the suture through the anchoring portion of the transvalvular band. In some embodiments, the method can include providing a trimming catheter configured to trim the suture.

In some embodiments, disclosed herein is a method for treating mitral valve regurgitation. The method can include percutaneously delivering a first subannular anchor coupled to a first suture, wherein the first suture extends through the annulus. The method can include percutaneously delivering a second subannular anchor coupled to a second suture, wherein the second suture extends through the annulus. The method can include cinching the first suture and the second suture with a transvalvular implant.

In some embodiments, cinching comprises cinching the posterior annulus toward the anterior annulus. In some embodiments, cinching facilitates proper leaflet coaptation. In some embodiments, the first suture extends in a straight path through a pilot hole in the posterior annulus. In some embodiments, the second suture extends in a straight path through a pilot hole in the anterior annulus. In some embodiments, the method can include delivering a third subannular anchor coupled to a third suture, wherein the third suture extends through the annulus. In some embodiments, the method can include delivering a fourth subannular anchor coupled to a fourth suture, wherein the fourth suture extends through the annulus. In some embodiments, the first suture and the third suture are coupled to a first end of the transvalvular implant and the second suture and the fourth suture are coupled to a second end of the transvalvular implant. In some embodiments, the first suture and the third suture are coupled to the posterior annulus and the second suture and the fourth suture are coupled to the anterior annulus. In some embodiments, the method can include ablating tissue to create a pilot hole to deliver the first anchor subannularly. In some embodiments, the method can include sequentially delivering the first subannular anchor and the second subannular anchor.

In some embodiments, disclosed herein is a system for delivering and anchoring an implant to a valve annulus. The system can include an anchor catheter configured to deliver a subannular anchor to a valve annulus of a heart of a patient. In some embodiments, the anchor catheter can include a portion configured to create a hole in the valve annulus through which the anchor catheter delivers the subannular anchor. In some embodiments, the subannular anchor comprises a first configuration in which the subannular anchor has a low profile to be delivered through the hole and a second configuration in which the subannular anchor is expanded. In some embodiments, the subannular anchor comprises a suture. The system can include a transvalvular implant configured to be delivered by sliding the transvalvular implant along the suture toward the valve annulus. In some embodiments, the transvalvular implant includes a first anchoring portion. In some embodiments, the suture is configured to extend through the first anchoring portion.

In some embodiments, the system can include a locking clip configured to be delivered by sliding the locking clip along the suture toward the valve annulus. In some embodiments, the anchor catheter is configured to deliver a plurality of subannular anchors. In some embodiments, the anchor catheter is configured to deliver four subannular anchors. In some embodiments, the anchor catheter is configured to deliver two subannular anchors on each leaflet. In some embodiments, the subannular anchor has a star configuration in which a plurality of prongs fold outward. In some embodiments, the subannular anchor compresses with tension, wherein the anchor catheter applies tension to compress the subannular anchor in the first configuration. In some embodiments, the transvalvular implant comprises the first anchoring portion and a second anchoring portion, and a central portion therebetween, wherein the central portion comprises a convex arcuate shape and comprises a plurality of crossing struts encapsulated by a material. In some embodiments, the transvalvular implant comprises the first anchoring portion and a second anchoring portion, and a central portion therebetween, wherein each anchoring portion is configured to accept sutures connected to subannular anchors therethrough. In some embodiments, the system can include a trimming catheter, wherein the trimming catheter is configured to slide along the suture after the transvalvular implant is delivered and trims the excess suture. In some embodiments, the system can include a catheter configured to allow transseptal access. In some embodiments, at least one catheter is steerable. In some embodiments, the system can include a means for suture management. In some embodiments, the system can include a lumen for each suture. In some embodiments, the system can include four lumens, each lumen configured to receive a suture connected to a subannular anchor. In some embodiments, the system can include a sleeve for each suture. In some embodiments, the system can include four sleeves, each sleeve configured to receive a suture connected to a subannular anchor. In some embodiments, the anchor catheter is configured to apply energy to create the hole.

BRIEF DESCRIPTION OF THE DRAWINGS

FIG. 3 is a bottom view of the normal mitral valve of FIG. 1 during systole looking from the left atrium to the left ventricle.

FIG. 4 is a bottom view of the normal mitral valve of FIG. 2 during diastole looking from the left atrium to the left ventricle.

FIG. 5 is a cross-sectional schematic view of the normal mitral valve of FIG. 1 during systole, illustrating the depth of the coaption zone.

FIG. 6 is a cross-sectional schematic view of the normal mitral valve of FIG. 2 during diastole.

FIG. 43A is a schematic view of the distal end of a percutaneous deployment catheter having a self-expandable implant positioned therein.

FIG. 43B is a schematic view as in FIG. 43A, with the implant partially deployed from the catheter.

FIG. 43C is a schematic view of the deployment catheter showing the implant fully expanded at the deployment site, but still tethered to the deployment catheter.

FIG. 43D is a side elevational view of the implant of FIG. 43C.

FIG. 43E is an end view taken along the line 43E-43E of FIG. 43D.

FIG. 44A is a side elevational perspective view of an anchor deployment catheter in accordance with the present invention.

FIG. 44B is a cross sectional view taken along the line 44B-44B of FIG. 44A.

FIG. 44C is a cross sectional side view of the anchor deployment catheter of FIG. 44A.

FIG. 45A is a schematic plan view of a self-expandable transvalvular band in accordance with the present invention.

FIG. 45B is a side elevational view of the transvalvular band of FIG. 45A shown in a reduced crossing profile (folded) configuration, and attached to three control wires.

FIG. 47D is a schematic view as in FIG. 47C, with the implant configured to move coaption earlier in the cardiac cycle.

FIG. 47E is a schematic view of the implant of FIG. 47D, with the deployment catheter removed.

FIG. 48A is schematic cross sectional view of a transapical deployment device positioned across the mitral valve.

FIG. 48B is a schematic view of the device of FIG. 48A, with tissue anchors engaged at the mitral valve annulus.

FIG. 48C is a schematic view as in FIG. 48B, with the deployment catheter withdrawn through the mitral valve.

FIG. 48D is a schematic view as in FIG. 48C, in an embodiment having a transventricular support.

FIGS. 49A through 49G illustrate an implantation sequence for a transvalvular band at the mitral valve, via a transapical access.

FIGS. 52A through 52C illustrate a transvalvular band, with a "t-tag" deployment system and suture tensioning feature.

FIG. 52D illustrates an embodiment of a plurality of tissue anchors looped together on a suture.

FIG. 63C are various views of an alternative embodiment of a needle and an energy tip.

DETAILED DESCRIPTION

Figure 1:
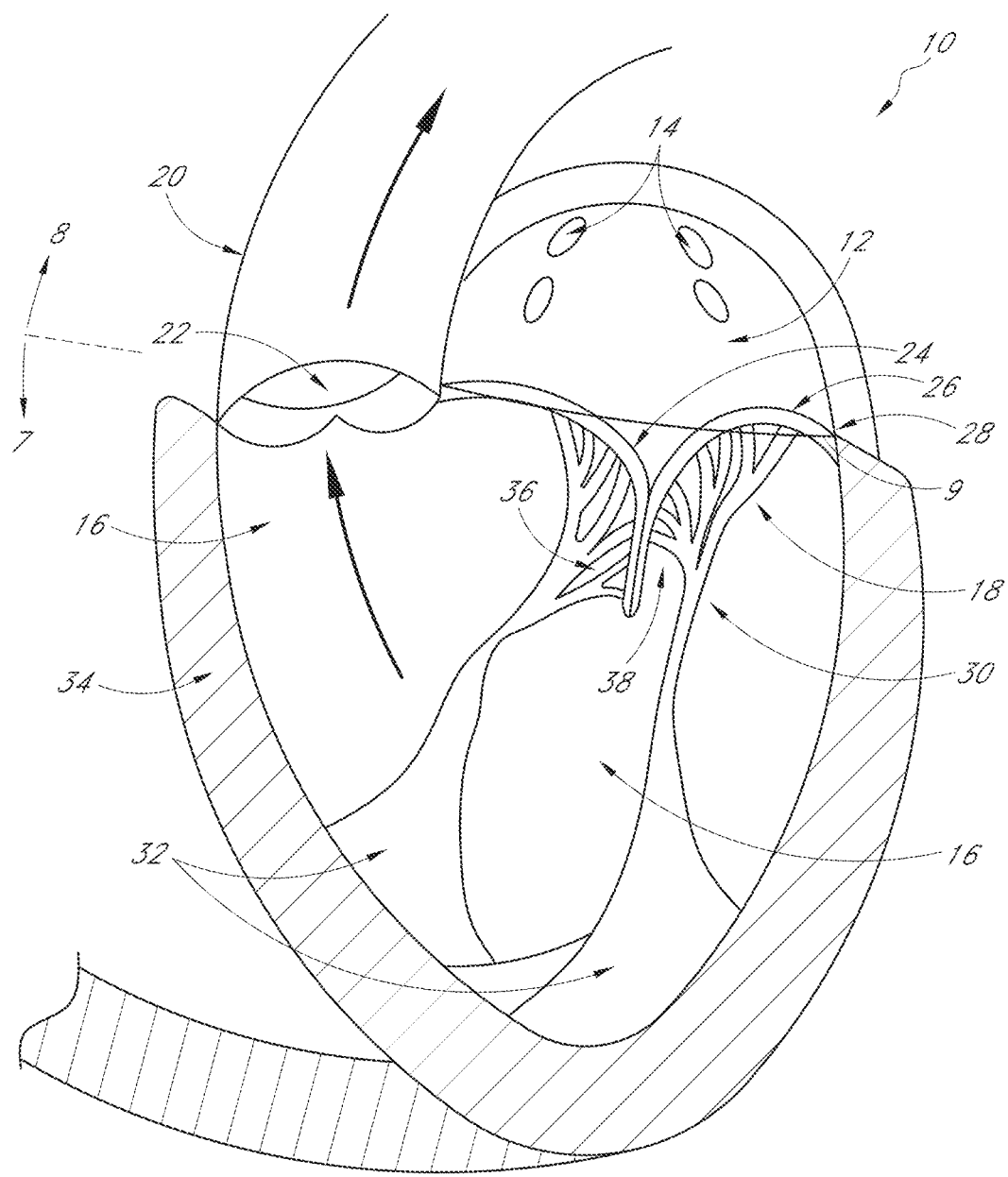
FIG. 1 is a simplified cross-sectional view of the heart with a normal mitral valve during systole. The intraannular plane is illustrated relative to supraannular and infrannular.

FIG. 1 illustrates a cross-sectional view of the heart 10 with a normal mitral valve 18 in systole. As illustrated, the heart 10 comprises the left atrium 12 which receives oxygenated blood from the pulmonary veins 14 and the left ventricle 16 which receives blood from the left atrium 12. The mitral valve 18 is located between the left atrium 12 and left ventricle 16 and functions to regulate the flow of blood from the left atrium 12 to the left ventricle 16. During ventricular diastole, the mitral valve 18 is open which allows blood to fill the left ventricle 16. During ventricular systole, the left ventricle 16 contracts, which results in an increase in pressure inside the left ventricle 16. The mitral valve 18 closes when the pressure inside the left ventricle 16 increases above the pressure within the left atrium 12. The pressure within the left ventricle 16 continues increasing until the pressure within the left ventricle 16 exceeds the pressure within the aorta 20, which causes the aortic valve 22 to open and blood to be ejected from the left ventricle and into the aorta 20.

The mitral valve 18 comprises an anterior leaflet 24 and a posterior leaflet 26 that have base portions that are attached to a fibrous ring called the mitral valve annulus 28. Each of the leaflets 24 and 26 has respective free edges 36 and 38. Attached to the ventricular side of the leaflets 24 and 26 are relatively inelastic chordae tendineae 30. The chordae tendineae 30 are anchored to papillary muscles 32 that extend from the intraventricular septum 34. The chordae tendineae 30 and papillary muscle 32 function to prevent the leaflets 24 and 26 from prolapsing and enable proper coaptation of the leaflets 24 and 26 during mitral valve 18 closure. Also shown schematically is line 9 through the valve annulus 28 representing the intraannular plane. Arrow 8 points supraannularly, toward the left atrium 12, while arrow 7 points infraannularly, toward the left ventricle 16.

Figure 2:
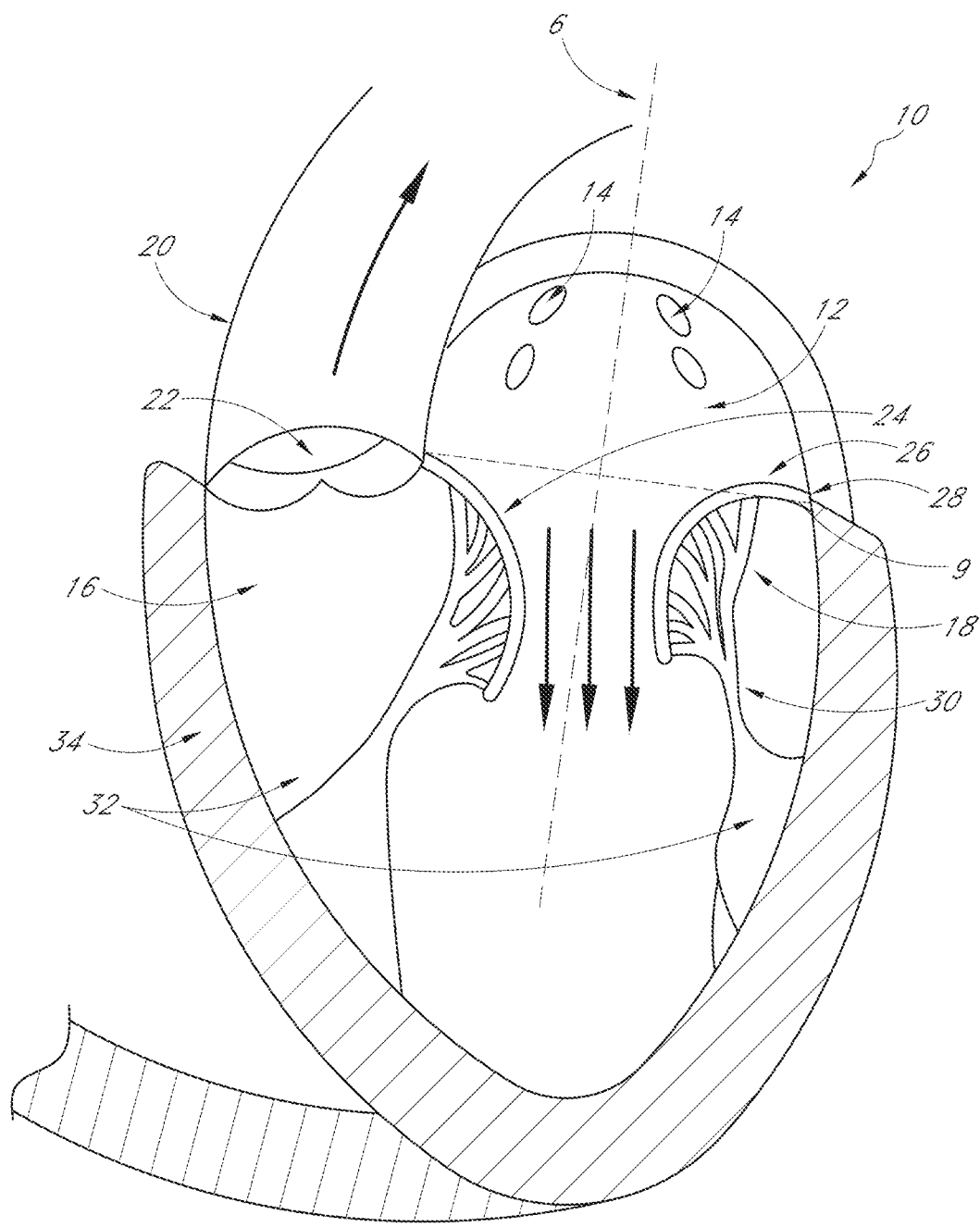
FIG. 2 is a cross-sectional view of the heart with a normal mitral valve during diastole. The axis of the mitral valve is illustrated, and shown piercing the intraannular plane.

FIG. 2 illustrates a cross-sectional view of the heart 10 with a normal mitral valve 18 in diastole. After the left ventricle 16 has ejected the blood into the aorta, the left ventricle relaxes, which results in a drop in pressure within the left ventricle 16. When the pressure in the left ventricle 16 drops below the pressure in the aorta 20, the aortic valve 22 closes. The pressure within the left ventricle 16 continues dropping until the pressure in the left ventricle 16 is less than the pressure in the left atrium 12, at which point the mitral valve 18 opens, as shown in FIG. 2. During the early filling phase, blood passively fills the left ventricle 16 and this accounts for most of the filling of the left ventricle 16 in an individual at rest. At the end of the filling phase, the left atrium 12 contracts and provides a final kick that ejects additional blood into the left ventricle. Also shown is intraannular plane 9 as described above, and line 6 representing the longitudinal axis 6 of the valve 18.

FIG. 3 illustrates a bottom view of normal mitral valve 18 in systole, looking from the left atrium and to the left ventricle. As shown, the anterior leaflet 24 and posterior leaflet 26 are properly coapted, thereby forming a coaptive edge 40 that forms a seal that prevents retrograde flow of blood through the mitral valve 18, which is known as mitral regurgitation. FIG. 4 illustrates a bottom view of normal mitral valve 18 in diastole. FIG. 5 provides a side cross-sectional view of a normal mitral valve 18 in systole. As shown in FIG. 5, the valve leaflets 24 and 26 do not normally cross the plane P defined by the annulus and the free edges 36 and 38 coapt together to form a coaptive edge 40.

FIG. 5 also illustrates a coaption zone 41. Preferably the depth of coaption (length of zone 41 in the direction of blood flow, in which the leaflets 24 and 26 are in contact) is at least about 2 mm or 5 mm, and is preferably within the range of from about 7 mm to about 10 mm for the mitral valve.

Thus, implantation of the devices in accordance with the present invention preferably achieves an increase in the depth of coaption. At increase of at least about 1 mm, preferably at least about 2 mm, and in some instances an increase of at least about 3 mm to 5 mm or more may be accomplished.

Figure 19A:
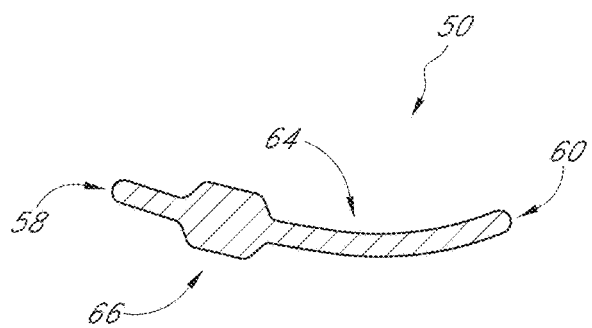
FIGS. 19A and B show a perspective view of yet another embodiment of a transvalvular band, with a widened coaptive edge support portion.
Figure 19B:
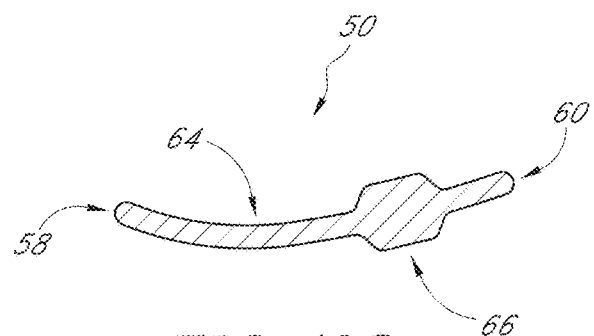

In addition to improving coaption depth, implantation of devices in accordance with the present invention preferably also increase the width of coaptation along the coaption plane. This may be accomplished, for example, by utilizing an implant having a widened portion for contacting the leaflets in the area of coaption such as is illustrated in connection with FIGS. 19A and 19B below. A further modification of the coaptive action of the leaflets which is accomplished in accordance with the present invention is to achieve early coaption. This is accomplished by the curvature or other elevation of the implant in the ventricle direction. This allows the present invention to achieve early coaption relative to the cardiac cycle, relative to the coaption point prior to implantation of devices in accordance with the present invention.

FIGS. 4 and 6 illustrate normal mitral valve 18 in diastole. As shown, the anterior leaflet 24 and posterior leaflet 26 are in a fully opened configuration which allows blood to flow from the left atrium to the left ventricle.

Figure 7:
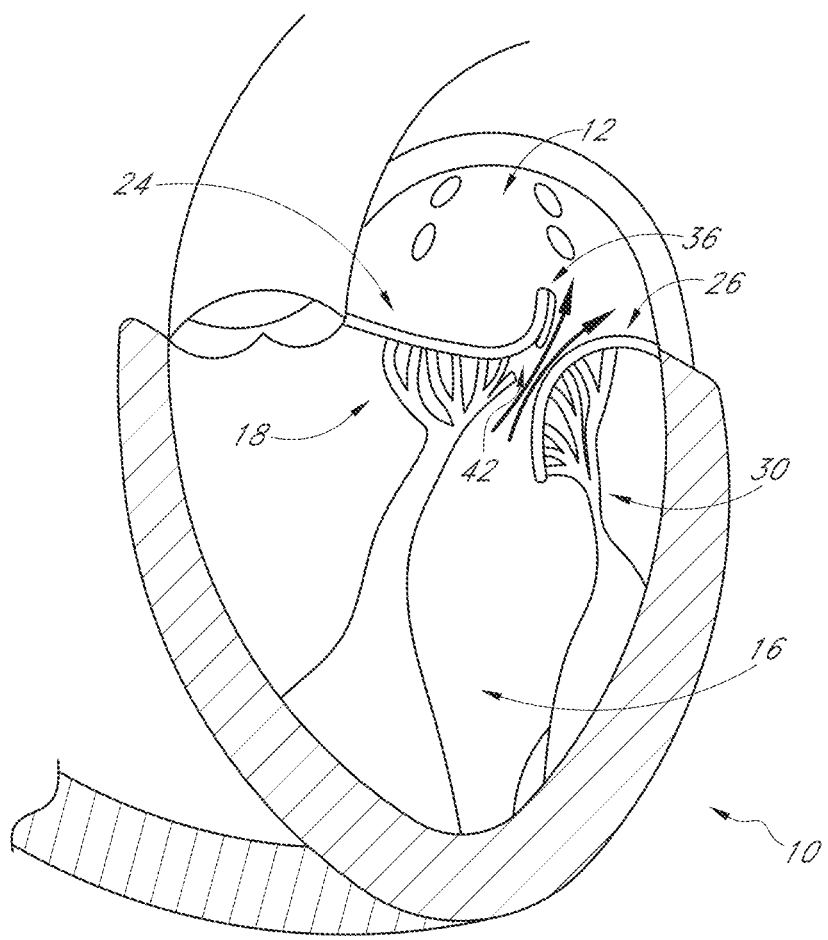
FIG. 7 is a cross-sectional view of the heart during systole showing a mitral valve with a prolapsed anterior leaflet caused by the rupture of the chordae tendineae attached to the anterior leaflet.
Figure 8:
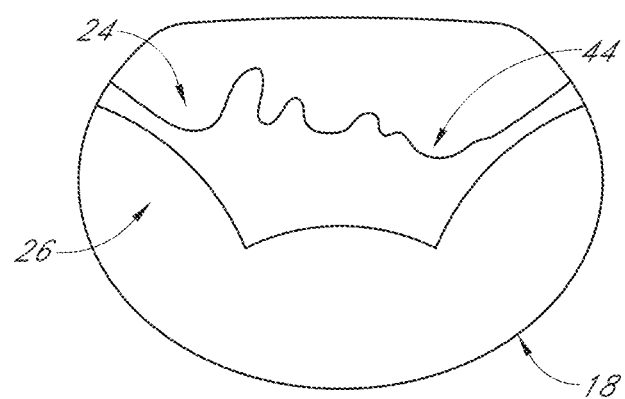
FIG. 8 is a bottom view of the mitral valve of FIG. 7 having a prolapsed anterior leaflet looking from the left atrium to the left ventricle.

FIGS. 7 and 8 illustrate a heart 10 in systole where the anterior leaflet 24 of the mitral valve 18 is in prolapse. Anterior leaflet 24 prolapse can be caused by a variety of mechanisms. For example, as illustrated in FIG. 7, rupture 42 of a portion of the chordae tendineae 30 attached to the anterior leaflet 24 can cause the free edge 36 of the anterior leaflet 24 to invert during mitral valve 18 closure. As shown in FIG. 8, inversion 44 of the anterior leaflet 24 can prevent the mitral valve leaflets 24 and 26 from properly coapting and forming a seal. This situation where the free edge 36 of the anterior leaflet 24 crosses into the left atrium 12 during mitral valve 18 closure can lead to mitral regurgitation.

Figure 9:
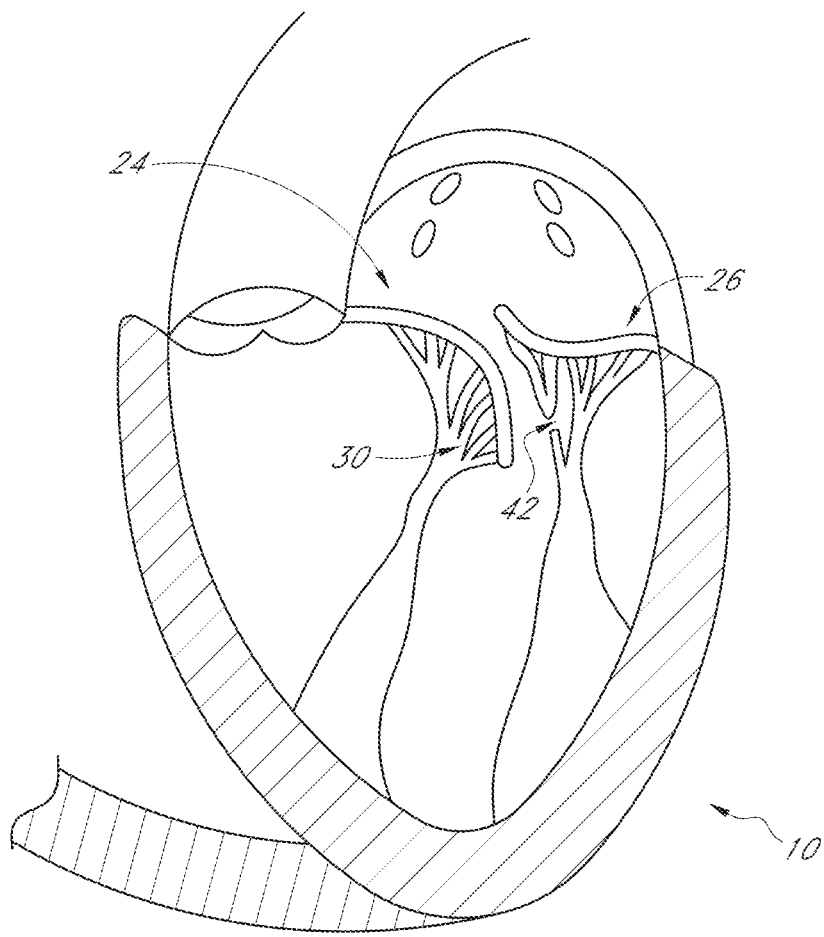
FIG. 9 is a cross-sectional view of the heart during systole showing a mitral valve with a prolapsed posterior leaflet caused by the rupture of the chordae tendineae attached to the posterior leaflet.
Figure 10:
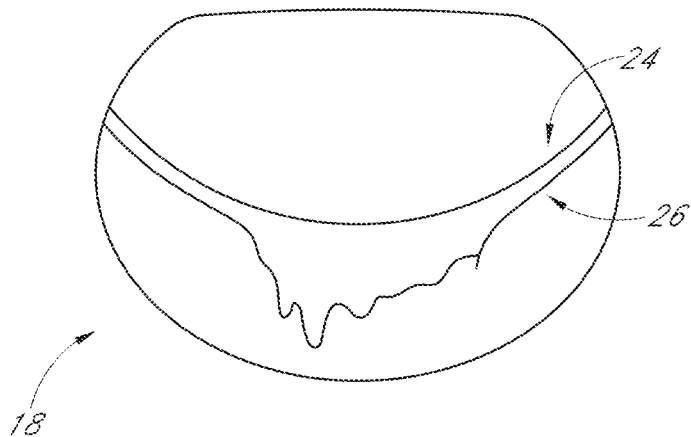
FIG. 10 is a bottom view of the mitral valve of FIG. 9 having a prolapsed posterior leaflet looking from the left atrium to the left ventricle.

Similarly, FIGS. 9 and 10 illustrate posterior leaflet 26 prolapse caused by a rupture of the chordae tendineae 30 attached to the posterior leaflet 26. In this case, the posterior leaflet 26 can invert and cross into the left atrium 12 during mitral valve 18 closure. The inversion of the posterior leaflet 26 prevents the mitral valve leaflets 24 and 26 from properly coapting and forming a seal, which can lead to mitral regurgitation.

Figure 11:
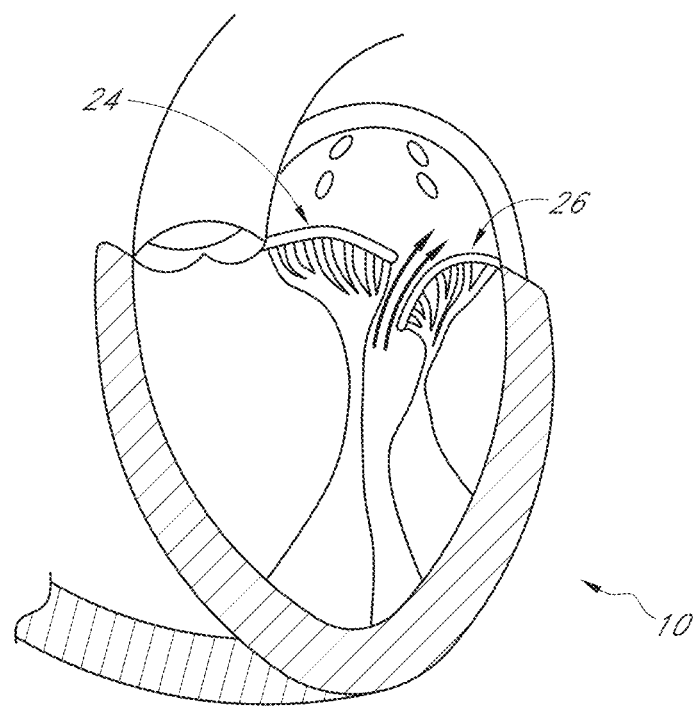
FIG. 11 is a cross-sectional view of the heart during systole showing a mitral valve with anterior leaflet prolapse.
Figure 11A:
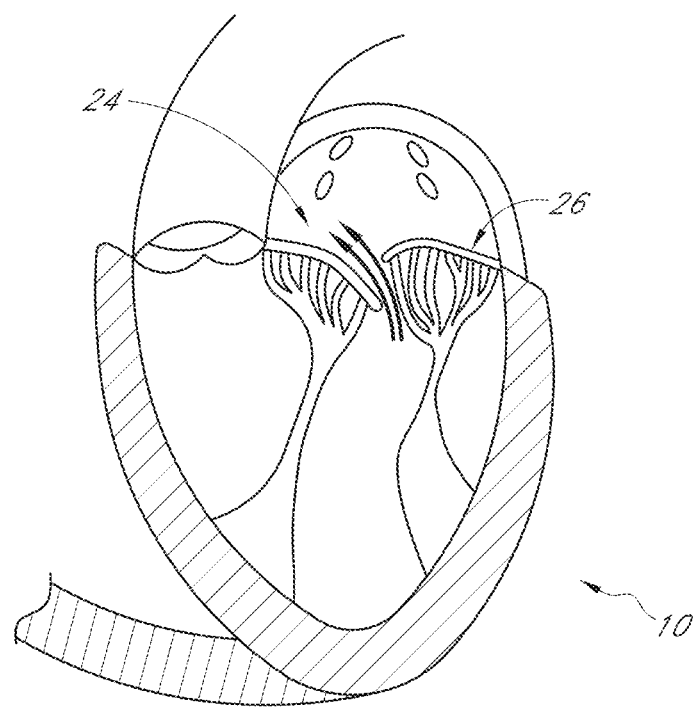
FIG. 11A is a cross sectional view as in FIG. 11, showing posterior leaflet prolapse.
Figure 11B:
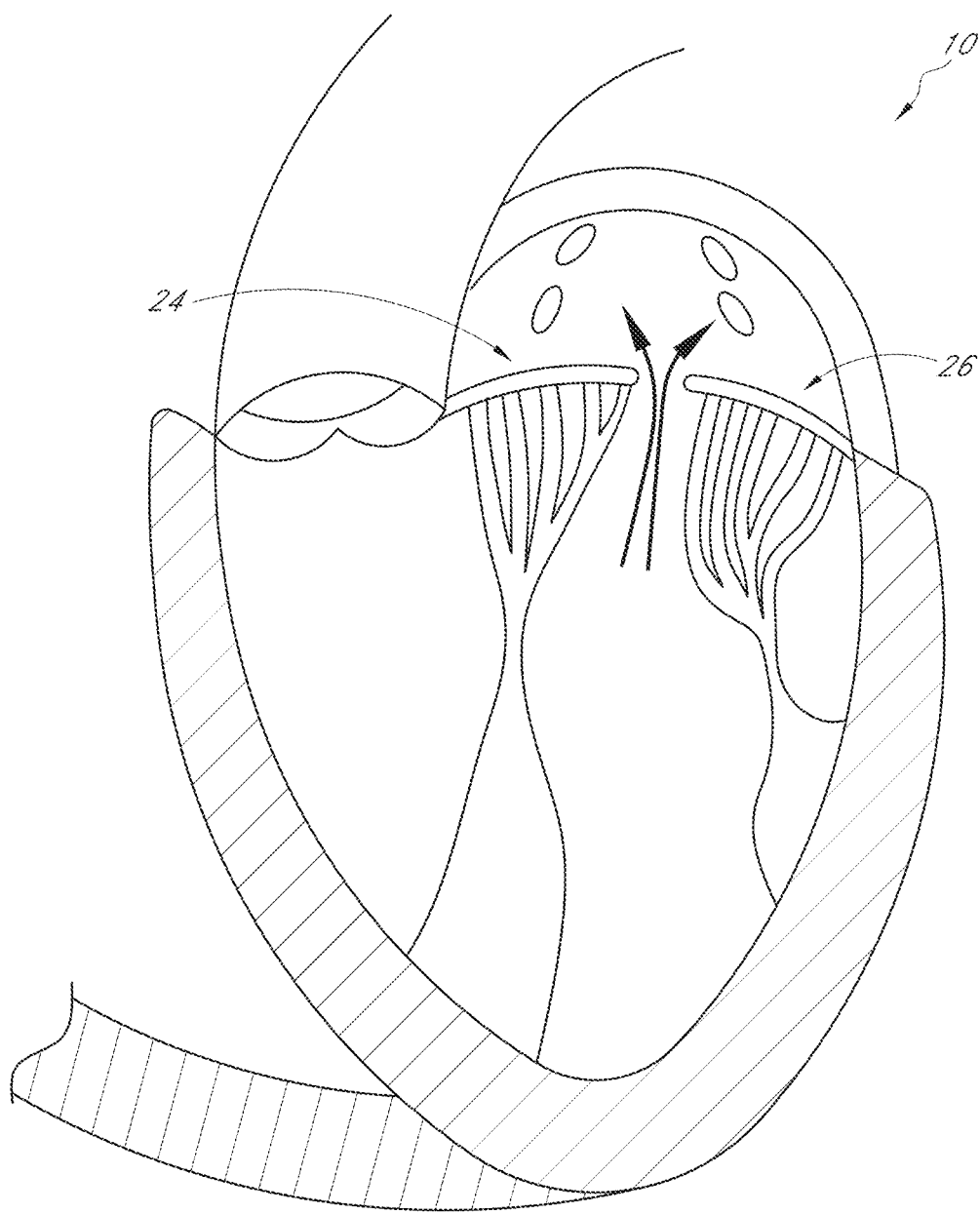
FIG. 11B is a cross sectional view as in FIG. 11, showing bileaflet prolapse with mitral regurgitation.
Figure 11C:
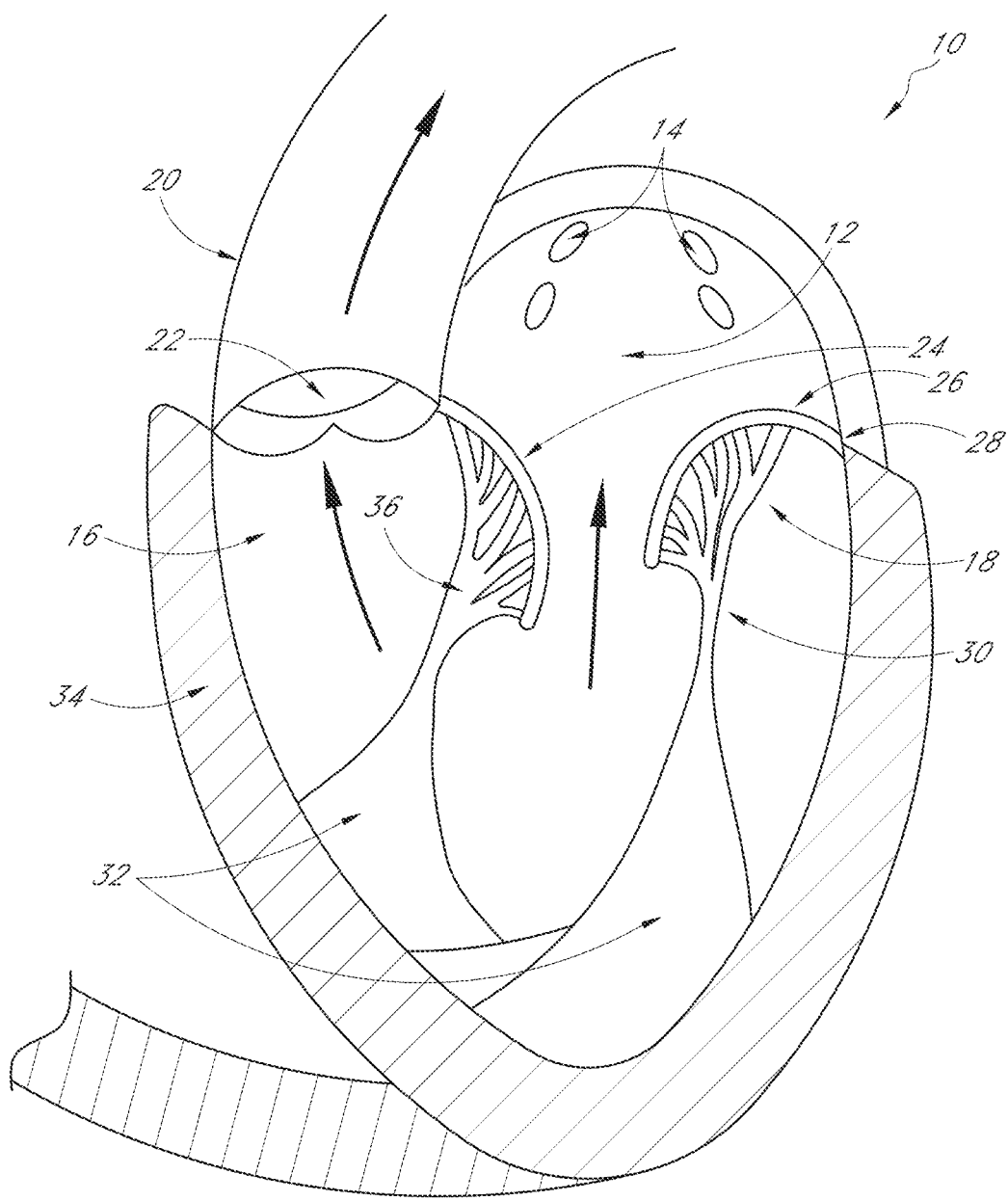
FIG. 11C illustrates a dilated mitral annulus with little or no coaption of both leaflets causing central mitral regurgitation in ischemic cardiomyopathy.

Mitral regurgitation can also be caused by an elongated valve leaflet 24 and 26. For example, an elongated anterior leaflet 24, as shown in FIG. 11, can prevent the valve leaflets 24 and 26 from properly coapting during mitral valve 18 closure. This can lead to excessive bulging of the anterior leaflet 24 into the left atrium 12 and misalignment of the free edges 36 and 38 during coaptation, which can lead to mitral regurgitation.

Figure 12:
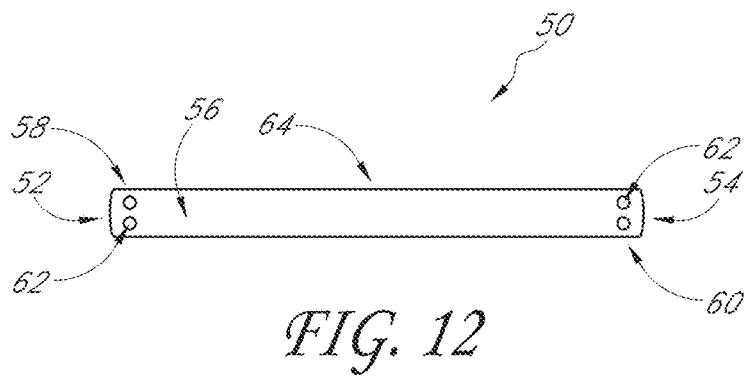
FIG. 12 is a top view of an embodiment of a transvalvular band.
Figure 13:
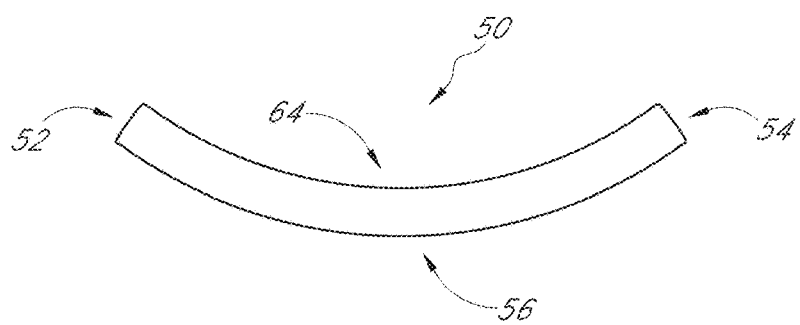
FIG. 13 is a side view of the transvalvular band of FIG. 12.

One embodiment of a transvalvular band 50 that would improve mitral valve leaflet 24 and 26 coaptation and prevent or reduce mitral regurgitation is illustrated in FIGS. 12 and 13. FIG. 12 provides a top view of the transvalvular band 50 while FIG. 13 provides a side view of the transvalvular band 50. In this embodiment, the transvalvular band 50 comprises an elongate and curved structure with a first end 52, a second end 54, a central portion 64 located between the two ends 52 and 54, and a length that is capable of extending across the annulus. The leaflet contact surface 56 is convex along the longitudinal axis, as best illustrated in FIG. 13. In other embodiments, the leaflet contact surface 56 can have a different shape and profile. For example, the contact surface 56 can be concave, straight, a combination of convex, concave and/or straight, or two concave or straight portions joined together at an apex. As illustrated in FIG. 12, the transvalvular band 50 can have a substantially constant width between the first end 52 and the second end 54. The first end 52 has a first anchoring portion 58 and the second end 54 has a second anchoring portion 60.

The anchoring portions 58 and 60 can have holes 62 for sutures that allow the transvalvular band 50 to be secured to the annulus. Alternatively, in other embodiments the anchoring portions 58 and 60 can have other means for securing the transvalvular band 50 to the annulus. For example, the anchoring portions 58 and 60 can be made of a membrane or other fabric-like material such as Dacron or ePTFE. Sutures can be threaded directly through the fabric without the need for distinct holes 62. The fabric can be attached to the other portions of the transvalvular band 50 by a variety of techniques. For example, the fabric can be attached to the other portions of the transvalvular band 50 with the use of an adhesive, by suturing, by tying, by clamping or by fusing the parts together. Another non-limiting technique of securing the transvalvular band to the annulus is to coat a malleable metal basis material, which creates structure for securing a skeleton of the transvalvular band, with a polymer such as silicone and bonding a material, such as PET (i.e., Dacron) velour for comprehensive tissue ingrowth when desired.

Figure 14:
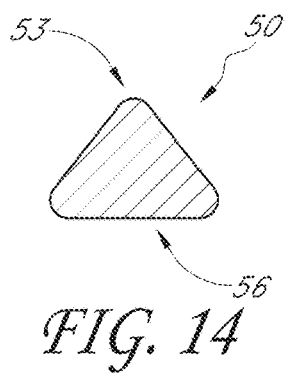
FIG. 14 is a cross-sectional view of a transvalvular band with a triangular cross-section.
Figure 15:
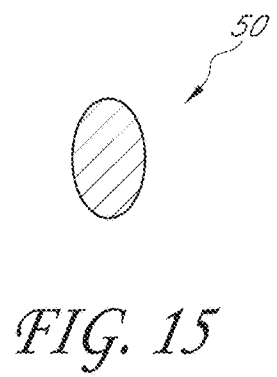
FIG. 15 is a cross-sectional view of a transvalvular band with an oblong cross-section.
Figure 16:
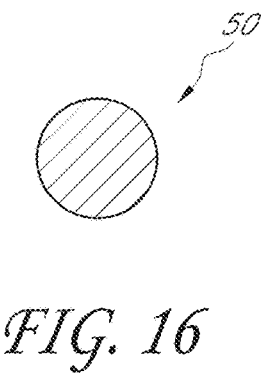
FIG. 16 is a cross-sectional view of a transvalvular band with a circular cross-section.
Figure 17:
FIG. 17 is a cross-sectional view of a transvalvular band with a rectangular cross-section.

The central portion of the transvalvular band 50 can have a variety of cross-sectional shapes, as illustrated in FIGS. 14-17. For example, the cross sectional shape can be substantially rectangular, circular, oblong or triangular. The edges of the transvalvular band 50 can be rounded or otherwise configured so that the transvalvular band 50 presents an atraumatic surface 51 to the valve leaflets. In some embodiments, the cross-section can be oriented in a particular fashion to enhance performance of the transvalvular band 50. For example as shown in FIG. 14, a transvalvular band 50 with a triangular cross section can be designed so that a relatively larger surface 56 of the triangle contacts the valve leaflets while a lower profile leading edge 53 of the triangle opposite the surface 51 faces the left atrium. This configuration allows a larger surface area to make contact with and support the mitral valve leaflets, while also presenting a more streamlined shape that provides less resistance to blood flowing from the left atrium to the left ventricle. Decreasing the resistance to blood flow is desirable because it can reduce turbulence and reduce the impedance of the transvalvular band 50 on the filling of the left ventricle. Similarly, the transvalvular bands 50 with an oblong or rectangular cross-section can be oriented to either increase the surface area for contact with the valve leaflets, or be oriented to reduce the resistance to blood flow.

The dimensions of the transvalvular band 50 will vary, depending upon the specific configuration of the band 50 as well as the intended patient. In general, transvalvular band 50 will have an axial length from first end 52 to second end 54 within the range of from about 20 mm to about 32 mm. In one embodiment, intended for a typical male adult, the axial length of the transvalvular band 50 is about 24 mm to 26 mm. The width of the transvalvular band 50 in the central zone 64 may be varied depending upon the desired performance, as will be discussed herein. In general, the trailing surface 51 against which leaflets will seat is preferably large enough to minimize the risk of erosion resulting from repeated contact between the closed leaflets and the implant. The width of the leading edge 53 is preferably minimized, as discussed above, to minimize flow turbulence and flow obstruction. In general, widths of the surface 51 measured perpendicular to the flow of blood are presently contemplated to be less than about 5 mm, and often within the range of from about 5 mm to about 10 mm in the zone of coaptation.

Figure 18:
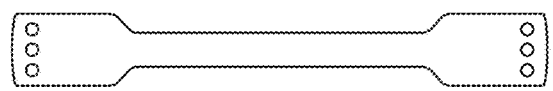
FIG. 18 is a top view of another embodiment of a transvalvular band.

In some embodiments as illustrated in FIG. 18, the central portion 64 of the transvalvular band 50 can be narrower in width, measured perpendicular to blood flow than the first and second anchoring portions 58 and 60. By narrowing the central portion 64, the resistance to blood flow can be reduced. However, narrowing the central portion 64 reduces the surface area of the leaflet contact surface 56 that supports the valve leaflets.

In the embodiment illustrated in FIG. 18, the narrowed central portion 64 is separated from the first anchoring portion 58 and second anchoring portion 60 by a first shoulder 57 and second shoulder 59. The length of the central portion 64, between first shoulder 57 and second shoulder 59 can be less than about 50% of the overall length of the device, or less than about 30% of the overall length of the device if it is desired to minimize the obstruction in the center of the flow path, while presenting a wider transverse surface for supporting the leaflets when the valve is closed. Alternatively, the length of the central zone 64 may be greater than 50%, and in some embodiments greater than 75% of the overall length of the implant.

In some embodiments as illustrated in FIGS. 19A, 19B, 21 and 23, a coaptive edge support portion 66 of the central portion 64 of the transvalvular band 50 can be wider than the adjacent portions of the transvalvular band 50, leading up to and potentially including the first and second anchoring portions 58 and 60. By increasing the width and surface area of the coaptive edge support portion 66, more support can be provided to the valve leaflets at the coaptive edge. This increased support can increase the width of leaflet coaption. The other portions of the central portion 64 can remain narrow to reduce the resistance to blood flow. The support portion 66 can be located at a fixed position or adjustable along the transvalvular band so that its position can be optimized by the surgeon and then secured at a fixed point such as by suturing, or removed if deemed unnecessary.

In one implementation of the invention, the transvalvular band comprises a first component for primary reduction and a second component for fine adjustment. For example, the device illustrated in FIG. 19A may be provided with an adjustable (e.g. slidable) support portion 66. The transvalvular band may be positioned across the annulus as has been described herein, and hemodynamic function of the valve may be evaluated. The support portion 66 may thereafter be adjusted along the length of the transvalvular band to treat residual leakage or otherwise optimize the functionality of the implant such as by increasing the zone of coaptation. The second component (e.g. support portion 66) may thereafter be fixed with respect to the transvalvular band such as by sutures, clips, adhesives, or other techniques known in the art. Alternatively, the second portion may be separate from and connectable to the transvalvular band such as stitching, clips, suturing or other technique known in the art.

In addition, the coaptive edge support portion 66 can be offset from the center of the transvalvular band 50, to reflect the asymmetry between the anterior leaflet and the posterior leaflet. For example, the coaptive edge support portion 66 can be positioned closer to the first anchoring portion 58 than to the second anchoring portion 60. In certain embodiments, the edge support portion 66 will be centered about a point which is within the range of from about 20% to about 45% of the overall length of the implant from the closest end.

Figure 20:
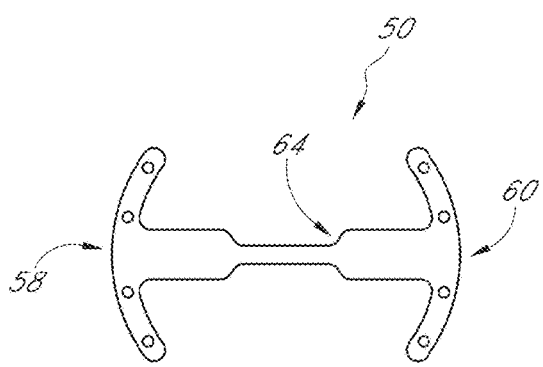
FIGS. 20-23 are top views of other embodiments of a transvalvular band.

FIG. 20 illustrates another embodiment of a transvalvular band 50 that is a modification of the transvalvular band 50 shown in FIG. 18. As illustrated in FIG. 20, the transvalvular band 50 has a narrow central portion 64 that provides relatively low resistance to blood flow. However, the first and second anchoring portions 58 and 60 extend further in a lateral direction, and can be arcuate to conform to the mitral valve annulus. These laterally extended anchoring portions 58 and 60 provide additional anchoring of the transvalvular band 50 and can help improve the stability of the device after implantation. The laterally extending anchoring portion 58 and 60 may be provided with any of a variety of structures for facilitating anchoring to the valve annulus. For example, they may be provided with a plurality of apertures 61, for conventional stitching or to receive any of a variety of clips or tissue anchors. The anchoring portions may alternatively be provided with any of a variety of barbs or hooks, or may be provided with a fabric covering such as a Dacron sleeve to facilitate sewing. Further, in some embodiments, this sewing ring may have an elastomeric core upon which the Dacron is secured to provide a more compliant structure to hold the implant. Measured in the circumferential direction (transverse to the longitudinal axis of the implant 50) the laterally extending anchoring portions will have an arc length of greater than about 5 mm, and, in some embodiments, greater than about 1 cm. Arc lengths of at least about 2 cm, and, in some embodiments, at least about 3 cm may be utilized, depending upon the desired clinical performance.

Figure 21:
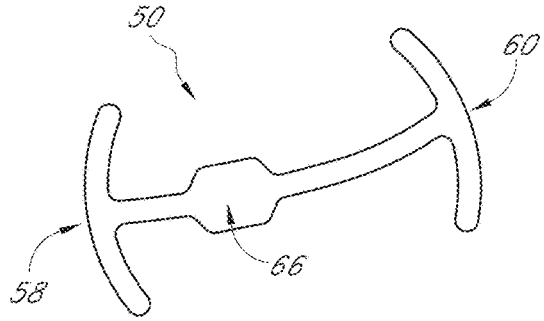

FIG. 21 illustrates another embodiment of a transvalvular band 50 with the extended anchoring portions 58 and 60 and a wider, offset coaptive edge support portion 66. This embodiment has the benefit of additional stability provided by the extended anchoring portions 58 and 60 and enhanced support of the coaptive edge.

Figure 22:
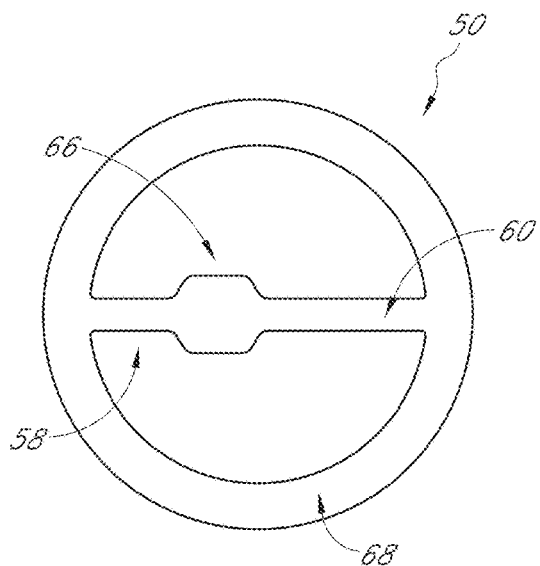
Figure 23:
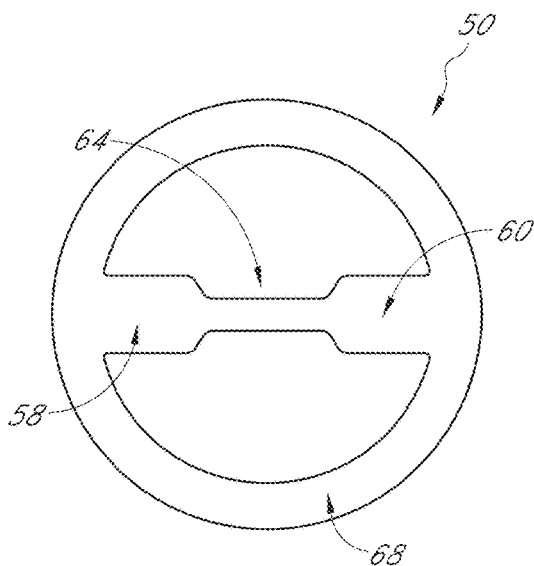

FIGS. 22 and 23 illustrate another embodiment of a transvalvular band 50 which is combined with an annular ring 68. The annular ring 68 can be used as both a support for the transvalvular band 50 and, if desired, also to help stabilize the size and shape of the mitral valve annulus itself. In some embodiments, the annular ring 68 can be used to reduce the size of the mitral valve annulus and to bring the mitral valve leaflets closer together. This can be accomplished by, for example, suturing the mitral valve annulus to an annular ring 68 of smaller diameter. In addition, the annular ring 68 provides additional support and stability to the transvalvular band 50. The anchoring portions 58 and 60 of the transvalvular band 50 can be formed integrally with the annular ring 68, or the anchoring portions 58 and 60 can be attached to the annular ring by a variety of means, such as suturing, bonding, adhesives, stapling and fusing. FIG. 22 discloses an embodiment with a narrow central portion 64 while FIG. 23 discloses an embodiment with a wider, offset coaptive edge support portion 66.

Figure 23A:
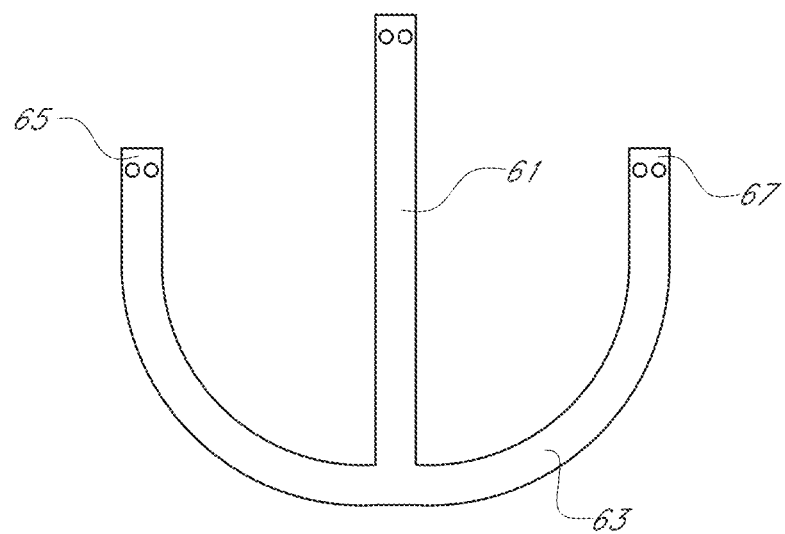
FIG. 23A shows a central mitral transvalvular band with posterior annuloplasty ring.

FIG. 23A illustrates a further implementation of the invention, adapted to treat ischemic mitral regurgitation with posterior annuloplasty. A transvalvular band 61 is provided for spanning the leaflet coaption plane as has been described herein. Any of the features described in connection with other transvalvular bands disclosed herein may be incorporated into the transvalvular band 61.

An arcuate posterior annuloplasty support 63 is connected to the transvalvular band 61, and adapted to extend for an arc length along the native annulus. In the illustrated embodiment, the support 63 extends through an arc of approximately 180°, extending from a first trigone attachment zone 65 to a second trigone attachment zone 67. The attachment zones may be provided with sewing apertures, a fabric covering, or other structure for facilitating attachment to tissue. In general, the transvalvular band 61 will have dimensions similar to those described elsewhere herein. The transverse dimension from first trigone zone 65 to second trigone zone 67 may be varied depending upon the size of the native annulus, but will generally be within the range of from about 35 mm to about 45 mm.

Figure 23B:
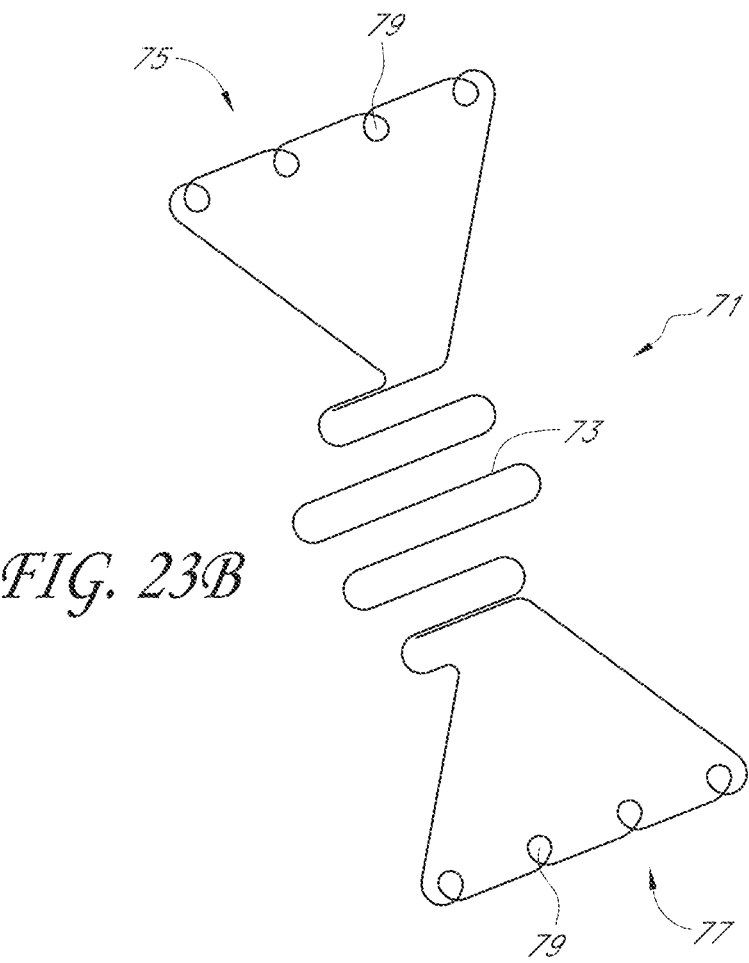
FIG. 23B shows an intraannular band formed from a length of wire.

Referring to FIG. 23B, there is illustrated a transvalvular band in accordance with the present invention, formed from a single length or several lengths of flexible wire. The bend angles and orientation of the struts in the illustrated embodiment may be readily altered, to accommodate the desired axes of compression which may be desirable for a particular deployment procedure.

In general, the transvalvular band 71 comprises an elongate flexible wire 73 formed into a serpentine pattern, for providing a support for the valve leaflets as has been discussed herein. Although not illustrated in FIG. 23B, the wire 73 may be formed such that it bows or inclines in the direction of the ventricle to achieve early closure as is discussed elsewhere herein. The wire 73 may extend into a first connection section 75 and a second connection section 77. Each of the connection sections 75 and 77 may be provided with a plurality of eyelets 79, to receive sutures for attaching the implant to the valve annulus. The implant may be formed from any of a variety of flexible materials, including various polymers described elsewhere herein as well as titanium, titanium alloy, Nitinol, stainless steel, elgiloy, MP35N, or other metals known in the art. This design has an advantage of providing a relatively large support footprint against the valve leaflets, while at the same time optimizing the area of open space to permit maximum blood flow therethrough. The design may be treated or coated with silicone or other suitable material to eliminate untoward effects such as thrombosis or corrosion. Treatments may be sequential and include more than one listed but not limited to electropolishing, harperization, tumbling, pickling, plating, encapsulation or physical vapor deposition of appropriate materials.

FIGS. 24-27 illustrate side views of transvalvular bands 50 with different inclinations. One of the objectives of the present invention is to not merely provide support to the leaflets during systole, but to elevate the plane of coaption in the direction of the ventricle, to cause early coaption (closure) relative to the cardiac cycle, as is discussed elsewhere herein. The variation in conditions, and other patient to patient variations may warrant production of the transvalvular band of the present invention in an array of sizes and/or configurations, so that clinical judgment may be exercised to select the appropriate implant for a given case. Alternatively, the transvalvular band may be provided in an adjustable form or a modular form so that an implant of the desired configuration can be constructed or modified intraoperatively at the clinical site. In a three segment embodiment, such as that illustrated in FIGS. 24 through 27, a central segment may be provided for positioning within the center of the flow path, or centered on the coaptive edges of the leaflets. First and second end portions may be connected to the central portion, for supporting the central portion relative to the tissue anchors. First and second end portions may be provided in a variety of lengths and curvatures, enabling construction of a relatively customized modular implant as may be desired for a particular patient.

Figure 24:
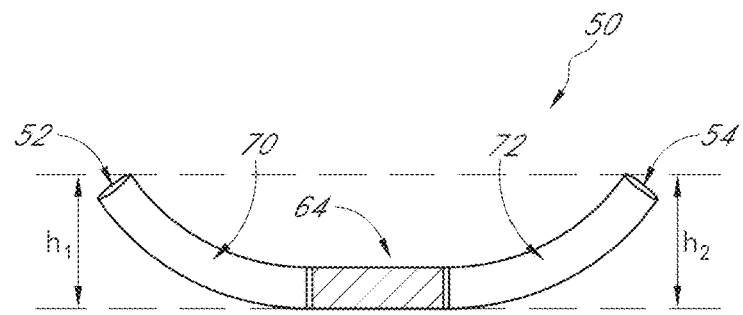
FIGS. 24-27 are side views of other embodiments of a transvalvular band.

For example, FIG. 24 illustrates a transvalvular band 50 with a central portion 64 and two gently angled arm portions 70 and 72. The first and second ends 52 and 54 are displaced from the central portion 64 by a height, h1 and h2, respectively. In FIG. 24, h1 and h2 are about equal and can range from about 0 mm to about 10 mm. Preferably h1 and h2 will be at least about 2 mm and will often be at least about 4 mm or 6 mm or more, but generally no more than about 10 mm or 12 mm.

Figure 25:
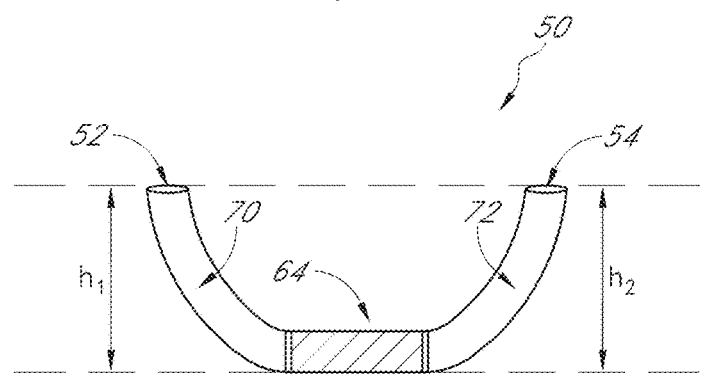
Figure 26:
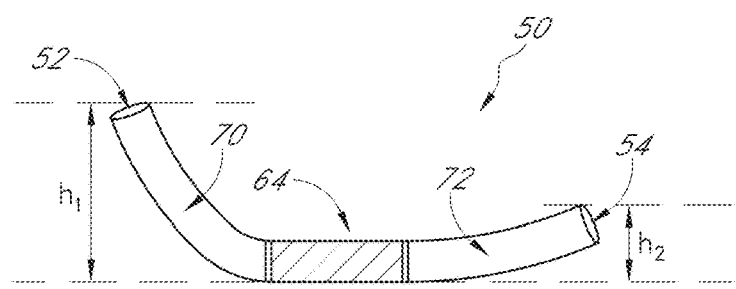
Figure 27:
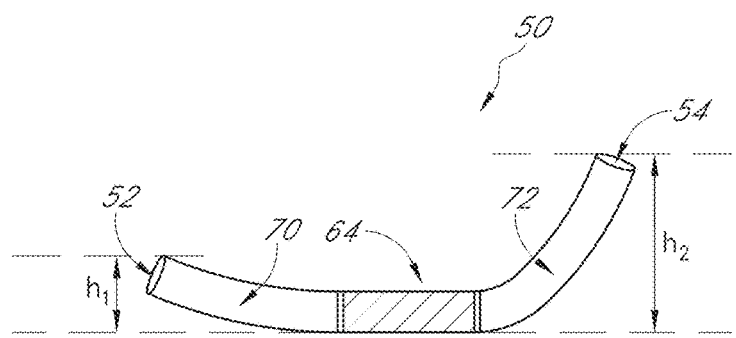

FIG. 25 illustrates a transvalvular band 50 with a central portion 64 and two sharply angled arm portions 70 and 72. The first and second ends 52 and 54 are displaced from the central portion 64 by a height, h1 and h2, respectively. In FIG. 25, h1 and h2 are about equal and can range from about 8 mm to about 12 mm. FIG. 26 illustrates a transvalvular band 50 with a central portion 64, a highly angled first arm 70 and a gently angled second arm 72. The first and second ends 52 and 54 are displaced from the central portion 64 by a height, h1 and h2, respectively. In FIG. 26, h1 is greater than h2. The h1 ranges from about 6 mm to about 10 mm, while h2 ranges from about 2 mm to about 6 mm. FIG. 27 illustrates a transvalvular band 50 with a central portion 64, a gently angled first arm 70 and a highly angled second arm 72. The first and second ends 52 and 54 are displaced from the central portion 64 by a height, h1 and h2, respectively. FIG. 27, may be a mirror image of FIG. 26.

The transvalvular band 50 can be made of any of a variety of materials that are compatible with implantation within a patient's body and which has the requisite structural integrity to support the mitral valve leaflets. For example, suitable materials include titanium, titanium alloys, stainless steel, stainless steel alloys, nitinol, elgiloy, MP35N, other metals and alloys, ceramics, and polymers such as PTFE, polycarbonate, polypropylene, UHMWPE, HDPE, PEEK, PEBAX and the like.

In order to reduce the thrombogenicity of the transvalvular band 50, the transvalvular band 50 can be provided with a smooth surface or appropriately micro-texture the surface in some embodiments, such as via a porous or microporous structure. Other factors such as surface chemistry, energy, morphology, macrofeatures, and general material properties matching the in situ needs can also be considered in tailoring the surface of the band. In addition, the transvalvular band 50 can be coated with a variety of substances to reduce thrombogenicity. For example, the transvalvular band 50 can be coated with a antithrombogenic agent such as heparin, a polymer such as PTFE, or a polymer conjugated with heparin or another antithrombogenic agent. Heparin coatings can be achieved in a variety of methods, one of which may be to coat or drip the prosthesis in TDMAC-heparin (Tridodecylmethylammonium heparinate).

As illustrated in FIGS. 28-31, the transvalvular band 50 is implanted in the plane of the mitral valve annulus 28 in a patient suffering from anterior leaflet 26 prolapse caused by the rupture 42 of the chordae tendineae 30 attached to the anterior leaflet 26. Although a prolapsed anterior leaflet 26 is illustrated, it should be understood that the method described herein is also applicable for treating other types of prolapse, such as posterior leaflet prolapse and prolapse caused by elongated leaflets 24 and 26. The transvalvular band 50 can be attached to the annulus 28 by a variety of techniques, such as sutures, anchors, barbs, stapes, self-expanding stents, or other techniques that are known or are apparent to those of skill in the art.

Figure 29:
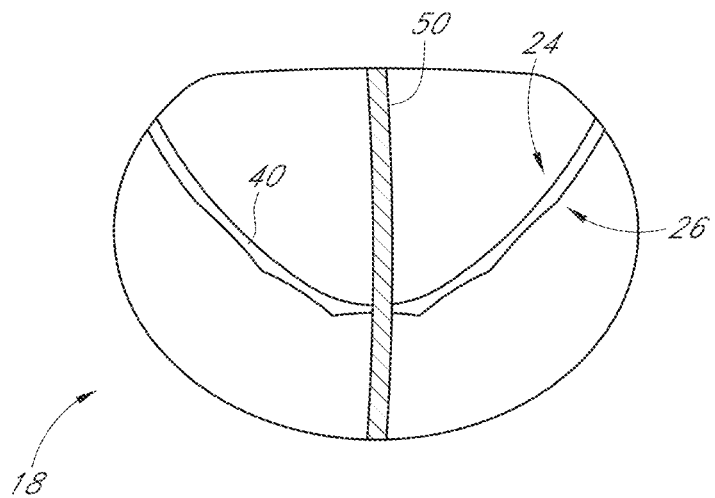
FIG. 29 is a bottom view of the mitral valve of FIG. 28 during systole with a transvalvular band implanted in the mitral annulus looking from the left atrium to the left ventricle.
Figure 31:
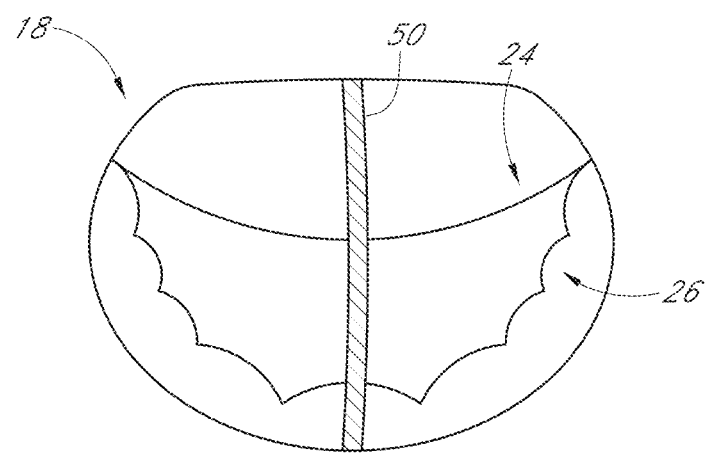
FIG. 31 is a bottom view of the mitral valve of FIG. 30 during diastole with a transvalvular band implanted in the mitral annulus looking from the left atrium to the left ventricle.

As best illustrated in FIGS. 29 and 31, the transvalvular band 50 is oriented in the annulus 28 so that the transvalvular band 50 is positioned approximately transversely to the coaptive edge 42 formed by the closure of the mitral valve leaflets 24 and 26. The transvalvular band 50 can also be positioned over the prolapsed portion of the anterior leaflet 26 so that the transvalvular band 50 can directly support the prolapsed portion of the anterior leaflet 24 and keep the anterior leaflet 24 inferior to the plane of the mitral valve annulus 28, i.e., elevated in the direction of the ventricle or of antegrade flow, thereby preventing or reducing prolapse and mitral regurgitation.

Figure 28:
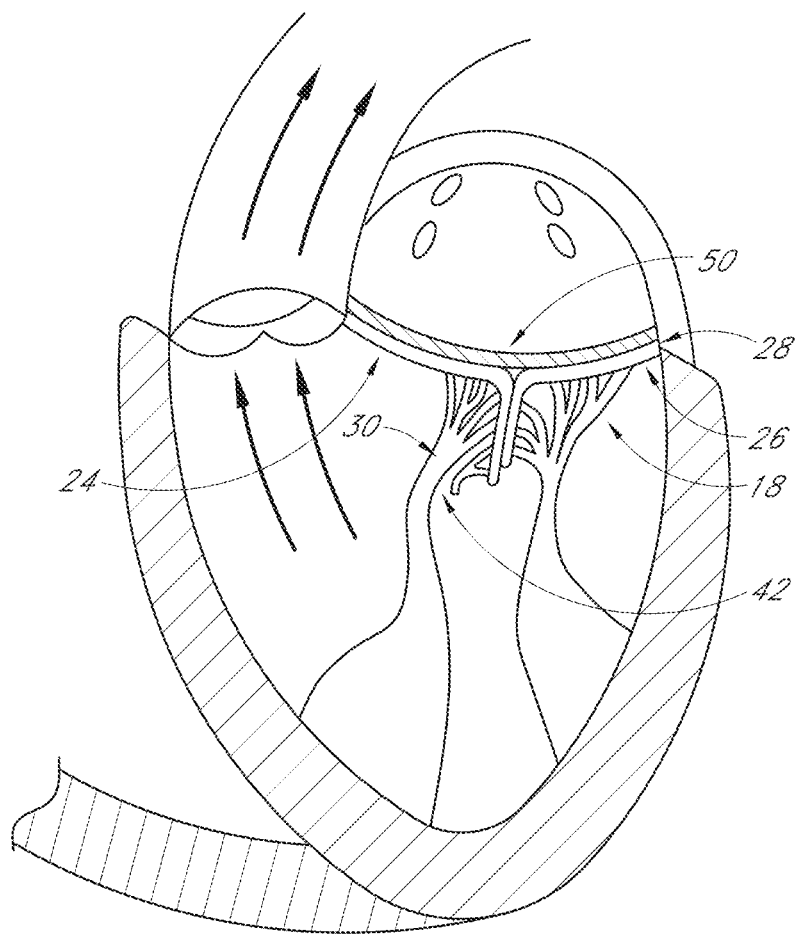
FIG. 28 is a cross-sectional view of a heart during systole with a transvalvular band implanted in the mitral annulus.

FIGS. 28 and 29 illustrate the effect of the transvalvular band 50 on the mitral valve 18 during systole. As shown, both the anterior leaflet 24 and the posterior leaflet 26 are supported by the transvalvular band during closure of the mitral valve 18. The arcuate transvalvular band 50 functions to keep both leaflets 24 and 26 inferior to the plane of the annulus 28 and enables the leaflets 24 and 26 to form a coaptive edge 40. Although a single transvalvular band 50 has been illustrated, in some embodiments, multiple transvalvular bands 50 such as two or three or more can be implanted across the annulus 28 to provide additional support to the mitral valve leaflets 24 and 26.

Figure 30:
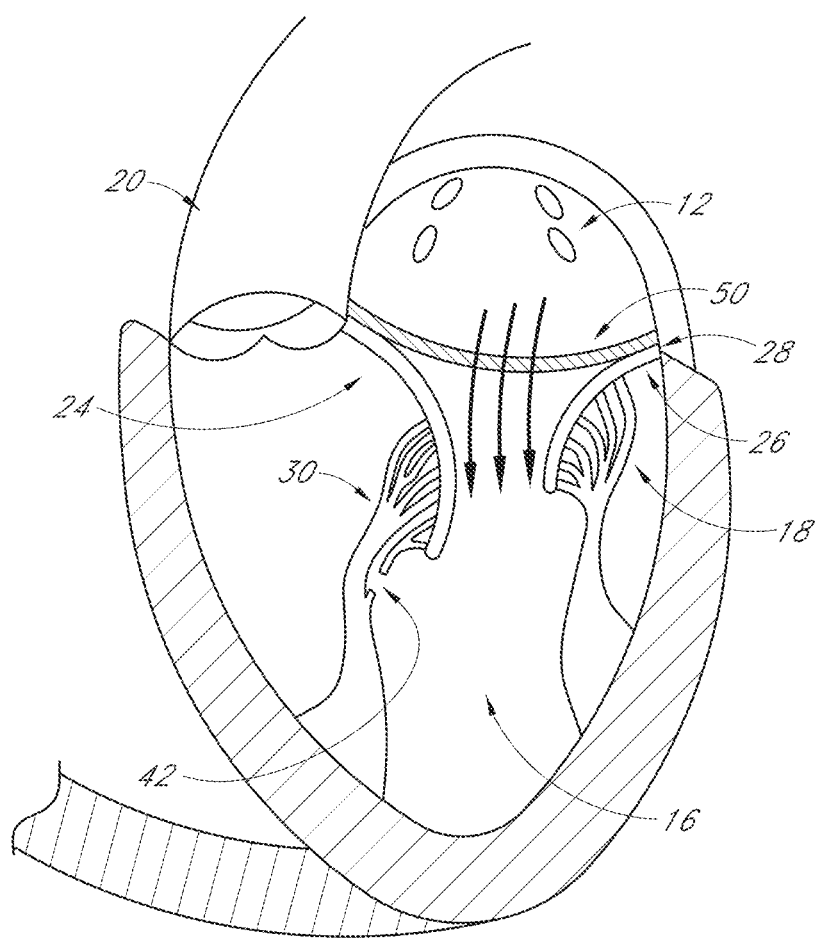
FIG. 30 is a cross-sectional view of a heart during diastole with mitral valve and a transvalvular band implanted in the mitral annulus.

FIGS. 30 and 31 illustrate the effect of the transvalvular band 50 on the mitral valve 18 during diastole. During diastole, the mitral valve 18 opens so that blood can fill the left ventricle 16 from the left atrium 12. As best illustrated in FIG. 31, the transvalvular band 50 obstructs only a small portion of the mitral valve 18 opening, and therefore, does not cause excessive resistance to blood flow.

Figures 32, 33:
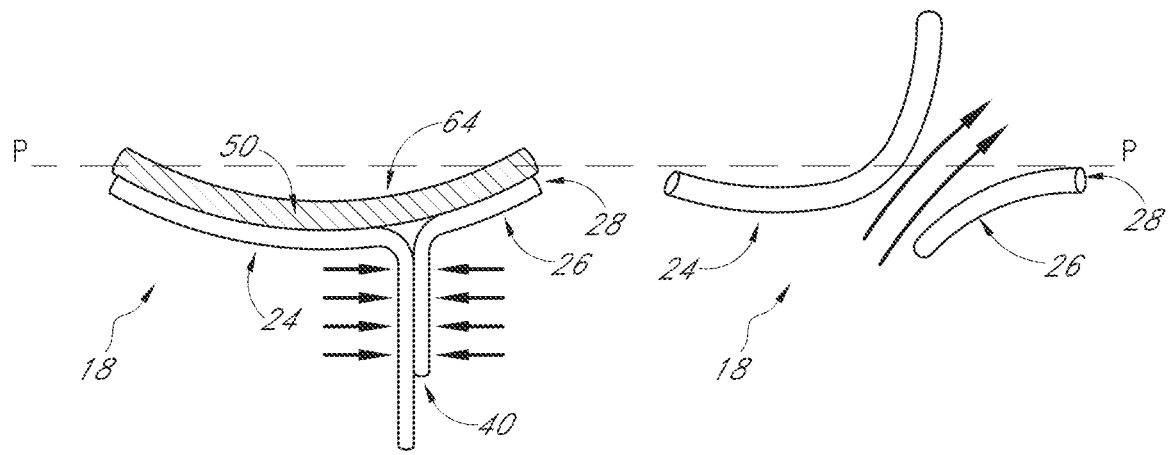
FIG. 32 is a cross-sectional schematic view of the mitral valve of FIG. 28 during systole with a transvalvular band implanted in the mitral annulus.
FIG. 33 is a cross-sectional schematic view of the mitral valve of FIG. 32 during systole without the transvalvular band implanted in the mitral annulus.
Figures 34, 35:
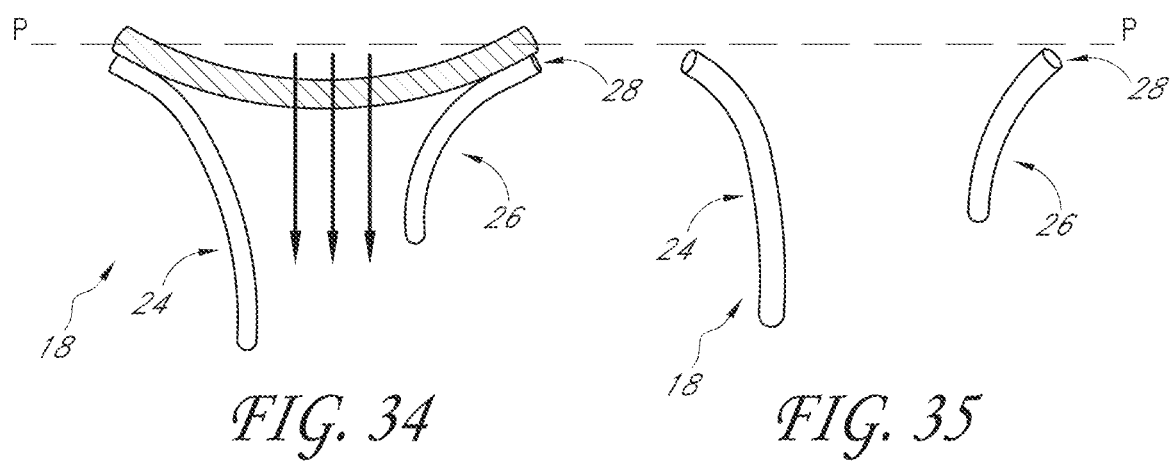
FIG. 34 is a cross-sectional schematic view of the mitral valve of FIG. 30 during diastole with the transvalvular band implanted in the mitral annulus.
FIG. 35 is a cross-sectional schematic view of the mitral valve of FIG. 34 during diastole without the transvalvular band implanted in the mitral annulus.

FIGS. 32-35 are cross-sectional side views of the mitral valve 18 with and without the support of the transvalvular band 50. During systole, the mitral valve 18 closes. Without the transvalvular band 50, the anterior leaflet 24 crosses the plane P defined by the mitral valve annulus 28 and prolapse, which leads to mitral regurgitation, as shown in FIG. 33. However, by implanting the transvalvular band 50 in the annulus 28 such that the arcuate transvalvular band 50 arches towards the left ventricle and the central portion 64 is displaced from the plane P, the anterior leaflet 24 is prevented from prolapsing above the plane P thus eliminating or reducing retrograde flow (shown in FIG. 33). The leaflets 24 and 26 rest upon the transvalvular band 50 and the pressure exerted by the blood upon the distal portion of the leaflets 24 and 26 form the coaptive edge 40. As illustrated in FIGS. 34 and 35, the performance of the mitral valve 18 during diastole is not substantially affected by the transvalvular band 50.

Figure 36:
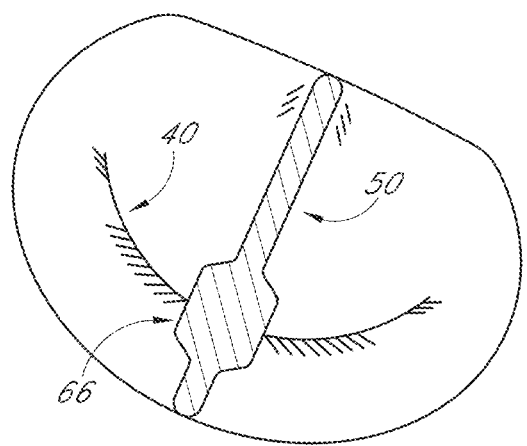
FIG. 36 is a bottom view of the mitral valve during systole with another embodiment of the transvalvular band implanted in the mitral annulus looking from the left atrium to the left ventricle.
Figure 38:
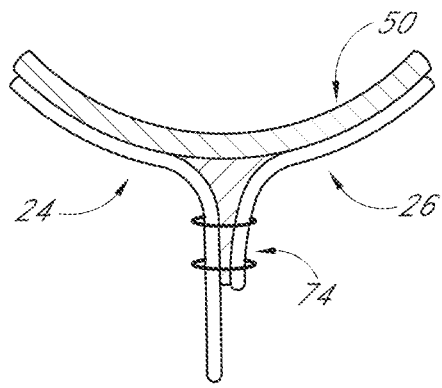
FIG. 38 is a cross-sectional schematic view of the mitral valve treated with the transvalvular band of FIG. 37 and an Alfieri type procedure.

Although the method of implanting and positioning the transvalvular band 50 has been illustrated with one embodiment of the transvalvular band 50, other embodiments as described above can also be used. For example, FIG. 36 illustrates a transvalvular band 50 with a wider, offset coaptive edge support portion 66 that has been implanted in the mitral valve annulus. As shown, the coaptive edge support 66 is offset so that it positioned to support the coaptive edge of the mitral valve 18. In addition, the transvalvular band 50 can be used in conjunction with other devices and procedures, such as a separate or integrally attached annular or annuloplasty ring described above. In addition, the transvalvular band 50 can be used in conjunction with the Alfieri procedure, where the tips of the mitral valve leaflets 24 and 26 are sutured 74 together, as shown in FIG. 38.

Figure 37:
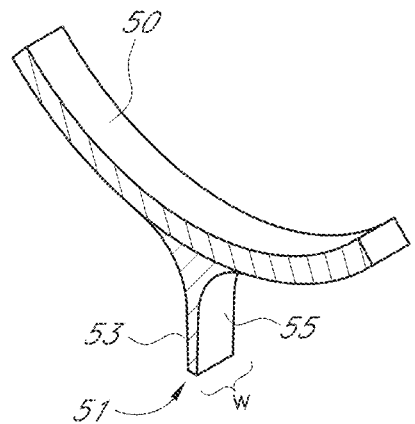
FIG. 37 is a cross-sectional view of a transvalvular band with a transverse leaflet support.

Referring to FIG. 37, there is illustrated a perspective view of a transvalvular band 50 having a transverse projection or support 51 extending in the direction of the ventricle or in the direction of diastolic blood flow, which could be considered antegrade. The support 51 has a width W, which may be at least about 3 mm, and in some embodiments, at least about 5 mm, and in other embodiments at least about 1.0 cm. The projection 51 may be utilized without an Alfieri stitch, so that the leaflets of the mitral valve close against opposing side walls 53 and 55 of the projection 51. The projection 51 thus helps center the closure of the leaflets, as well as controlling the width of coaption. In addition, the band 50 is illustrated as convex in the direction of the ventricle, to accomplish early closure as has been discussed herein.

The transvalvular band in accordance with the present invention can be implanted via an open surgical procedure, via thoracotomy (e.g. transapically) or alternatively, via a percutaneous procedure using a translumenally implantable embodiment. In the translumenally implantable embodiment, one or more transvalvular bands can be attached to a self-expandable support structure, such as a self-expandable ring or self-expandable stent having a relatively short axial length relative to its expanded diameter. The transvalvular band and the compressed self-expandable support structure are loaded into a catheter with a retractable outer sheath which is inserted percutaneously and advanced translumenally into or across the mitral valve. The retractable outer sheath can be retracted to allow the self-expandable support structure to expand adjacent or against the annulus, thereby positioning the one or more transvalvular bands in about the plane of the mitral annulus. Each transvalvular band can be characterized by a longitudinal axis, and the transvalvular band is oriented in the mitral valve such that the longitudinal axis of the transvalvular band in oriented substantially transversely to the coaptive edge of the mitral valve.

By "percutaneous" it is meant that a location of the vasculature remote from the heart is accessed through the skin, such as using needle access through, for example, the Seldinger technique. However, it may also include using a surgical cut down procedure or a minimally invasive procedure. The ability to percutaneously access the remote vasculature is well-known and described in the patent and medical literature.

Depending on the point of vascular access, the approach to the mitral valve may be antegrade and require entry into the left atrium via the pulmonary vein or by crossing the interatrial septum. Alternatively, approach to the mitral valve can be retrograde where the left ventricle is entered through the aortic valve. Once percutaneous access is achieved, the interventional tools and supporting catheter(s) will be advanced to the heart intravascularly where they may be positioned adjacent the target cardiac valve in a variety of manners, as described elsewhere herein. While the methods will preferably be percutaneous and intravascular, many of the implants and catheters described herein will, of course, also be useful for performing open surgical techniques where the heart is beating or stopped and the heart valve accessed through the myocardial tissue. Many of the devices will also find use in minimally invasive procedures where access is achieved thoracoscopically and where the heart will usually be stopped but in some instances could remain beating.

Figure 39:
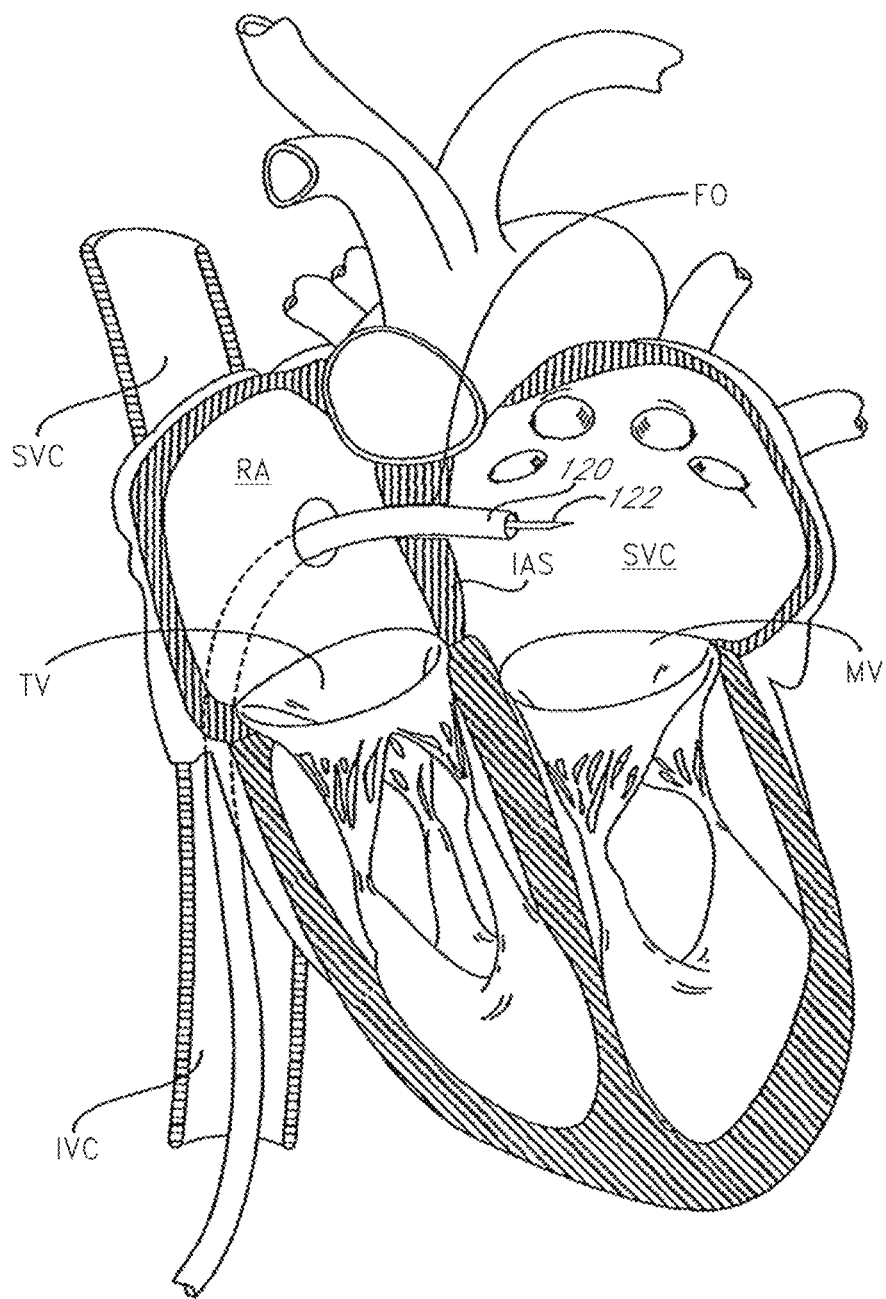
FIG. 39 is a schematic cross-sectional view of the heart, showing a typical antegrade approach to the mitral valve by way of a transseptal crossing.

A typical antegrade approach to the mitral valve is depicted in FIG. 39. The mitral valve MV may be accessed by a standard approach from the inferior vena cava IVC or superior vena cava SVC, through the right atrium RA, across the interatrial septum IAS and into the left atrium LA above the mitral valve MV. As shown, a catheter 120 having a needle 122 may be advanced from the inferior vena cava IVC into the right atrium RA. Once the catheter 120 reaches the interatrial septum IAS, the needle 122 may be advanced so that it penetrates through the septum at the fossa ovalis FO or the foramen ovale into the left atrium LA. At this point, a guidewire may be advanced out of the needle 122 and the catheter 120 withdrawn.

Figure 40:
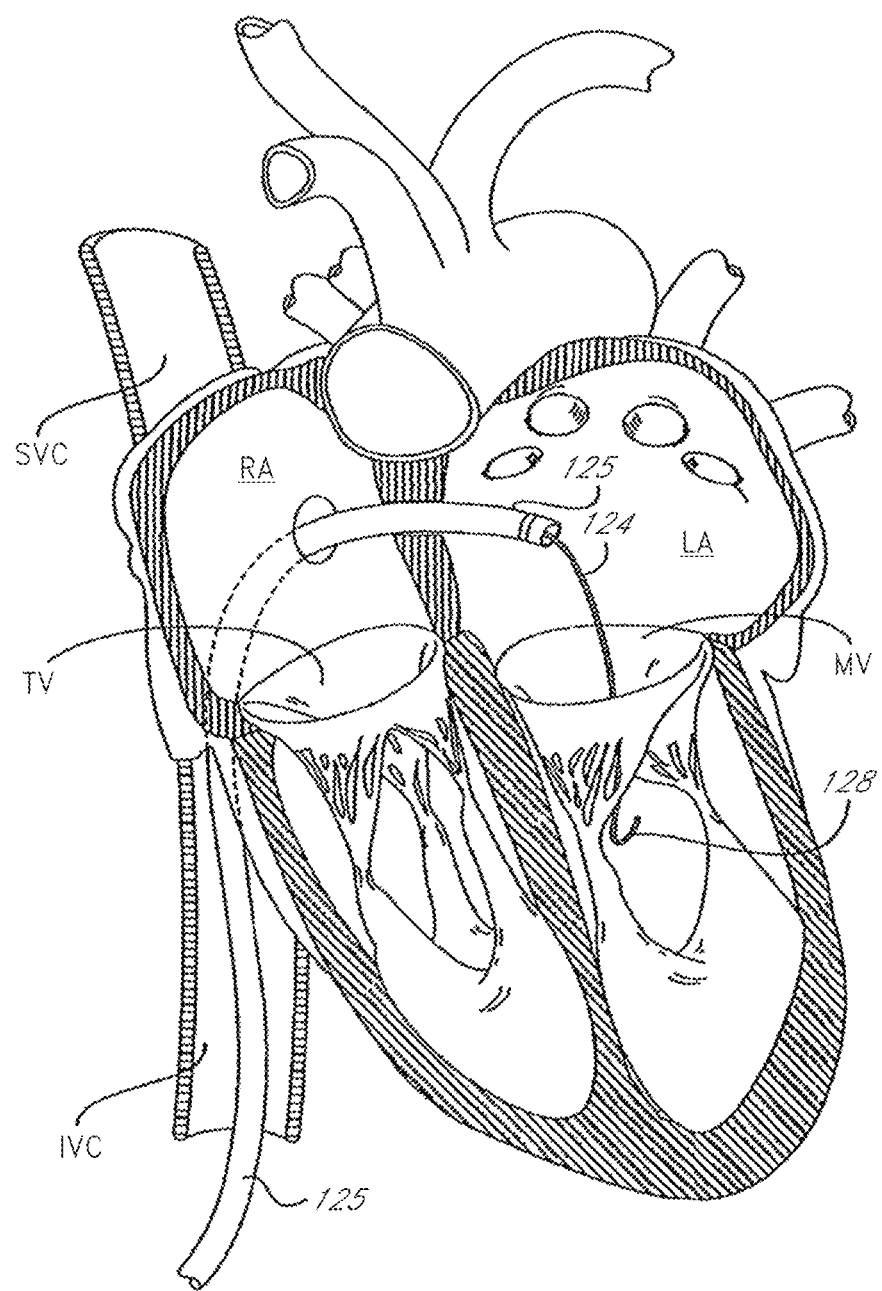
FIG. 40 is a cross sectional view as in FIG. 39, showing placement of a guidewire through the mitral valve.

As shown in FIG. 40, access through the interatrial septum IAS will usually be maintained by the placement of a guide catheter 125, typically over a guidewire 124 which has been placed as described above. The guide catheter 125 affords subsequent access to permit introduction of the tool(s) which will be used for performing the valve or tissue modification, as described in more detail below.

Figure 41:
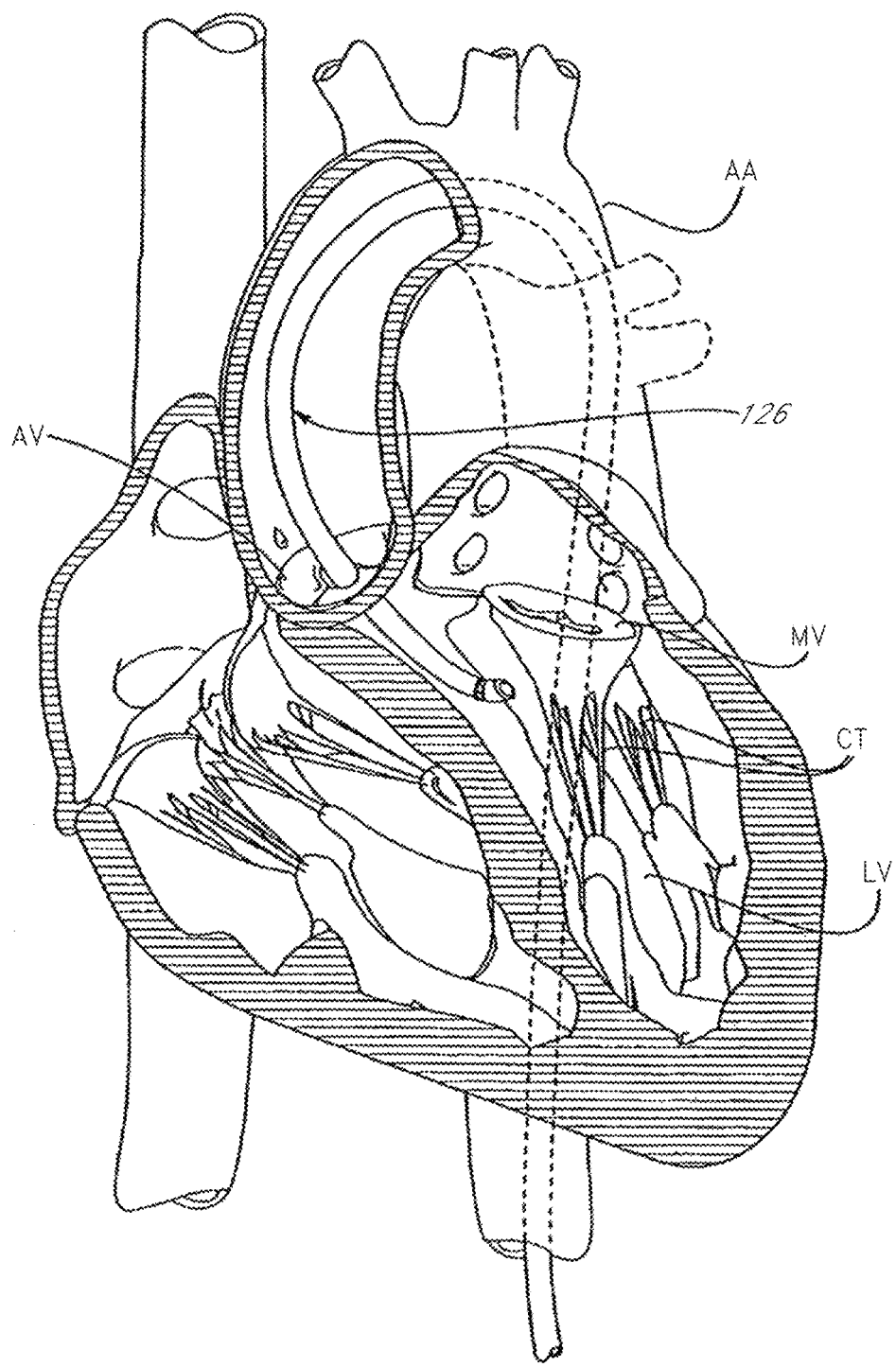
FIG. 41 is a cross sectional view of the heart showing a typical retrograde approach to the mitral valve by way of a femoral artery access.
Figure 42:
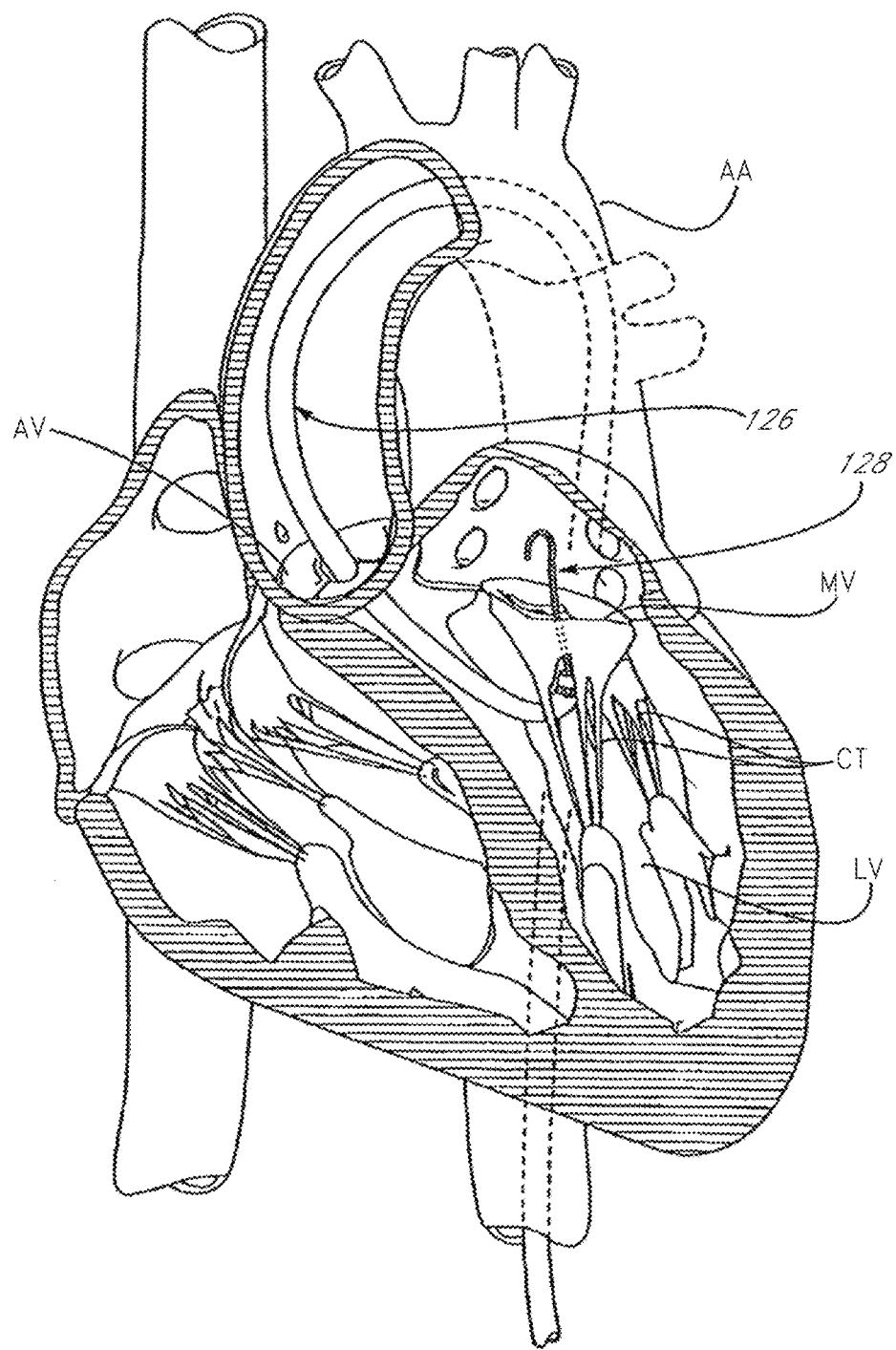
FIG. 42 shows a retrograde approach as in FIG. 41, with a guidewire placed across the mitral valve.

A typical retrograde approach to the mitral valve is depicted in FIG. 41. Here the mitral valve MV may be accessed by an approach from the aortic arch AA, across the aortic valve AV, and into the left ventricle below the mitral valve MV. The aortic arch AA may be accessed through a conventional femoral artery access route, as well as through more direct approaches via the brachial artery, axillary artery, or a radial or carotid artery. As shown in FIG. 42, such access may be achieved with the use of a guidewire 128. Once in place, a guide catheter 126 may be tracked over the guidewire 128. The guide catheter 126 affords subsequent access to permit introduction of the tool(s) which will be used for performing the valve modification, as described in more detail below.

In some cases, access routes to the mitral valve may be established in both antegrade and retrograde approach directions. This may be useful when, for instance, grasping is performed with the use of specific devices introduced through one route and fixation is achieved with the use of separate devices introduced through another route. In one possible situation, the transvalvular band may be introduced via a retrograde approach. While the transvalvular band is held in place, a fixation tool may be introduced via an antegrade approach to fix the transvalvular band in place. The access pathways for the transvalvular band and fixation tool may alternatively be reversed. Thus, a variety of access routes may be used individually or in combination with the methods and devices of the present invention.

Referring to FIG. 43A, there is illustrated a schematic view of a percutaneously deliverable implant in accordance with one aspect of the present invention. The deployment system includes a deployment catheter 200, only a distal end of which is illustrated herein. Deployment catheter 200 is configured in accordance with known technology for accessing the mitral valve, utilizing conventional dimensions and the materials known to those of skill in the art. In general, the deployment catheter 200 comprises an elongate flexible tubular body 202 extending between a proximal end (not illustrated) and a distal end 204. The proximal end is provided with a proximal manifold, including access portals such as luer connectors in communication with each functional lumen in the catheter 200.

The distal end 204 is provided with a distally facing opening 208, which is in communication with the proximal end via a central lumen 206.

Positioned within the central lumen 206 is a collapsed implant 210. Implant 210 is transformable between a first, radially reduced configuration such as for positioning within the deployment catheter 200 and a second, radially enlarged configuration (see FIG. 43C) for positioning at the treatment site. Transformation of the implant from the first configuration to the second configuration may be accomplished under positive force, such as via balloon dilatation. Alternatively, as illustrated herein, transformation is accomplished by self-expansion of the implant 210 in response to removal of the constraint provided by the tubular body 202.

In general, the implant 210 comprises a frame or anchor component 212 and a leaflet support component 214. Leaflet support component 214 may comprise any of a variety of structures similar to those described previously herein as the annular band, configured or reconfigured such that the annular band may be radially reduced for positioning within a deployment catheter and subsequently radially enlarged for spanning the mitral valve. The implant 210 additionally comprises an anchor component, for anchoring the leaflet support 214 at the treatment site. In the illustrated embodiment, anchor 212 is schematically illustrated as a zigzag wire or filament structure, which is radially expansible following removal of the constraint. However, any of a variety of configurations may be utilized for the anchor 212.

Referring to FIG. 43B, the outer tubular flexible body 202 is shown partially retracted from the implant, permitting the implant to begin to radially expand. FIG. 43C illustrates further retraction of the tubular body 202, to fully release the anchor 212 at the deployment site. As illustrated, anchor 212 radially expands within the left atrium. The leaflet support 214 extends approximately transversely to the coaptive edge of the mitral valve leaflets, and is convex or inclined in the direction of the mitral valve to advance the coaptation of the mitral valve leaflets in the direction of the ventricle as has been described elsewhere herein.

As seen in FIG. 43A, the implant 210 is controlled by at least one control line 216. Control line 216 extends throughout the length of the deployment catheter 200, and to at least one control on or near the proximal manifold. This enables proximal retraction of the flexible body 202 with respect to the implant 210, and control of implant 210 prior to final detachment from the deployment system.

Referring to FIG. 43C, at least a first control wire 216, a second control wire 218, and a third control wire 220 are illustrated connected to the anchor 212. Control wires 216, 218 and 220 enable manipulation of the implant into its final desired position, and, if necessary, proximal retraction of the implant back within the deployment catheter should the decision be made to remove the implant prior to final detachment.

Prior to final detachment of the implant 210, additional anchoring structures may be engaged to retain the implant at its desired implanted location. For example, anchor 212 may be provided with any of a variety of tissue anchors or barbs, for engaging the mitral valve annulus or the base of the leaflets or other adjacent anatomical structures. Alternatively, separate tissue anchors may be advanced through the deployment catheter 200, and utilized to secure the anchor 212 to the adjacent tissue. Suitable anchors are preferably enlargeable from a first, reduced cross sectional configuration for traveling through the deployment catheter 200 and piercing tissue, to a second, enlarged configuration for resisting removal from the tissue. In the embodiment illustrated in FIG. 43C, no secondary anchoring structures are illustrated for simplicity.

Once the position of the implant 210 has been verified and found acceptable, and the determination of whether to introduce secondary anchoring structures has been made, the control wires 216, 218 and 220 are detached from the anchor 212, and the deployment catheter 200 is removed from the patient. Detachment of the control wires from the implant 210 may be accomplished in any of a variety of ways, such as by electrolytic detachment, detachment by thermal elevation of a softenable or meltable link, mechanical detachment such as by rotating the control wire such that a threaded end of the control wire is threadably disengaged from the anchor 212, or other detachment techniques depending upon the desired functionality and profile of the system.

Referring to FIG. 43D, there is illustrated a side elevational view of the implant 210 in an unconstrained (e.g., bench top) expanded configuration. The anchor 210 comprises a plurality of struts 222, which are joined at a first end by a plurality of apices 224 and a second end by a plurality of apices 226 to produce a zigzag structure sometimes referred to as a "Z stent" configuration. This configuration is convenient and well understood in the intravascular implant arts, although any wide variety of structures may be utilized. For example, zigzag wire patterns, woven wire patterns, or sinusoidal wire patterns may be utilized. Laser cut wall patterns such as from tubing stock may also be utilized, and may be provided with any of a wide variety of complex wall patterns. In general, nickel titanium alloys such as any of a variety of nitinol alloys are preferred. However, depending upon the wall pattern, stainless steel, elgiloy, certain polymers or other materials may also be utilized. Heat treatment may be required to anneal and shape set an alloy such as Nitinol. Other alloys may require only annealing to relieve stresses incurred during prior processing.

Referring to FIG. 43E, there is illustrated an end view of the implant shown in FIG. 43D to show the transverse configuration of the transvalvular band portion of the implant. In this illustration, the transvalvular band comprises a plurality of struts 230 which are connected to the anchor 212 at junctions 232. Struts 230 may in turn be divided into a bifurcated section 234 or other configuration to increase the effective footprint of the transvalvular band measured along the coaptive edge of the valve, while minimizing obstruction to blood flow therethrough. The coaptive edge of the valve, as implanted, will preferably be approximately aligned with the transverse axis 236 illustrated in FIG. 43E of the band, as implanted. The axis of coaption of the mitral valve is preferably parallel to axis 236 in the implanted configuration, but may be within about 45°, preferably within about 20°, and most preferably within about 10° of the axis 236.

Referring to FIGS. 44A and 44B, there is illustrated an anchor deployment catheter which may be utilized to provide either primary or secondary anchoring of the anchor structure 212 to adjacent tissue. Anchor deployment catheter 250 comprises an elongate flexible tubular body 252, configured to access the vicinity of the mitral valve. Tubular body 252 extends between a proximal end 254 and a distal end 256. Distal end 256 is provided with a distal opening 258, enabling access to a central lumen 260. An elongate flexible core wire 262 extends from the proximal end 254 throughout most of the length of the lumen 260 to a distal surface 264. See FIG. 44C. The proximal end of the core wire 262 is provided with a control 266 that enables axial reciprocal movement of the core wire 262 within the central lumen 260.

A tissue anchor 268 may be positioned within the distal end of the delivery catheter 250. In use, manipulation of the control 266, such as by distal axial advance relative to the tubular body 252, distally, axially advances the core wire 262 to expel the anchor 268 through the distal opening 258. Distal opening 258 is preferably provided with a bevel or angled cut to provide a sharpened distal tip 270. This enables distal axial advance of the distal tip 270 into tissue at a desired site, so that the control 266 may be manipulated to deploy all or a portion of the anchor 268 into the target tissue.

Any of a variety of tissue anchors 268 may be utilized, depending upon the desired configuration of the implant and the implant anchor interface. In the illustrated embodiment, the anchor 268 is configured as a double "t-tag" anchor. A first tissue engaging element 272 is connected to a second implant engaging element 274 by a filament 276. In use, the distal tip 270 is positioned within the tissue of the mitral valve annulus. Control 266 is manipulated to deploy the first element 272 beneath the surface of the tissue. The tubular body 252 is thereafter proximally retracted, enabling the second element 274 to engage the implant and retain it against the adjacent tissue.

The anchor delivery catheter 250 may be advanced through the deployment catheter 200, and/or along a guide such as a guidewire or support wire. In the illustrated embodiment, the anchor deployment catheter 250 is provided with a guide lumen 278 allowing the anchor delivery catheter to track along a guidewire. Guide lumen 278 is defined by a tubular wall 280. Tubular wall 280 may extend the entire length of the anchor delivery catheter 250, such as by forming the catheter body as a dual lumen extrusion. Alternatively, tubular wall 280 may be provided with an axial length that is short relative to the overall length of the catheter, such as no more than about 3 cm and preferably no more than about 2 cm in length. This allows the anchor delivery catheter to ride along a guidewire in a monorail or rapid exchange manner as will be illustrated below.

Referring to FIGS. 45A and 45B, there is illustrated an implant configured for use with the anchor delivery catheter described above. In general, the implant comprises a first leaflet support 292 and a second leaflet support 294, separated by a flexible connection 296. Flexible connection 296 permits the implant 290 to be folded within a deployment catheter, and later expanded in a manner that permits the implant 290 to function as a transvalvular band as described. The implant 290 may be manufactured in any of a variety of ways, such as using a wire frame or by laser cutting from sheet stock as will be appreciated by those of skill in the art.

In the illustrated embodiment, a first and second flexible connection 296 reside in a plane configured to be substantially parallel to the axis of coaption the as implanted orientation. The lateral edges of the each of the first leaflet support 292 and second leaflet support 294 are provided with at least one and preferably two or three eyes 298, fabric patches, or other anchor attachment structure, for receiving a tissue anchor.

Referring to FIG. 45B, the implant of FIG. 45A is illustrated in a partially collapsed configuration, flexed about the flexible connection 296. In addition, control wires 300, 302 and 304 are illustrated releasably connected to the implant 290. Control wires 300, 302 and 304 may be utilized to advance the implant 290 from the deployment catheter such as catheter 200 described above, and manipulate the implant until the anchors have been fully deployed. Thereafter, control wires 300, 302 and 304 may be removed such as by electrolytic detachment, melting a polymeric link, unscrewing a threaded connection, or other detachment mechanism depending upon the desired functionality of the device.

Referring to FIGS. 46A through 46E, there is illustrated a sequence of deploying an implant at the mitral valve from an antegrade direction. The implant 290 may be similar to that illustrated in FIGS. 45A and 45B, or have wall patterns or characteristics of other implants disclosed elsewhere herein. In general, the implant 290 is deployed from the catheter 200 in the sequence illustrated in FIGS. 46A through 46C. The surrounding anatomy has been eliminated for simplicity.

Figure 46A:
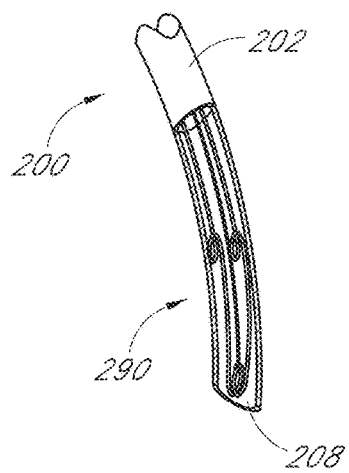
FIG. 46A is a cut-away perspective view of the distal end of a deployment catheter having a self-expandable implant contained therein.
Figure 46B:
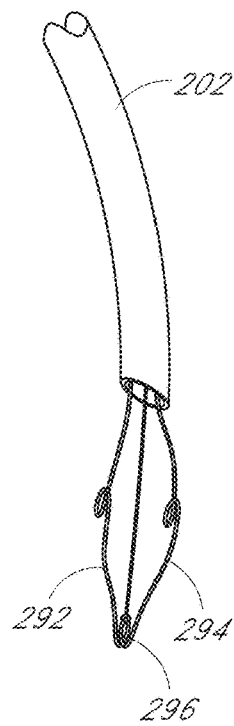
FIG. 46B is a deployment catheter as in FIG. 46A, with the implant partially deployed.
Figure 46C:
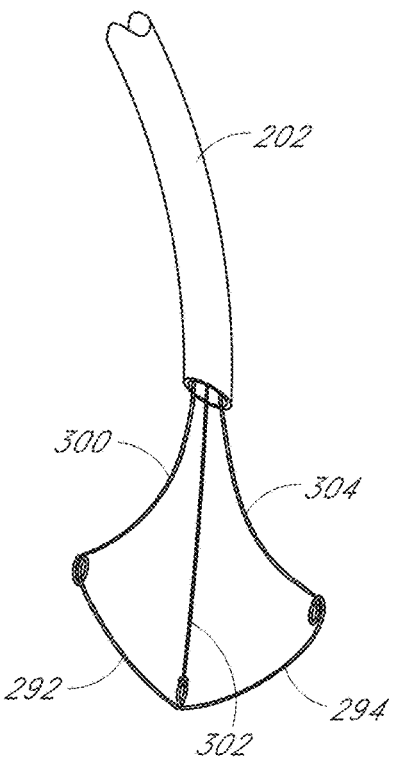
FIG. 46C is a view as in FIG. 46B, showing the implant released from the deployment catheter, but connected to three control wires.
Figure 46D:
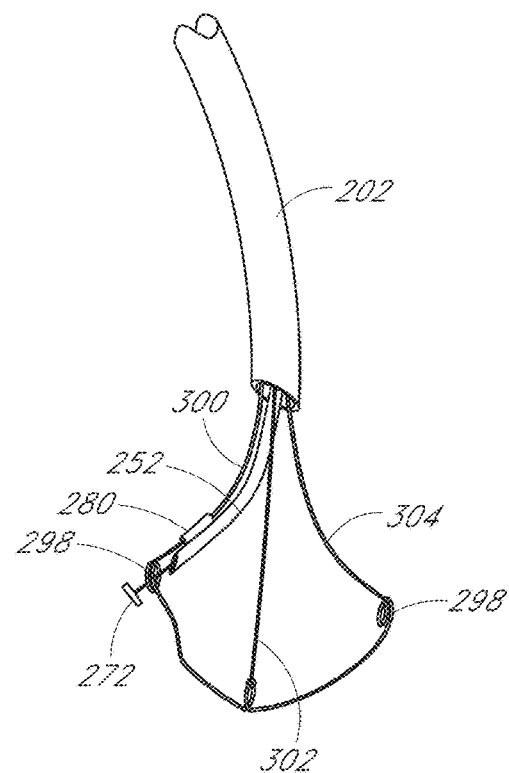
FIG. 46D is a view as in FIG. 46C with a tissue anchor deployment catheter.

Referring to FIG. 46D, the anchor delivery catheter 250 is advanced onto the proximal end of one of the control wires 300, such that the control wire 300 is axially moveably positioned within guide lumen 278. This enables the anchor delivery catheter 250 to be advanced along the control wire 300 in a monorail or rapid exchange configuration as is understood in the catheter arts. Anchor delivery catheter 250 is advanced along the control wire 300 until the distal tip 270 advances through the eye 298 or fabric tab or other attachment structure, and into the adjacent tissue of the base of the mitral valve leaflet or mitral valve annulus. The control 266 is manipulated such as by distal advance to advance the first anchor element 272 out of the distal opening 258 and into the tissue as illustrated in FIG. 46D.

The anchor delivery catheter 250 is thereafter proximally withdrawn to position the distal opening 258 on the device proximal side of the eye 298, and the core wire 262 is further distally advanced to deploy the second anchor element 274 from the distal opening 258 of the anchor delivery catheter 250. Anchor delivery catheter 250 may thereafter be proximally withdrawn from the patient. Either the same or a different anchor delivery catheter 250 may thereafter be advanced along the third control wire 304, enabling deployment of another tissue anchor as is illustrated in FIG. 46E.

Figure 46E:
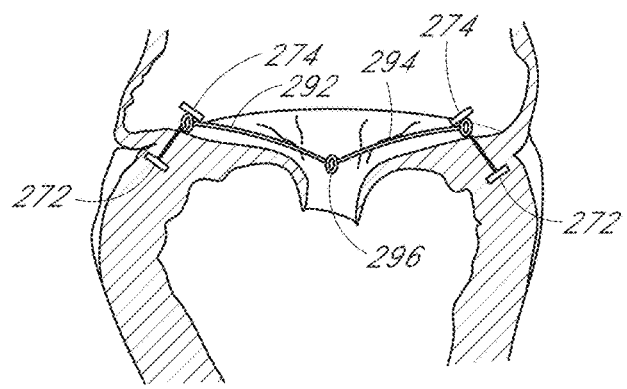
FIG. 46E is a cross sectional view of a mitral valve, having an implant anchored in place and the deployment catheter removed.

The implant 290 is illustrated in FIG. 46E as having a central portion inclined in the direction of the ventricle to support the leaflets as has been discussed elsewhere herein. This configuration may be retained by the inherent bias built into the structure and materials of the implant 290. Alternatively, the configuration of inclining in the direction of the ventricle may be retained by active intervention such as by providing a mechanical interlock, in situ heat weld with capacitive discharge/electrolytic weld, application of a clip or other locking structure by way of control wire 302 or simply by the mechanical forces attributable to the mitral valve annulus, which prohibit lateral expansion of the device sufficient for the flexible connection 296 to invert in the direction of the atrium. Alternatively, an implantable control wire (not illustrated) may be introduced, to connect the implant 290 such as in the vicinity of the flexible connection 296 to the opposing wall of the ventricle, as will be described in connection with a transapical implementation of the invention described below.

Figure 47C:
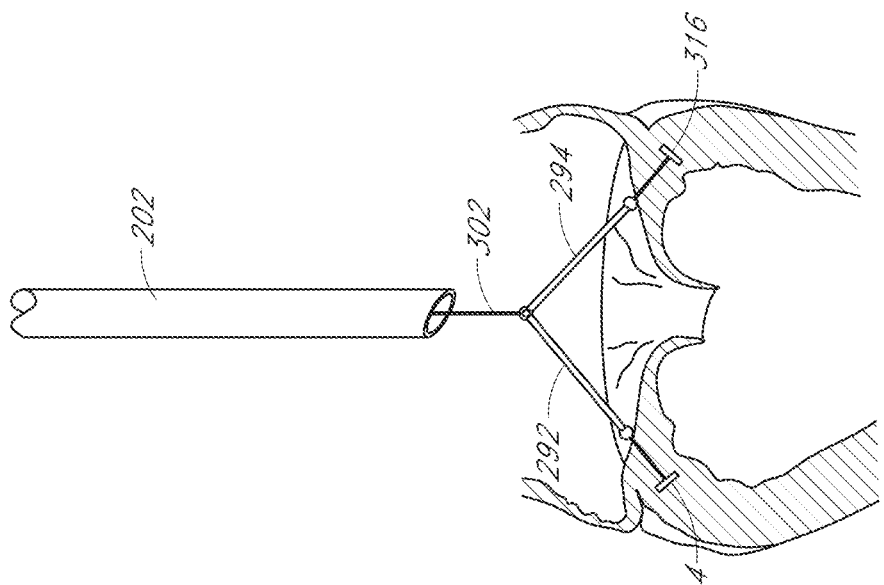
FIG. 47C is a schematic view as in FIG. 47B, with the tissue anchor deployment guides removed.

A further implementation of the invention is illustrated in connection with FIGS. 47A through 47E. Referring to FIG. 47A, the first control line 300 and third control line 304 have been replaced by a first guide tube 310 and a second guide tube 312. First guide tube 310 and second guide tube 312 each has the double function of controlling deployment of the implant, as well as enabling introduction of a tissue anchor therethrough. This avoids the use of a separate tissue anchor deployment catheter such as that described above.

Figure 47B:
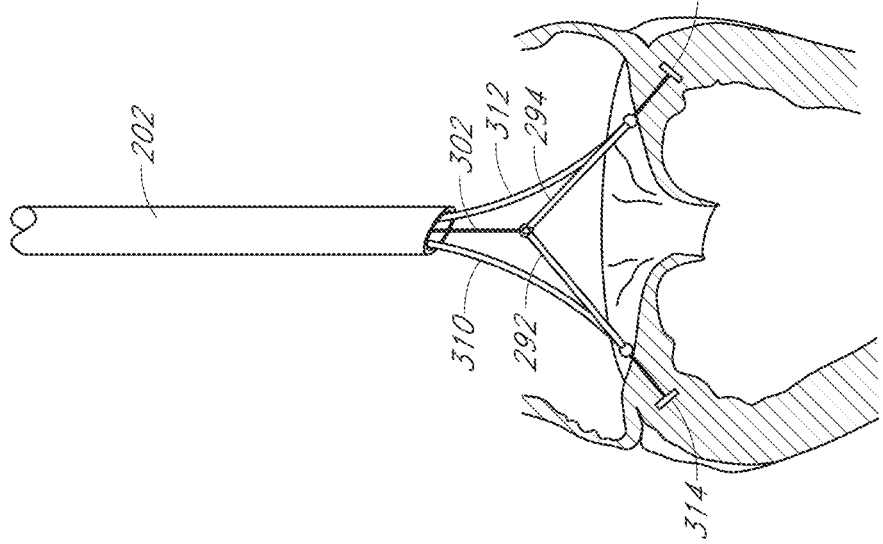
FIG. 47B is a schematic view of the catheter and implant of FIG. 47A, during implantation at the mitral valve.
Figure 47A:
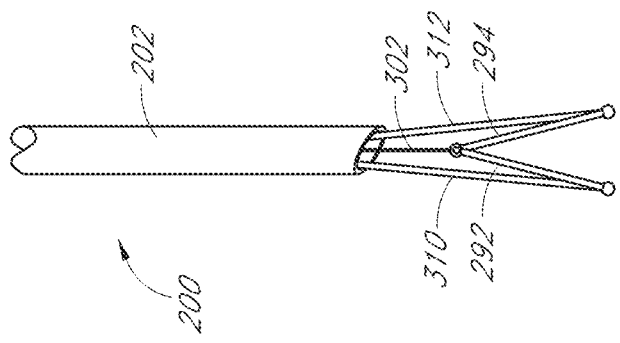
FIG. 47A is a side elevational view of the distal end of a deployment catheter, having an implant partially deployed therefrom.

As illustrated in FIG. 47B, once the implant is provisionally positioned in the vicinity of the mitral valve, a first tissue anchor 314 is deployed through the first guide tube 310. A second tissue anchor 316 is deployed through the second guide tube 312. The tissue anchors may comprise "T" tag type constructions, pigtail or corkscrew constructions, or any of a variety of other soft tissue anchors known in the art. In general, tissue anchors utilized for the present purpose are preferably transformable from a first, reduced cross-sectional configuration to a second, radially enlarged cross-sectional configuration to enable deployment through a small needle or tube and then provide a relatively higher resistance to pull out. Radial enlargement may be accomplished by angular movement of a portion of the anchor, or by physical expansion in a radial direction.

Referring to FIG. 47C, the first guide tube 310 and second guide tube 312 have been removed following deployment of the tissue anchors. The guide tubes may be removed using any of a variety of detachment techniques disclosed elsewhere herein. Either before or after removal of the guide tubes, distal pressure on either the tubular body 202 or the control wire 302 inverts the implant from the configuration shown in FIG. 47C to the final configuration shown in FIGS. 47D and E. The inverted configuration of FIGS. 47D and E may be retained by the mechanical bias imparted through the anchoring to the mitral valve annulus, or using techniques described elsewhere herein. The control wire 300 is thereafter detached from the implant, as illustrated in FIG. 47E.

Any of a variety of the implants of the present invention may alternatively be introduced across the ventricle, such as in a transapical approach. The retrograde approach to the mitral valve will necessitate certain modifications to both the implant and the deployment system, as will be appreciated by those of skill in the art in view of the disclosure herein.

For example, a transventricular approach is illustrated in FIGS. 48A through 48D. A deployment catheter 320 is introduced into the ventricle, and retrograde through the mitral valve to position the distal opening 208 within the atrium. An implant is carried within the deployment catheter 320, as has been described elsewhere herein. In general, the implant comprises a first leaflet support 292 and a second leaflet support 294 separated by a flexible zone or pivot point.

In the retrograde implementation of the invention, the first and second leaflet supports are flexible or pivotable with respect to the longitudinal axis of the control wire 300, such that they may be moved between a first configuration in which there are substantially parallel with the axis of the control wire 300, and a second position, as illustrated in FIGS. 48A through 48D, in which they are inclined radially outwardly from the longitudinal axis of the control wire 300 in the device proximal direction. The implant may thus reside within the deployment catheter 320 when the first leaflet support 292 and second leaflet support 294 are in the first, reduced crossing profile configuration, with each of the tissue anchors 314 and 316 pointing in a device proximal direction. In this embodiment, the tissue anchor 314 may be permanently affixed to or integral with the first leaflet support 292 and the second anchor 316 may be similarly carried by the second leaflet support 294.

Once the distal end of the deployment catheter 320 has been positioned within the atrium, the control wire 300 may be distally advanced to advance the anchors 314 and 316 beyond the distal opening 208. This releases the implant and allows the angle between the first and second leaflet supports to be increased, so that the tissue anchors 314 and 316 may be aimed at the desired tissue anchor target sites. Proximal retraction on the control wire 300 may be utilized to seat the tissue anchors within the target tissue, as illustrated in FIG. 48B.

Further proximal traction on the control wire 300 may be utilized to invert the implant into the configuration illustrated in FIG. 48C. At that point, the control wire 300 may be severed from the implant as has been discussed elsewhere herein. Alternatively, the deployment catheter 320 may be proximally retracted leaving the control wire 300 secured to the implant, and a second portion of the control wire may be secured to a tissue anchor 322 within or on the epicardial surface of the ventricle. Anchor 322 may comprise any of a variety of structures, such as a pledget, button, or other structure that provides a footprint against the epicardial surface to resist retraction of the control wire 300 into the ventricle. The control wire 300 may thereafter be severed proximally of its securement to the anchor 322, leaving the control wire 300 and anchor 322 in position to span the ventricle and retain the configuration of the implant as illustrated in FIG. 48D.

In all the foregoing embodiments, the final configuration of the implant within the mitral valve is illustrated in a highly schematic form, and the angle and degree of inclination into the direction of the ventricle may be significantly greater than that illustrated herein depending upon the desired clinical performance. The transvalvular band inclination can be highly advantageous in some embodiments in providing clinical benefit as it facilitates "physiologic coaptation" in a preferred manner as its surface mimics the three dimensional feature created by the leaflets as they would have coapted in a healthy native valve.

Figure 49H:
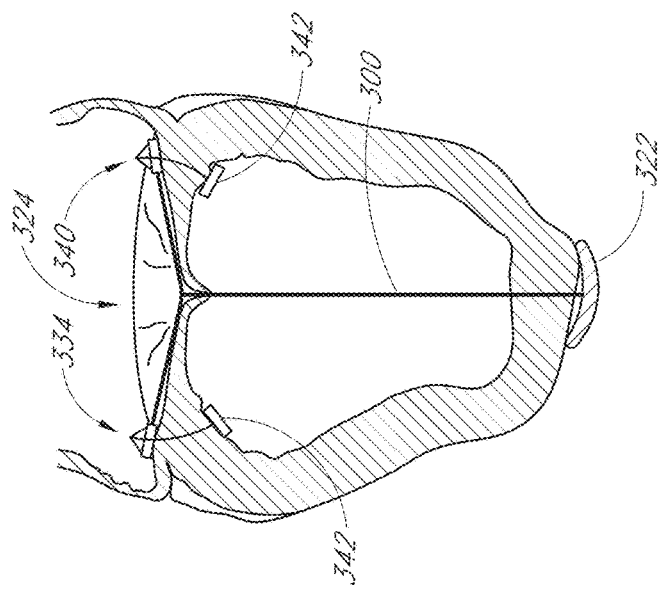
FIG. 49H shows an alternate end point, in which the transvalvular band is additionally provided with a transventricular truss and an epicardial anchor.

Referring to FIGS. 49A through 49H, there is illustrated a transapical approach to the mitral valve, and deployment of a transvalvular band in accordance with the present invention. As illustrated in FIG. 49A, a deployment catheter 320 has been introduced such as via thoracotomy, and advanced retrograde through the mitral valve. A transvalvular band 324 has been deployed distally from the catheter 320, and is illustrated in FIG. 49A in an expanded configuration within the left atrium. Expansion of the transvalvular band 324 from a reduced cross-sectional profile for positioning within the catheter 320 to the enlarged cross-sectional profile illustrated in FIG. 49A may be accomplished either under mechanical force, such as by dilatation of an inflatable balloon or other mechanical mechanism. Preferably, however, transvalvular band 324 is self-expandable so that it converts from the reduced profile to the enlarged profile automatically upon deployment from the distal end of the catheter 320.

In the illustrated embodiment, the transvalvular band 324 comprises an arcuate central portion 325, which is convex in the direction of the ventricle. See FIGS. 49A and 49B. The transvalvular band 324 is provided with a first attachment structure 326 and a second attachment structure 328. Attachment structures 326 and 328 may comprise any of a variety of structures disclosed herein, such as tissue anchors, including hooks or barbs. In one implementation of the invention, the first attachment structure 326, and second attachment structure 328 each comprise a target for receiving an anchor as will be disclosed below. Suitable targets for the present purpose include woven or non-woven fabrics, polymers, or other materials or constructions which permit a needle or sharpened anchor to penetrate therethrough, as will be discussed. In one implementation of the invention, each of the attachment structures comprises a Dacron mesh, having a frame for supporting the mesh and securing the mesh to the transvalvular band 324.

Referring to FIG. 49B, there is illustrated a perspective view of the transvalvular band 324 illustrated in FIG. 49A. The transvalvular band 324 comprises a central section 325, convex in the direction of the ventricle for affecting leaflet closure as has been described herein. Central section 325 is formed by a frame 327, which comprises at least one strut 329 extending between the first attachment structure 326 and second attachment structure 328. In the illustrated embodiment, three struts extend generally parallel to each other, defining at least two elongate openings therebetween. One or two or four or more transverse elements 331 may be provided, such as to enhance structural integrity of the construct. At least a first control wire 300 and, optionally a second or third or fourth control wire 300 is releasably attached to the transvalvular band 324, to enable manipulation of the band into position as shown in FIG. 49C. Control wire 300 is releasably connected to the transvalvular band 324 at a connection point 301. The connection at point 301 may be established by threadable engagement, an electrolytically detachable link or weld, or other detachment mechanism. Electrolytically detachable deployment systems are known, among other places, in the neurovascular embolic coil and stent arts, and suitable systems are disclosed in U.S. Pat. No. 5,976,131 to Guglielmi, et al.; U.S. Pat. No. 6,168,618 to Frantzen; and U.S. Pat. No. 6,468,266 to Bashiri, et al., the disclosures of which are hereby incorporated in their entireties herein by reference The first attachment structure 326 comprises a support 333 carried by the frame 327. In the illustrated embodiment, support 333 comprises an enclosed loop, having a central opening filled or covered by a mesh 337. The support 333 may alternatively comprise any of a variety of structures, such as a single linear element, sinusoidal or zigzag pattern, depending upon the desired performance. In the illustrated embodiment, the support 333 is conveniently provided in the form of a loop, to facilitate holding mesh 337 in a generally planar configuration, and support the mesh so that it may be punctured by an anchor, suture or other retention structure. A second support 335 is similarly provided with a mesh 337, to facilitate attachment. The mesh 337 may conveniently be a layer or pad of Dacron or other material, such as an integration of a silicone core with a Dacron jacket, which facilitates both piercing by an attachment structure, as well as tissue in-growth for long term retention. The first support 333 and second support 335 may comprise a radio opaque material, or be provided with radio opaque markers to enable aiming the anchor deployment system into the mesh 337 under fluoroscopic visualization.

Once the transvalvular band 324 has been brought into the position illustrated in FIG. 49C, the first attachment structure 326 and second attachment structure 328 may be secured to the adjacent tissue using any of a variety of clips, staples, barbs, sutures, or other structure which may be conveniently pierced through the mesh 337 and/or looped around the first and second supports 333, 335. The retention element may be approached from either the side of the left atrium, the ventricle, or epicardially, such as by way of a minimally invasive puncture on the chest wall. In the implementation of the method described below, the example of advancing the retention elements from the left ventricle will be described.

Referring to FIG. 49C, proximal traction on the catheter 320 and on the control wire 300, pulls the transvalvular band 324 snuggly against the left atrial side of the mitral valve, such that the first attachment structure 326 and second attachment structure 328 are seated against the valve annulus.

Referring to FIG. 49D, a first anchor guide 330 and a second anchor guide 332 have been distally advanced from the distal end of the catheter 320. Anchor guides 330 and 332 may be alternatively associated with or carried by the catheter 320 in a variety of ways. For example, the first and second anchor guides 330 and 332, may be pivotably carried by the catheter 320, such that they may be inclined radially outwardly from the longitudinal axis of the catheter in the distal direction.

In the illustrated embodiment, the first and second anchor guides comprise a wire or tube for directing an anchor as will be discussed. The wire or tube of the anchor guide may comprise any of a variety of materials, such as nickel titanium alloys (e.g. nitinol) which may be preset to assume a position similar to that illustrated in FIG. 49D upon distal advance from the catheter 320. The first and second anchor guides may be provided with radio-opaque markers, or may be constructed from a radio-opaque material, to permit fluoroscopic guidance. In the illustrated embodiment, the first and second anchor guides are in the form of tubes, for axially slidably receiving a tissue anchor and tissue anchor deployment structures therein.

Referring to FIG. 49E, a retention element in the form of a first anchor 334 is illustrated as having been distally advanced from the first anchor guide 330, through the tissue in the vicinity of the mitral valve annulus, and through the first attachment structure 326. Penetration of the first anchor 334 through the first attachment structure 326 may be accomplished while providing proximal traction on the control wire 300.

The first anchor 334 is provided with at least one and preferably two or four or more transverse elements 336 to resist proximal retraction of the first anchor 334 back through the opening formed in the first attachment structure 326. The transverse element or surface 336 may be provided on any of a variety of structures, such as an umbrella-type structure, t-tag, barbs, or other anchoring configuration which can pass in a first direction through an opening formed in the first attachment structure 326, but resist retraction in a second, opposite direction, back through the first attachment structure 326.

The transverse element 336 is carried by a filament 338, which extends through the adjacent myocardial tissue. Filament 338 may comprise any of a variety of materials, such as a monofilament or multi-filament structure made from polypropylene, any of a variety of other known suture materials such as polyethylene, or metals such as stainless steel, nitinol, and others known in the art. The filament 338 may be a mono-filament structure or a multi-filament structure which may be braided or woven, depending upon the desired clinical performance. At least a second, similar anchor 340 is introduced on the opposing side of the mitral valve.

Figure 49G:
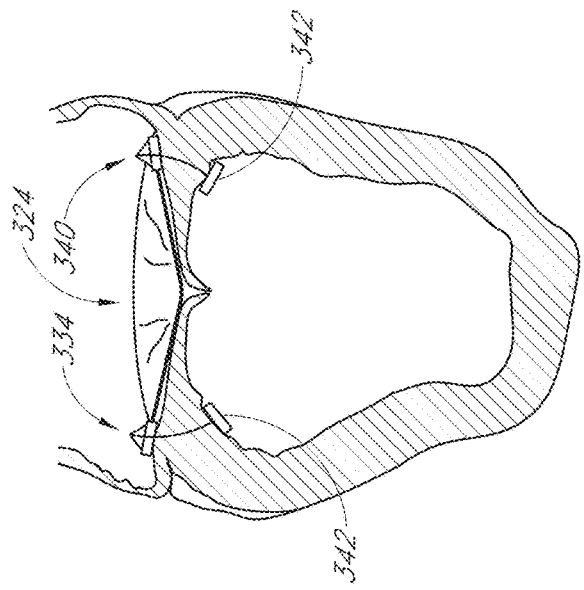
Figure 49F:
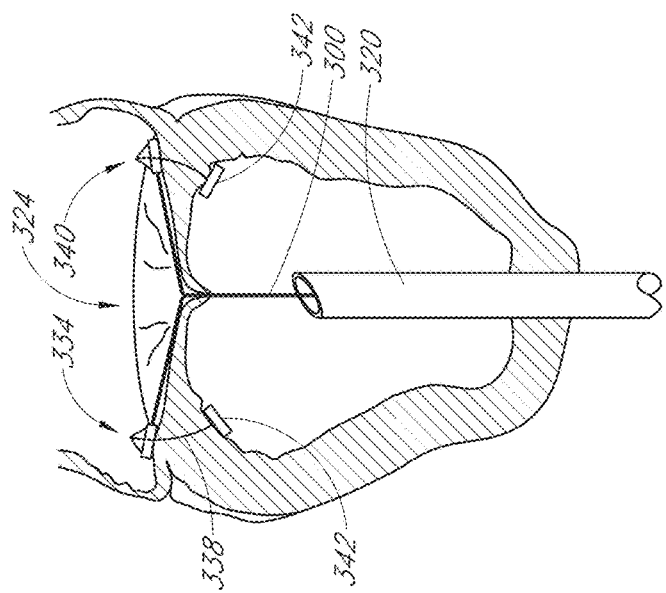

Referring to FIG. 49F, a second transverse element 342 is shown secured to or carried by the ventricular end of the filament 338, to provide a secure anchoring through the tissue wall for the transvalvular band. A similar structure is provided on the opposing side of the mitral valve. Although only a first and second anchoring systems has been described above, additional anchoring systems, such as a total of four or six or eight or more, typically in even numbers to produce bilateral symmetry, may be used. The number and configuration of tissue anchors will depend upon the configuration of the transvalvular band, as will be apparent to those of skill in the art in view of the disclosure herein.

As shown in FIG. 49F, the anchors have been fully deployed and the first anchor guide 330 and second anchor guide 332 have been proximally retracted into the catheter 320.

Referring to FIG. 49G, the control wire 300 may thereafter be detached from the transvalvular band and removed. Detachment of control wire 300 may be accomplished in any of a variety of ways, as has been described elsewhere herein.

Alternatively, the control wire 300 may be left in place as is illustrated in FIG. 49H. Control wire 300 is secured to an epicardial anchor 322, to provide a transventricular truss, as has been described.

Figure 50A:
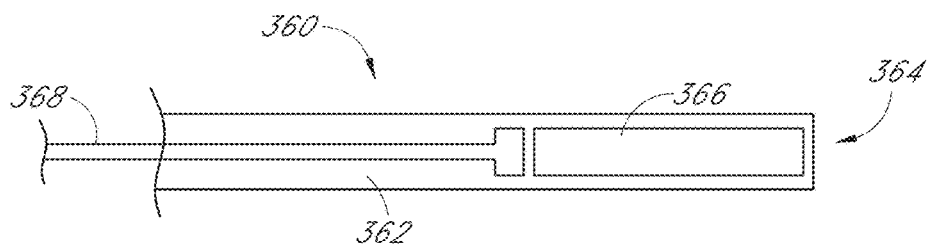
FIG. 50A is a side elevational schematic view of the distal end of a deployment catheter, having a rolled up transvalvular band therein.
Figure 50B:
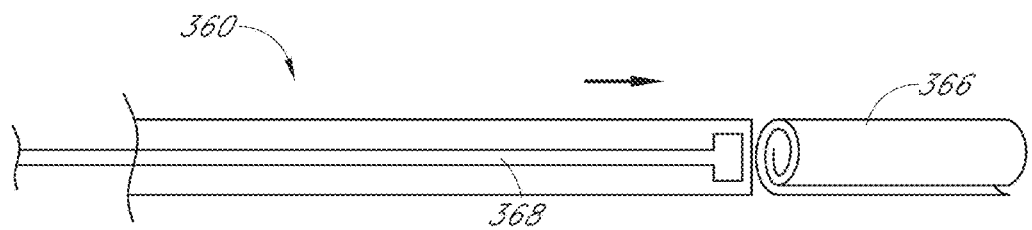
FIG. 50B is an illustration as in FIG. 50A, following distal deployment of the transvalvular band.

Referring to FIGS. 50A and 50B, there is illustrated a side elevational schematic view of the distal end of a deployment catheter 360 which may be adapted for use in either the transapical delivery of FIGS. 49A-49H, or any other delivery mode described herein. In the illustrated embodiment, the deployment catheter 360 includes an elongate tubular body having a central lumen 362, opening at a distal end 364. Carried within the central lumen 362 is a transvalvular band 366, in a rolled-up configuration. Transvalvular band 366 is maintained in a rolled-up configuration by the constraint imposed by the deployment catheter 360. However, upon distal advance of the push element 368 to deploy the transvalvular band 366 beyond the distal end 364, as illustrated in FIG. 50B, the transvalvular band 366 unrolls under its natural bias into a predetermined configuration for implantation across the mitral valve.

Figure 51A:
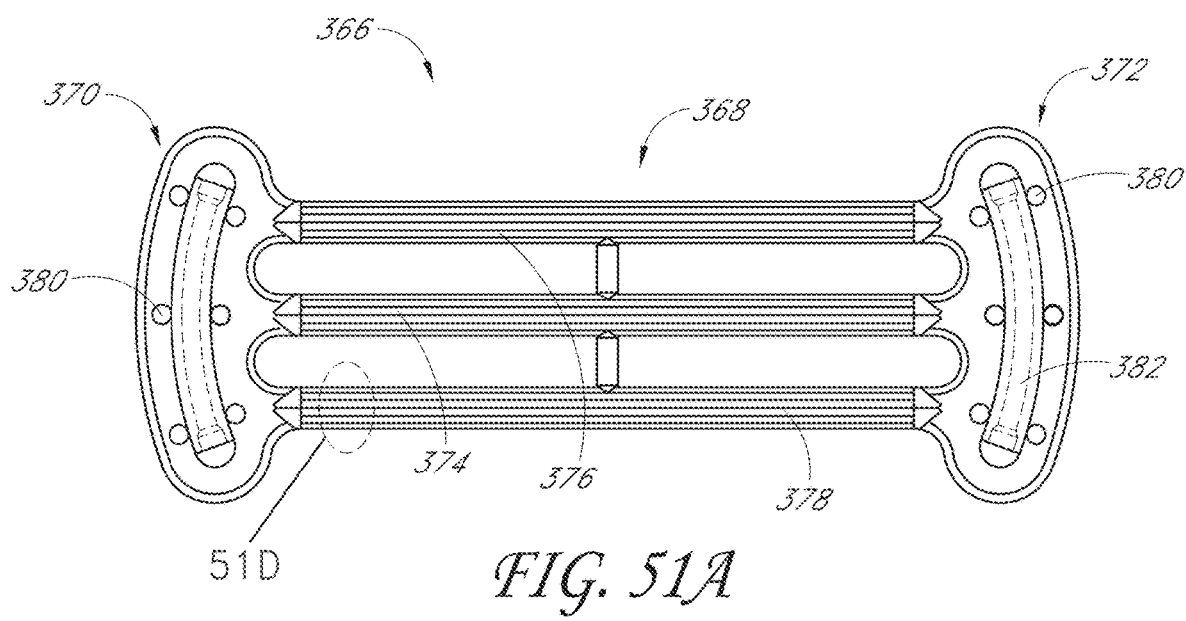
FIGS. 51A and 51B illustrate top plan views and side views of a transvalvular band in accordance with the present invention.

One configuration for the transvalvular band is shown rolled out in plan view in FIG. 51A. However, any of a variety of alternative transvalvular band configurations disclosed herein can be utilized with the catheter of FIGS. 50A and 50B.

Referring to FIG. 51A, there is illustrated a transvalvular band 366 having a central portion 368 for spanning the coaptive edges of the mitral valve. A first attachment zone 370 and a second attachment zone 372 are provided on opposing ends of the central portion 368.

The central portion comprises at least a first strut 374 for spanning the mitral valve as has been discussed. In the illustrated embodiment, a second strut 376 and a third strut 378 are provided, spaced apart to increase the width of the contact footprint with the valve leaflet but permit blood flow therethrough. A first end of each of the struts 374, 376, and 378 are connected at the first attachment zone 370, and the second ends of the three struts are connected at the second attachment zone 372.

The first and second attachment zones may be provided with a reinforcing element 382, to facilitate long term attachment. Apertures 380 are illustrated, which may be provided to allow manual suturing when the transvalvular band 366 is intended for use in an open surgical procedure. Alternatively, apertures 380 may be configured for attachment using an anchor deployment catheter when intended for use in a translumenal or transapical deployment. Each of the first, second and third ribs may be provided with a central core, such as a nitinol or stainless steel wire or ribbon, and an outer coating such as a polycarbonate urethane with or without copolymers like silicone, silicone coating, or a fabric such as PET, ePTFE, polyethylene, or a hybrid of, for example, the aforementioned materials impregnated silicone coating, to reduce the risk of abrasion of the mitral valve leaflets A close-up view of circled zone 51D of FIG. 51A is illustrated in FIG. 51D.

Figure 51B:
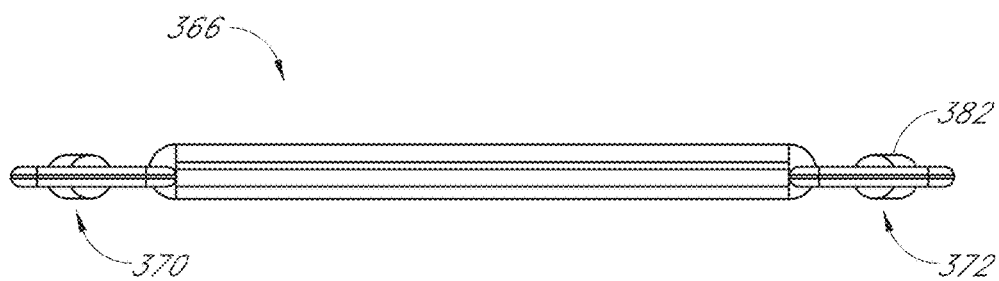
Figure 51C:
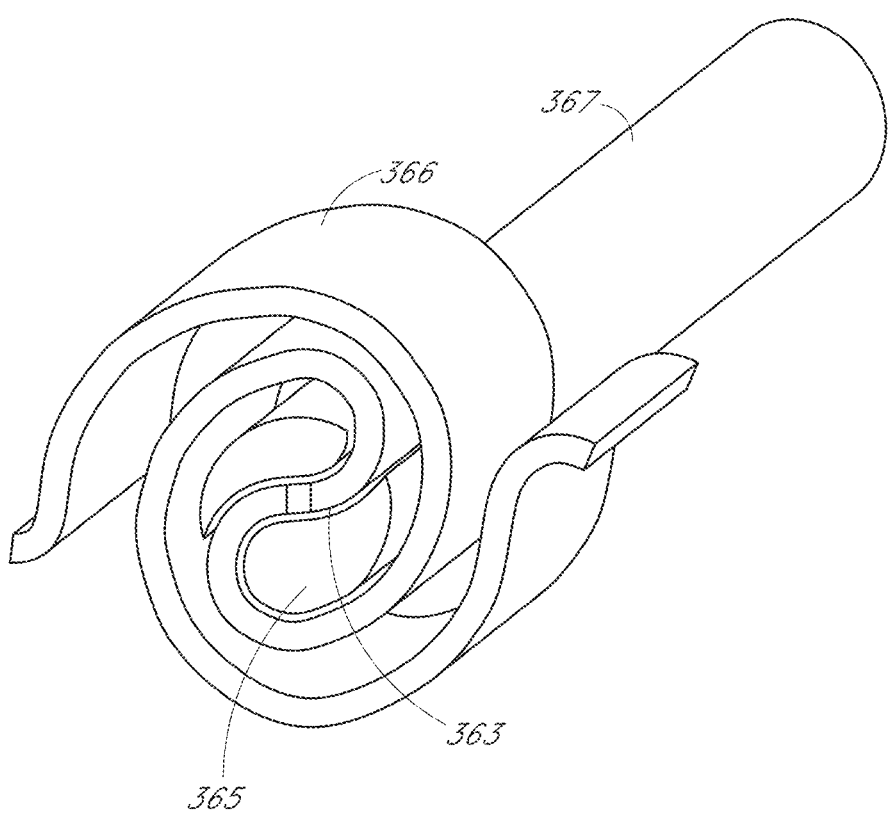
FIG. 51C illustrates a perspective view of one embodiment of a transvalvular band in a rolled-up configuration and mounted on a delivery mandrel.
Figure 51D:
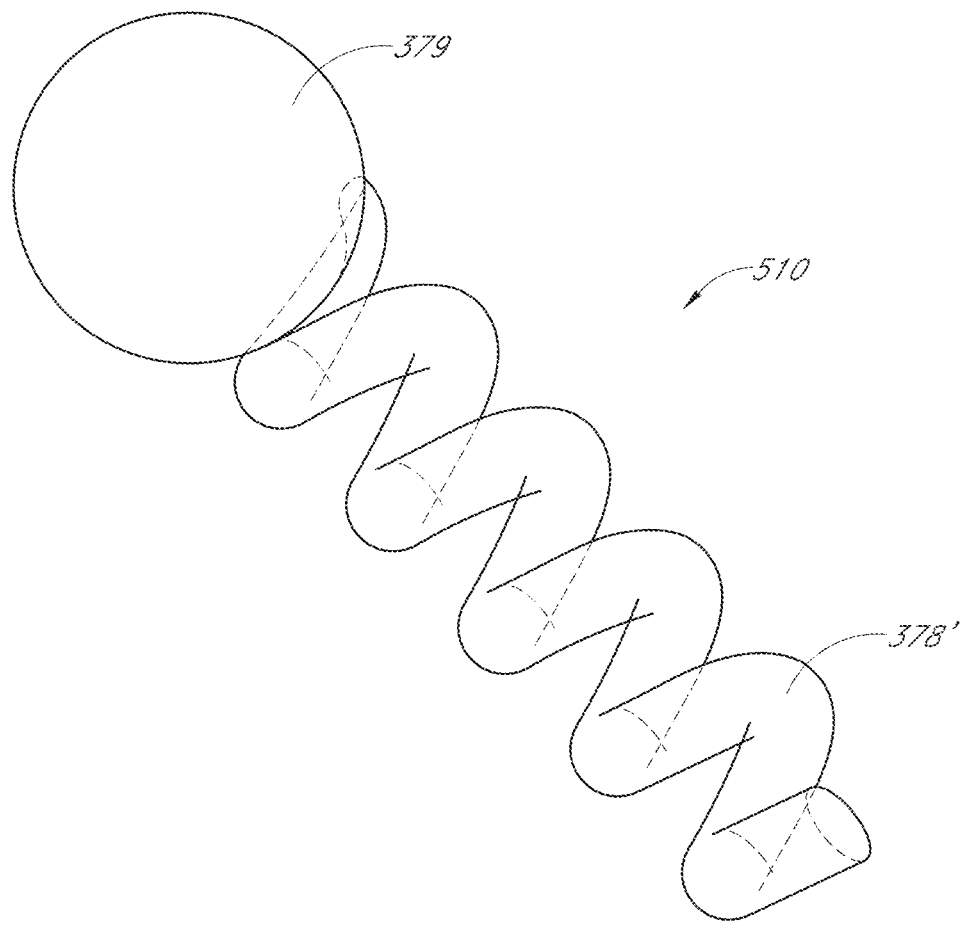
FIG. 51D illustrates a view of at least a non-linear portion of a strut of FIG. 51B.

FIG. 51D illustrates one embodiment of a fatigue-resistant terminal portion of a proximal and/or distal end of one, two, or more of the struts 374, 376, 378 illustrated in FIG. 51D. The terminal portion 51D may have a non-linear portion 378' and a head portion 379. The non-linear portion could be a coil with a helical, zig-zag, or any other generally non-linear shape to advantageously provide increased fatigue resistance for the struts. In some embodiments, at least a portion of the terminal portion 51D is embedded in an elastomer such as silicone, polycarbonate, urethane, or the like to further improve fatigue tolerance. In some embodiments, the terminal portion 51D may have a straight-line length that is less than 20%, 15%, 10%, 5%, or less of the strut. In some embodiments, the terminal portion 51D may have a straight-line length that is at least about 5%, 10%, 15%, 20%, 25%, or more of the length of the strut, or could even cover the entire length of one, two, or more struts 374, 376, 378 from first attachment zone 370 to second attachment zone 372 (e.g., a strut without a linear portion). Head portion 379 is operably connected to non-linear portion 378' and the portions may be integrally formed. The head portion 379 could be spherical, ovoid, square, rectangular, triangular, or a variety of other shapes. Head portion 379 is in turn operably connected to first attachment zone 370 and/or second attachment zone 372. In some embodiments, the head portion 379 is not attached to an attachment zone but rather terminates as a free end of one or more of the struts 374, 376, 378.

FIG. 51B is a side elevational view of the transvalvular band 366 of FIG. 51A, shown in a flat configuration. However, as has been discussed elsewhere herein, the transvalvular band will typically be provided with a curvature such that it advances the mitral valve leaflets in the direction of the ventricle and provides for physiologic coaptation.

FIG. 51C illustrates a perspective view of a transannular band 366 in a rolled-up configuration for delivery, similar to that illustrated in FIG. 50B. The band can be rolled in a variety of ways, such as capturing the band 366 at or near the center (near 363) and rolling it such that both ends are drawn inward as shown. In some embodiments, the band could be rolled up like a scroll, or folded into a "V", "W", or a variety of other shapes. In some embodiments, at least a portion of the band 366 resides within one or more slots 363 or movable jaw-like elements on the distal end 363 of a mandrel 367 or other elongate body within a delivery catheter. Actuation of the jaw-like elements to release the band 366, distal movement of a pusher tube, retraction of the mandrel 367 relative to another catheter, or other mechanism can be employed to deploy the band 366. In some embodiments, turning the mandrel a desired distance, such as about 90 degrees, can help facilitate unfurling of the band 366 for deployment.

Referring to FIGS. 52A-52C, there is illustrated a transvalvular band in accordance with the present invention having a tissue attachment system which may be adapted for either percutaneous or open surgical use. The transvalvular band comprises a central zone 368 carrying a first attachment zone 370 and a second attachment zone 372 as has been described.

A tissue anchor 390, such as a "t-tag" anchor includes a transverse element 392 and an elongate flexible suture 394. As used herein, the term "suture" is not limited to its normal definition, but also includes any of a wide variety of elongate flexible filaments, including polymeric, metal, combinations of both as well as monofilament and multifilament structures. Multifilament structures may be braided, woven, or otherwise configured, depending upon the desired performance.

The suture 394 is illustrated to extend through a first guide 396 in the second attachment zone 372. For simplicity, only a single anchoring system will be disclosed herein. However, it should be appreciated that the anchoring system may be utilized on both ends of the central zone 368, and more than one, such as two or three or more, anchors 390 may be utilized on each attachment zone.

The suture 394 is illustrated as extending through first guide 396, and then through a lock 398 which will be described below. The free end 402 of the suture 394 is further advanced through a second guide 400. Depending upon the intended use of the system, the free end 402 may extend proximally throughout the length of the deployment catheter, where it may be manipulated such as by proximal traction in order to tighten the second attachment zone 372 with respect to the transverse element 392. Thereafter, the free end 402 may be severed in the vicinity of the second attachment zone 372 or elsewhere.

Referring to FIG. 52C, details of the lock 398 may be seen. In general, the lock 398 includes an aperture 404 through which the suture 394 may extend. An engaging element 406 is exposed to the interior of the aperture, for permitting the suture to advance in a first direction through the aperture 404 but resist movement of the suture 394 in an opposite direction through the aperture 404. In the illustrated embodiment, the engaging element 406 is a sharpened point or spike configured to mechanically pierce or engage the suture 394.

The foregoing structure permits the free end 402 to be proximally withdrawn away from the second attachment zone 372 in a manner that draws the transverse element 392 closer to the second attachment zone 372. However, traction on the transverse element 392 causes the suture 394 to engage the engaging element 406, and prevents the transverse element 392 from pulling away from the second attachment zone 372.

Referring to FIG. 52D, illustrated is a suture 394 which can be looped through one, two, or more transverse elements 392 of anchors. The suture 394 looped through the anchor can function as a pulley, where appropriate traction on the suture 394 can tighten the anchors into place. Having a plurality of anchors as shown connected on one loop, such as, for example, 2, 3, 4, 5, or more anchors, can advantageously allow one cinching maneuver to tighten all of the anchors at once.

Referring back to FIG. 52A, an anchor deployment tool 408 is illustrated. Deployment tool 408 may comprise an elongate flexible wire having a proximal end 410 and a distal end 412. The deployment tool 408 may extend throughout the length of a percutaneous translumenal catheter, with the proximal end 410 exposed or attached to a control to allow axial reciprocal movement of the deployment tool 408. The distal end 412 is releasably positioned within an aperture 414 on a first end of the transverse element 392. A second end of the transverse element 392 is provided with a sharpened point 416.

In use, distal axial advance of the deployment tool 408 is utilized to drive the transverse element 392 into a target tissue, to a desired depth. Once the desired depth has been achieved, proximal retraction on the deployment tool 408 proximally retracts the distal end 412 out of the aperture 414, allowing removal of the deployment tool 408 but leaving the transverse element 392 behind within the target tissue. Proximal traction on the free end 402 of the suture 394 enables tightening of the transvalvular band with respect to the transverse element 392. Once a desired level of tightening has been achieved, releasing the free end 402 allows engaging element 406 to lock the suture 394 against further release, thereby holding the transvalvular band into position.

Figure 53:
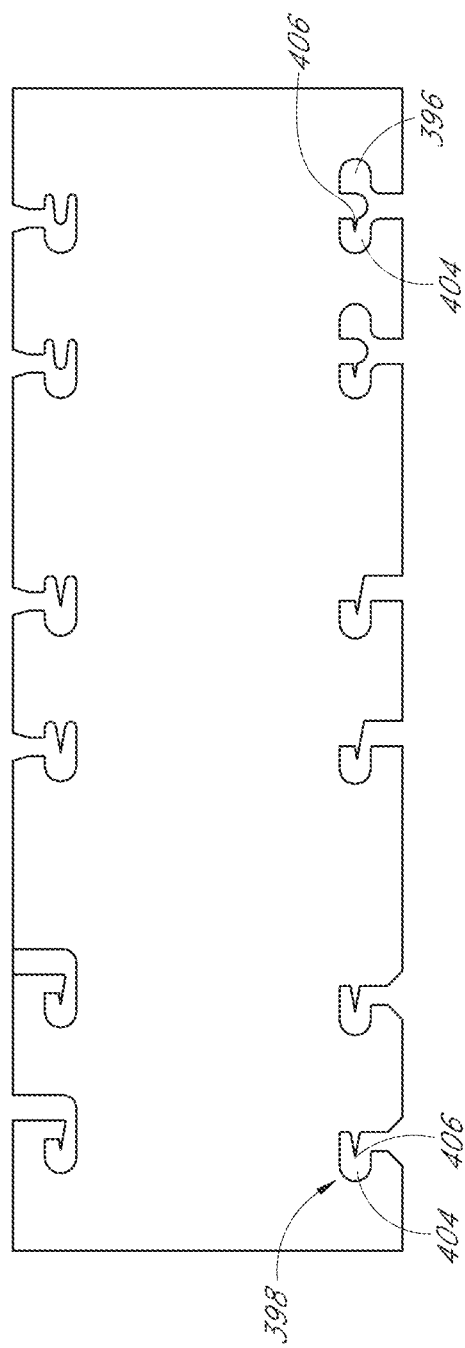
FIG. 53 is a side elevational perspective view of a transvalvular band in accordance with the present invention.

Although the lock 398 is illustrated as an enclosed aperture, alternative lock embodiments may involve access from a lateral edge of the implant. This permits side-loading of the suture into the lock, which may in some instances be desired over an enclosed aperture which requires end loading of the suture through the aperture. A variety of alternative side-loading lock configurations is illustrated in FIG. 53.

Figure 54:
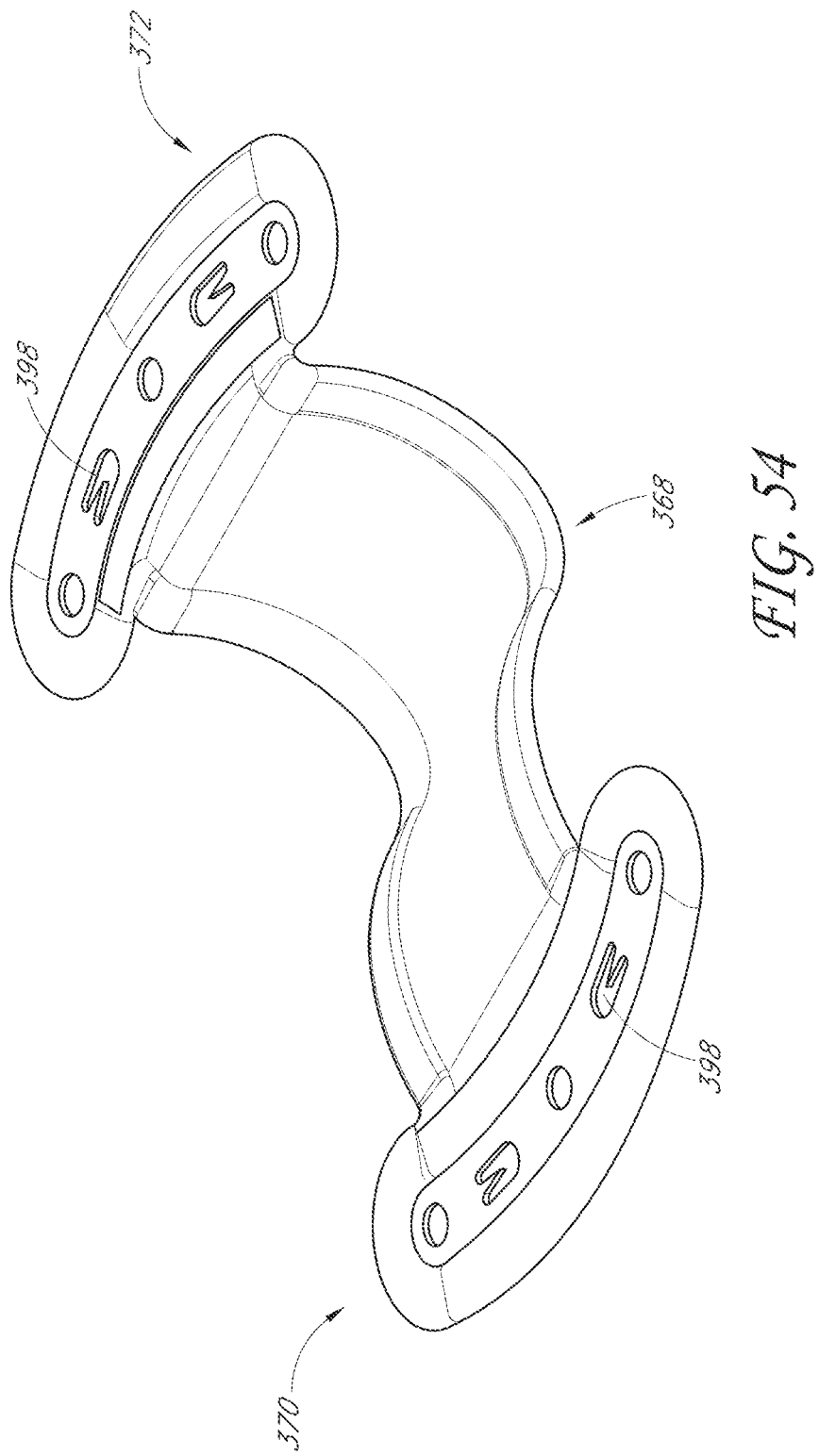
FIG. 54 is a schematic illustration of various suture lock configurations for use on transvalvular bands of the present invention.

Referring to FIG. 54, there is illustrated a perspective view of an alternate transvalvular band in accordance with the present invention. In this embodiment, the central section 368 is provided with an asymmetrical curvature, to provide asymmetrical support to the mitral valve leaflets. Along the width or central portion of the transvalvular band, this provides a contour mimicking the three-dimensional shape of the coapted mitral valve in a healthy native valve, and provides a physiologic analog thereby promoting correct anatomy during coaptation.

Figure 55:
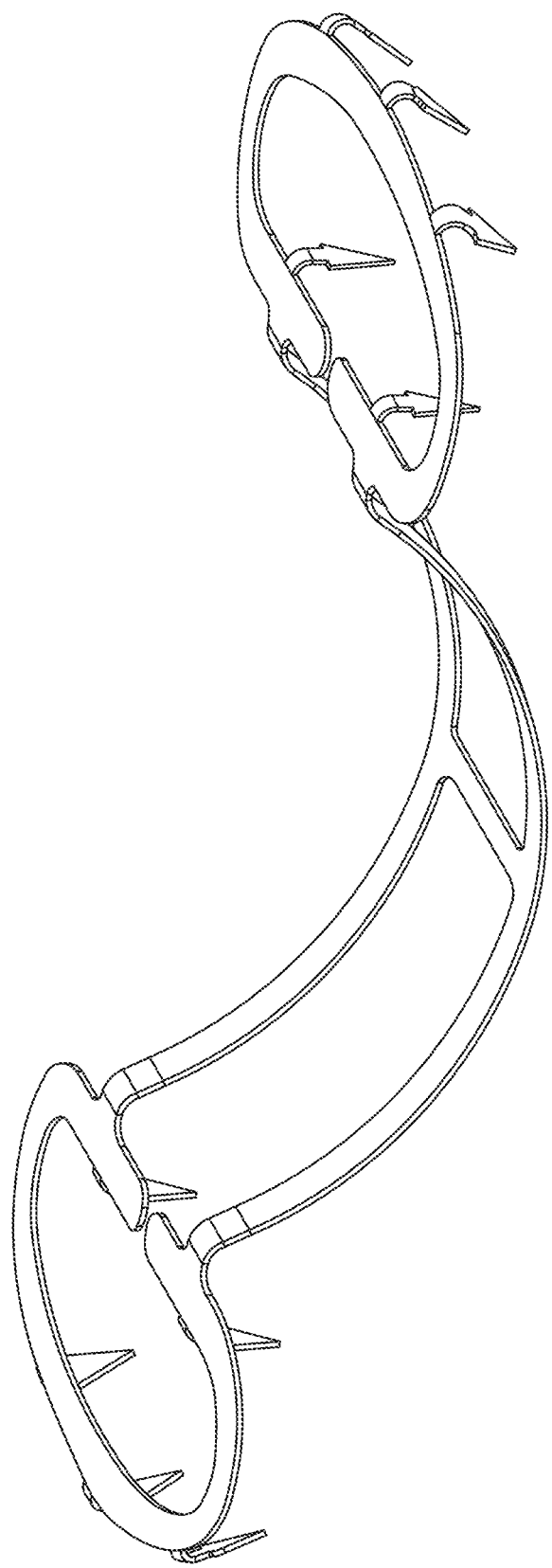
FIG. 55 is a side elevational perspective view of a transvalvular band, having barbed tissue anchors thereon.
Figure 56:
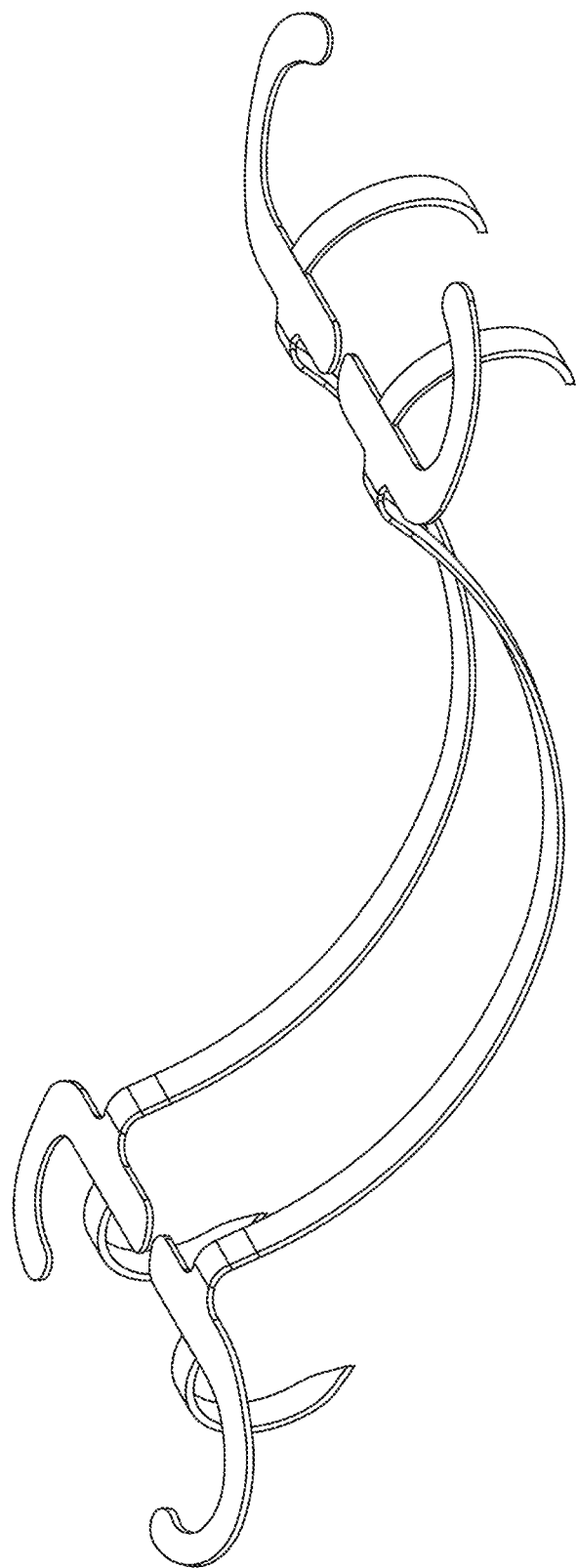
FIG. 56 is a side elevational perspective view of a transvalvular band in accordance with the present invention, having arcuate tissue anchors thereon.

FIGS. 55 and 56 illustrate alternative transvalvular bands in accordance with the present invention. In these embodiments, the attachment zones are provided with tissue anchors configured to pierce the tissue of the valve annulus. In general, the tissue anchors each comprise a pointed end, for penetrating tissue and a retention structure for resisting removal of the tissue anchor from the tissue. The retention element in FIG. 55 is in the form of a first or second barb or shoulder, as will be understood by those skilled in the art. The retention feature of the transvalvular band illustrated in FIG. 56 comprises an arcuate configuration for the tissue-piercing structure. Compression from the closure of the valve leaflets against the convex side of the central zone will tend to impart a circumferential force on the tissue anchors, advancing the distal point further in the direction of its own arcuate path. This construction tends to allow the natural forces of closure of the mitral valve to increase the retention of the tissue anchor within the adjacent tissue. In some embodiments, the barbs can be used as a primary anchor that can be crimped or otherwise secured in place. In other embodiment, the barbs could act as positioning features, to temporarily hold the band in place while verifying the position. The band could then be anchored in a secondary step, such as using a crimp, staple, suture, or other anchor as described herein. In some embodiments, the barbs can be self-locking upon penetration through tissue.

Figure 56A:
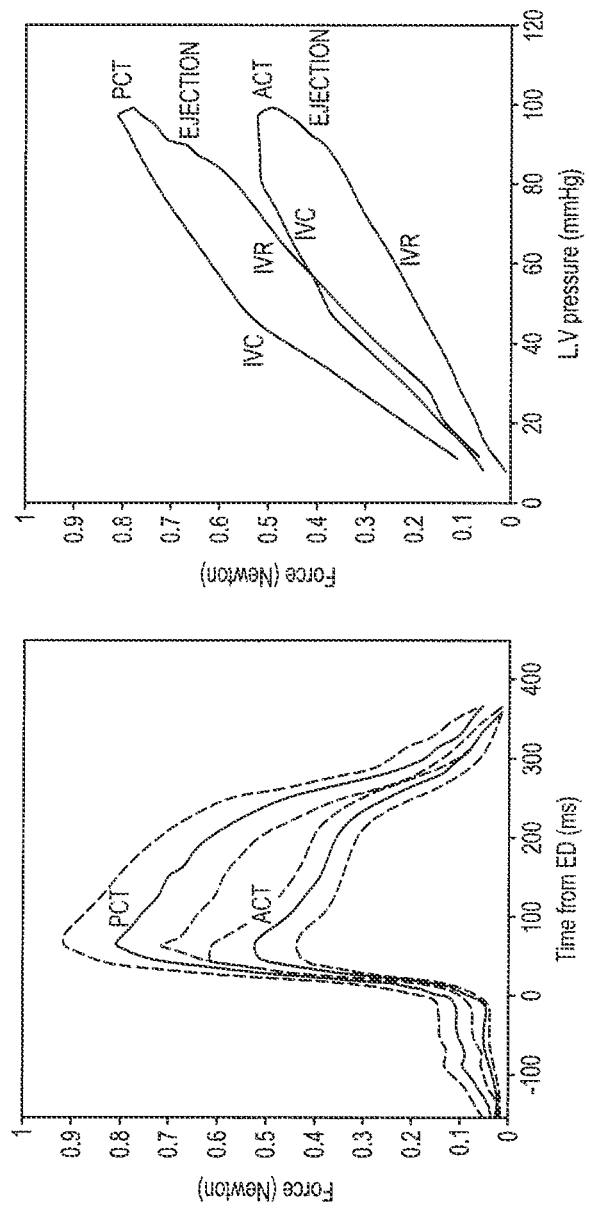
FIGS. 56A-B are graphs illustrating data regarding chordal physiologic force experiments.
Figure 56B:
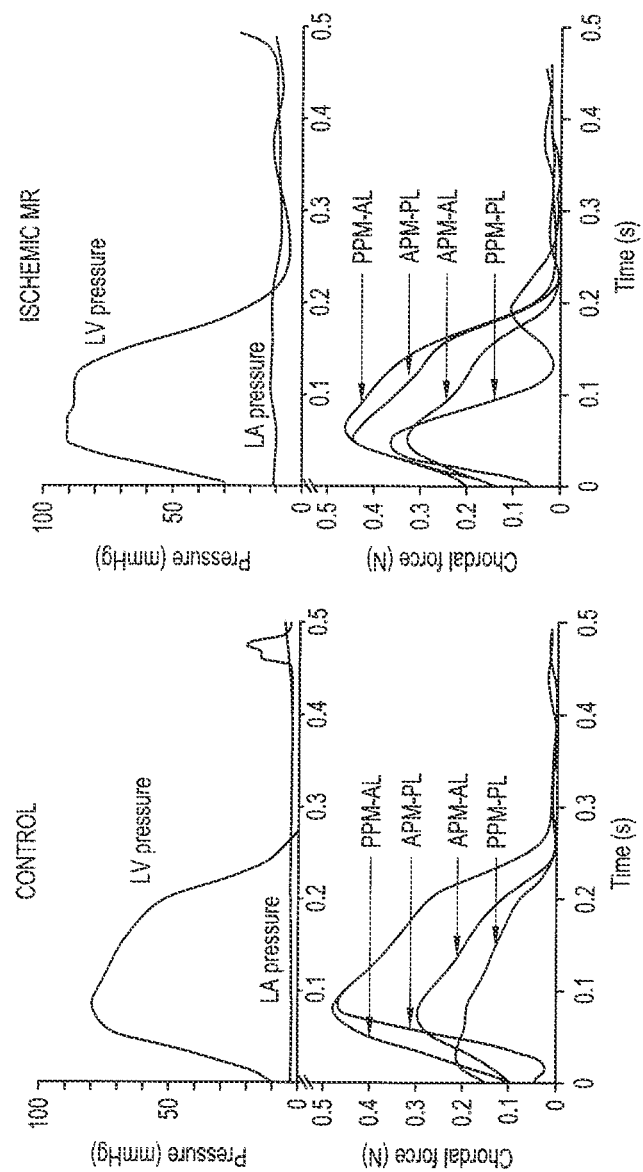

In some embodiments, disclosed is a transvalvular band that provides resistance to coaptation in the same manner as the chordae provides resistance to coaptation in a continuously nonlinear fashion, like a viscoelastic response. This band could have a configuration such as described and illustrated above, and could have material properties or additional features to provide non-linear resistance to coaptation. Such embodiments could retain a curvature mimicking the natural three dimensional surface of the coapted mitral valve yet could displace in the retrograde direction up to the anatomically correct plane of coaption when appropriate. The direction of displacement, for example, with respect to the mitral valve is better described in the atrial direction during systole to provide a cushioned impact for the valve leaflets as opposed to the leaflets striking a ridged implant structure and remodeling in a potentially deleterious fashion such as fibrosis or thinning around impact edges. FIG. 56A is reproduced from Nielsen et al, Circulation 2003; 108:486-491, *Influence of Anterior Mitral Leaflet Second-Order Chordae Tendineae on Left Ventricular Systolic Function*, which is hereby incorporated by reference in its entirety, illustrating a bilinear relationship between LV pressure and chordal tension during isovolumic contraction, a decrease in chordal tension despite high LV pressure during ejection, and an almost linear decline during isovolumic relaxation. FIG. 56B is reproduced from Nielsen et al, J Thorac Cardiovasc Surg 2005; 129:525-31, *Imbalanced chordal force distribution causes acute ischemic mitral regurgitation: Mechanistic insights from chordae tendineae force measurements in pigs*, which is incorporated by reference in its entirety. These figures demonstrate that chordae force with respect to time increases and then decays in a non-linear manner during systole. A band mimicking this performance could benefit the valvular surface as it returns its coaptive forces to a near normal state. In some embodiments, a band could cushion or physiologically reduce or prevent physical stress caused by repetitive contact with the coaptive leaflet surfaces. The band could accomplish this by virtue of construction such as chambered struts that may or may not be filled with a media such as a fluid. These chambers would be enclosed and impermeable or substantially impermeable to blood or blood component penetration within a lifetime. Another method of cushioned coaption would be a device that allows some flexing during coaption. This flexibility could be designed based upon strut material, thickness, width, inferior and superior cross-section such as a ripple, or encapsulation material such as an elastomer or elastomeric foam. The foam material could be sealed by an exterior polymer of equal overall flexibility. Additional embodiments would be coils (such as illustrated in FIG. 51D above) or coils within coils to produce unique nonlinear displacement signatures or tubes such as Nitinol laser cut tubes that could optionally be filled with a polymer. Yet another embodiment would include struts that loop towards the ventricle crossing itself. This loop would also create this nonlinear resistance to coaption by its spring force. In other embodiments, the band can proceed down to the chordae and devices can be adapted to shorten or augment the chordae to achieve natural physiology. Devices of this manner can be, for example, crimped bands with elastomer bodies between the crimped bands. The elastomeric bodies would replicate the deficient portion of the chordae to mimic the correct force curve during coaptation. This may provide enough benefit in some grades of the disease so as to provide palliative care or resolve it.

Figure 57A:
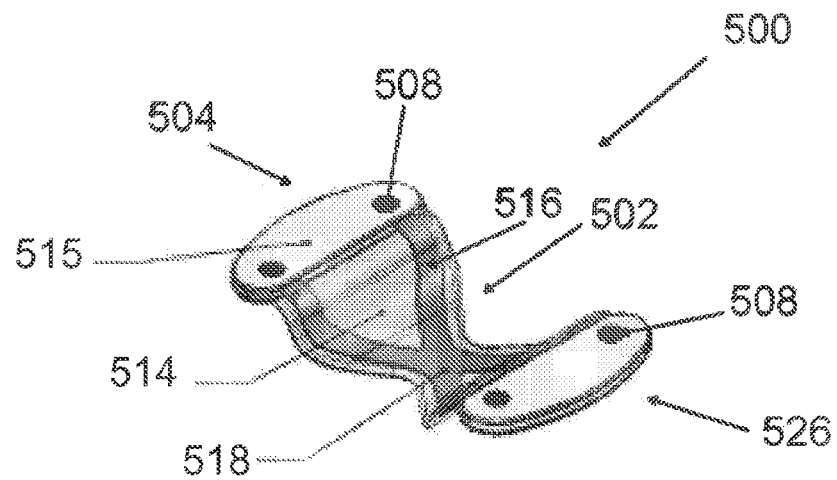
FIGS. 57A-D illustrate another embodiment of a transvalvular band.

FIGS. 57A-D illustrate another embodiment of a transvalvular band 500, which can also be referred to herein as a transvalvular bridge, e.g., a mitral bridge. FIG. 57A is a perspective view of a transvalvular bridge 500 according to some embodiments of the invention. The transvalvular bridge 500 can include a first attachment structure 504 at a first end of the bridge 500 and a second attachment structure 526 at a second end of the bridge 500, both attachment structures 504, 526 of which can include a variety of structures as discussed elsewhere herein for anchoring to the valve annulus. As illustrated, the attachment structures 504, 526 can have one or more layers 515 of a velour material such as a Dacron mesh and having a underlying frame for supporting the mesh and securing the mesh to the transvalvular band 500. The velour could be 6111 Polyester Double Velour Fabric in some embodiments. The mesh material can advantageously promote tissue ingrowth in some embodiments. The attachment structures 504, 526 can also include one or a plurality of apertures 508 which can be configured to allow for suturing therethrough, to attach the transvalvular bridge 500 to the valve annulus.

Still referring to FIG. 57A, the transvalvular bridge 500 can also include an arcuate central portion 502 which can be generally convex in the direction of the ventricle. As illustrated, the central portion 502 can include a plurality of struts 516 that cross and form a generally "X" shape at intersection zone or junction 518. The struts 516 can be made of any appropriate material, such as a metal, e.g., a shape memory metal such as Nitinol. The struts 516 as well as the spaces 514 in between the struts 516 can be treated or coated, e.g., encapsulated with silicone or another appropriate material as described elsewhere herein, in order to eliminate untoward effects such as thrombosis or corrosion.

Figure 57B:
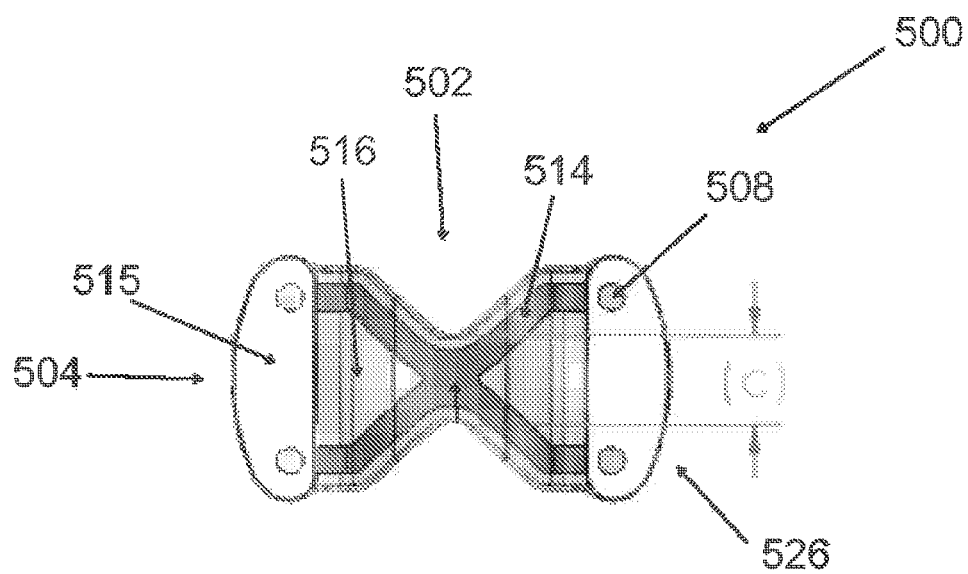

FIG. 57B is a top view of the transvalvular bridge 500 of FIG. 57A. As shown, the central portion 502 spans between the first attachment portion 504 and the second attachment portion 526, and can have a transverse width laterally that is substantially the same as that of the attachment portions 504, 526, but can become narrower toward the center toward intersection zone 518. In some embodiments, the width C in the central intersection zone 518 (measured perpendicular to blood flow) is between about 20% and about 80%, such as between about 25% and about 50%, or about 20%, 25%, 30%, 35%, 40%, 45%, 50%, 55%, 60%, 65%, 70%, or 75% of the width of the central portion 502 just proximate to the attachment portions 504, 526, and can gradually narrow toward the center as illustrated. In some embodiments, the width C in the central intersection zone 518 can be between about 4 mm and about 7 mm, such as between about 5 mm and about 6 mm, or about 5 mm, about 5.2 mm, about 5.4 mm, about 5.6 mm, about 5.8 mm, or about 6 mm, or ranges incorporating any of the foregoing values. By narrowing the central portion 502, the resistance to blood flow can advantageously be reduced.

Figure 57C:
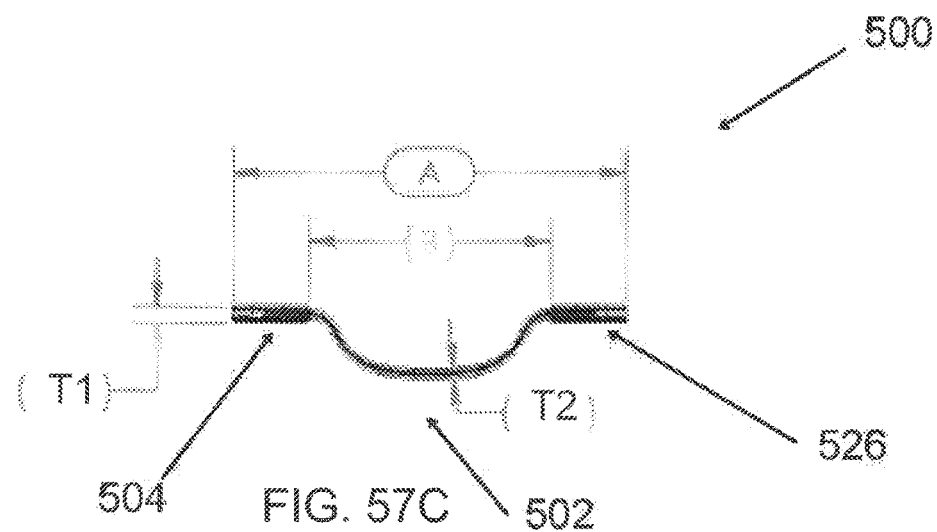

FIG. 57C is a side view of the transvalvular bridge 500 illustrated and described in connection with FIGS. 57A-B. In some embodiments, the thickness T2 of the central portion 502 can be defined by the strut 516 and the encapsulation layer 514 surrounding the strut. In some embodiments, the thickness T1 of the attachment portions 504, 526 can be defined by the ends of the struts 516, an encapsulation layer 514 surrounding the strut 516, and/or the velour material layer(s) 515 as previously described. The attachment portions 504, 526 can have a relatively greater thickness than the thickness of the central portion 502. In some embodiments, the attachment portions 504, 526 can have a thickness that is between about 25% and about 75% greater than that of the central portion 502, such as between about 40% and about 60% greater, or about 25%, 30%, 40%, 45%, 50%, 55%, 60%, 65%, 70%, or 75% greater than the thickness of the central portion 502. In some embodiments, the central portion 502 can have a thickness T1 of between about 0.5 mm and about 1.0 mm, such as about 0.6 mm, 0.7 mm, or 0.8 mm, or ranges incorporating any of the foregoing values. In some embodiments, the attachment portions 504, 526 can have a thickness of between about 0.8 mm and about 1.3 mm, such as about 0.9 mm, 1.0 mm, 1.05 mm, 1.07 mm, 1.1 mm, or 1.2 mm, or ranges incorporating any of the foregoing values.

Still referring to FIG. 57C, the transvalvular bridge 500 can have an entire axial length A in some embodiments of between about 15 mm and about 40 mm, such as between about 20 mm and about 32 mm depending on the patient's anatomy. The central portion 502 of the transvalvular bridge 500 can have an axial length in some embodiments of between about 8 mm and about 24 mm, such as between about 12 mm and about 20 mm in some embodiments.

Figure 57D:
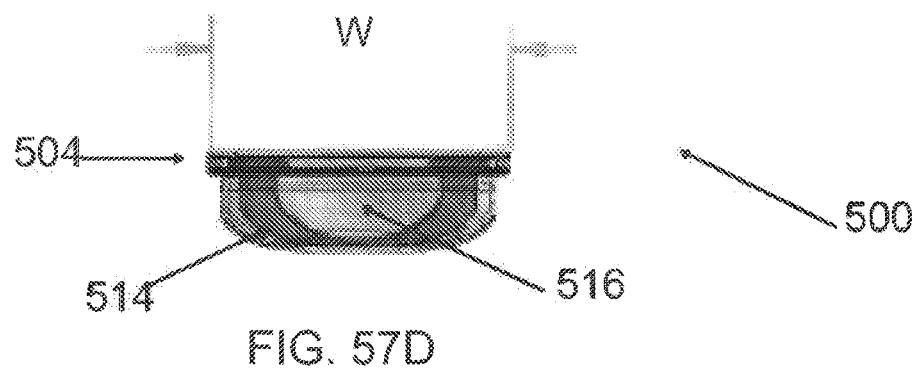

FIG. 57D illustrates an end view of the transvalvular bridge 500 illustrated and described in connection with FIGS. 57A-C above, showing the struts 516, silicone encapsulation layer 514, and attachment portion 514. In some embodiments, the width W of the attachment structures 504, 526 can be between about 10 mm and about 20 mm, and about 15 mm in some embodiments.

Figure 57E:
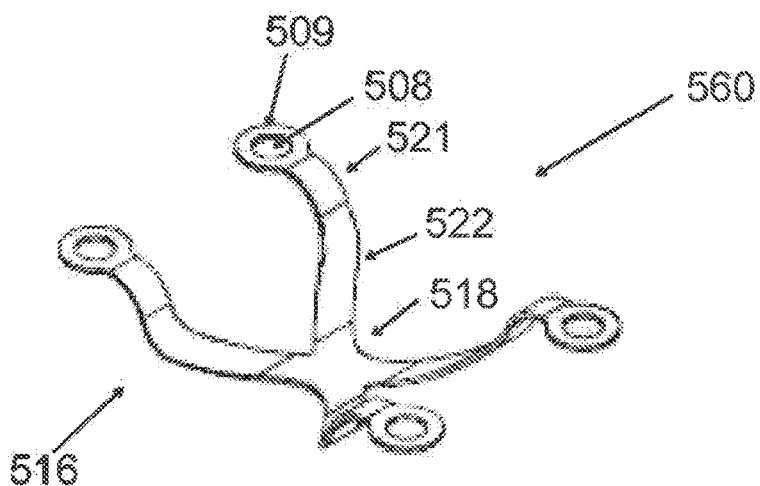
FIGS. 57E-H illustrate views of the underlying skeleton layer of the transvalvular band, according to some embodiments.
Figure 57F:
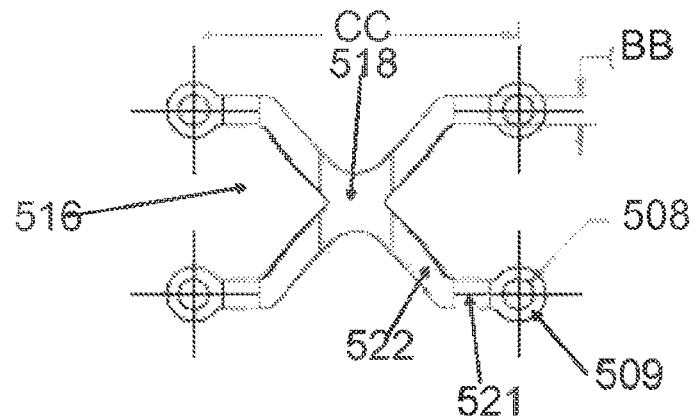
Figure 57G:
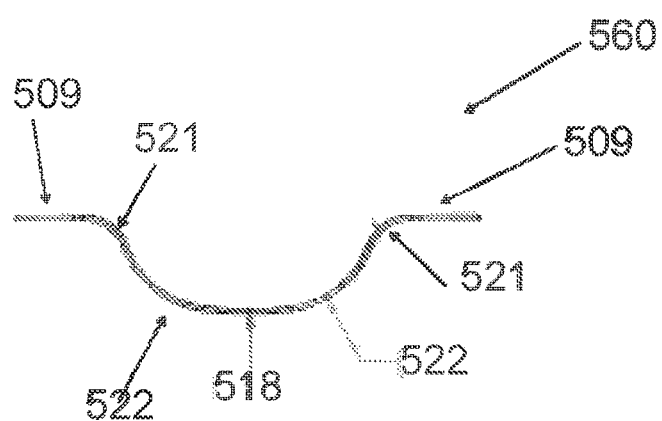
Figure 57H:
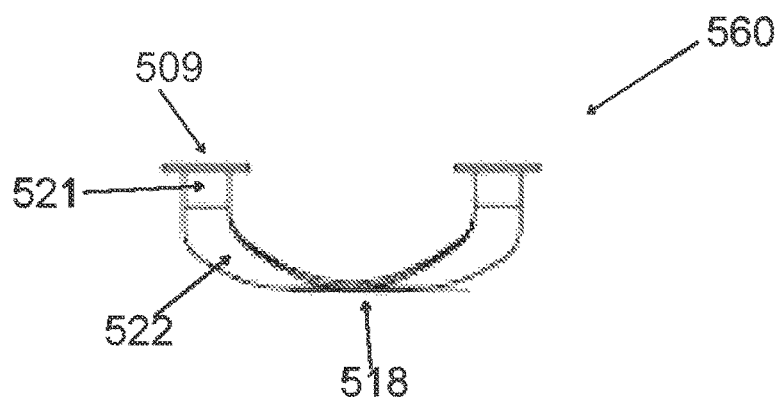

FIGS. 57E-H illustrate views of the underlying skeleton layer 560 of the transvalvular bridge 500, and can be formed of a shape set Nitinol skeleton that can be convex in the direction of the ventricle as previously described. FIG. 57E is a perspective view of the shape memory skeleton 560 of the transvalvular bridge 500, which can include struts 516 that cross at intersection zone 518 as previously described. The lateral ends of the skeleton 560 can include rings 509 defining apertures 508 that can be utilized for suturing as previously described. The skeleton layer 560 contribution to the central portion 502 of the transvalvular band 500 can include lateral curved transition zone 521 of the struts 516, which has a first curvature; which is in turn connected to medial curved transition zone 522 of the strut 516 which has a second curvature different from the first curvature; and the intersection zone 518 which includes the vertex of the arcuate central portion 502. FIG. 57F is a top view of the skeleton layer 560 of FIG. 57E. As illustrated, in some embodiments the lateral curved transition zones 521 of the struts 516 can, while configured to slope downwardly as shown, can run substantially parallel to the longitudinal axis of the skeleton 560 (and that of the transvalvular bridge 500), while the medial curved transition zone 522 can be oblique to the longitudinal axis of the skeleton 560 and the transvalvular bridge 500. In some embodiments, the axial length CC of the skeleton layer 560 can be between about 13 mm and about 25 mm, and the width BB of each strut 516 can be between about 1 mm and about 2 mm, such as between about 1.3 mm and about 2.0 mm. FIG. 57G is a side view, and FIG. 57H is an end view of the shape set Nitinol skeleton of FIGS. 57E-F.

As described above, the mitral valve and supporting structures are composed of the valve annulus, two leaflets, chordae tendineae, and papillary muscles. The anterior and posterior leaflets, oriented in the septal-lateral direction, provide for closing the valve opening during systole. During systole, the annulus and valvular surface create a saddle shape optimizing forces during closure by arching. The chordae and papillary muscles work together to limit the leaflet coaptation to the intraannular plane.

Qualitative Motion and Load on the Mitral Bridge: The mitral valve has a saddle shape. As the saddle gets deeper, the commissures drop, and the anteroposterior diameter contracts. This contraction results in a compressive load on the transvalvular bridge. During this contraction, the pressure behind the leaflets causes them to contact the transvalvular bridge strut. In some embodiments, the mitral bridge is configured to withstand a total circumferential or compressive force applied to the Mitral Bridge of at about or at least about 0.35N, 0.40N, 0.45N, 0.50N, or about 0.368N per cardiac cycle in some embodiments. In some embodiments, the Mitral Bridge can be configured to tolerate a septal-lateral displacement of about or at least about 0.4 mm, 0.5 mm, or 0.6 mm during the cardiac cycle. • As such, the mitral bridge can be configured to withstand load in cyclic fatigue without damage allowing long term function; maintain an AP diameter or septal-lateral diameter for early coaptation eliminating regurgitation; and/or maintain an AP diameter facilitating LV remodeling.

Quantitative Leaflet Loads: The force acting on a papillary muscle can be, in some embodiments, between 3.97 and 6.42 N dependent upon systolic pressure typically ranging between 120 and 200 mmHg. There are two papillary muscles. If both muscles were not functioning, the load acting on the mitral valve leaflets would be 13 N. The force transferred to the mitral bridge can be calculated by using the ratio of the total orifice area to the area of the mitral bridge strut. The orifice and MB strut areas are typically 1000 mm$^2$ and 100 mm$^2$, respectively. The resulting load on the MB strut is about 1.3 N. This is the load that the mitral bridge would see if the chordate and papillary muscles were not absorbing any load. Therefore, in some embodiments, the mitral bridge can be configured to withstand a leaflet load of between about 1N and about 2N, or about or at least about 1.2N, 1.3N, 1.4N, or 1.5N to withstand loads without damage, allowing for long-term function.

Quantitative Motion on the Mitral Bridge: Based upon a six month Chronic Porcine Study of the mitral bridge, the echo analysis of that study showed no perceptible displacement of device from the Septal-Lateral (SL) plane. However, in some embodiments the mitral bridge can be configured to tolerate a displacement of about 0.5 mm in compression and tension. The average force to displace a device ±0.5 mm is between about 0.80N and about 0.85N, such as about 0.8358N in tension; and between about 0.60N and about 0.70N, such as about 0.63808N in compression. The forces found are over double the circumferential forces. The mitral bridge can be configured, when implanted, to withstand such forces and continue to stably function to improve valve coaptation without being damaged, displaced, or substantially displaced as noted above. The mitral bridge can thus be configured to tolerate, in some embodiments, a tension force of about or at least about 0.75N, 0.80N, 0.85N, 0.90N, 0.95N, 1.00N, or more. The mitral bridge can thus be configured to tolerate, in some embodiments, a compression force of about or at least about 0.55N, 0.60N, 0.65N, 0.70N, 0.75N, 0.80N, or more.

FIGS. 58-70 illustrate a system of delivery catheters 600 configured for use with the mitral devices described herein. While the system of delivery catheters 600 is described herein for use with the transvalvular bridge 500, any of the mitral devices described herein can be used with the devices and methods described herein. Referring back to FIG. 57A, the transvalvular bridge 500 comprises the first attachment structure 504 at the first end of the bridge 500 and the second attachment structure 526 at the second end of the bridge 500. The arcuate central portion 502 permits the transvalvular bridge 500 to be folded or otherwise compressed for delivery within a deployment catheter, and later expanded in a manner that permits the transvalvular bridge 500 to function as described. The attachment structures 504, 526 can include one or a plurality of apertures 508 which can be configured to allow for suturing therethrough, to attach the transvalvular bridge 500 to the valve annulus. In the illustrated embodiment, each of the attachment structures 504, 526 comprises two apertures 508.

Figure 58:
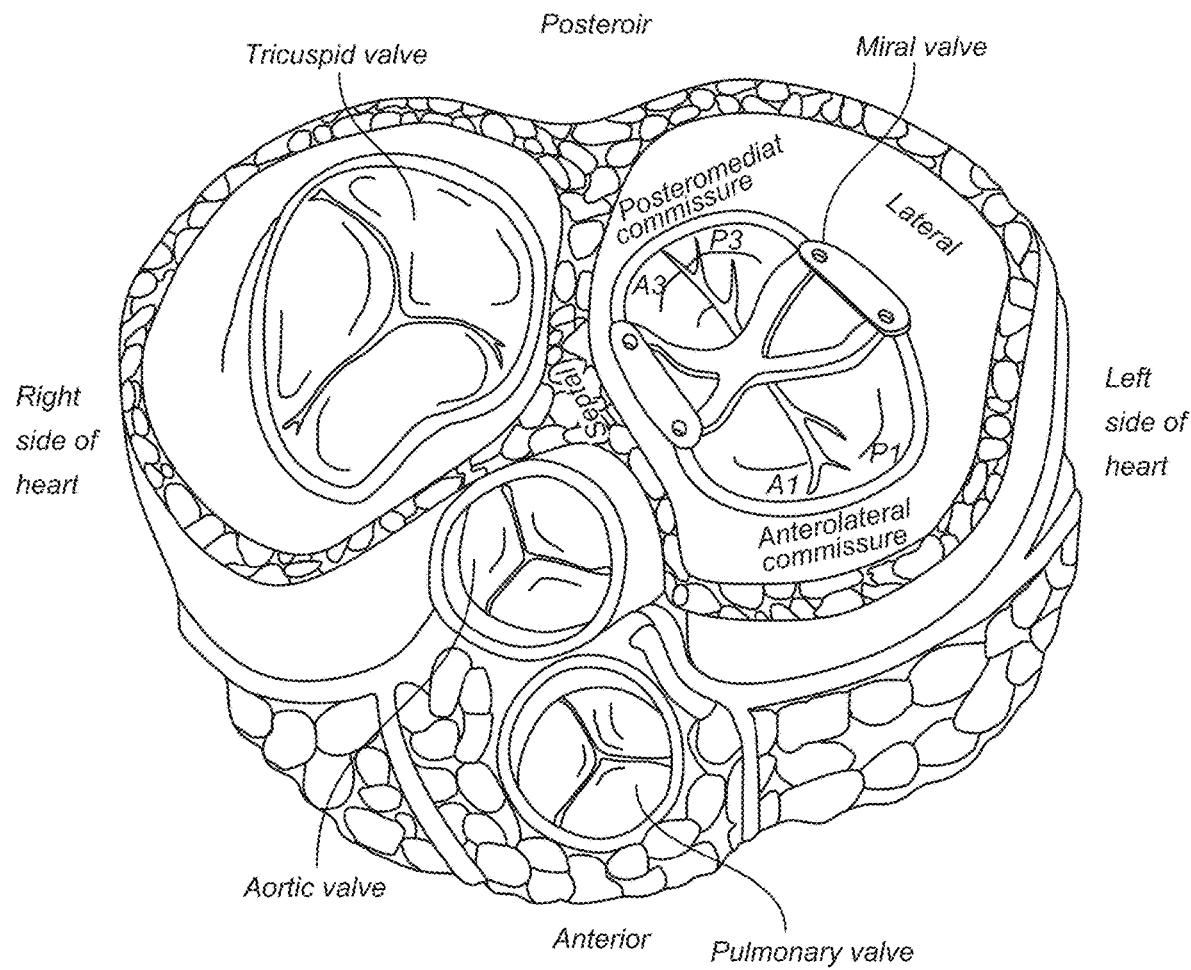
FIG. 58 is a simplified cross-sectional view of the heart.

FIG. 58 illustrates features of the anatomy of the heart. A system of cardiovascular catheters 600 is used to percutaneously deliver the transvalvular bridge 500 to the mitral valve for the repair of the mitral valve. The transvalvular bridge 500 can be securely attached to the mitral valve annulus at four points, that is P1, P3, A1, and A3. Locations A1 and A3 can be located on the anterior leaflet. Locations P1 and P3 can be located on the posterior leaflet. The locations P1, P3, A1, and A3 can correspond to the apertures 508 in the attachment structures 504, 526 of the transvalvular bridge 500. The transvalvular bridge 500 can be secured to provide coaptation of the mitral valve leaflets. The coaptation can be observable via various visualization techniques.

Figure 59A:
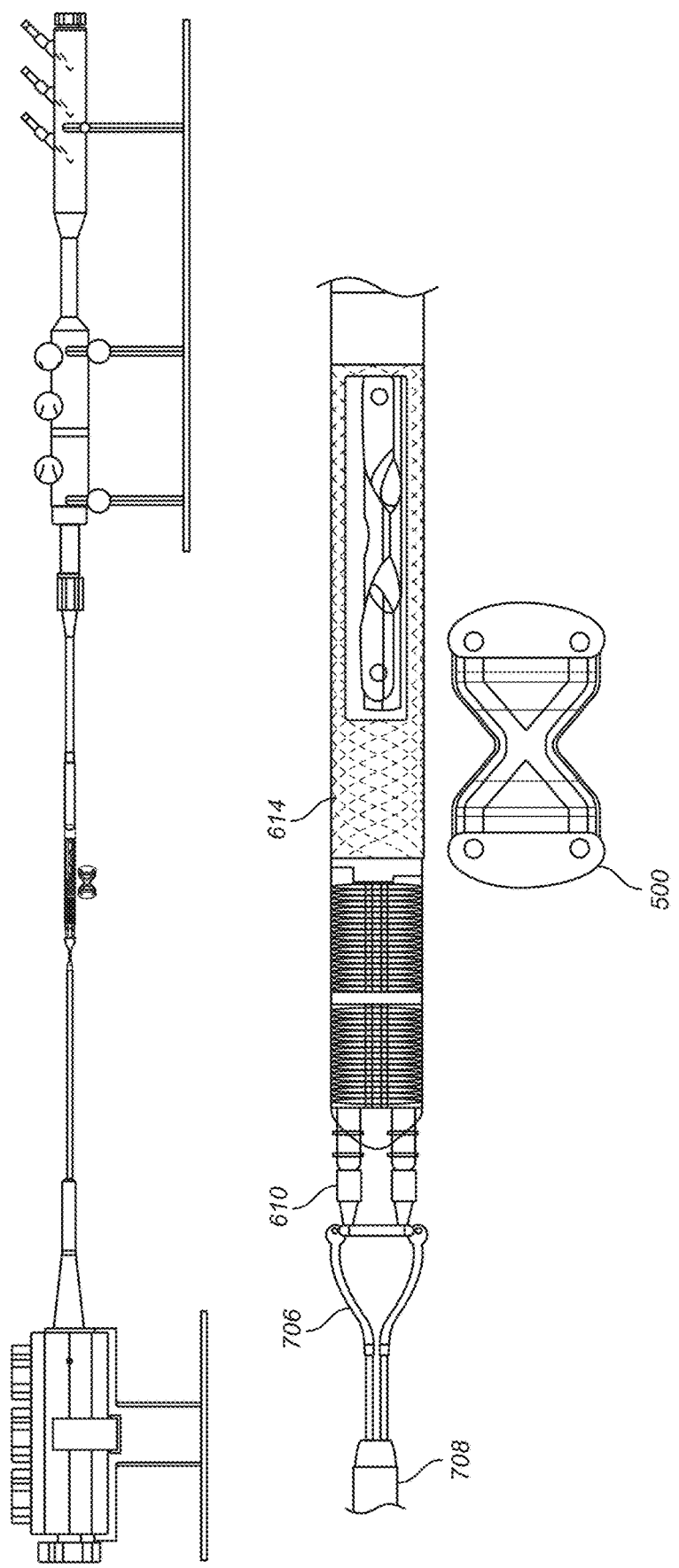
FIGS. 59A-59C are views of a catheter system, according to some embodiments.
Figure 59B:
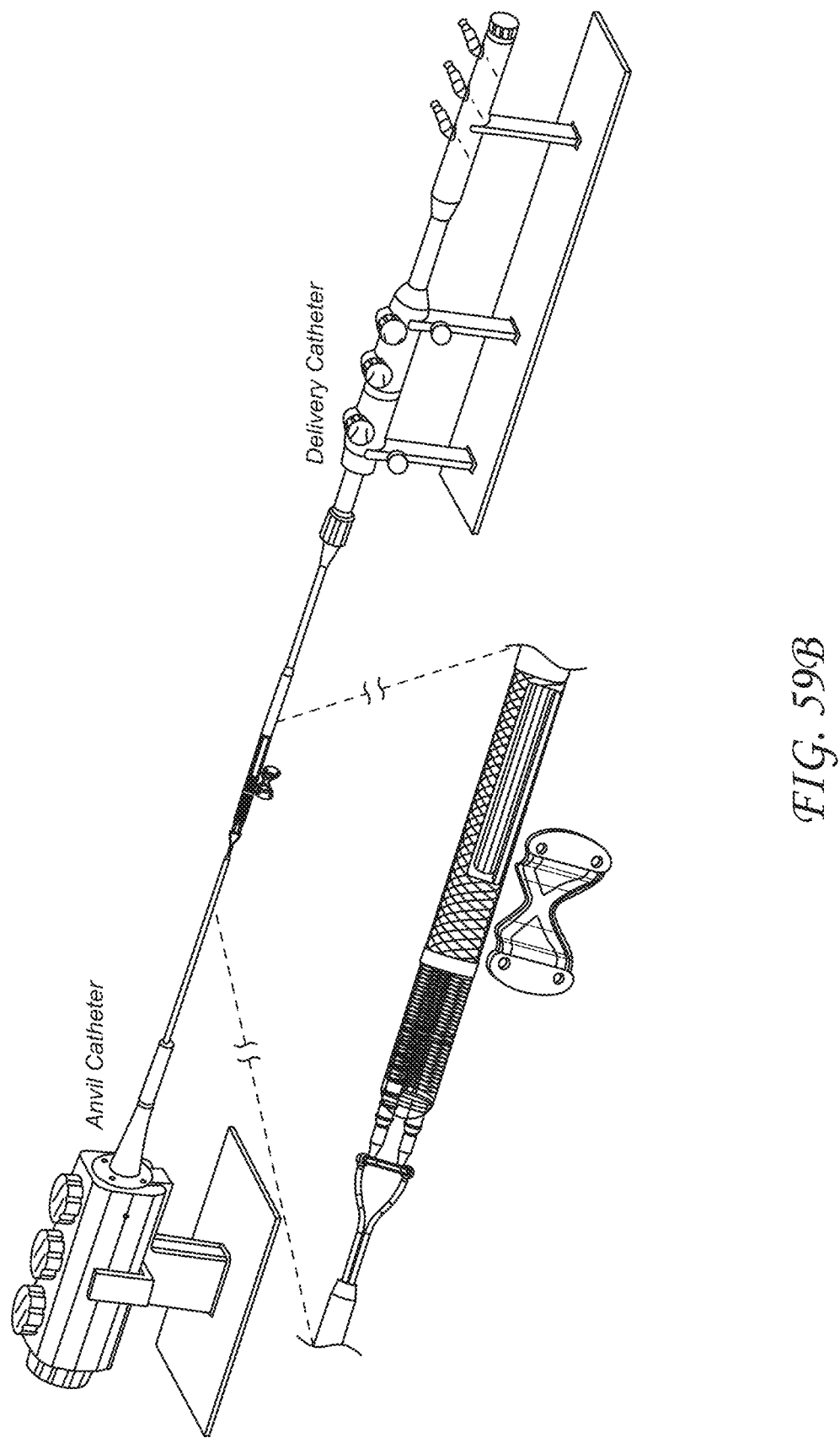
Figure 59C:
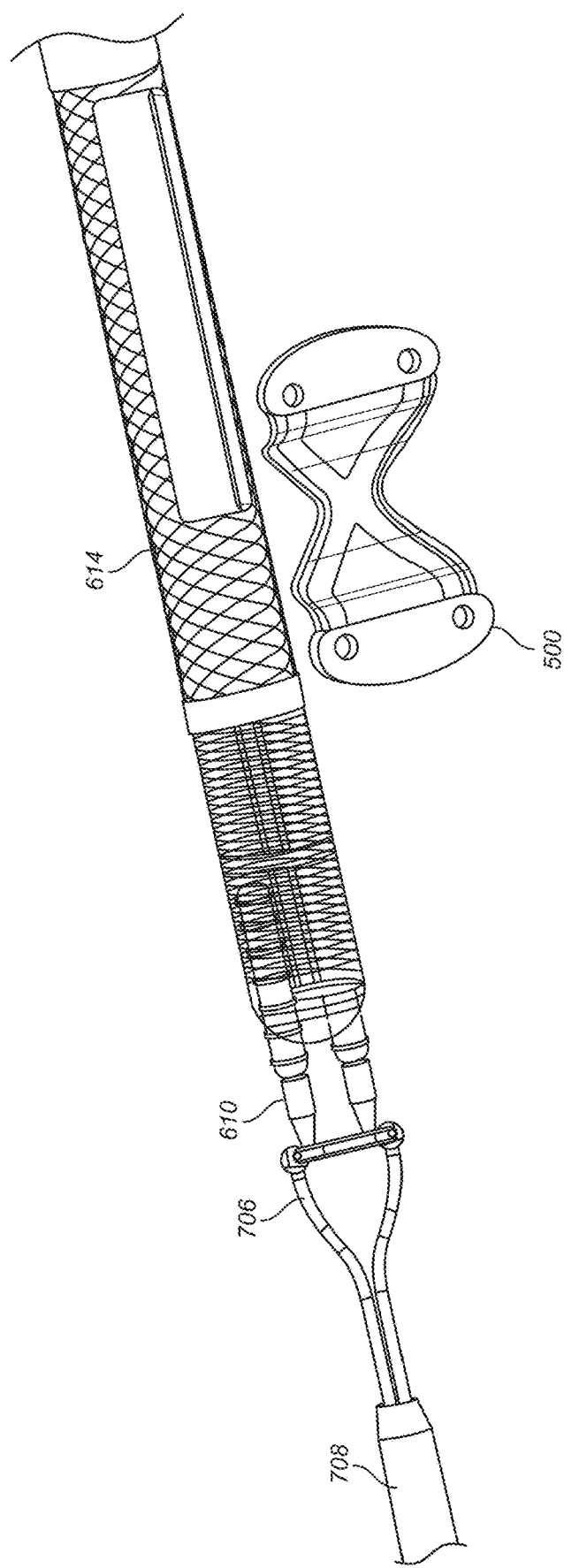

FIGS. 59A-59C illustrate features of the cardiovascular catheters 600. The cardiovascular catheters 600 described herein are intended for transcatheter implantation of the transvalvular bridge 500. This method is in contrast to an open-surgical implantation. An overview of the transcatheter implantation of the transvalvular bridge 500 can include one or more of the following steps. The patient can be anesthetized. An introducer catheter 602 can be introduced through the femoral vein. The introducer catheter 602 can be any commercially available introducer catheter. The method can include the step of inserting the introducer catheter 602. Imaging can be used throughout the procedure to ensure proper positioning. Imaging techniques can include fluoroscopy and 2D/3D/4D TTE imaging modalities. In some methods of use, a guide catheter 604 can be positioned in the right ventricle. In some methods of use, the guide catheter 604 can be positioned in the right atrium. The guide catheter 604 can be 12F but other dimensions are contemplated. A septal needle 606 can be inserted through the guide catheter 604. The septal needle 606 can puncture through the atrial septum. The puncture can be located at the 12 o'clock position, proximate the fossa ovalis. The guide catheter 604 can allow for subsequent dilation and advancement of the guide catheter 604. The guide catheter 604 can be advanced into the left atrium.

The needle catheter 610 can be delivered through the guide catheter 604. The needle catheter 610 can include multiple components, as described herein. The needle catheter 610 can be positioned to deliver a retainer 612. The position for delivery may be located at approximately P3. The needle catheter 610 can deliver the retainer 612 via sub-annular puncture. The needle catheter 610 can deliver the retainer 612 via a pressure or force. The needle catheter 610 can deliver the retainer 612 by applying electrical energy to create a hole. The hole can be created in the annulus. The hole can be created in a leaflet. One or more holes can be created. The needle catheter 610 or a portion thereof can be pushed through the hole. The retainer 612 can be positioned and delivered by being pushed from the needle catheter 610. The retainer 612 can be deployed. The needle catheter 610 can be withdrawn. A suture tail of the retainer 612 can be left exteriorized through the venous access. The process can be repeated to deploy one or more additional retainers 612. The additional retainers 612 can be placed at approximately P1, A1 and A3. In some methods of use, two or more retainers 612 are deployed simultaneously. In some methods of use, two or more holes are created simultaneously.

The transvalvular bridge 500 can be loaded into a deployment catheter 614. The transvalvular bridge 500 can be crimped to fit within the deployment catheter 614. The deployment catheter 614 can be delivered near the annulus. The transvalvular bridge 500 can be deployed. A dilator 616 can be delivered through the deployment catheter 614. The dilator 616 can allow for suture management and cinching.

The transvalvular bridge 500 can be secured by advancing a clip 620. The clip 620 can be advanced via a pusher 622. The clip 620 can be advanced toward the transvalvular bridge 500. The pusher 622 can extend through the deployment catheter 614. The suture can be trimmed via a trimming catheter 624. The trimming catheter 624 can extend through the deployment catheter 614. The implantation of the transvalvular bridge 500 can be viewed through imaging techniques. The cardiovascular catheters 600 can be withdrawn. The incision can be closed.

In some embodiments, one or more catheter can be transseptal (TS) catheters. The transseptal catheters can include catheters delivered via the atrial septum. The transseptal catheters can include the introducer catheter 602. The introducer catheter 602 can be a transfemoral introducer. The transseptal catheters can include the guide catheter 604. The transseptal catheters can include needle catheter 610. The transseptal catheters can include the deployment catheter 614. The transseptal catheters can include the dilator 616. The one or more transseptal catheters can deploy on the atrial side of the mitral valve (in other words, upstream in the direction of blood flow of a cardiac valve).

In some embodiments, the system 600 can include one or more transapical (TA) catheters. The transapical catheters can include an introducer 702. The transapical catheters can include a guide catheter 704. The transapical catheters can include an anvil delivery catheter 706. The transapical catheters can include a cinching catheter 708. The one or more transapical catheters can deploy on the ventricular side of the mitral valve (in other words, downstream in the direction of blood flow of a cardiac valve). The one or more transseptal catheters and the one or more transapical catheters can deploy on opposite sides of the annulus. The deployment of the system 600 can be considered a hybrid approach.

Figure 60:
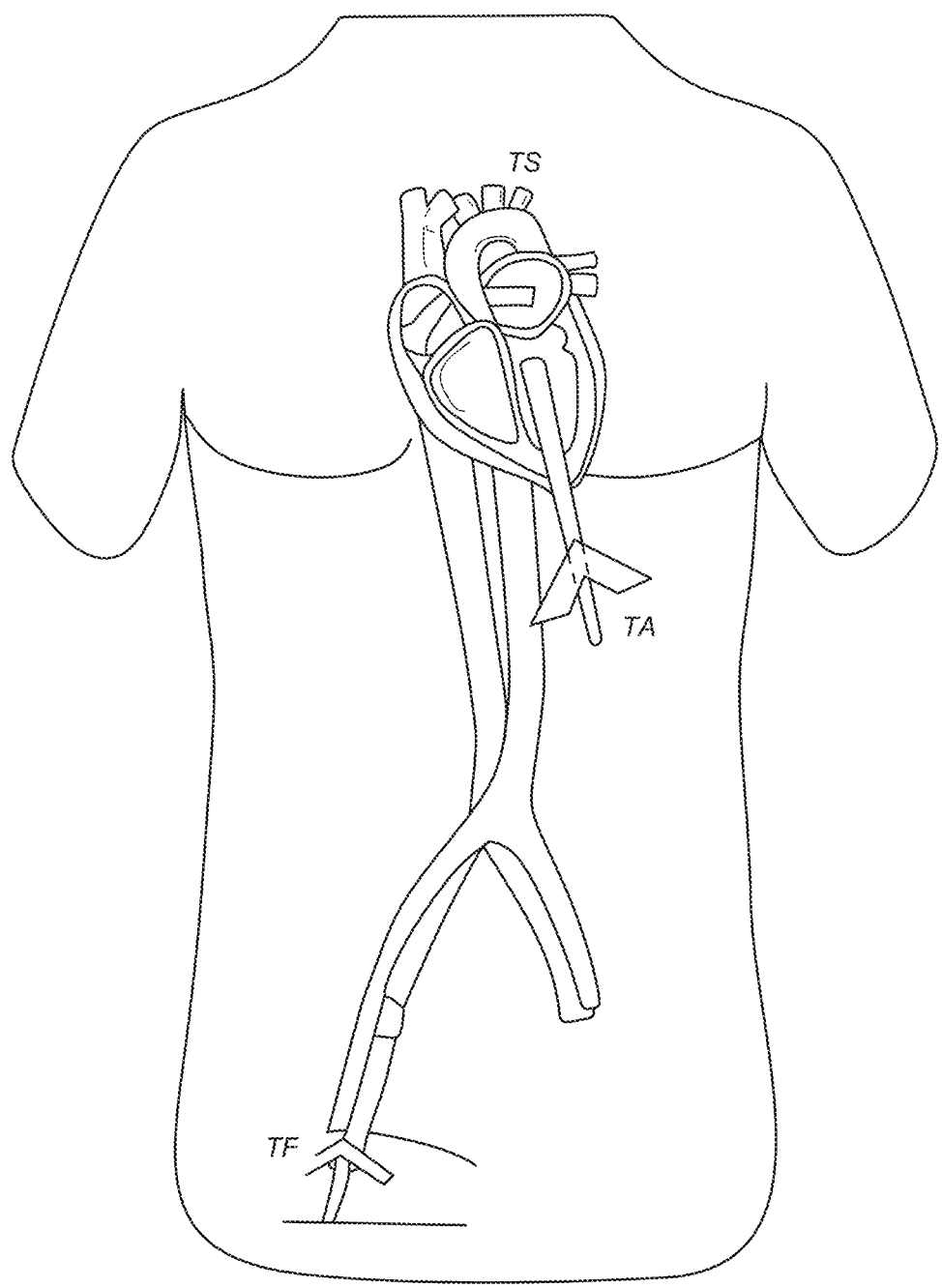
FIG. 60 illustrates examples of access locations.

FIG. 60 illustrates the locations of insertion for the one or more transseptal catheters and the one or more transapical catheters. The method can include one or more of the following steps. The introducer catheter 602 can be inserted through a transfermoral approach. The introducer catheter 602 can be inserted through a transseptal approach. The introducer 702 can be inserted through a transapical approach. The guide catheter 604 can be inserted through a transfermoral approach. The guide catheter 604 can be inserted through a transseptal approach. The guide catheter 704 can be inserted through a transapical approach. The deployment catheter 614 can be inserted through a transseptal approach. The anvil delivery catheter 706 can be inserted through a transapical approach. The needle catheter 610 can be inserted through a transseptal approach. The cinching catheter 708 can be inserted through a transapical approach. The dilator 616 can be inserted through a transseptal approach.

The deployment of the sutures can be through a transseptal approach. The suture retrieval can be through a transapical approach. The suture count and management can be through a transapical approach. The cinching can be through a transapical approach. The deployment of the transvalvular bridge 500 can be through a transseptal approach. The knotting can be through a transapical approach. The suture can be cut through a transapical approach. The withdrawal of the one or more catheters can be through a transseptal approach. The withdrawal of the one or more catheters can be through a transapical approach. The closure can be through a transapical approach and/or through a transseptal approach.

In some embodiments, the delivery is through a singular location. The method can include delivery of the one or more transseptal catheters. The introducer catheter 602 can be inserted at described herein. The guide catheter 604 can be inserted as described herein. In the atrium, the needle catheter 610 can be deployed. In the atrium, the deployment catheter 614 can be deployed. In the subvalvular region, the anvil delivery catheter 706 can be deployed. In the subvalvular region, the cinching catheter 708 can be deployed. The anvil delivery catheter 706 can be inserted transaortically. The anvil delivery catheter 706 can be inserted through a transmitral approach via transseptal access.

Figure 61A:
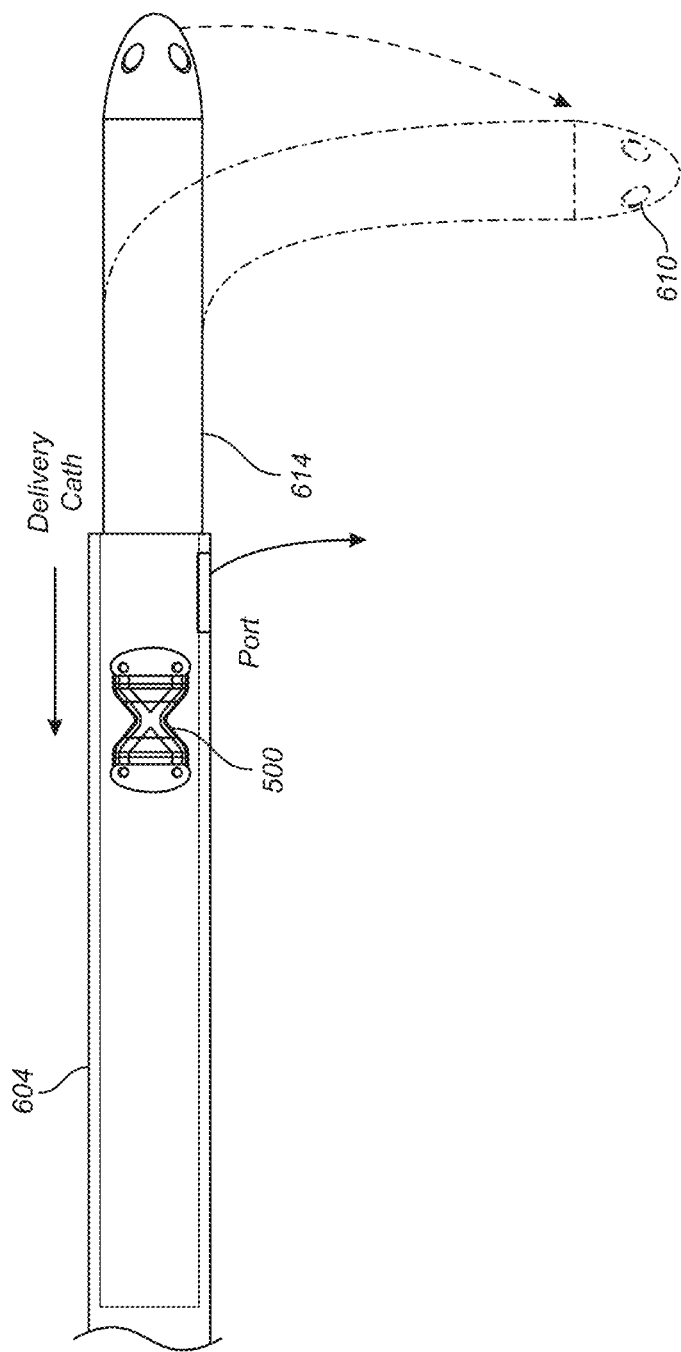
FIGS. 61A-61G illustrates various features of the catheter system, according to some embodiments.
Figure 61B:
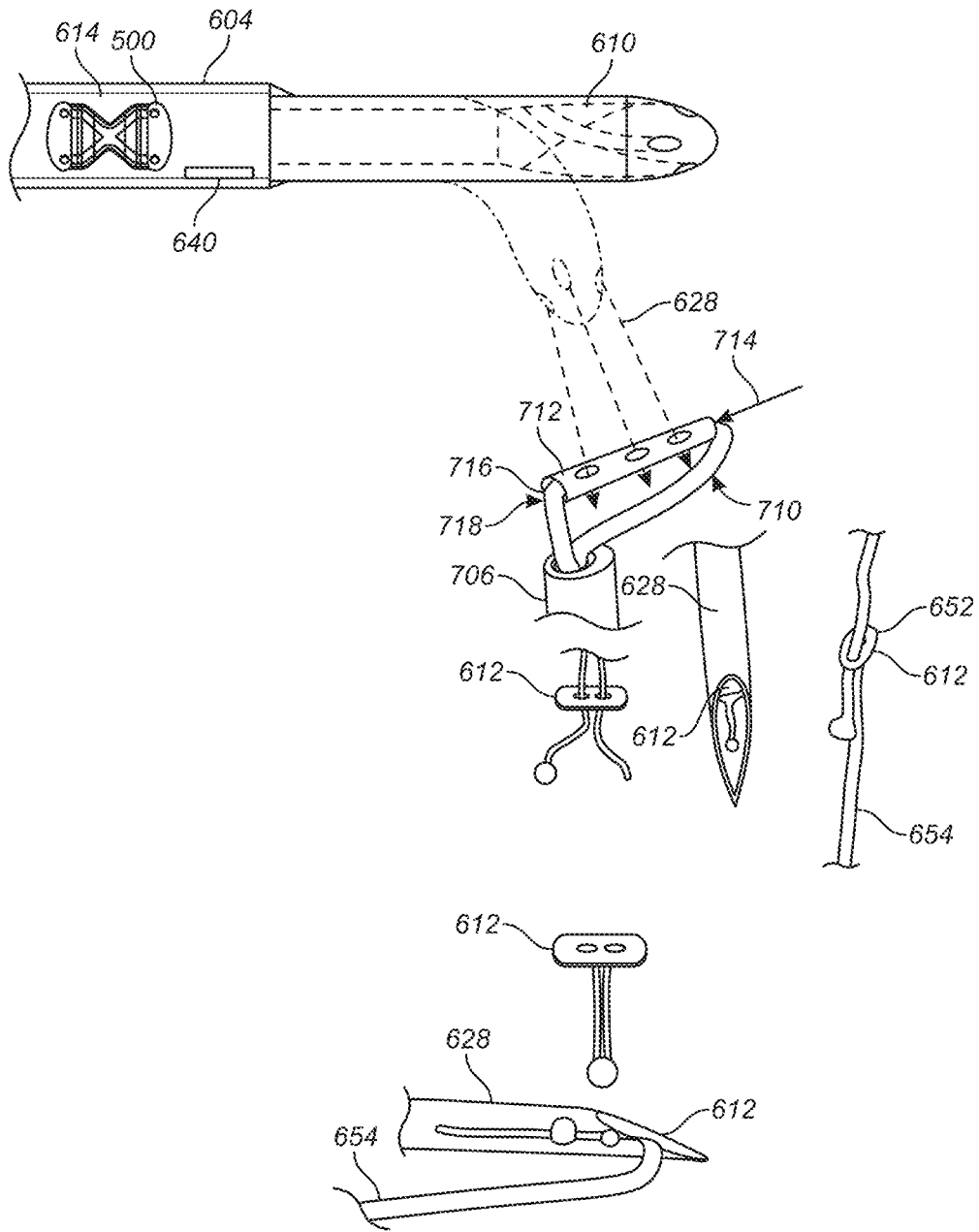

FIGS. 61A-61G illustrates an example of the hybrid approach. FIG. 61A shows an embodiment of transseptal (TS) catheters. The guide catheter 604 is shown as a sheath. The deployment catheter 614 extend through the guide catheter 604 to the atrium to deploy the transvalvular bridge 500. The needle catheter 610 can extend through the guide catheter 604 to the atrium. Referring to FIG. 61B, the needle catheter 610 can deploy one or more needles 628. In the illustrated embodiment, the needle catheter 610 deploys three needles 628. In some embodiments, three retainers 612 are deployed by the three needles 628. In some embodiments, six retainers 612 are deployed (e.g., two sets of three retainers 612). In some embodiments, the needle catheter 610 deploys six needles 628. The six needles 628 can correspond to six retainers 612.

The deployment catheter 614 can include a port 640. The port 640 can allow deployment of the transvalvular bridge 500. The transvalvular bridge 500 can exit the deployment catheter 614 through the port 640. The port 640 can be located on a side surface of the deployment catheter 614.

The retainers 612 can be coupled to the transvalvular bridge 500 prior to deployment of the transvalvular bridge 500. In some embodiments, a suture 654 of the retainer 612 extends through an aperture 508 of the transvalvular bridge 500. In some embodiments, two or more sutures corresponding to two or more retainers are coupled to the transvalvular bridge 500 prior to deployment.

The one or more needles 628 can be designed to interact with an anvil 710. The anvil 710 can be delivered to a sub annular location via the anvil delivery catheter 706. The anvil 710 can include one or more slots 712. In some embodiments, the number of slots 712 can correspond to the number of needles 628. In the illustrated embodiment, the anvil 710 includes three slots 712. The slot 712 can be sized and shaped to accept the needle 628 therethrough. The needle 628 can extend through the anvil 710 in a direction transverse to the longitudinal axis 714 of the anvil 710.

The anvil 710 is designed to be deployed to support the annulus. The anvil 710 can have a first configuration wherein the longitudinal axis 714 of the anvil 710 is generally parallel to a longitudinal axis of the anvil delivery catheter 706. The longitudinal axis 714 of the anvil 710 can be coaxial with the longitudinal axis of the anvil delivery catheter 706. The first configuration can be a low profile configuration. The anvil 710 can be deployed within the left ventricle. The anvil 710 can be pivoted. The anvil 710 can have a second configuration wherein the longitudinal axis 714 of the anvil 710 is generally perpendicular to a longitudinal axis of the anvil delivery catheter 706. The anvil 710 can lie against the annulus. The anvil 710 can support the annulus. The slot 712 of the anvil 710 can be in position to accept the needle 628. The second configuration can be a deployed configuration. The anvil 710 can include a lock 716. The lock 716 can maintain the position of the anvil 710 in the second configuration. The lock 716 can maintain the position of the anvil 710 relative to a control arm 718. The anvil 710 can be hinged relative to the control arm 718. In some embodiments, the control arm 718 is rigid. In some embodiments, the control arm 718 is flexible. The angle between the anvil 710 and the control arm 718 can be approximately ninety degrees. Other configurations are contemplated (e.g., 30 degrees, 40 degrees, 50 degrees, 60 degrees, 70 degrees, 80 degrees, 90 degrees, 100 degrees, 110 degrees, 120 degrees, etc.). The anvil 710 can lock at 290 degrees.

As described herein, the retainer 612 can be loaded into the needle 628. The retainer 612 can include a pledget 652. The retainer 612 can include the suture 654. The needle can deliver the retainer 612 through the slot 712 in the anvil 710. The retainer 612 can be considered an uncrimped suture tag. The retainer 612 can include a suture pinch point.

Figure 61C:
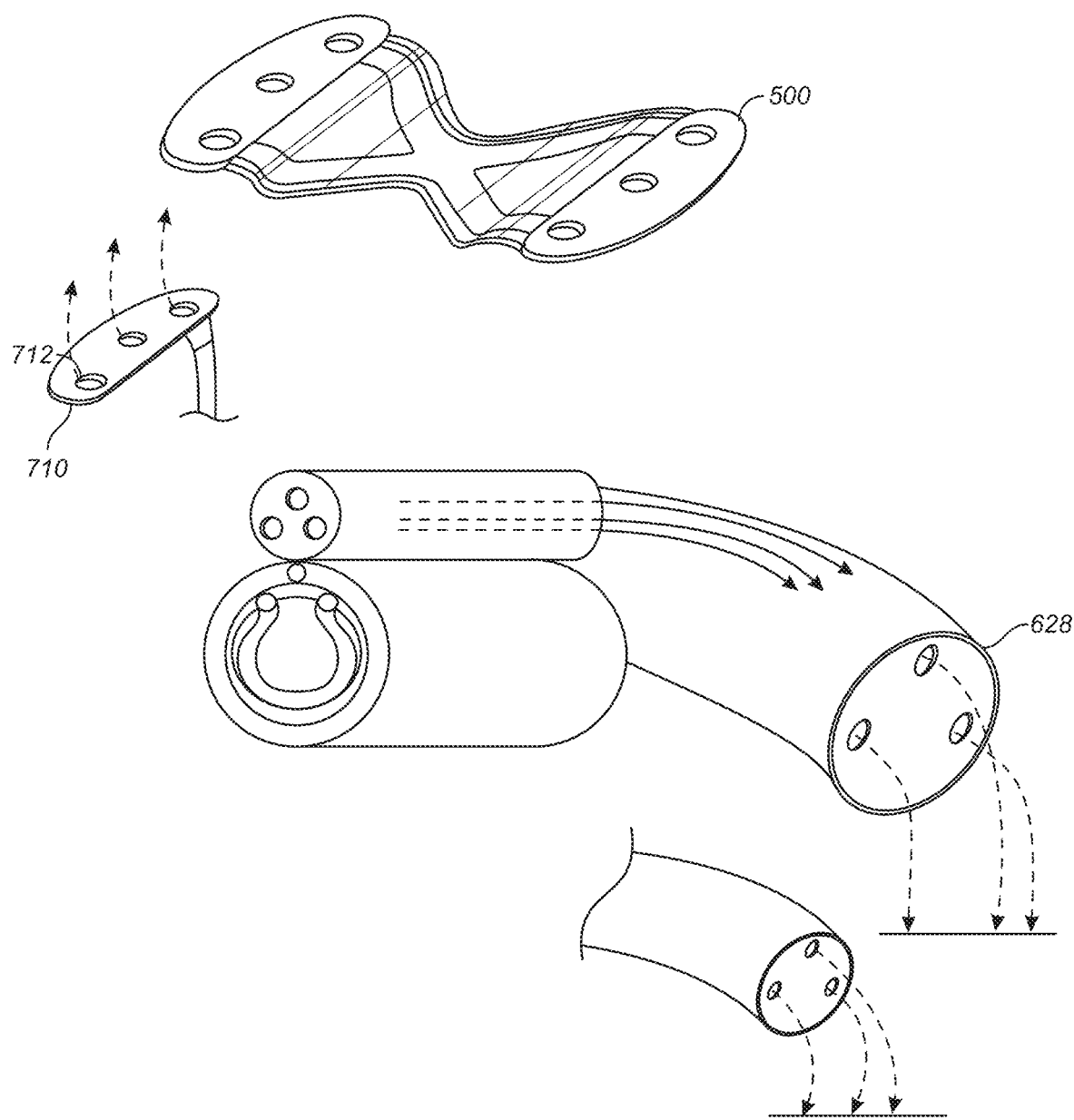

FIG. 61C illustrates the trajectory of the needle 628. In some embodiments, the one or more needles 628 extend along a straight path through the needle catheter 610. In some embodiments, the one or more needles 628 extend in a straight path from the needle catheter 610. The trajectory of the needle 628 can be linear. In some embodiments, the one or more needles 628 extend along a non-linear, curved or helical path through the needle catheter 610. In some embodiments, the one or more needles 628 extend in non-linear path from the needle catheter 610. The trajectory of the needle 628 can be non-linear. As described herein, the needle catheter 610 can be steerable. The needle catheter 610 can curve. The curvature of the needle catheter 610 can align the trajectory of the one or more needles 628 with the slots 712 in the anvil 710. In some embodiments, two or more needles 628 are designed to be simultaneously inserted into two or more slots 712. In some embodiments, two or more needles 628 are designed to deliver retainers 712 simultaneously through two or more slots 712.

Figure 61E:
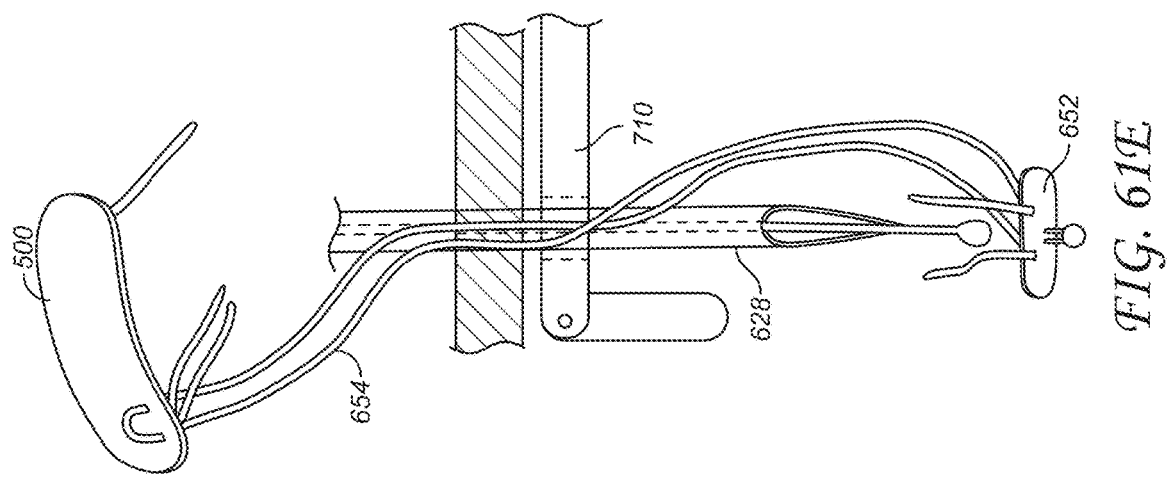
Figure 61D:
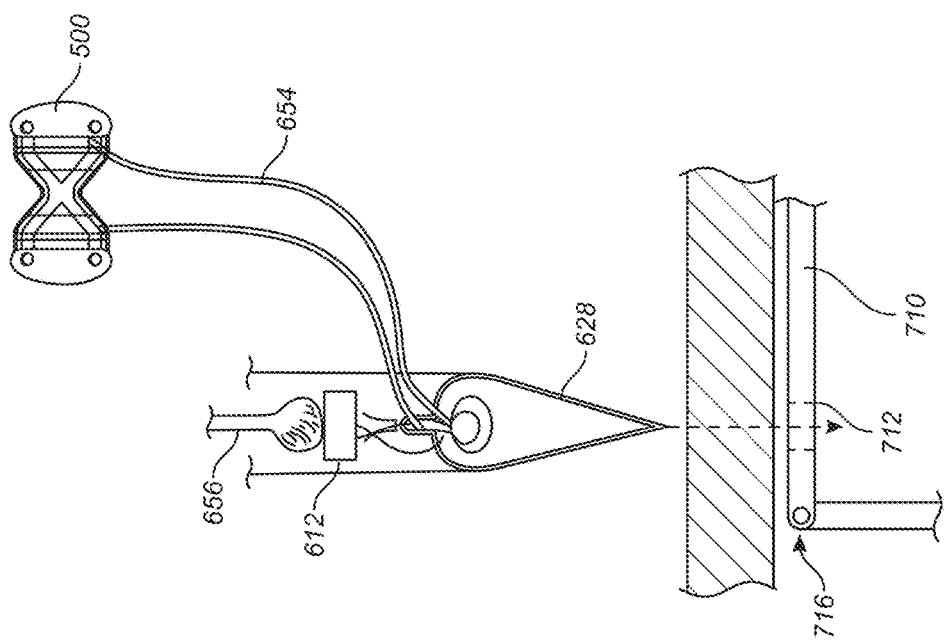

FIGS. 61D and 61E illustrates a method of using the anvil 710. The anvil 710 can be moved into position relative to the annulus. The anvil 710 can be pivoted relative to the control arm 718. The anvil 710 can be locked relative to the control arm 718. In the locked configuration, the anvil 710 supports a larger cross-section of the annulus. The needle 628 can be aligned with the slot 712 of the anvil 710. The retainer 612 can be disposed within the needle 628. The suture 654 of the retainer 612 can be coupled to the transvalvular bridge 500. The suture 654 can span from the needle catheter 610 to the transvalvular bridge 500. A plunger 656 can be disposed within the needle catheter 610. The anvil 710 can be held in position via the lock 716 during delivery of the retainers 612.

The needle 628 can be advanced to puncture the annulus, as described herein. The needle 628 can be advanced such that the needle 628 burns a hole in the annulus, as described herein. The needle 628 can be advanced through the slot 712 of the anvil 710. The needle 628 can deliver the retainer 612 through the annulus. The plunger 656 can be advanced to push the retainer 612 through the needle 628. The plunger 656 can cause the retainer 612 to enter the left ventricle. The retainer 612 can be subannular. The suture 654 of the retainer 612 can span from the retainer 612 to the transvalvular bridge 500. The suture 654 of the retainer 612 can span the annulus from the left ventricle to the left atrium.

Figure 61F:
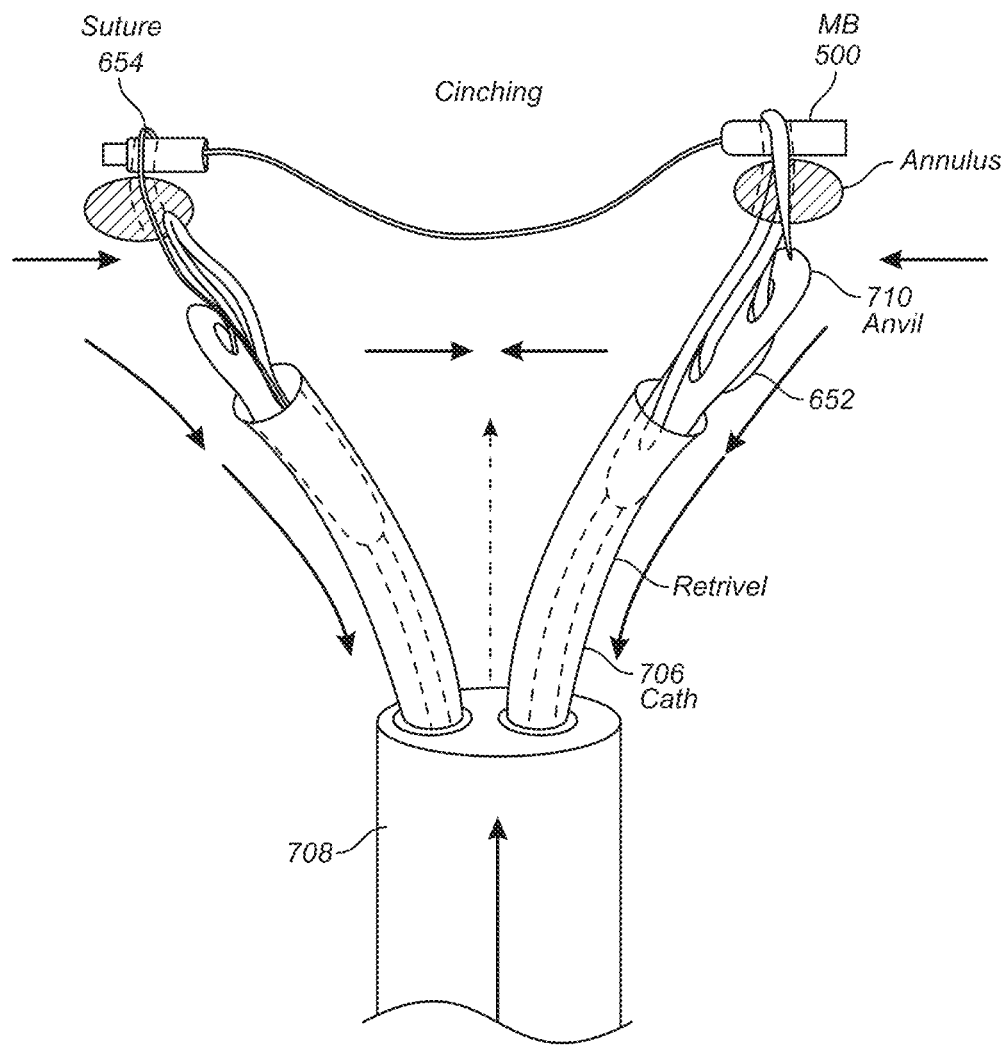

FIG. 61F illustrates the cinching catheter 708. The transvalvular bridge 500 can be deployed and positioned relative to the annulus. As described herein, the transvalvular bridge 500 can be coupled to the suture 654 of the retainer 612. The suture 654 can extend through the annulus from the pledget 652. The anvil 710 can separate the pledget 652 from the annulus after the retainer 612 is deployed. The anvil 710 can be retracted into the anvil delivery catheter 706. The anvil 710 causes the pledget 652 to move toward the anvil delivery catheter 706. The cinching catheter 708 can cause the anvil delivery catheter 706 to move inward. In the illustrated embodiment, the cinching catheter 708 controls two anvil delivery catheters 706. The cinching catheter 708 can cause the two anvil delivery catheters 706 to move toward each other. The cinching catheter 708 can cause the two anvil delivery catheters 706 to become more linear or straighter. The cinching catheter 708 can cause the transvalvular bridge 500 to be cinched. The cinching catheter 708 can cause the transvalvular bridge 500 to be cinched. The cinching catheter 708 can cause the attachment structures 504, 526 of the transvalvular bridge 500 to move toward each other.

Figure 61G:
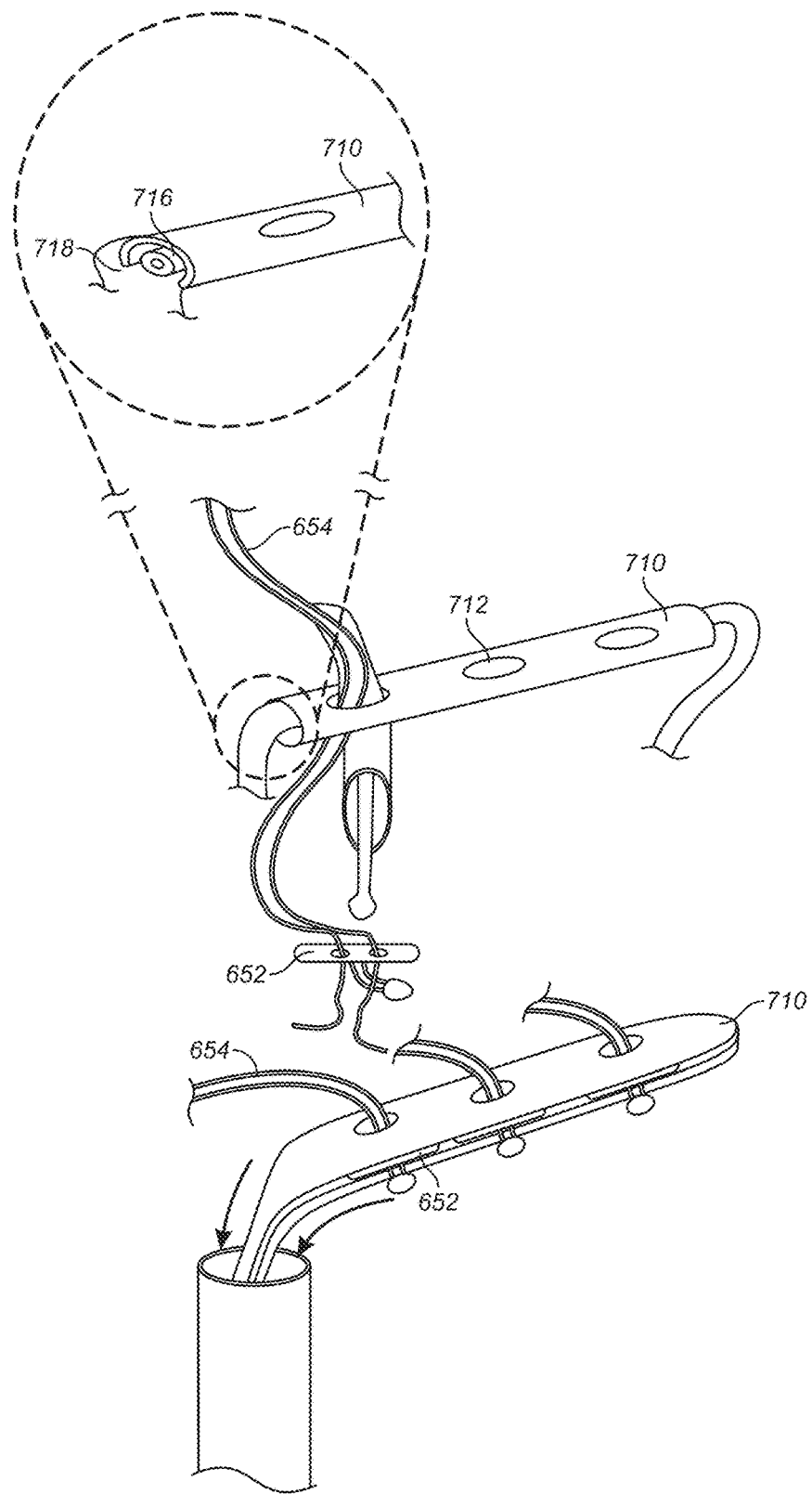

FIG. 61G illustrates a method. The method can include one or more of the following steps. The method can include the step of holding all of the sutures 654. The anvil 710 can enable one or more retainers 612 to be held. In the illustrated embodiment, three retainers 612 are held by the anvil 710. The method can include withdrawal of the anvil 710. The anvil 710 can be retracted into the anvil delivery catheter 706. The method can include withdrawal of the anvil delivery catheter 706. The anvil delivery catheter 706 can be withdrawn into the cinching catheter 708. The method can include removal of the pledget 652 or tag. The pledget 652 can be removed while the suture 654 is held in position. In some methods of use, the suture 654 is held in tension from the ventricular side of the annulus. In some methods of use, the suture 654 is held in tension from the atrial side of the annulus. The method can include loading a suture fastening system such as a COR-KNOT device (LSI Solutions, Inc., Victor, N.Y.). The method can include loading a pledget. The method can including cinching. The cinching can apply tension to the transvalvular bridge 500. The cinching can apply tension to the pledget 652. The cinching can apply tension to the suture 654. The cinching can apply tension to the anvil 712. The cinching can move one or more components of the system into position. The method can include deploying the suture fastening system.

Figure 62:
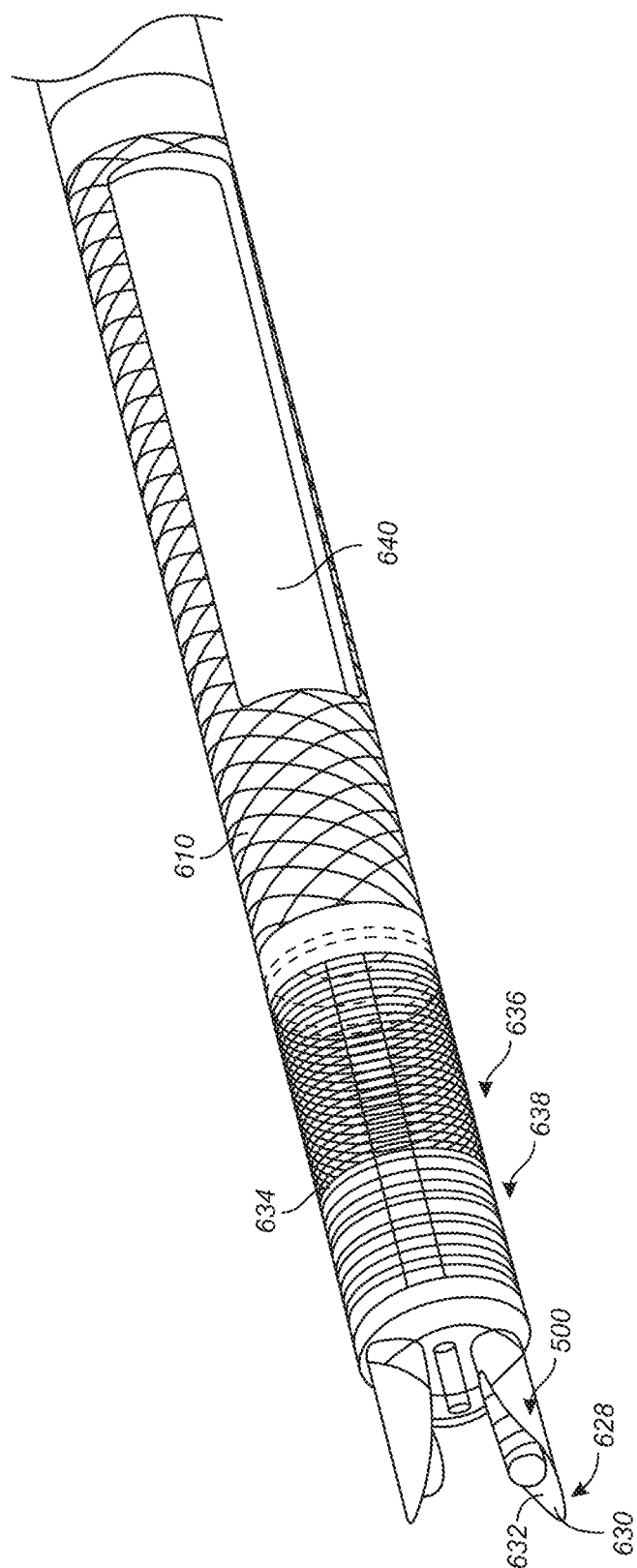
FIG. 62 is a side perspective view of an embodiment of a needle catheter.

FIG. 62 illustrates the needle catheter 610. The needle catheter 610 can include the needle 628. The illustrated embodiment includes two needles 628 but other configurations are contemplated (e.g., one needle, two needles, three needles, four needles, five needles, six needles, etc.). The two needles 628 can be similar or identical. The two needles 628 can be oriented to be a mirror image. The needle 628 can be designed for puncturing the annulus. The needle 628 can include a sharpened tip 630. The sharpened tip 630 can be any design to allow for puncture. In the illustrated embodiment, the sharpened tip 630 is tapered from an inside surface to an outside surface. The needle 628 can be cylindrical. The needle 628 can include a lumen 632. In some embodiments, the transvalvular bridge 500 can be disposed within the needle catheter 610. In some embodiments, the transvalvular bridge 500 can be designed to span the distance from between the needles 628. In some embodiments, the transvalvular bridge 500 can be designed to be deployed by advancing through the end of the needles 628.

The needle catheter 610 can use fluid pressure to deliver the needle 628. In some methods of use, the needle catheter 610 can allow for hydraulic or compressed air delivery of the needle 628. The needle catheter 610 can include a flexible pressure vessel 634. The flexible pressure vessel 634 can include a fluid chamber. The fluid can be gas or liquid. The fluid can be air. The flexible pressure vessel 634 can be flexible to enable the needle catheter 610 to flex or turn. The flexible pressure vessel 634 can allow components to apply a pressure or force on other components within the needle catheter 610. The needle catheter 610 can include a pressure plate 636 for an internal pusher or plunger. The pressure plate 636 allows a pressure or force to be applied to the internal pusher or plunger. For instance, a pressure or force can be applied to move the retainer 612. For instance, a pressure or force can be applied to move the transvalvular bridge 500. The needle catheter 610 can include a pressure plate 638 for the needle 628. The pressure plate 638 can allow a pressure or force to be applied to the needle 628. For instance, a pressure or force can be applied for sub-annular puncture. The needle catheter 610 can include a catheter port 640. The catheter port 640 can allow the flexible pressure vessel 634 to be filled with fluid.

Figure 63A:
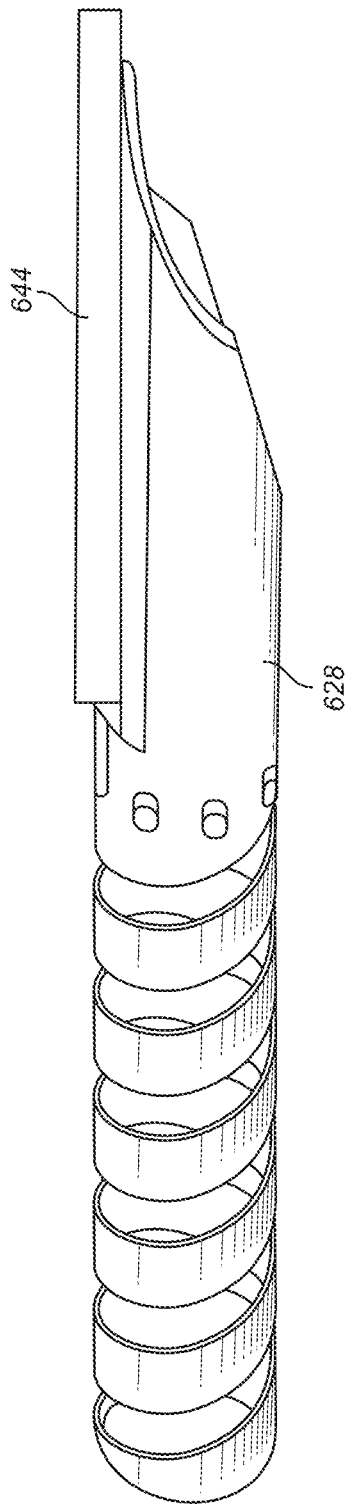
FIG. 63A is a side perspective view of an embodiment of a needle and an energy tip.
Figure 63B:
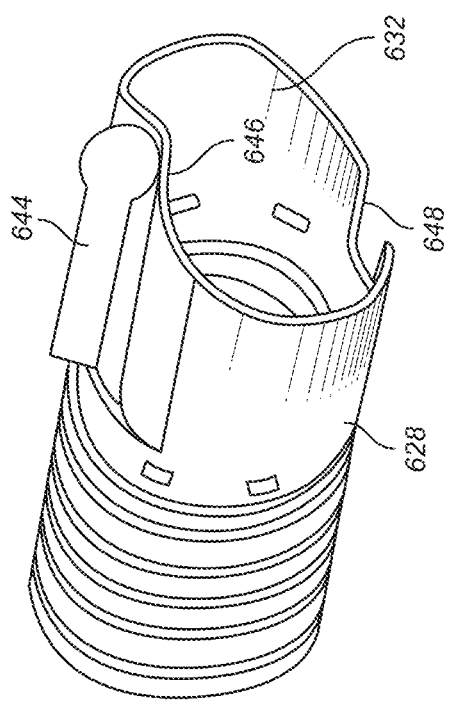
FIG. 63B is a front perspective view of the needle and the energy tip of FIG. 63A.

FIGS. 63A and 63B illustrate perspective views of the needle 628. The needle 628 can include an energy tip 644. The energy tip 644 can delivery energy such as RF energy to the tissue. The energy tip 644 can be an electrode. The energy tip 644 can be coupled to the needle 628. The energy tip 644 can be integrally formed with the needle 628. The energy tip 644 can be located within a detent 646 of the needle 628. The detent 646 can enable the energy tip 644 to be partially or entirely disposed within the detent 646. The detent 646 can change the cross-sectional shape of the lumen 632 as shown in FIG. 60B. The energy tip 644 can be designed to burn through the annulus. The energy tip 644 can be designed to the puncture through the annulus. The energy tip 644 can be located at the distalmost edge of the needle 628. The energy tip 644 can protrude past the distalmost edge of the needle 628 such that the energy tip 644 is the first to contact the annulus. The needle 628 can include a slot 648.

FIG. 63C illustrate various additional views of the needle 628. Referring to FIG. 60C, the energy tip 644 can be a sleeve. The energy tip 644 can partially surround the needle 628. The energy tip 644 can be coupled to an energy source (not shown). The energy source can supply the energy tip 644 with energy such as electrical energy. The energy tip 644 can convert the electric energy to RF energy. The energy tip 644 can enable RF heating. The energy tip 644 can enable the application of a high-frequency or radiofrequency electric current to biological tissue such as the annulus. The energy tip 644 can allow the tissue to be cut. The energy tip 644 can also coagulate blood or blood vessels or cauterize the tissue. The needle catheter 610 can include a sheath (not shown) which covers the needles 628 during delivery. The sheath can cover the energy tip 644.

In some methods of use, the user locates the position and uses low force for penetration of the needle 628. In some methods of use, the energy tip 644 can be a guide for the incising needle 628. The energy tip 644 can be collinear with the needle 628. The initial penetration can be with the energy tip 644. The secondary penetration can be with the needle 628. The energy tip 644 can be co-linear with the needle catheter 610. The energy tip 644 can be co-axial with the needle catheter 610. In some embodiments, suction is used to locate and provide puncture counterforce.

Figure 64A:
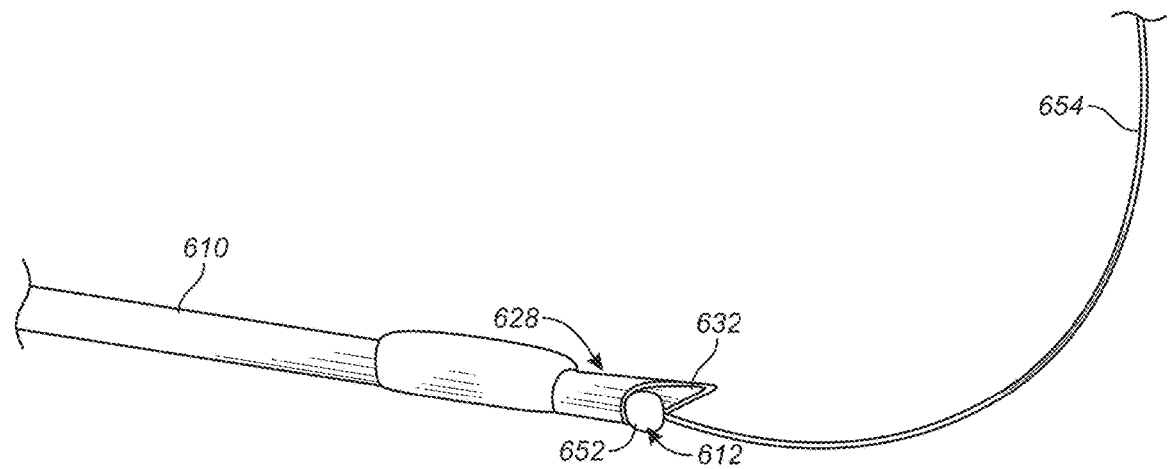
FIGS. 64A-64E are various perspective views of the delivery of a retainer, according to some embodiments.
Figure 64B:
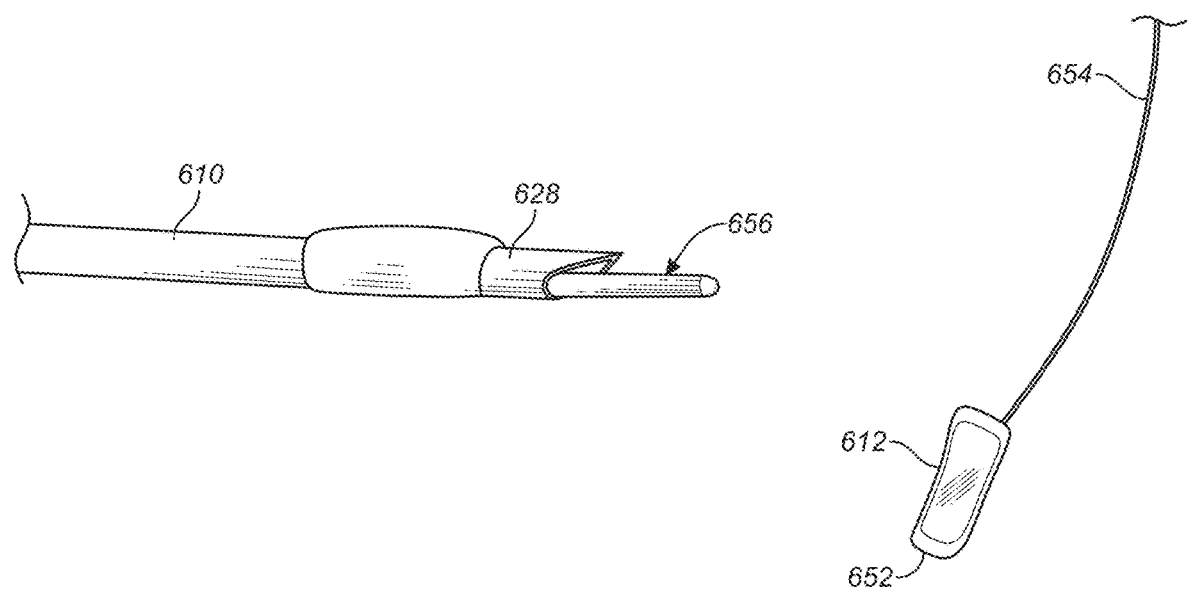

FIGS. 64A and 64B illustrate the deployment of the retainer 612. The retainer 612 can include the pledget 652. The pledget 652 can be cylindrical or any shape known in the art (rectangular, square, oval, elliptical, etc.). The pledget 652 can be shaped to be disposed within the lumen 632 of the needle 628. The pledget 652 can be formed from a plastic or polymer materials. The pledget 652 can comprise polytetrafluorethylene (PTFE). The pledget 652 can be sterile and non-absorbable. The retainer 612 can include the suture 654. The pledget 652 can be coupled the suture 654. The suture 654 can be formed from a plastic or polymer materials. The suture 654 can comprise polyethylene terephthalate (PET). The suture 654 can be any size known in the art. In the illustrated embodiments, the suture 654 is size 2 (2-0). The retainer 612 can secure the transvalvular bridge 500 in the annulus. The retainer 612 can be used to replicate open implants. The retainer 612 can be disposed within the needle catheter 610. The retainer 612 can be a self-locking slice for single column. The retainer 612 can be double locked by the clip 620. The retainer 612 can hold the transvalvular bridge 500 in place. The retainer 612 can hold greater than the suture strength in the annulus.

Referring to FIG. 64A, the retainer 612 can be loaded into the lumen 632 of the needle 628. The suture 654 can be attached to the pledget 652 before being loaded into the needle 628. The retainer 612 can be disposed in a first orientation. In the first orientation, the pledget 652 of the retainer 612 can have a longitudinal axis aligned with the longitudinal axis of the lumen 632 of the needle 628. The suture 654 can extend from the distal end of the needle 628. The suture 654 can extend through the slot 648 of the needle 628. The suture 654 can extend toward the proximal end of the needle 628. The suture 654 can be held within the needle catheter 610 during delivery. The retainer 612 can be disposed in the needle 628 during delivery through the annulus.

In the first orientation, the pledget 652 of the retainer 612 can have a longitudinal axis aligned with the longitudinal axis of the hole created by the needle 628. As described herein, the energy tip 644 can burn a hole in the annulus. The needle 628 can enlarge the hole created by the energy tip. The needle 628 can puncture the annulus. The needle 628 can be delivered through the hole. The retainer 612 can be delivered through the hole created by the energy tip 644. The retainer 612 can be delivered through the hole created by the needle 628.

Referring to FIG. 64B, the retainer 612 can be deployed. The needle catheter 610 can include the plunger 656. The plunger 656 can be advanced along the lumen 632 of the needle 628. The plunger can push the retainer 612 out of the needle 628. The pledget 652 of the retainer 612 can be plunged out of the needle 628. The pledget 652 can be disposed on the other side of the annulus. The suture 654 of the retainer 612 can span the annulus. The retainer 612 can be disposed in a second orientation. In the second orientation, the pledget 652 of the retainer 612 has a longitudinal axis not aligned with the longitudinal axis of the lumen 632 of the needle 628. In some methods of use, the longitudinal axis of the pledget 652 is ninety degrees from the longitudinal axis of the lumen 632 of the needle 628. In some methods of use, the longitudinal axis of the pledget 652 is transverse to the longitudinal axis of the lumen 632 of the needle 628. In some methods of use, the pledget 652 is rotated during deployment. The needle catheter 610 can be withdrawn after deployment of the retainer 612. Referring back to FIG. 60, the pressure plate 636 allows a pressure or force to be applied to the plunger 656. The pressure plate 636 can enable the plunger 656 to deploy the retainer 612.

Referring to FIG. 62, the needle catheter 610 can deliver two retainers 612. In some methods of use, the needle catheter 610 can be moved to another location. The needle catheter 610 can deliver two additional retainers 612. In some methods of use, the needle catheter 610 can deliver four retainers 612. The needle catheter 610 can create the number of holes corresponding to the number of apertures 508 of the transvalvular bridge 500. In the illustrated embodiment, the needle catheter 610 can create four holes corresponding to the four apertures 508 of the transvalvular bridge 500. After the retainers 612 are deployed, four sutures 654 can span the annulus.

Figure 64C:
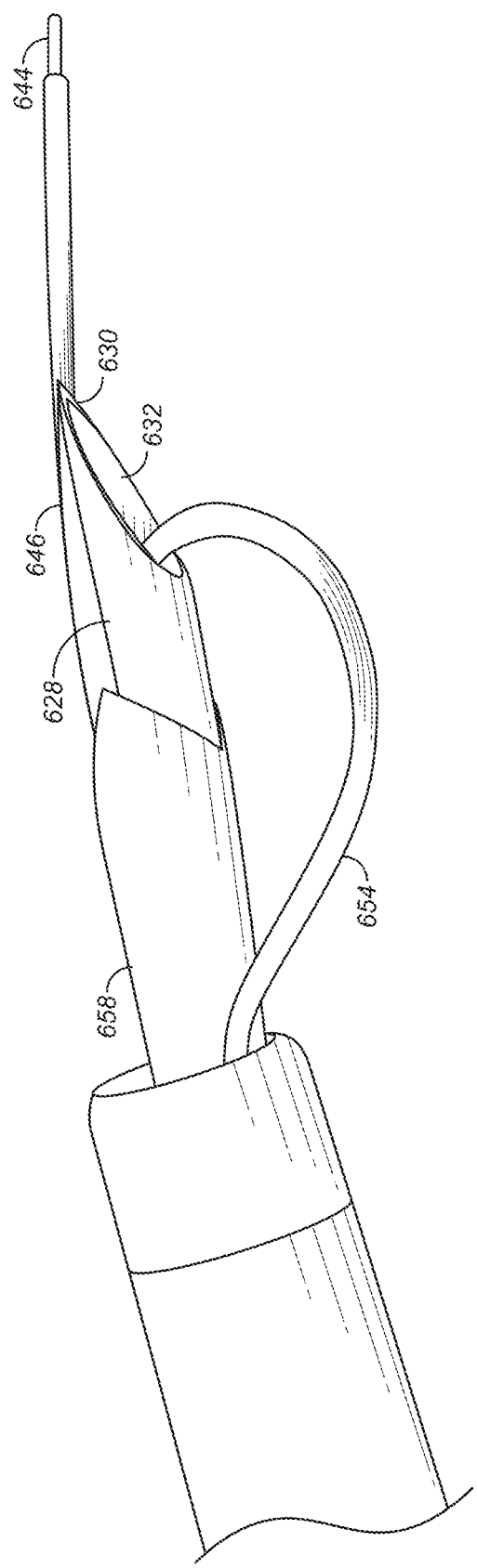
Figure 64D:
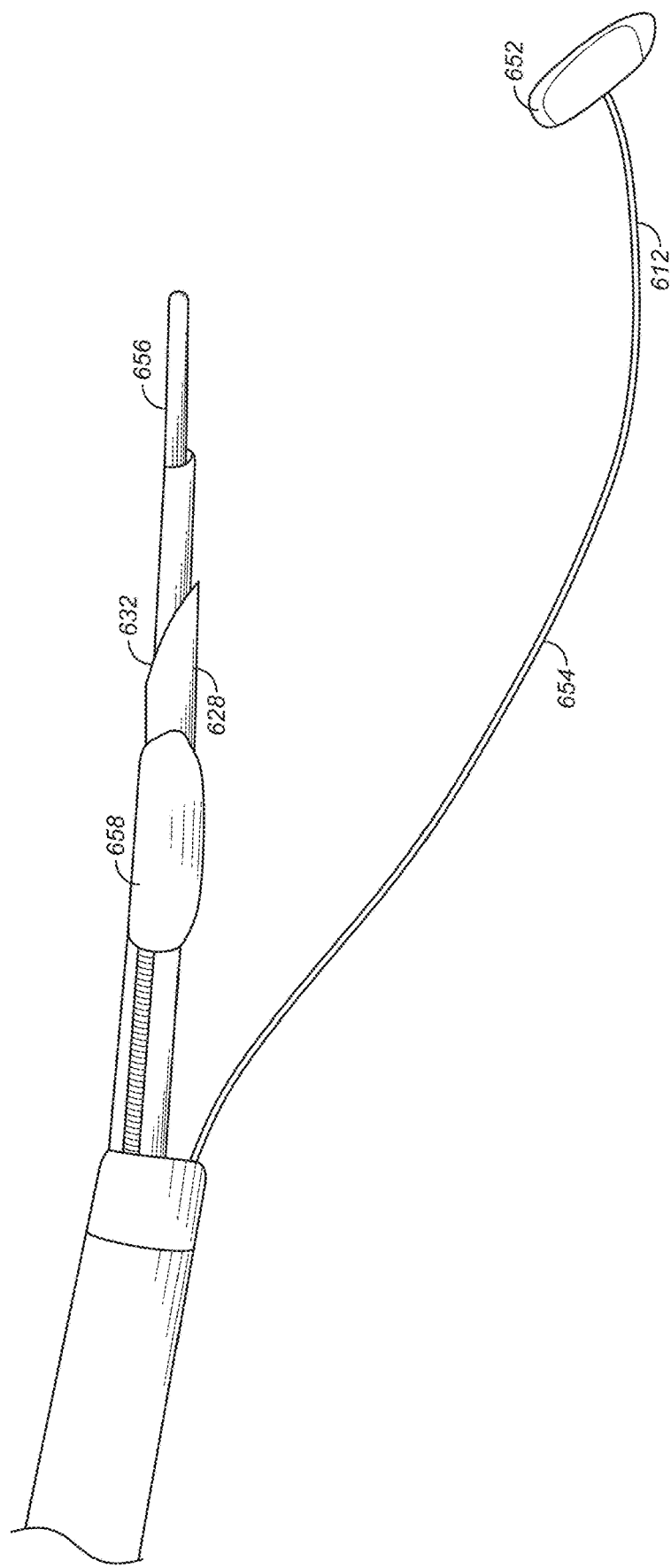
Figure 64E:
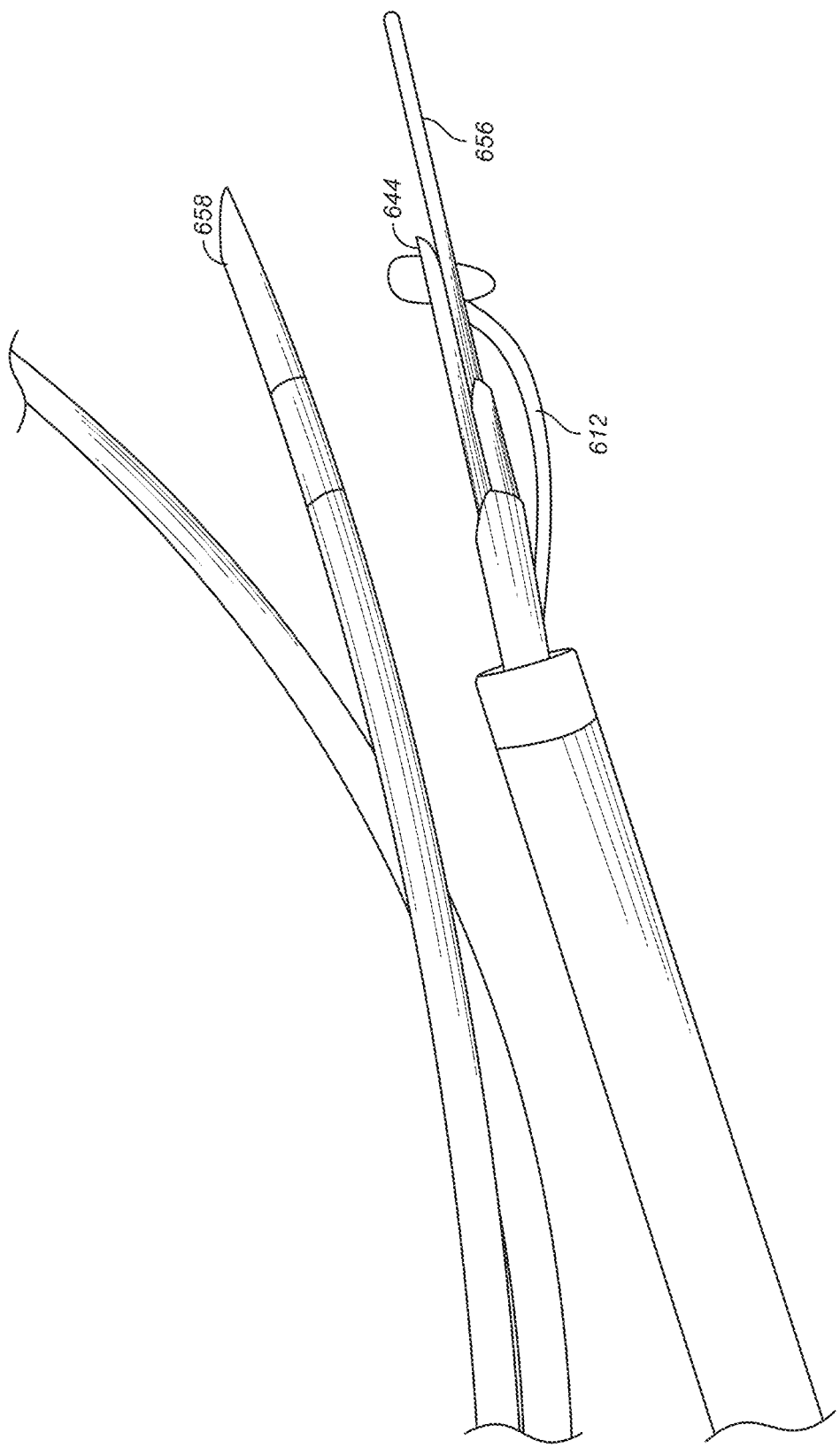

FIG. 64C-64E show a single needle catheter 658. The single needle catheter 658 can include any of the features of needle catheter 610. The single needle catheter 658 can include the needle 628. The needle 628 can include the sharpened tip 630. The needle 628 can include the lumen 632. The single needle catheter 658 can include the energy tip 644. The needle 628 can include the detent 646. Referring to FIG. 64D, the single needle catheter 658 can be designed to deliver the retainer 612. The single needle catheter 658 can deliver one retainer 612. The single needle catheter 658 can include the plunger 656. The plunger 656 can extend through the lumen 632 of the needle 628 to deploy the retainer 612. FIG. 64E shows various components decoupled.

Figure 65A:
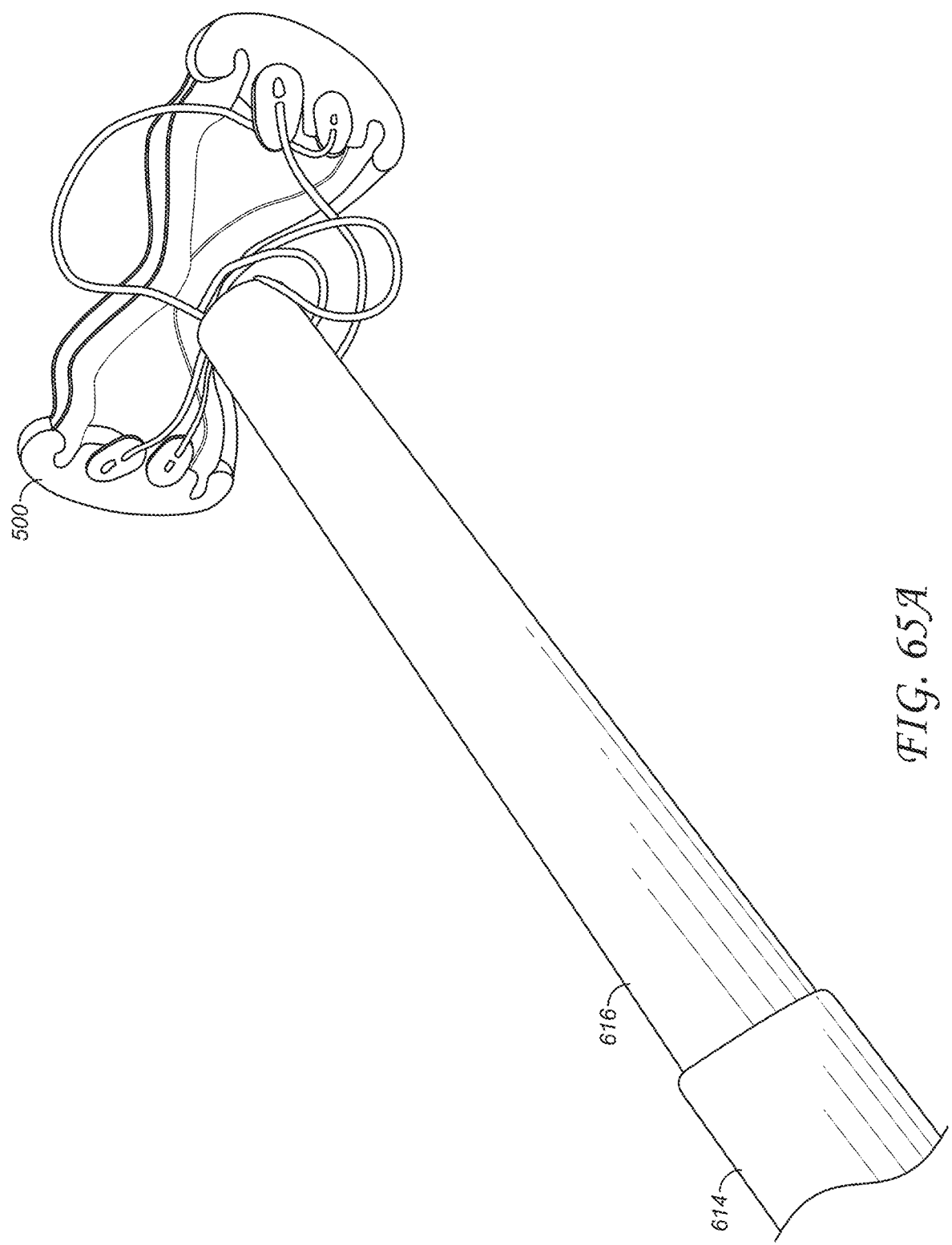
FIGS. 65A-65H are various perspective views of the delivery of a transvalvular bridge, according to some embodiments.

FIG. 65A-65G illustrate the deployment of the transvalvular bridge 500. The transvalvular bridge 500 can be deployed via the deployment catheter 614. In some embodiments, the transvalvular bridge 500 can include an asymmetric feature to wrap the transvalvular bridge 500 around with a sheath. The transvalvular bridge 500 can be cinched to reduce diameter. The transvalvular bridge 500 can be folded within the deployment catheter 614 such that an inner diameter of the deployment catheter 614 is available for passage of other devices. The output of crimping creates a capsule encompassing the transvalvular bridge 500. The transvalvular bridge 500 can be deployed with the use of the dilator 616. The transvalvular bridge 500 can be unsheathed from the deployment catheter 614. The transvalvular bridge 500 can be deployed such as by unrolling the transvalvular bridge 500. Referring to FIG. 65A, the dilator 616 can move the transvalvular bridge 500 toward the annulus. The dilator 616 can maintain the position of the one or more sutures 654 relative to the transvalvular bridge 500. The dilator 616 can function to allow for suture management. The dilator 616 can function to cinch the sutures 654. The dilator 616 can also function to cinch the transvalvular bridge 500.

Figure 65B:
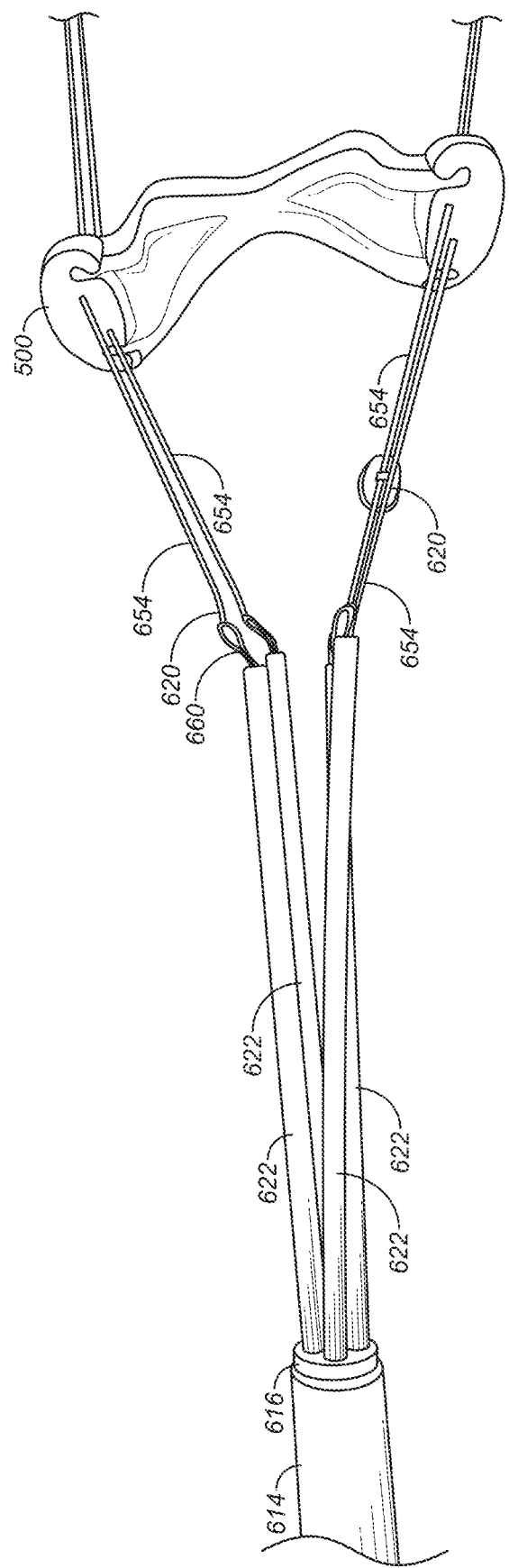

Referring to FIG. 65B, the deployment catheter 614 can be moved away from the transvalvular bridge 500. The dilator 616 can be partially withdrawn into the deployment catheter 614. The deployment catheter 614 can include a plurality of pushers 622. Each pusher 622 can include a lumen 660. In some embodiments, each retainer 612 can include a single suture 654. In some embodiments, each retainer 612 can include two or more sutures 654. Prior to delivery of the transvalvular bridge 500, each suture 654 can be passed through a lumen 660 of the pusher 622. The pusher 622 can extend along a length of the suture 654. The deployment catheter 614 can include the one or more pushers 622. In the illustrated embodiment, the dilator 616 can include four pushers 622 for the four sutures 654. The number of pushers 622 can correspond to the number of retainers 612 deployed. The number of pushers 622 can correspond to the number of sutures 654 deployed.

Figure 65C:
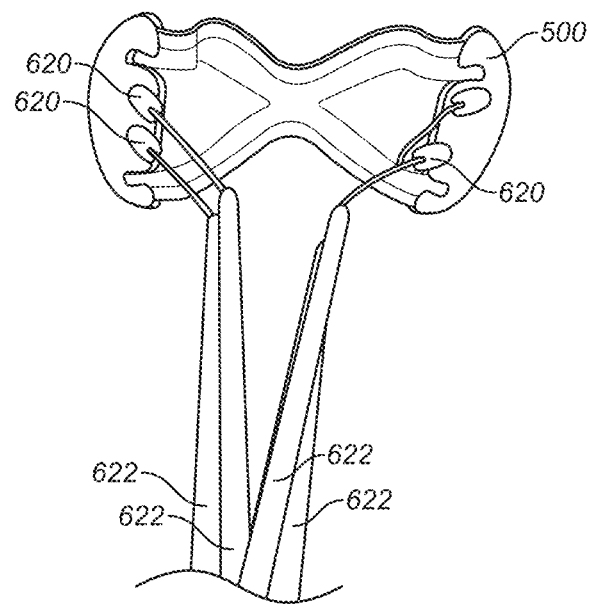
Figure 65D:
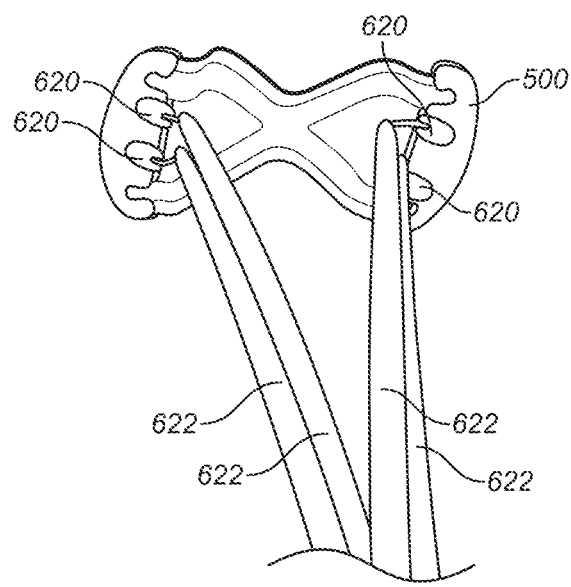

Referring to FIG. 65C, the pusher 622 can be moved toward the transvalvular bridge 500. In some methods of use, two or more pusher 622 can move simultaneously. In some methods of use, one or more pushers 622 are moved independently of another pusher 622. The one or more pushers 622 are moved toward the transvalvular bridge 500 as shown in FIG. 65D. The pusher 622 can be flexible to be deflected outward when moved toward the transvalvular bridge 500. The pusher 622 can follow the path of the suture 654 disposed within the lumen 660. As the pusher 622 is moved toward the transvalvular bridge 500, the suture 654 can be managed. The suture 654 can straighten. The suture 654 can be detangled. The pusher 622 can cinch the suture 654. The one or more pushers 622 can move the transvalvular bridge 500 into position. The one or more pushers 622 can move the transvalvular bridge 500 against the annulus. The one or more pushers 622 can move the transvalvular bridge 500 such that the apertures 508 align with holes created by the needle catheter 610. The one or more pushers 622 can move the transvalvular bridge 500 such that the apertures 508 align with P1, P3, A1, and A3 described herein.

In some embodiments, each suture 654 can include a single clip 620. Prior to delivery of the transvalvular bridge 500, each suture 654 can be passed through the clip 620. Prior to delivery of the transvalvular bridge 500, each suture 654 can be passed through the clip 620 prior to passing the suture 654 through the lumen 660 of the pusher 622. The clip 620 can be disposed on the suture 654. Referring back to FIGS. 65B and 65C, the clip 620 can be disposed between the transvalvular bridge 500 and the end of the pusher 622. The number of clips 620 can correspond to the number of sutures 654. In the illustrated embodiment, four clips 620 are deployed.

Figure 65E:
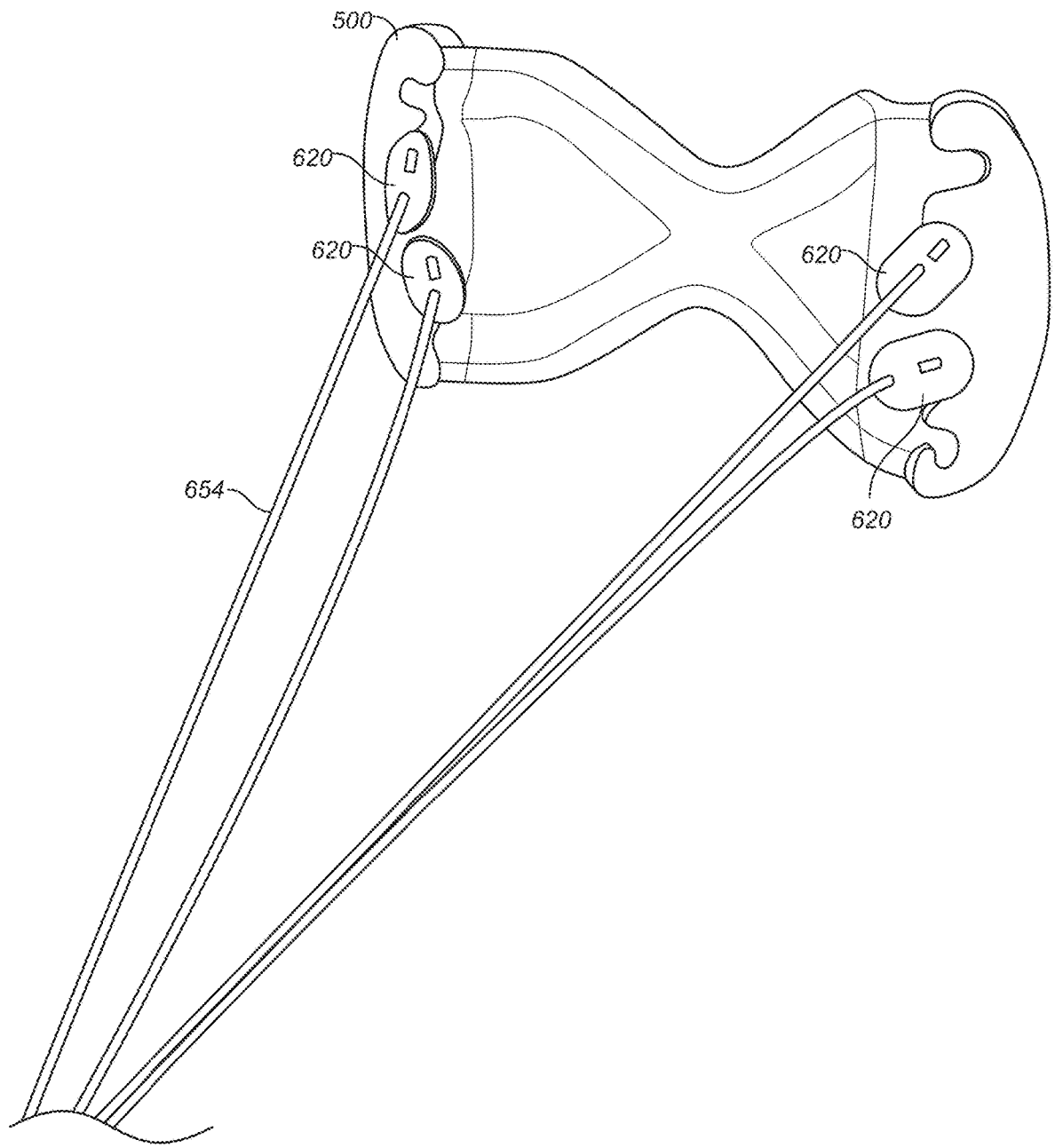

Referring to FIG. 65D, the pusher 622 can advance the clip 620. As the pusher 622 is advanced toward the transvalvular bridge 500, the clip 620 can be advanced toward the transvalvular bridge 500. The clip 620 can be located near a distal end of the pusher 622 as the pusher 622 is advanced. Referring to FIG. 65E, the clip 620 can be pushed against the transvalvular bridge 500. The pusher 622 can be withdrawn.

Figure 65F:
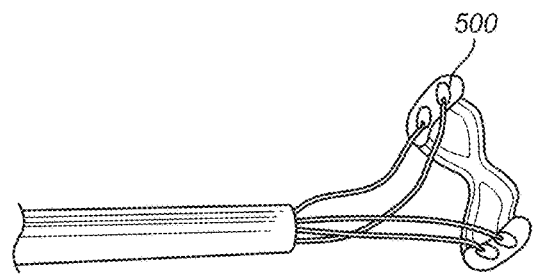
Figure 65G:
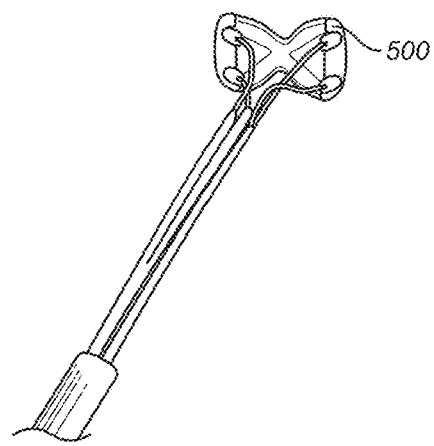
Figure 65H:
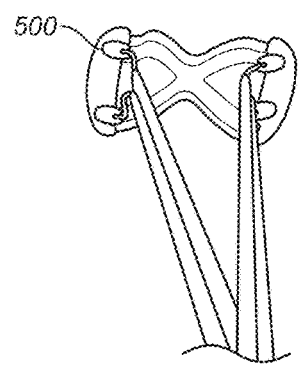

FIGS. 65F-65G show various other perspective views of deploying the transvalvular bridge 500.

Figure 66A:
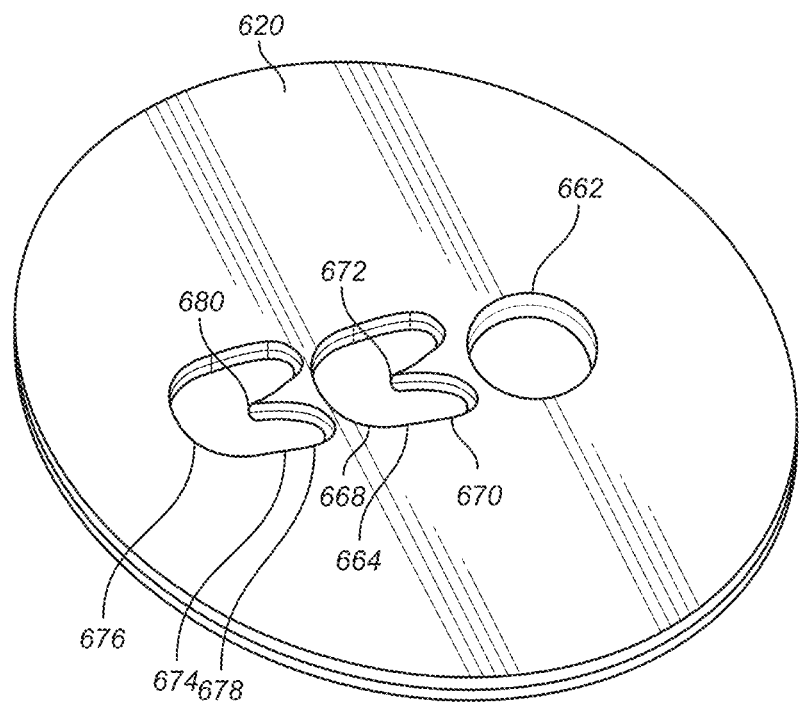
FIG. 66A is a front perspective view of a clip.
Figure 66B:
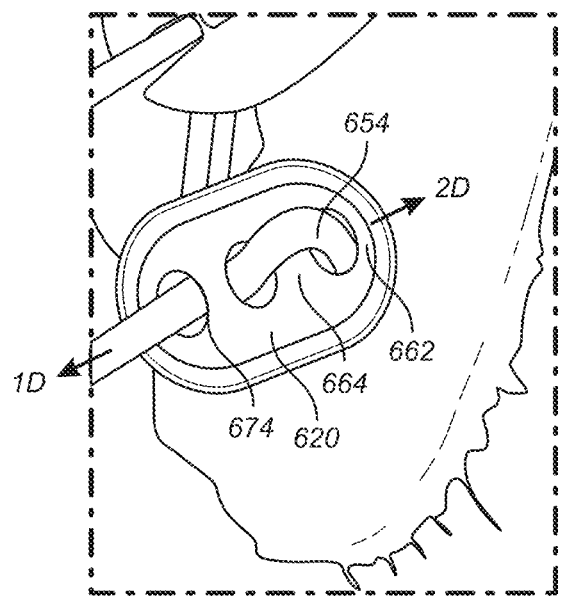
FIG. 66B is a front perspective view of the clip of FIG. 66A and a suture, according to some embodiments.

FIGS. 66A and 66B illustrates the clip 620. The clip 620 can include any cross-sectional shape including circular, oval, elliptical or other rounded configuration. The round edges may reduce trauma to the surrounding tissue. Other cross-sectional shapes are contemplated include triangular, square, rectangular, or other polygonal shape. The clip 620 can include a first aperture 662. The first aperture 662 can be circular, oval, elliptical or other rounded configuration.

The clip 620 can include a second aperture 664. The second aperture 664 can include a rounded portion 668. The rounded portion 668 can be semi-circular, semi-oval, semi-elliptical or other rounded configuration. The rounded portion 668 can be approximately half of a circle. The rounded portion 668 can be approximately half of the second aperture 664. The second aperture 664 can include a catch portion 670. The catch portion 670 can include a protrusion 672. The protrusion 672 can extend inward from the second aperture 664. The protrusion 672 can be any cross-sectional shape such as triangular, square, rectangular, or other polygonal shape. In the illustrated embodiment, the protrusion 672 is triangular. The catch portion 670 can be approximately half of the second aperture 664.

The clip 620 can include a third aperture 674. The third aperture 674 can include a rounded portion 676. The rounded portion 676 can be semi-circular, semi-oval, semi-elliptical or other rounded configuration. The rounded portion 676 can be approximately half of a circle. The rounded portion 676 can be approximately half of the third aperture 674. The third aperture 674 can include a catch portion 678. The catch portion 678 can include a protrusion 680. The protrusion 680 can extend inward from the third aperture 674. The protrusion 680 can be any cross-sectional shape such as triangular, square, rectangular, or other polygonal shape. In the illustrated embodiment, the protrusion 680 is triangular. The catch portion 678 can be approximately half of the third aperture 674. The second aperture 664 and the third aperture 674 can be similar. The second aperture 664 and the third aperture 674 can be identical. The second aperture 664 and the third aperture 674 can be oriented such that the protrusion 672 of the second aperture 664 is coaxial with the protrusion 680 of the third aperture 674.

Referring to FIG. 66B, the suture 654 can be passed through the first aperture 662, the second aperture 664, and the third aperture 674. The suture 654 can be passed through the first aperture 662, the second aperture 664, and the third aperture 674 sequentially. The suture 654 can be passed through the first aperture 662, then through the second aperture 664, and then through the third aperture 674. The suture 654 can pass over the clip 620 between the first aperture 662 and the second aperture 664. The suture 654 can pass under the clip 620 between the second aperture 664 and the third aperture 674.

The suture 654 can be passed through the clip 620 in a first direction 1D. The suture 654 slides through the first aperture 662. The suture 654 slides through the rounded portion 668 of the second aperture 664. The suture 654 slides through the rounded portion 676 of the third aperture 674. The first direction can move the clip 620 toward the transvalvular bridge 500.

The suture 654 can be limited or prevented from passing through the clip 620 in a second direction 2D. As the suture 654 is pulled in the second direction, the protrusion 672 of the second aperture 664 can embed within the suture 654. As the suture 654 is pulled in the second direction, the protrusion 680 of the third aperture 674 can embed within the suture 654. The second direction can move the clip 620 away from the transvalvular bridge 500.

The clip 620 can be a one direction push and lock device. The clip 620 can allow travel of the suture 654 through the clip 620 in the first direction. The clip 620 can limit travel of the suture 654 through the clip 620 in the second, opposite direction. The clip 620 can be manufacture from a rigid material such as a metal. In the illustrated embodiment, the clip 620 comprises 316 stainless steel. The clip 620 can have a high tensile force. The clip 620 can break above the suture strength. The clip 620 can fit within the deployment catheter 614.

Figure 67A:
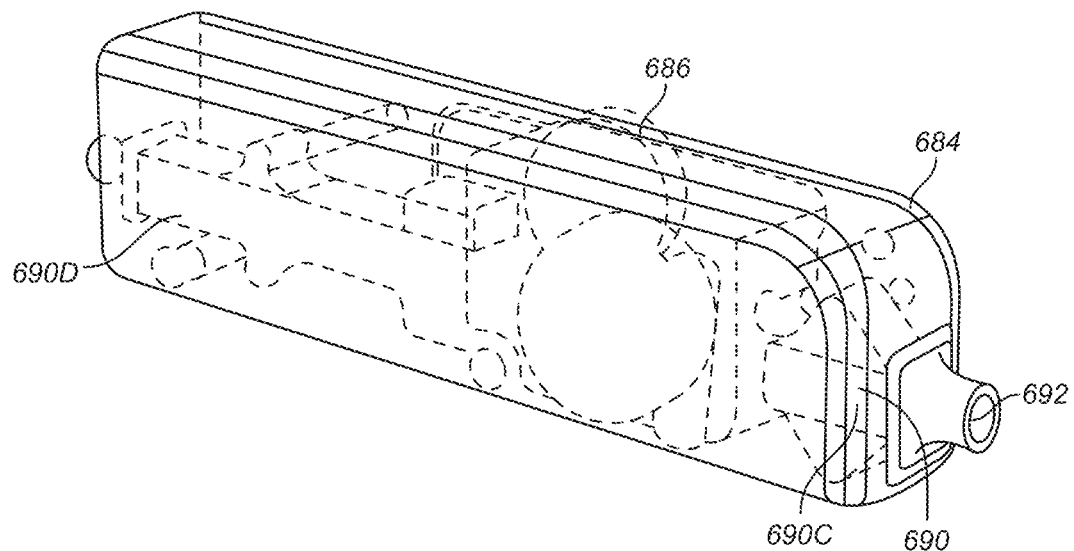
FIG. 67A is a side perspective view of a handle, according to some embodiments.
Figure 67B:
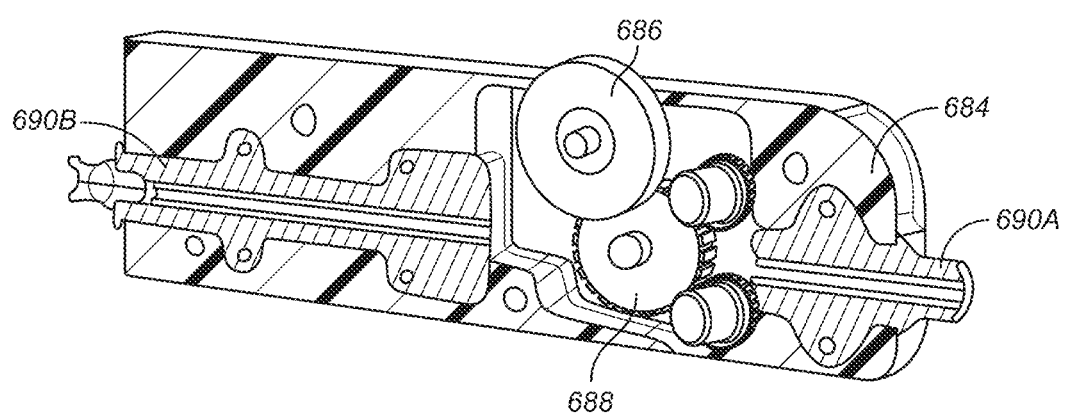
FIG. 67B is a cross-sectional perspective view of the handle of FIG. 67A.

FIGS. 67A and 67B illustrate a handle 684. The handle 684 can be any shape to facilitate grip by the user. The handle 684 can be designed to fit within the hand of the user. The handle 684 can be designed for use by the right hand, the left hand, or either the left hand or the right hand of the user. The handle 684 includes a wheel 686. The wheel 686 can be actuated by a finger of the hand of the user. The wheel 686 can be actuated by the thumb. As the wheel 686 is turned, the wheel 686 can actuate one or more gears 688 within the handle 684. The gears 688 can cause an action such as the twisting or turning motion of a catheter attached thereto.

Referring to FIG. 67B, the handle 684 can include an insert 690. The insert 690 can couple to the handle 684. The insert 690 can couple to a catheter. In some embodiments, the handle 684 can accept two or more inserts. In some embodiments, the handle 684 can be designed to couple to two or more catheters. Each catheter described herein can be designed to couple with an insert. The handle 684 can be considered a universal handle. The handle 684 can couple to each catheter described herein.

Referring to FIG. 67B, the handle 684 is shown in cross-section. The insert 690 can include multiple pieces 690A, 690B, 690C, 690D. The piece 690A can have a mirror image piece 690C. The piece 690B can have a mirror image piece 690D. The insert 690 can include a lumen 692. The lumen 692 can be formed from the piece 690A and the corresponding mirror image piece 690C. The lumen 692 can be formed from the piece 690B and the corresponding mirror image piece 690D. The lumen 692 can be sized to accept a catheter therewithin.

Figure 68A:
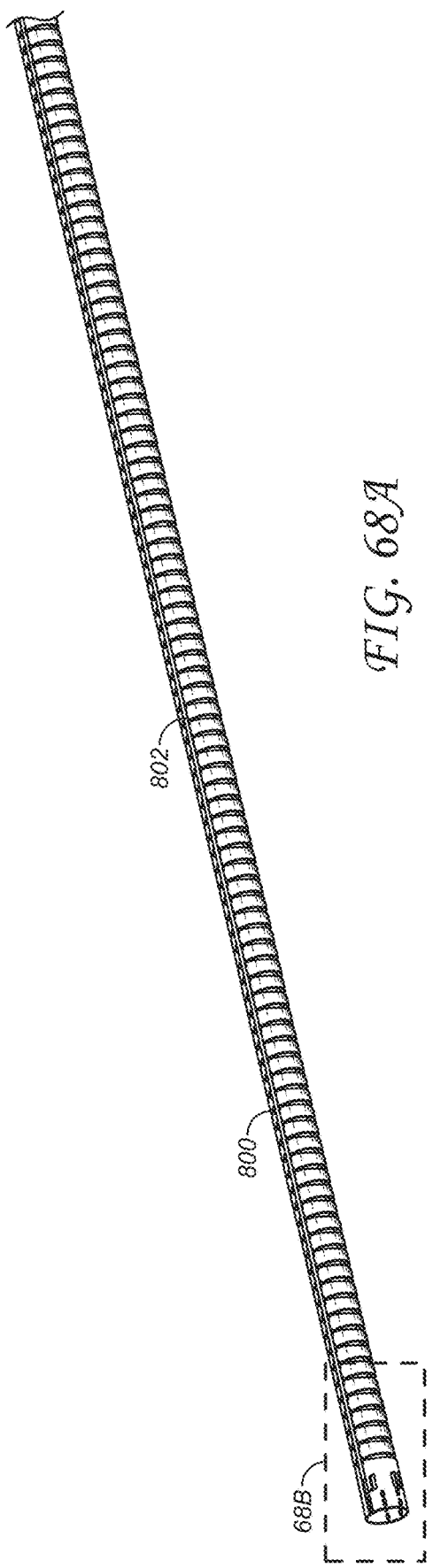
FIGS. 68A-68B are side perspective views of a steerable catheter, according to some embodiments.
Figure 68B:
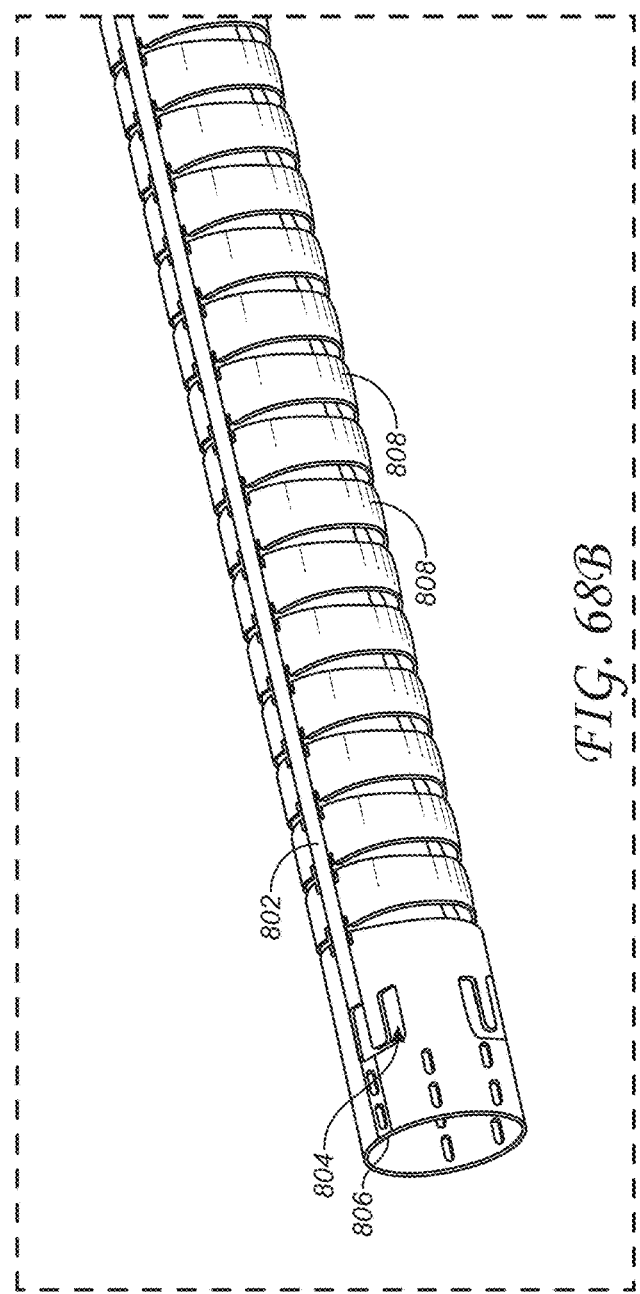

FIGS. 68A and 68B illustrate a steerable catheter 800. The steerable catheter 800 can be used with the handle 684. The steerable catheter 800 can be bi-direction. The steerable catheter 800 can move in at least two directions. The steerable catheter 800 can include a steering wire 802. In the illustrated embodiment, the steerable catheter 800 includes two steering wires 802. The steering wires 802 can be disposed 180 degrees from each other. The steering wire 802 can allow the steerable catheter 800 to collapse along steering wire 802. The steering wire 802 can cause the tip to flex or turn. The steerable catheter 800 can turn in two directions due to the two steering wires 802. Each steering wire 802 can include a steering wire attachment 804. The steering wire attachment 804 can couple the steering wire 802 to the steerable catheter 800. The steerable catheter 800 can include a distal end 806. The distal end 806 can be considered steerable. The user can actuate the steering wire 802 to cause the distal end 806 to turn.

The steerable catheter 800 can include a dog bone pattern. The steerable catheter 800 can include a plurality of ribs 808. The rib 808 can include two ends and a narrower middle section disposed therebetween. The ribs 808 can enable the steerable catheter 800 to flex. As the steerable catheter 800 is flexed, the space between adjacent ribs 808 becomes smaller. In some embodiments, the narrower middle section of two adjacent ribs 808 can touch. The design of the ribs 808 can impact the ability of the steerable catheter 800 to flex or rotate. The design of the ribs 808 can impact the radius of curvature of the steerable catheter 800.

Figure 68C:
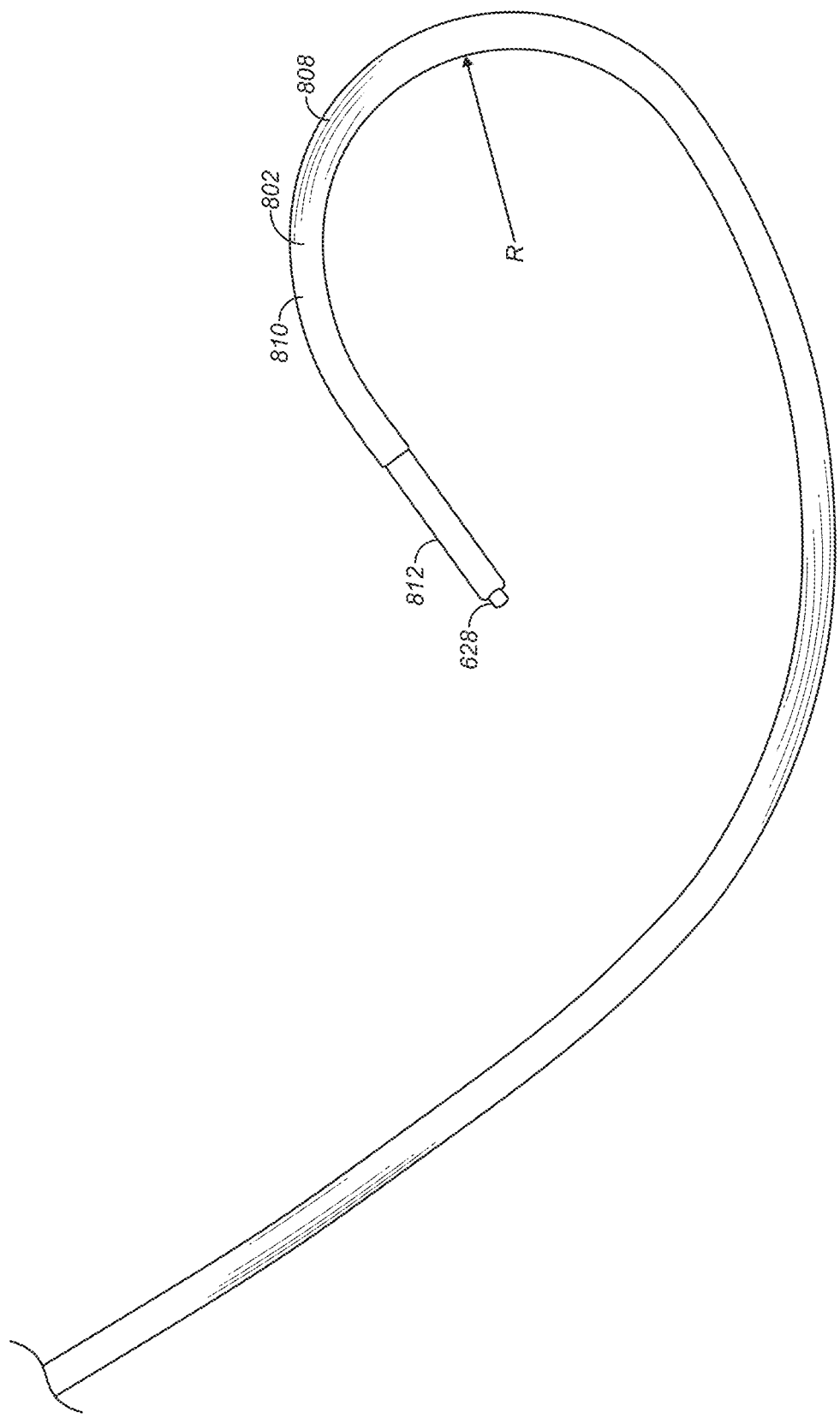
FIGS. 68C-68D are side perspective views of a steerable needle catheter.
Figure 68D:
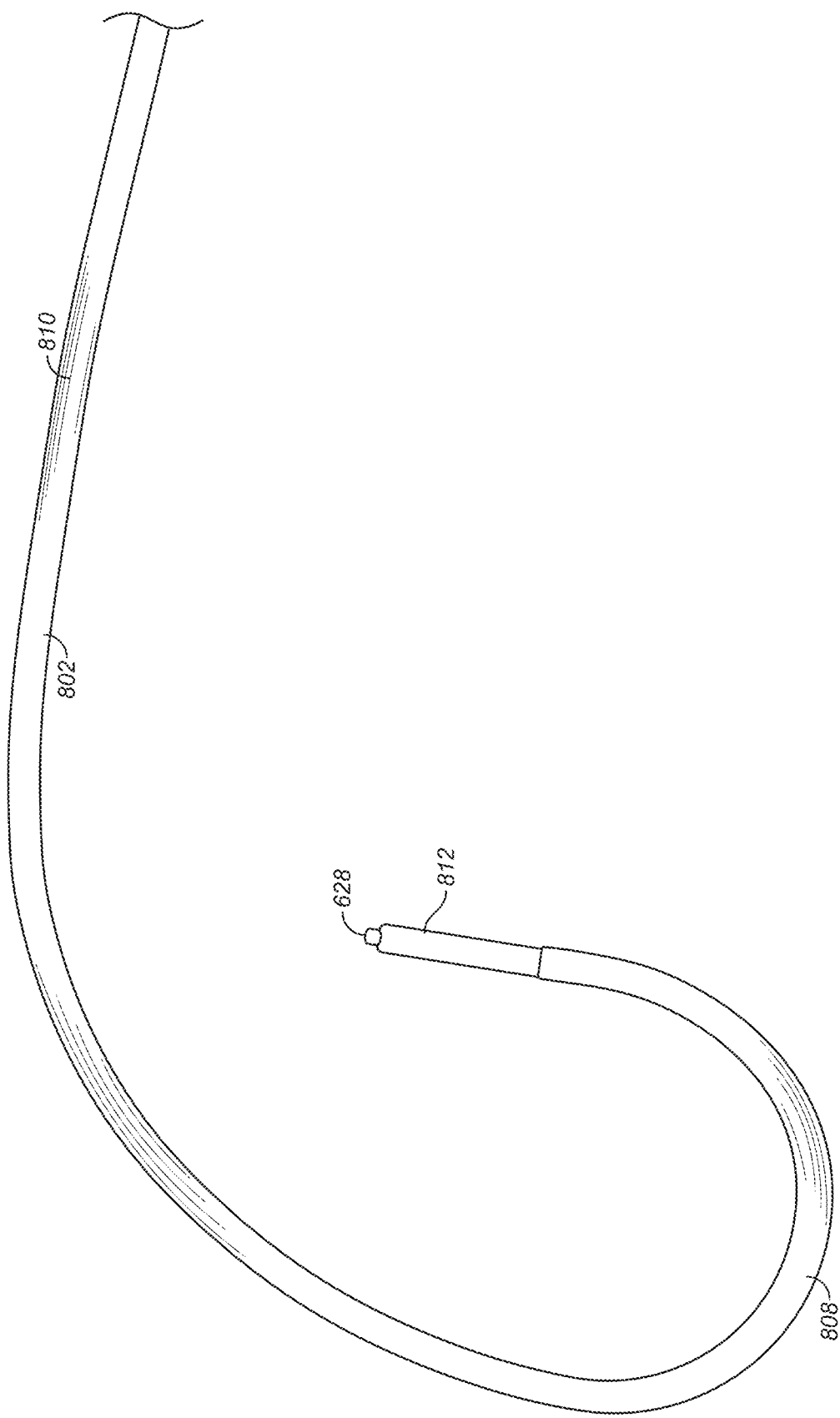

FIGS. 68C and 68D depict a steerable needle catheter 810. Any of the catheters described herein can include one or more features of the steerable catheter 800. The steerable needle catheter 810 can be bi-direction. The steerable needle catheter 810 can move in at least two directions. The steerable needle catheter 810 can include the steering wire 802. The steering wire 802 can allow the steerable needle catheter 810 to collapse along steering wire 802. The steering wire 802 can cause the tip to flex or turn. The steering wire 802 can be coupled to the steerable needle catheter 810. The steerable needle catheter 810 can include a dog bone pattern. The steerable needle catheter 810 can include a plurality of ribs 808.

Figure 68E:
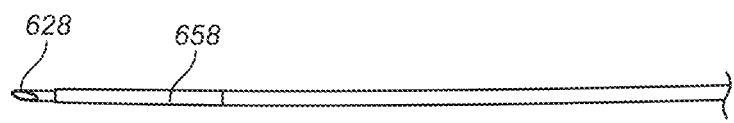
FIG. 68E is a perspective view of a needle catheter.

The steerable needle catheter 810 can include a radius of curvature R. In some embodiments, the steerable needle catheter 810 can allow the steerable needle catheter 810 to turn up to 180 degrees from the direction of travel. In some embodiments, the steerable needle catheter 810 can turn up to ninety degrees from the direction of travel. The ribs 808 can occur along a portion of the length of the steerable needle catheter 810. The ribs 808 can allow the portion of the steerable needle catheter 810 to curve. The steerable needle catheter 810 can be bi-directional. The steerable needle catheter 810 can include the single needle catheter 658 as described herein. The needle 628 can protrude from the sheath 812. The needle 628 can be sharpened. The needle 628 can be collinear with the steerable needle catheter 810. The energy tip 644 can be collinear with the steerable needle catheter 810. The steerable needle catheter 810 can facilitate immediate deployment. The single needle catheter 658 with the needle 628 is shown in FIG. 68E.

Figure 69A:
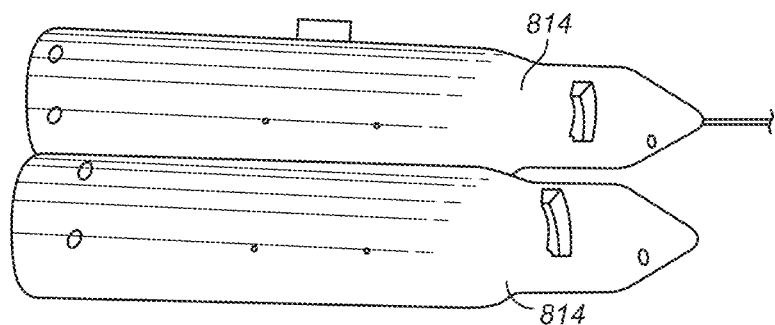
FIG. 69A-69B are perspective views of a handle, according to some embodiments.
Figure 69B:
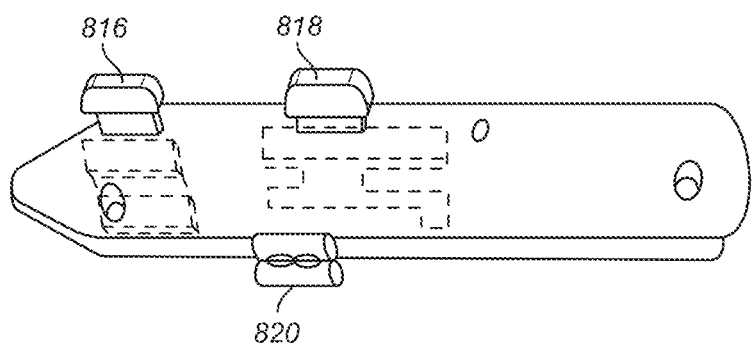

FIGS. 69A and 69B illustrate embodiments of a handle 814. The handle 814 can be designed to interact with any catheter described herein. The handle 814 can be designed to interact with the steerable needle catheter 810. The handle 814 can be any shape to facilitate grip by the user. The handle 814 can be designed to fit within the hand of the user. The handle 814 can be designed for use by the right hand, the left hand, or either the left hand or the right hand of the user.

The handle 814 can allow one or more functions. The handle 814 can include a user interface 816 to control the sheath 812. The sheath 812 can cover any of the catheters described herein. The sheath 812 can cover the needle 628. The handle 810 can include a user interface 818 to deploy. The user interface 818 can deploy any catheter or any catheter component described herein. In some embodiments, the user interface 818 can apply a force for the needle 628 to puncture the annulus. In some embodiments, the user interface 818 can apply a force for the energy tip 644 to apply energy to the annulus. The handle 818 can include a user interface 820 to articulate. The user interface 820 can articulate any catheter or any catheter component described herein. The user interface 820 can articulate the steerable needle catheter 810. The user interface 820 can cause the steerable needle catheter 810 to turn. Each of the user interfaces 816, 818, 820 can be a button, slide, wheel, or other device to enable movement as described herein. Each of the user interfaces 816, 818, 820 can be the same as or similar to another user interface. In the illustrated embodiment, the user interfaces 816, 818, 820 are slides. The handle 814 can be durable and ergonomic.

Figure 70:
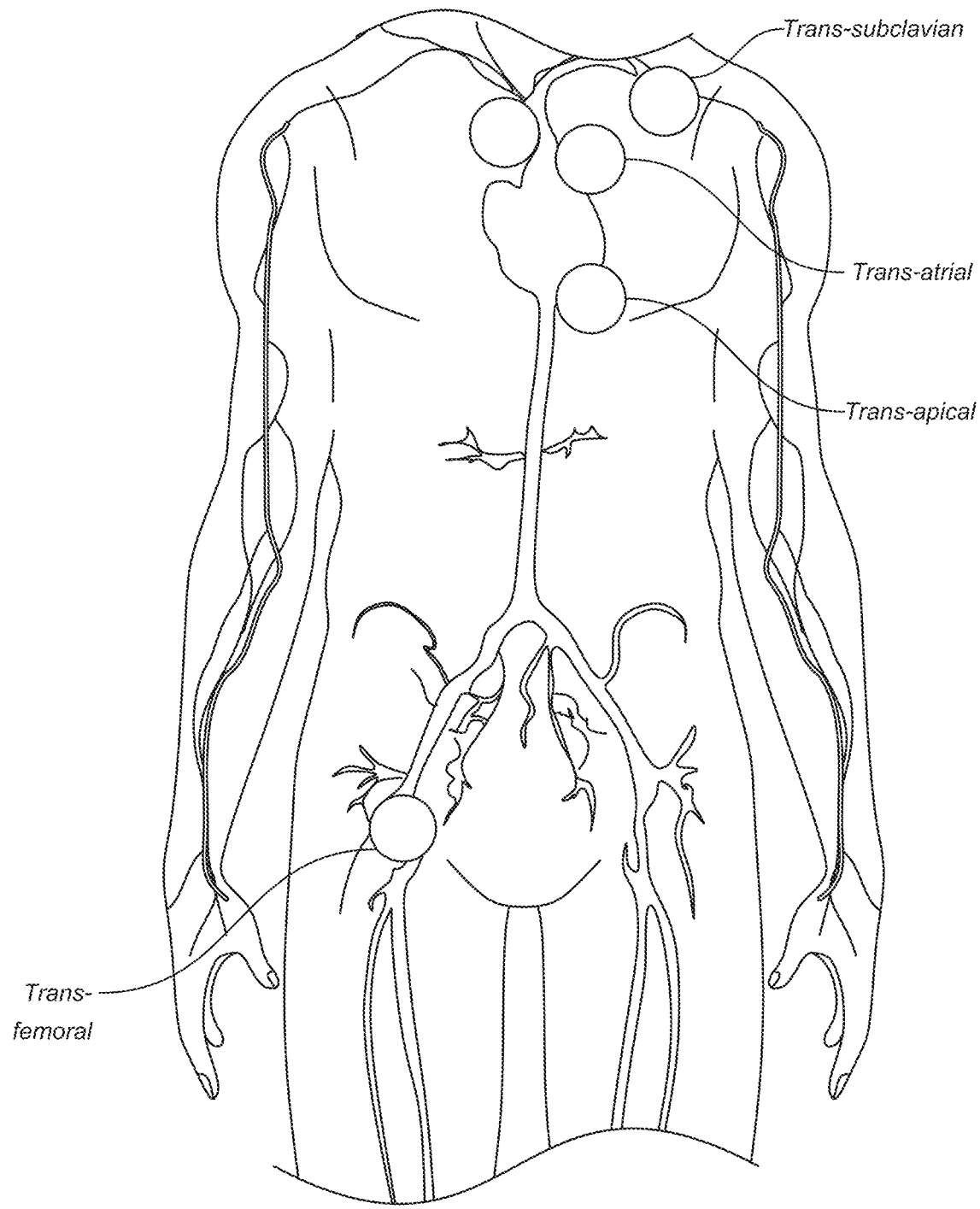
FIG. 70 is a simplified view of various access locations, according to some embodiments.

FIG. 70 shows various access locations. The systems and methods described herein can be used for any access location. The procedure approach and delivery system can be trans-femoral, trans-femoral and trans-apical, trans-apical, trans-apical and trans-atrial, trans-atrial, trans-subclavian, trans-subclavian and trans-apical, or any other approach known in the art.

Advantages can include any of the following. The systems and methods described herein can replicate open procedures. The systems and methods described herein can replicate open procedures related to the placement of the transvalvular bridge 500. The systems and methods described herein can replicate open procedures end-securement. The systems and methods described herein can guarantee suture placement. The systems and methods described herein can show the user, such as a surgeon, the suture count prior to first knot. The systems and methods described herein can provide positional identification of the sutures by valve nomenclature. The systems and methods described herein can be used with the devices described herein. The systems and methods described herein can be used with the transvalvular bridge 500. The systems and methods described herein can be conducted on a beating heart. The systems and methods described herein can be echogenic. The systems and methods described herein can prevent or limit occlusions. The systems and methods described herein can prevent or limit leaflet damage. The systems and methods described herein can prevent or limit chordae damage. The systems and methods described herein can allow for complete bail out until first suture is knotted. The systems and methods described herein can allow for complete identification and count of all catheter delivery components. The systems and methods described herein can allow for complete identification and count of all suture tail cuts. The systems and methods described herein can allow for hydraulic or compressed air delivery of the one or more needle 628. The systems and methods described herein can include a flexible pressure vessel and needles. The systems and methods described herein can include a flexible deployment of retaining system. The systems and methods described herein can allow for percutaneous securement by knot or ferrule locking device. The systems and methods described herein can allow for trans-apical and trans-septal hybrid delivery. The systems and methods described herein can allow for trans-septal and trans-aortic hybrid delivery.

The systems and methods described herein can have simple designs. One or more of the needle catheter 610, the deployment catheter 614, and the trimming catheter 624 can have a simple design. One or more of the needle catheter 610, the deployment catheter 614, and the trimming catheter 624 can include a single lumen. One or more of the needle catheter 610, the deployment catheter 614, and the trimming catheter 624 can include embedded catheter features. The needle catheter 610 can include a built in plunger 656. The deployment catheter 614 can include a built in pusher 622.

The method can include the step of inserting a sub-annular retainer 612. The method can include the step of inserting the energy tip 644 through the tissue of the heart. In some methods of use, the energy tip 644 is inserted through the annulus. In some methods of use, the energy tip 644 is inserted through the anterior leaflet. In some methods of use, the energy tip 644 is inserted through the posterior leaflet. The method can include the step of holding the energy tip 644 in position. The method can include the step of guiding the energy tip. The method can include the step of following the energy tip 644 with the needle catheter 610. The method can include the step of intraluminal deployment of the pledget 652. The pledget 652 can be coupled to the suture 654. The method can include the step of cinching the suture 654.

The method can include the step of positioning the mitral device. The mitral device can be any device described herein. In some methods of use, the method can include the step of positioning transvalvular bridge 500. The method can include the step of sliding the transvalvular bridge 500 out of the deployment catheter 614. The deployment catheter 614 can be a single lumen catheter. The method can include the step of parachuting the transvalvular bridge 500 down with the dilator 616. The method can include the step of moving the transvalvular bridge 500 toward the annulus. The method can include the step of cinching the suture 654.

The method can include the step of securely clipping the mitral device. The method can include the step of deploying the clip 620. The method can include the step of moving the clip 620 with a pusher 622. The method can include the step of securing the clip 620. The clip 620 can be a self-locking clip. The method can include the step of trimming the suture 654.

Figure 71:
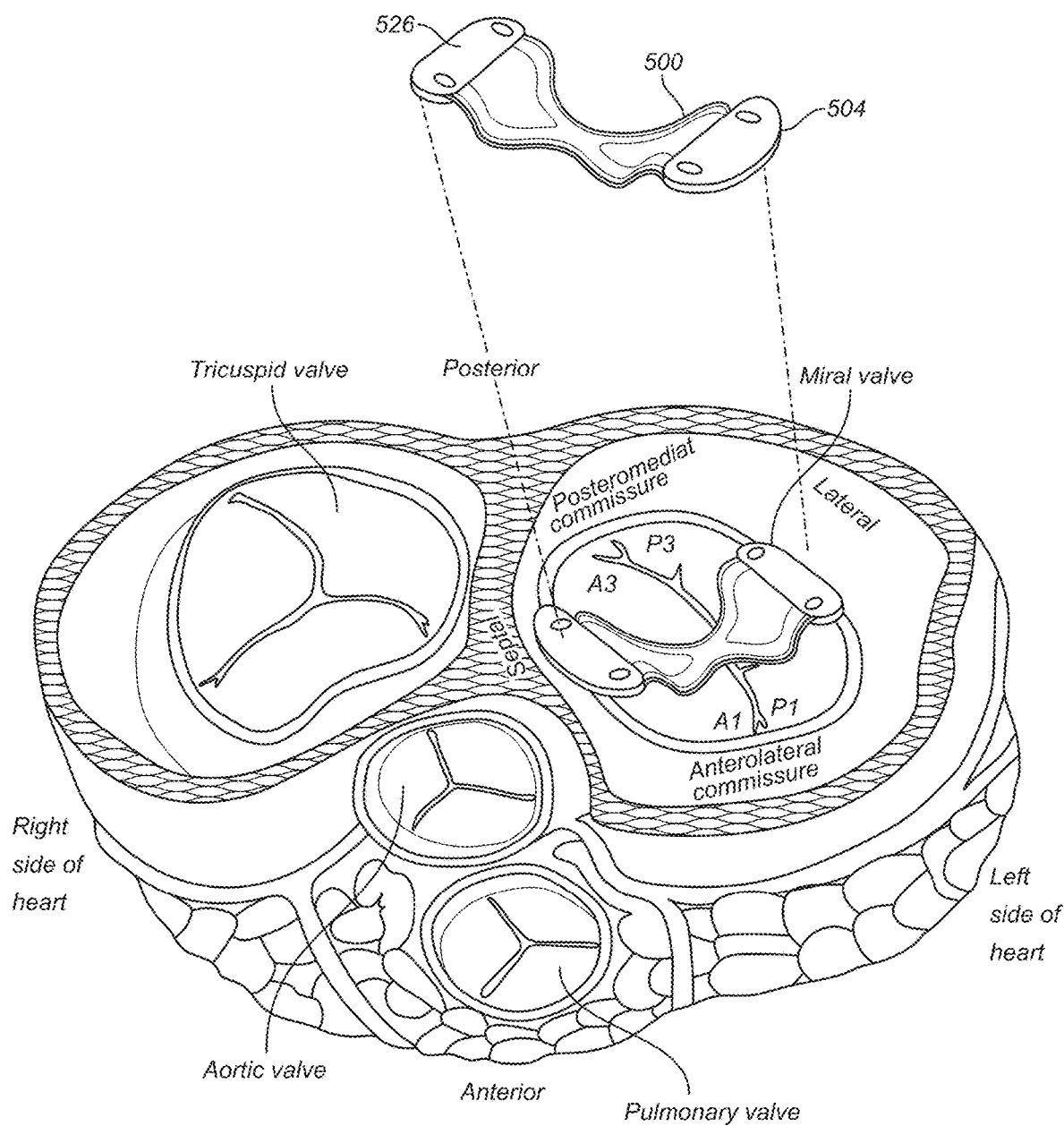
FIGS. 71-73 are simplified views of the heart and the location of the transvalvular band, according to some embodiments.
Figure 73:
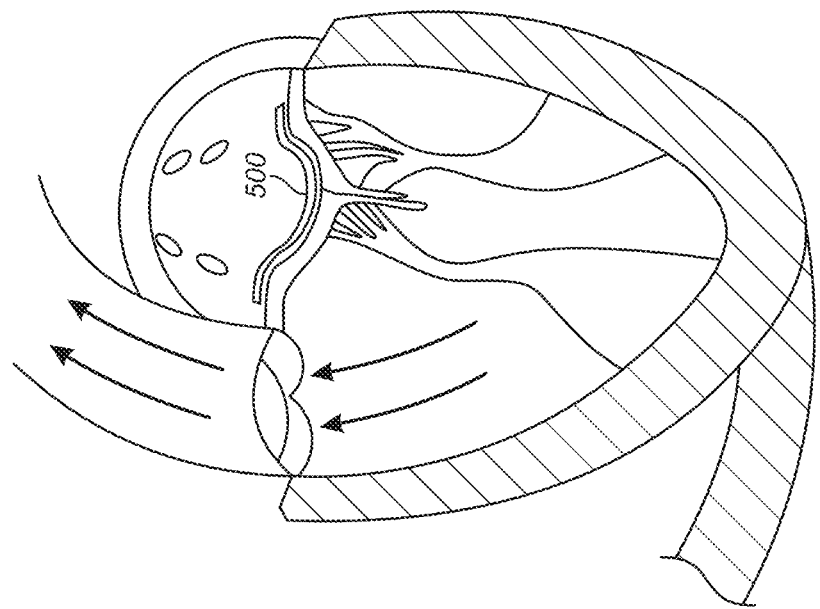
Figure 72:
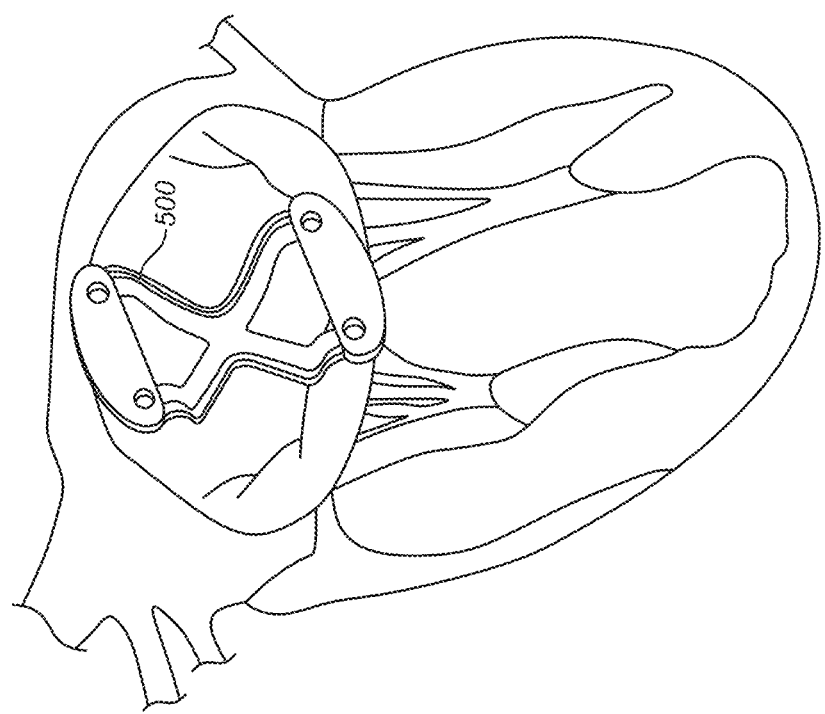
Figure 74:
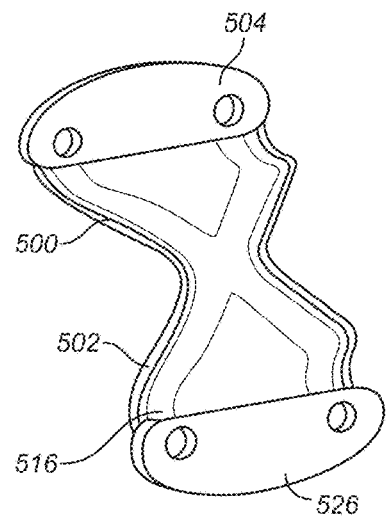
FIGS. 74-76 are views of the transvalvular band, according to some embodiments.
Figure 75:
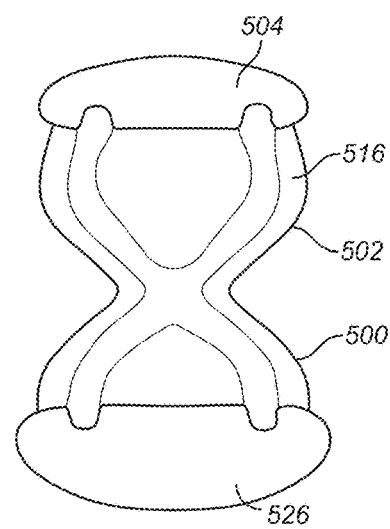
Figure 76:
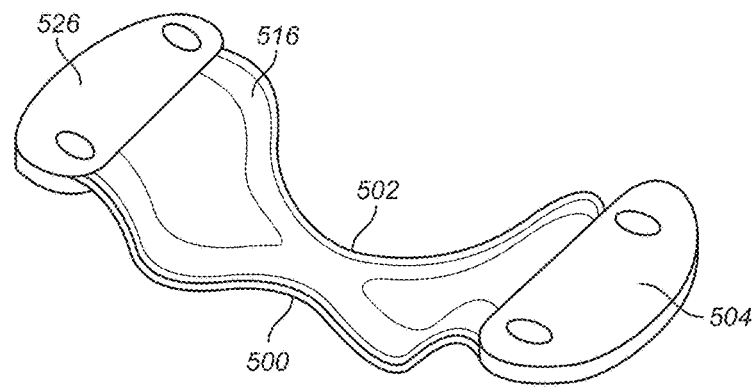

FIGS. 71-73 illustrates the transvalvular bridge 500 positioned within the heart. The transvalvular bridge 500 can include the first attachment structure 504 at a first end of the bridge 500 and the second attachment structure 526 at a second end of the bridge 500. The transvalvular band 500 serves both surgical and interventional markets. The same transvalvular band 500 can be used for both markets. The design of the transvalvular band 500 is shown in FIGS. 74-76. Systems and methods including tools and transcatheter systems are shown in FIGS. 77-96.

Mitral Regurgitation (MR) occurs when one of the four valves in the heart, the mitral valve, does not close properly, allowing blood to leak backwards. Mitral Regurgitation is the most common form of valvular heart disease. There are two types of Mitral Regurgitation: Functional Mitral Regurgitation (FMR) and Degenerative Mitral Regurgitation (DMR). The transvalvular bridge 500 can be used for Functional Mitral Regurgitation (FMR). The transvalvular bridge 500 can be used for Degenerative Mitral Regurgitation (DMR). Mitral Regurgitation may lead to shortness of breath and eventually heart failure. Mitral Regurgitation affects about 5% of the US population. Some estimates suggest 2.8M people suffer from Mitral Regurgitation in the US. Approximately 80,000 mitral valve surgeries are performed per year. Some estimates suggest that 41% are in need of intervention. Some estimates suggest that 41% are in need of intervention, either due to Functional Mitral Regurgitation (FMR) or Degenerative Mitral Regurgitation (DMR). Some estimates suggest a 5% conversion to percutaneous treatment for Mitral Regurgitation. There may be a need for a less invasive technology.

For annuloplasty rings, the procedure can be invasive, requiring open heart surgery. The procedure may require cardiopulmonary bypass. The procedure may require anticoagulants. There are disadvantages or limitations to current devices and procedures. The annuloplasty ring may not be optimal for anatomy. The annuloplasty ring flattens the annulus from a natural saddle shape. The annuloplasty ring may affect outcome. The limitations include that the procedure, and subsequent outcome, can be surgeon technique dependent.

For clips, a guide catheter is inserted through the femoral vein at the groin and is guided into the mitral valve. The clip delivery system delivers and deploys the implant. The clip holds and fastens the leaflets of the valve together. In this procedure, usually two clips are delivered. There are disadvantages or limitations to current devices and procedures. The large size of the catheter can be problematic. The entire length procedure is technically demanding. The long-term durability of the results of the device is unknown. The device cannot be used in patients with severe pathology of the mitral valve.

The transvalvular band 500 can overcome limitations of other devices. The transvalvular band 500 can be optimal for the anatomy. The transvalvular band 500 does not flatten the annulus in some embodiments, but rather conforms to the natural saddle shape. The transvalvular band 500 is not surgeon technique dependent in some cases. The shape of the transvalvular band 500 can be determined prior to surgery, for instance by selecting the transvalvular band 500 from a plurality of bands. In some methods of use, the transvalvular band 500 can be implanted in an open procedure. In some methods of use, the transvalvular band 500 can be implanted in a minimally invasive procedure. In some methods of use, the transvalvular band 500 can be implemented without cardiopulmonary bypass. In some methods of use, the transvalvular band 500 can be implemented without anticoagulants. In some methods of use, the transvalvular band 500 can be implemented with a plurality of anchor locations. In some methods of use, the transvalvular band 500 can be implemented with four anchor locations. In some methods of use, the transvalvular band 500 can be implemented with a plurality of spaced apart anchor locations. In some methods of use, the transvalvular band 500 can be implemented with a small, reduced diameter catheter system. In some methods of use, the transvalvular band 500 can be implemented with a short, non-technically demanding procedure. In some methods of use, the transvalvular band 500 can have long-term durability. In some methods of use, the transvalvular band 500 can be implemented in patients with severe pathology of the mitral valve. In some methods of use, the transvalvular band 500 implantation is simple and effective. In some methods of use, the transvalvular band 500 implantation is an alternative to annuloplasty in mitral valve repair.

The transvalvular band 500 can be a unique technology developed for the treatment of mitral valve regurgitation. The transvalvular band 500 in some cases can be configured to act as a transannular bridge in the septolateral dimension. The transvalvular band 500 can be configured to reduce annular dimensions back to normal and physiological needs. The unique design of the transvalvular band 500 in some embodiments allows it to be used in either a surgical (open-sternotomy or MIS) or transcatheter approach.

FIG. 71 illustrates the location of a transvalvular band 500 implanted in the heart. The transvalvular band 500 is positioned to span the mitral valve. FIG. 72 illustrates the transvalvular band 500 in the septolateral dimension. FIG. 73 illustrates the transvalvular band 500 illustrates another view of the position of the transvalvular band 500. The position of the transvalvular band 500 avoids the circumflex (Cx) coronary artery. The position of the transvalvular band 500 avoids the atrioventricular (AV) node. The position of the transvalvular band 500 avoids the aortic leaflets.

The design of the transvalvular band 500 according to some embodiments is shown in FIGS. 74-76. The transvalvular bridge 500 can include the first attachment structure 504 at a first end of the bridge 500 and the second attachment structure 526 at a second end of the bridge 500. In some embodiments, the first attachment structure 504 is a polyethylene terephthalate (PET) anchoring pad. In some embodiments, the second attachment structure 526 is a PET anchoring pad. In some embodiments, the first attachment structure 504 and the second attachment structure 526 can be similar or identical in shape. In some embodiments, the first attachment structure 504 and the second attachment structure 526 can be similar or identical in material. FIG. 74 shows the bottom view of the transvalvular band 500. FIG. 75 shows the top or annular view of the transvalvular band 500. FIG. 76 shows the perspective view of the transvalvular band 500.

The transvalvular bridge 500 can also include an arcuate central portion 502 which can be curved downward. The transvalvular bridge 500 is concave when implanted. The transvalvular bridge 500 can include a plurality of struts 516. The struts 516 can provide structural support to the transvalvular bridge 500. In some embodiments, the struts 516 form a generally X shape. The arcuate central portion 502 can be formed of silicon. The arcuate central portion 502 can be formed of Nitinol. In some embodiments, the arcuate central portion 502 can comprise a covering formed silicon with the struts 516 formed of Nitinol. The transvalvular bridge 500 can include infra-annular curvature. The transvalvular bridge 500 can include a silicon-nitinol bridge between the first and second attachment structures 504, 526. The transvalvular bridge 500 can be a silicone-Nitinol bridge. In some embodiments, the transvalvular bridge 500 can be a single piece. In some embodiments, the transvalvular bridge 500 can be multiple pieces coupled together. In some embodiments, the transvalvular bridge 500 can have no moving parts.

In some embodiments, the transvalvular bridge 500 can be in a plurality of sizes, for instance, 22 mm, 24 mm, 26 mm, 28 mm, 30 mm, or ranges incorporating any of the foregoing values. Other sizes are contemplated including 10 mm, 12 mm, 14 mm, 16 mm, 18 mm, 20 mm, 21 mm, 23 mm, 25 mm, 27 mm, 29 mm, 31 mm, 32 mm, 34 mm, 36 mm, 38 mm, 40 mm, or ranges incorporating any of the foregoing values. In some embodiments, two or more sizes of the transvalvular bridge 500 are provided. In some embodiments, five sizes of the transvalvular bridge 500 are provided. The transvalvular bridge 500 can include a centered infra-annular curvature. The transvalvular bridge 500 can be symmetric. The transvalvular bridge 500 can have one axis of symmetry. The transvalvular bridge 500 can have two axes of symmetry. The transvalvular bridge 500 can have three axes of symmetry. The transvalvular bridge 500 can have a plurality of axes of symmetry.

The transvalvular bridge 500 can form a continuous infra-annular curvature. The midpoint or vertex of the transvalvular bridge 500 can be centered. The midpoint or vertex of the transvalvular bridge 500 can be centered between the first and second attachment structures 504, 526.

In some methods of use, the transvalvular bridge 500 reduces the septolateral dimension. In some methods of use, the transvalvular bridge 500 reduces the distance between PPM and leaflet. In some methods of use, the transvalvular bridge 500 maintains the saddle shape of the annulus. In some methods of use, the transvalvular bridge 500 ensures early coaptation of leaflets. In some methods of use, the transvalvular bridge 500 is compliant to annular displacement. In some methods of use, the transvalvular bridge 500 is durable. In some embodiments, the transvalvular bridge 500 can withstand 400 million cycles. In some embodiments, the transvalvular bridge 500 can withstand 600 million cycles. In some embodiments, the transvalvular bridge 500 can withstand 1 billion cycles. In some embodiments, the transvalvular bridge 500 can withstand cycles with a displacement of 0.5 mm. In some embodiments, the transvalvular bridge 500 can withstand cycles with a displacement of −0.5 mm.

Figure 77:
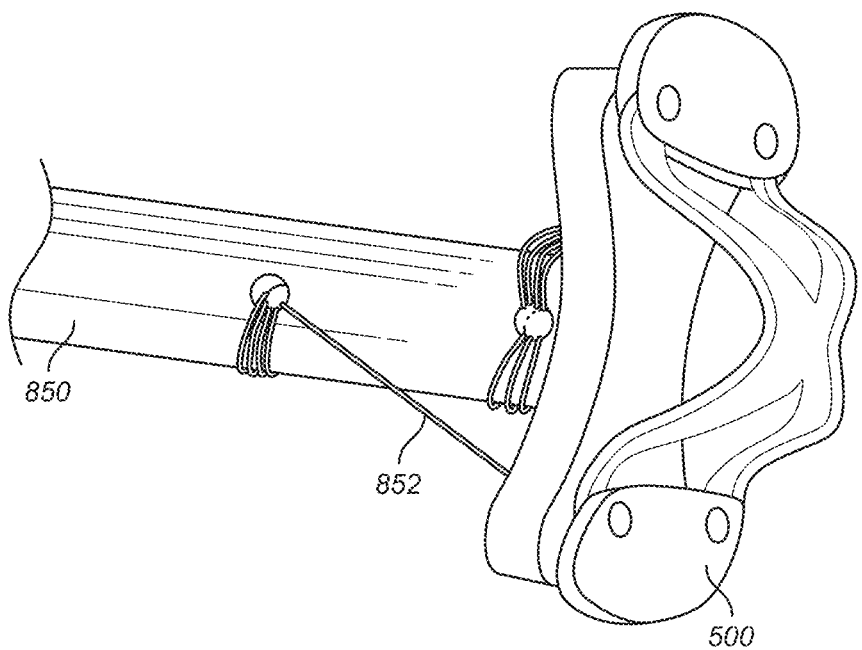
FIGS. 77-83 are views of an open procedure method, according to some embodiments.
Figure 78:
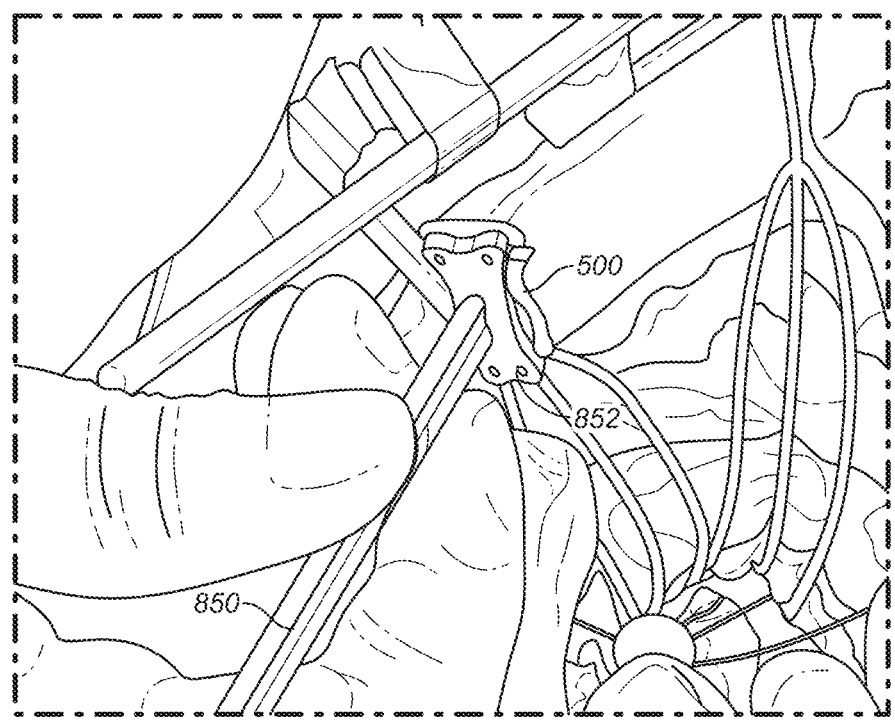

FIGS. 77-78 illustrate a transvalvular bridge 500 on a holder 850 with a holding suture 852. The holder 850 can include a flat region designed to abut the transvalvular bridge 500. The holder 850 can span the distance between the first and second attachment structures 504, 526. The holding suture 852 can couple the transvalvular bridge 500 to the holder 850. The holder 850 can be used to position the transvalvular bridge 500 relative to the heart. In some methods of use, removal or release of the holding suture 852 can allow the holder 850 to move away from the transvalvular bridge 500. In some methods of use, the holding suture 852 can extend through the attachment structures 504, 526. In some methods of use, the holding suture 852 can extend through one or more of the plurality of apertures 508 of the attachment structures 504, 526.

Figure 79:
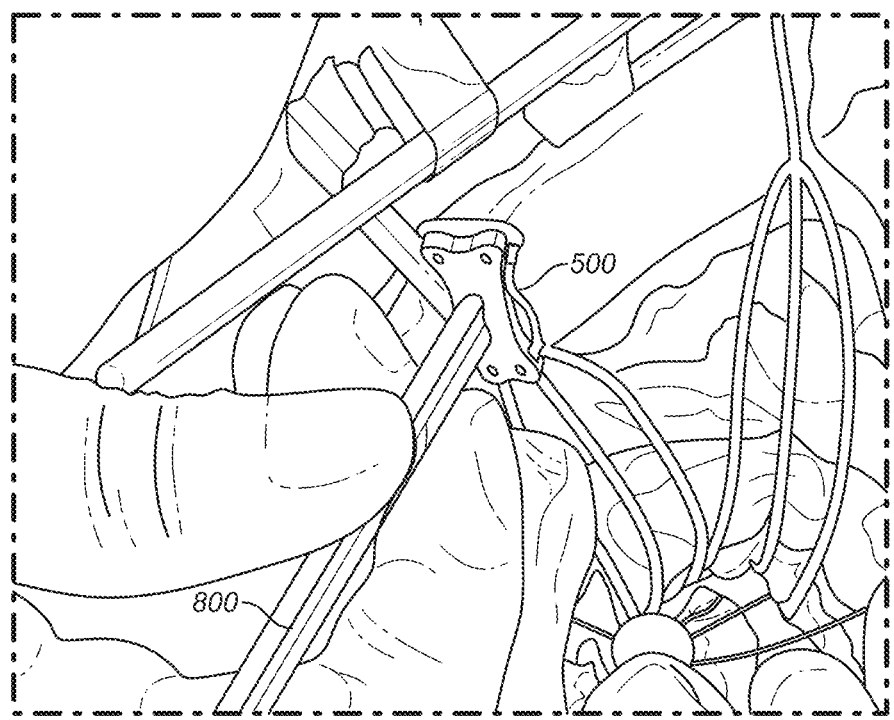
Figure 80:
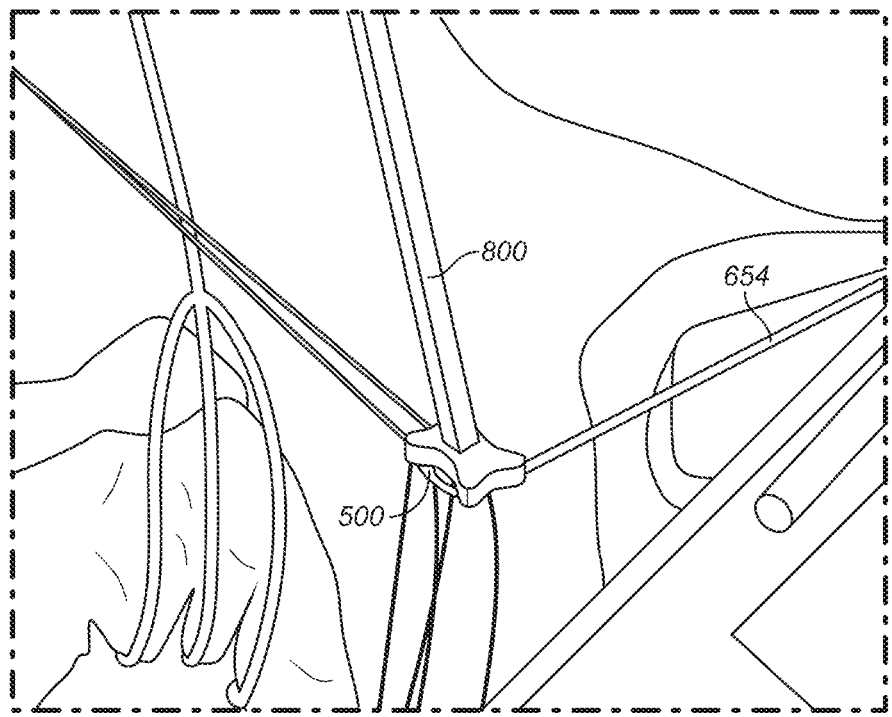
Figure 81:
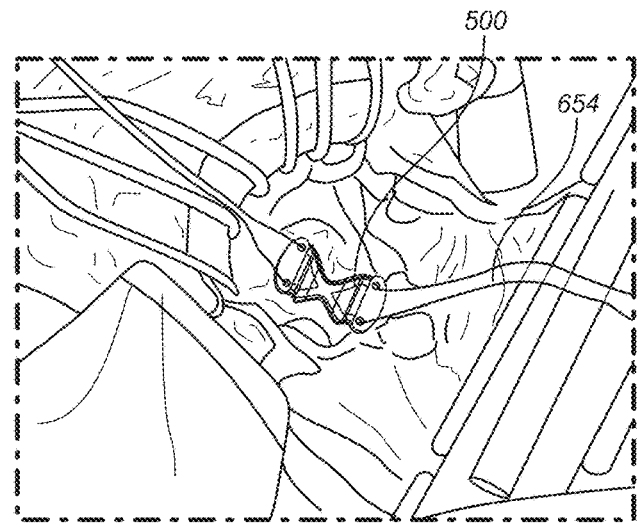
Figure 82:
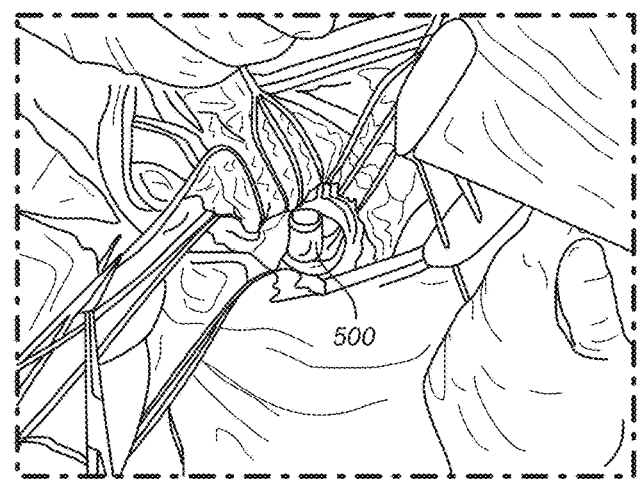
Figure 83:
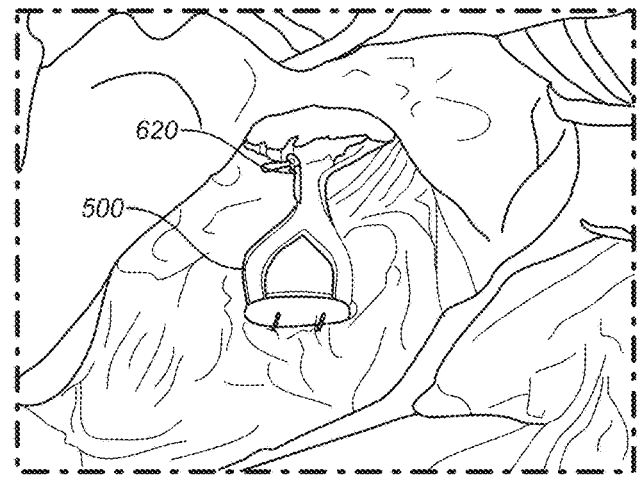

FIG. 77-83 illustrate an open procedure. FIG. 77 illustrates the position of the transvalvular bridge 500 on a holder 850. FIG. 78-79 illustrates the surgeon positioning the transvalvular bridge 500. The holder 850 facilitates placement of the transvalvular bridge 500. In some methods of use, the tissue is retracted to provide access to the mitral valve. FIG. 80 illustrates the position of the sutures 654 or other sutures described herein extending from the transvalvular bridge 500. As described herein, the retainer 612 can be loaded into the needle 628. The retainer 612 can include a pledget 652 and the suture 654. FIG. 81 illustrates the position of the transvalvular bridge 500 relative to the mitral valve. The surgeon moves the transvalvular bridge 500 toward the mitral valve until the transvalvular bridge 500 spans the mitral valve. The holder 850 can be removed. FIG. 82 illustrates the position of the transvalvular bridge 500. The transvalvular bridge 500 can be secured by advancing a clip 620. The clip 620 can be pushed along the suture 654 as described herein. FIG. 83 illustrates the position of the transvalvular bridge 500 after the transvalvular bridge 500 is secured.

Figure 84:
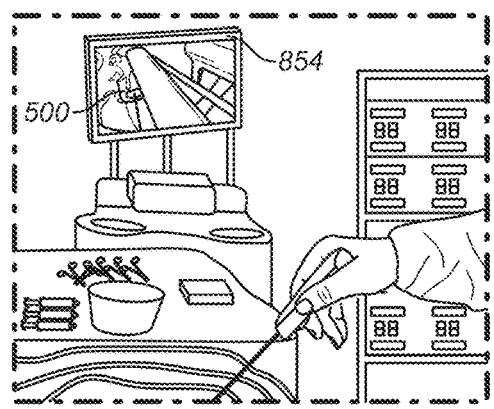
FIGS. 84-86 are views of a minimally invasive surgery method, according to some embodiments.
Figure 85:
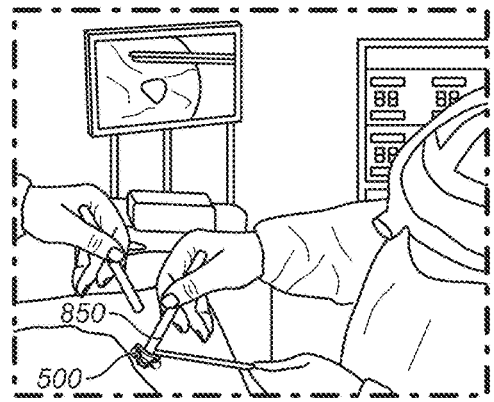
Figure 86:
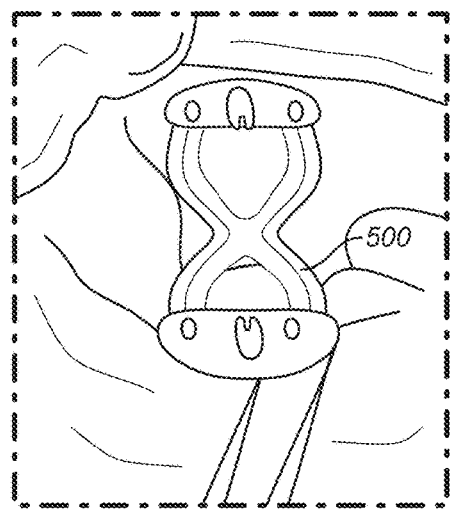

FIGS. 84-86 illustrate a minimally invasive surgical procedure. FIG. 84 illustrates a mini thoracotomy. The transvalvular bridge 500 can be delivered. FIG. 85 illustrates the transvalvular bridge 500 being inserted into the annulus. FIG. 86 illustrates transvalvular bridge 500 anchoring. The surgeon can ensure delivery of the transvalvular bridge 500 by viewing a display 854. The display 854 shows the positioning of the transvalvular bridge 500 during the minimally invasive surgical procedure.

In some methods of use, the transvalvular bridge 500 is placed between midpoints of A2-P2. In some methods of use, the transvalvular bridge 500 is placed at the annular level. In some methods of use, the attachment structures 504, 526 of the transvalvular bridge 500 are placed level with the annulus. In some methods of use, the transvalvular bridge 500 is placed with standard sutures. In some methods of use, the transvalvular bridge 500 is placed with suture 654 as described herein. In some methods of use, the transvalvular bridge 500 has rapid implantation. In some methods of use, the transvalvular bridge 500 is available in a plurality of sizes. In some methods of use, the transvalvular bridge 500 is in the range of 22 to 30 mm. In some methods of use, the transvalvular bridge 500 can achieve direct, non-planar septolateral dimension reduction. In some methods of use, the transvalvular bridge 500 can restore the annular saddle shape. In some methods of use, the transvalvular bridge 500 can facilitate preservation of leaflet curvature. In some methods of use, the transvalvular bridge 500 can facilitate preservation of annular function. In some methods of use, the transvalvular bridge 500 can promotes early coaptation. In some methods of use, the transvalvular bridge 500 can retrain the leaflet (prolapse) below the annular plane.

In some embodiments, the septolateral dimension is reduced by 10 percent. In some embodiments, the septolateral dimension is reduced by 15 percent. In some embodiments, the septolateral dimension is reduced by 20 percent. In some embodiments, the septolateral dimension is reduced by 25 percent. In some embodiments, the septolateral dimension is reduced by 30 percent. In some embodiments, the septolateral dimension is reduced an average of about 25 percent. In some embodiments, the septolateral dimension is reduced about 5 mm. In some embodiments, the septolateral dimension is reduced about 10 mm. In some embodiments, the septolateral dimension is reduced about 15 mm. In some embodiments, the septolateral dimension is reduced about 20 mm. In some embodiments, the septolateral dimension is reduced an average of about 10 mm. In some embodiments, the copatation height increases 2 mm. In some embodiments, the copatation height increases 3 mm. In some embodiments, the copatation height increases 4 mm. In some embodiments, the copatation height increases 5 mm. In some embodiments, the copatation height increases 6 mm. In some embodiments, the copatation height increases an average of about 4.5 mm. In some embodiments, the mean gradient increase 0.2 mm Hg. In some embodiments, the mean gradient increase 0.4 mm Hg. In some embodiments, the mean gradient increase 0.6 mm Hg. In some embodiments, the mean gradient increase 0.8 mm Hg. In some embodiments, the mean gradient increase 1.0 mm Hg. In some embodiments, the mean gradient increase an average of about 0.7 mm Hg. In a baseline study, about 60% of patients had moderate-severe mitral regurgitation before implantation. In a baseline study, about 40% of patients had—severe mitral regurgitation before implantation. After implantation about 60% of patients had no regurgitation and about 40% had mild regurgitation. Some estimates suggest that over 50% of patients with annuloplasty rings have moderate or severe regurgitation at two years.

The same transvalvular bridge 500 used in open or MIS surgery can be mounted in catheter for trans-septal delivery. The delivery, positioning, and anchoring can be optimized for trans-septal delivery and implantation.

Figure 87:
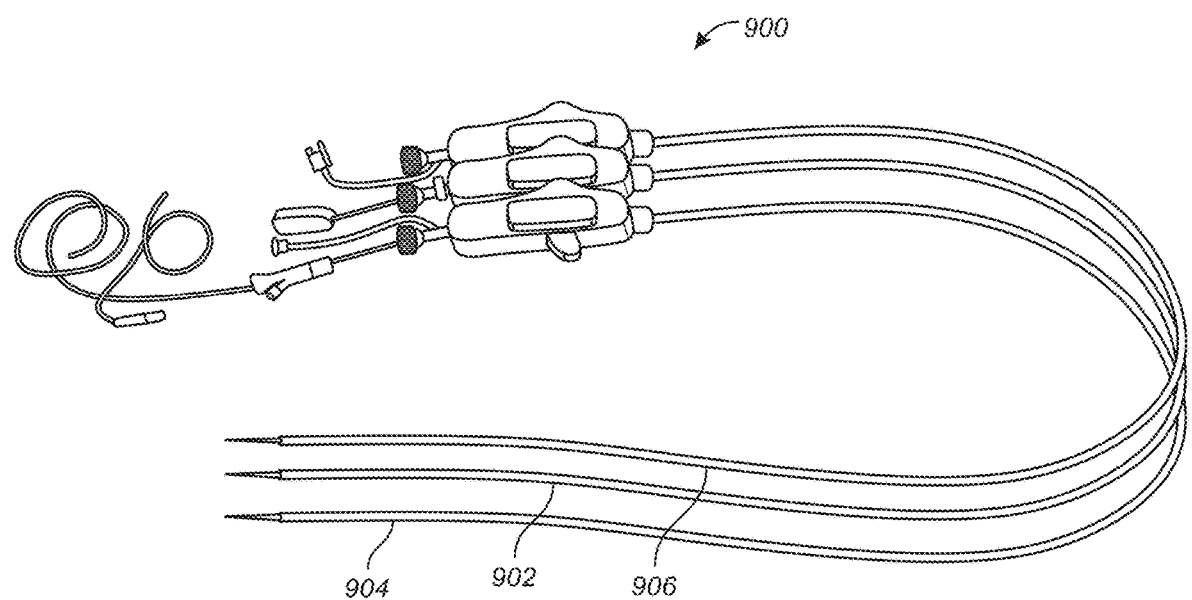
FIGS. 87-91 are views of a transcatheter system, according to some embodiments.

FIG. 87 illustrates a transcatheter system 900. The transcatheter system can deliver the transvalvular bridge 500 or any implant described herein. The transcatheter system 900 can include any of the features of the system of delivery catheters 600 described herein. The transcatheter system 900 can include any number of primary catheters. In some embodiments, the transcatheter system 900 can include four primary catheters. The transcatheter system 900 can include a pipeline catheter 902. The transcatheter system 900 can include a sheath & needle catheter 904. The transcatheter system 900 can include a delivery catheter & suture management catheter 906. The transcatheter system 900 can include a trimming catheter 908.

The transcatheter system 900 can include one or more catheters that include a single lumen. The transcatheter system 900 can include one or more catheters that include a plurality of lumens. The transcatheter system 900 can include embedded catheter features. For instance, the clip pushers described herein can be built into the delivery catheter & suture management catheter 906. The transcatheter system 900 can reduce complexity. The transcatheter system 900 can enable rapid progress and easy prototypes. The transcatheter system 900 can replicate open procedure. The transcatheter system 900 can allow delivery while the heart is beating. The transcatheter system 900 can deliver the transvalvular bridge 500 without cardiopulmonary bypass.

Figure 88:
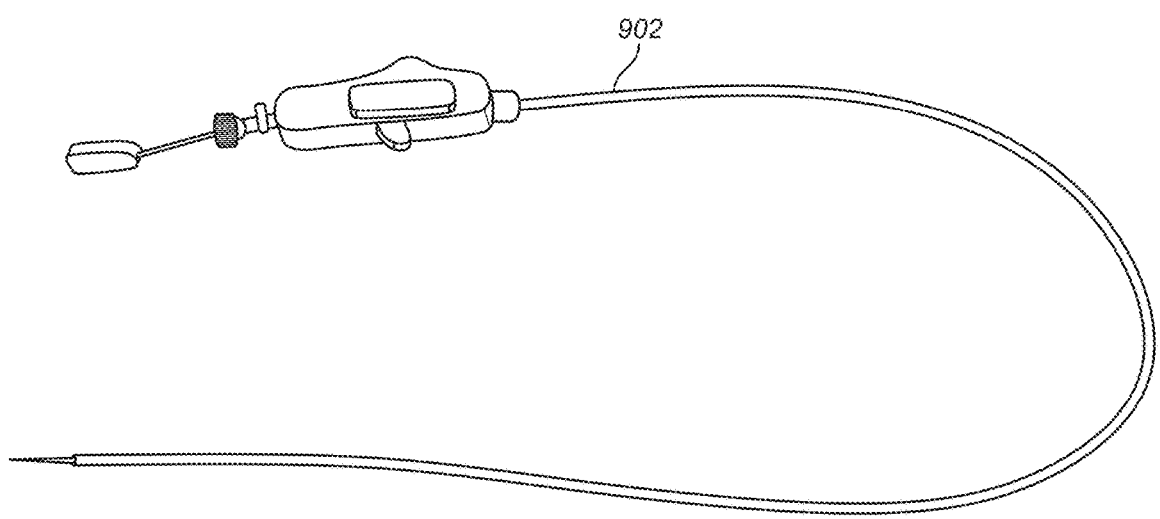

FIG. 88 illustrates the pipeline catheter 902, according to some embodiments. The pipeline catheter 902 can function as a guide and can be the primary conduit. The pipeline catheter 902 can have any size outer diameter and length. In some embodiments, the pipeline catheter 902 has an outer diameter of 14 Fr, 16 Fr, 18 Fr, 20 Fr, 22 Fr, 24 Fr, 26 Fr, 28 Fr, 30 Fr, 32 Fr, 34 Fr, or ranges incorporating any of the foregoing values, between 20-30 Fr, about 24 Fr, etc. In some embodiments, the pipeline catheter 902 has a length of 70 cm, 80 cm, 90 cm, 100 cm, 110 cm, 120 cm, 130 cm, or ranges incorporating any of the foregoing values, between 90-110 cm, about 100 cm, etc. The pipeline catheter 902 can have a single lumen. The pipeline catheter 902 can be steerable. For instance, a handle of the pipeline catheter 902 can control a flexible tip. The pipeline catheter 902 can be a 90° Bi-directional catheter. The pipeline catheter 902 can be axially stiff. The pipeline catheter 902 can hold a septal position. The pipeline catheter 902 can be an ultra-flexible dilator. In some embodiments, the pipeline catheter 902 can have a reduced outer diameter during delivery. In some embodiments, the pipeline catheter 902 can have a reduced outer diameter compared to other delivery catheters.

Figure 89A:
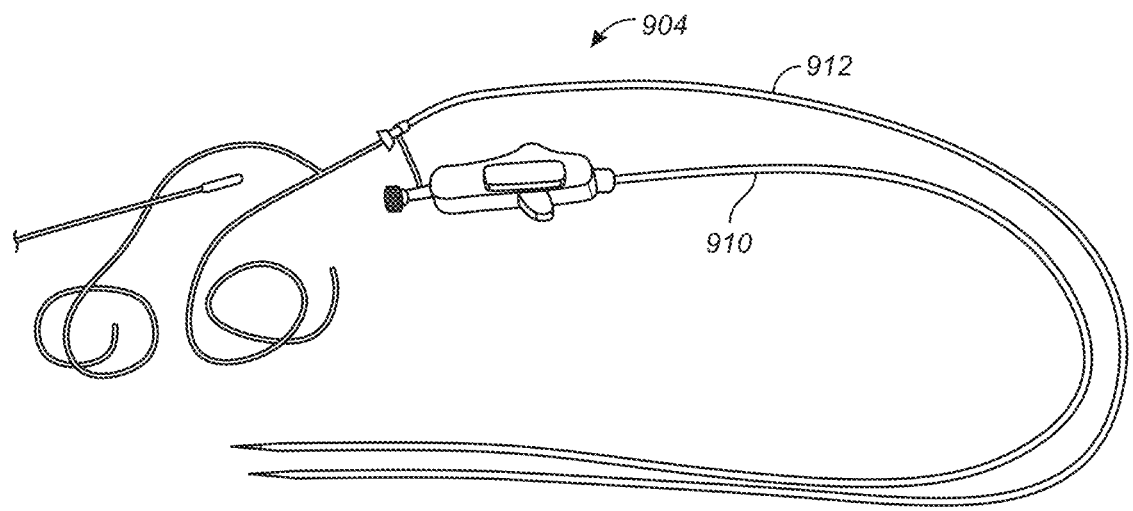
Figure 89B:
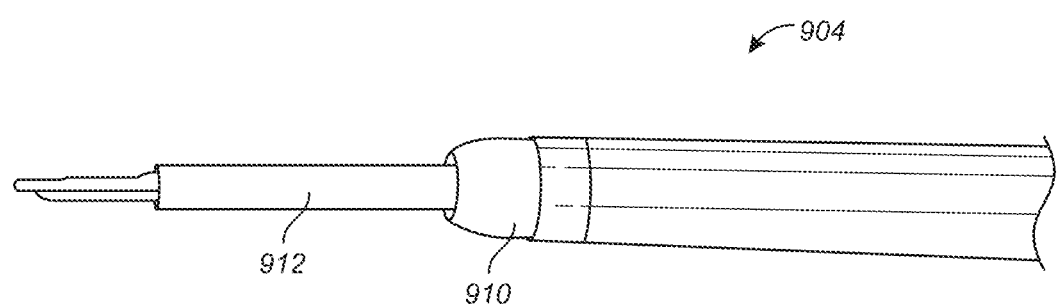

FIG. 89A illustrates a sheath & needle catheter 904. The sheath & needle catheter 904 can include a sheath 910 and a needle 912. The sheath 910 and the needle 912 are separated in FIG. 89A. FIG. 89B illustrate the distal end of the sheath & needle catheter 904. The needle 912 is disposed within the sheath 910 in FIG. 89B. The sheath 910 can have LA steering. The sheath 910 can have any size outer diameter and length. In some embodiments, the sheath 910 has an outer diameter of 2 Fr, 4 Fr, 6 Fr, 8 Fr, 10 Fr, 12 Fr, 14 Fr, 16 Fr, 18 Fr, 20 Fr, 22 Fr, 24 Fr, or ranges incorporating any of the foregoing values, between 10-20 Fr, about 8 Fr, etc. In some embodiments, the sheath 910 has a length of 70 cm, 80 cm, 90 cm, 100 cm, 110 cm, 120 cm, 130 cm, or ranges incorporating any of the foregoing values, between 100-120 cm, about 110 cm, etc. The sheath 910 can be steerable. The sheath 910 can be a 180° Bi-directional catheter. The sheath 910 can have any bend radius. In some embodiments, the sheath 910 has bend radius of 8 mm, 8.5 mm, 9 mm, 9.5 mm, 10 mm, 10.5 mm, 11 mm, 11.5 mm, 12 mm, 12.5 mm, 13 mm, 13.5 mm, 14 mm, 14.5 mm, 15 mm, 15.5 mm, 16 mm, 16.5 mm, 17 mm, or ranges incorporating any of the foregoing values, between 10-15 mm, about 12.5 mm, etc.

The needle 912 is designed to be disposed within the sheath 910. The needle 912 can include a needle and a needle sheath. The needle 912 can function for burn and retainer delivery. In some embodiments, the needle 912 has an outer diameter of 1 Fr, 2 Fr, 3 Fr, 4 Fr, 5 Fr, 6 Fr, 7 Fr, 8 Fr, 9 Fr, 10 Fr, 12 Fr, 14 Fr, 16 Fr, 18 Fr, 20 Fr, 22 Fr, 24 Fr, or ranges incorporating any of the foregoing values, between 1-10 Fr, about 5 Fr, etc. In some embodiments, the needle 912 has a length of 70 cm, 80 cm, 90 cm, 100 cm, 110 cm, 120 cm, 130 cm, 140 cm, 150 cm, or ranges incorporating any of the foregoing values, between 110-130 cm, about 120 cm, etc. The needle 912 can be axially stiff. The needle 912 can be a RF needle. The needle 912 can be designed to deliver RF energy to burn a hole in the annulus, as described herein. The needle 912 can facilitate flexible pusher deployment. FIG. 89B illustrates the coaxial sheath & needle catheter 904.

Figure 90A:
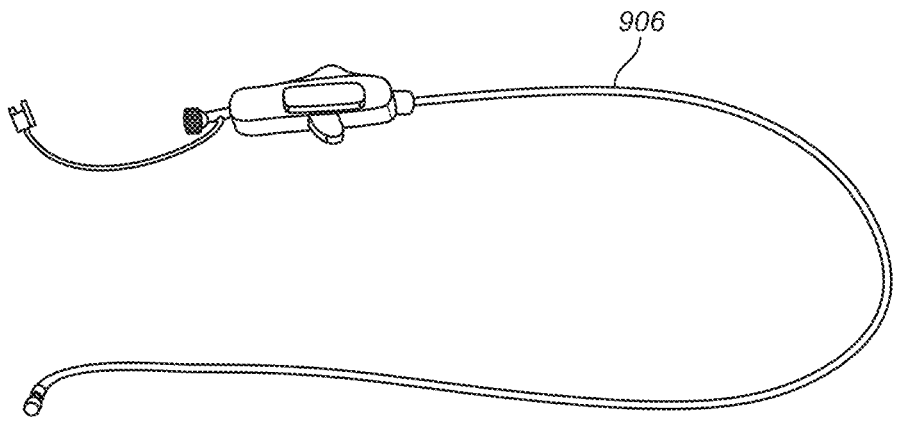
Figure 90B:
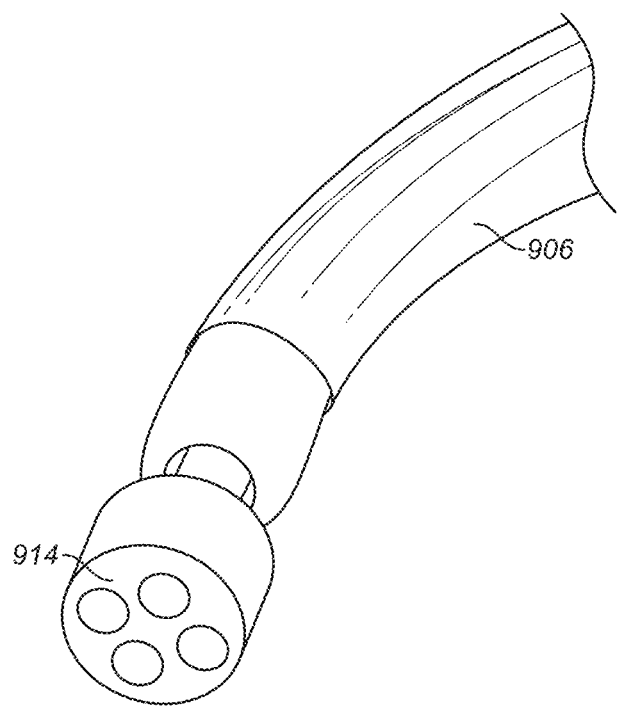

FIG. 90A illustrates the delivery catheter & suture management catheter 906. The delivery catheter & suture management catheter 906 can function for deployment of the transvalvular bridge 500 or any implant described herein. The delivery catheter & suture management catheter 906 can function for suture management and cinching. In some embodiments, the delivery catheter & suture management catheter 906 has an outer diameter of 1 Fr, 2 Fr, 3 Fr, 4 Fr, 5 Fr, 6 Fr, 7 Fr, 8 Fr, 9 Fr, 10 Fr, 12 Fr, 14 Fr, 16 Fr, 18 Fr, 20 Fr, 22 Fr, 24 Fr, or ranges incorporating any of the foregoing values, between 1-10 Fr, about 8 Fr, etc. In some embodiments, the delivery catheter & suture management catheter 906 has a length of 70 cm, 80 cm, 90 cm, 100 cm, 110 cm, 120 cm, 130 cm, 140 cm, 150 cm, or ranges incorporating any of the foregoing values, between 110-130 cm, about 120 cm, etc. The delivery catheter & suture management catheter 906 can be steerable. The delivery catheter & suture management catheter 906 can be a 180° Bi-directional catheter. The delivery catheter & suture management catheter 906 can have any bend radius. In some embodiments, the sheath 910 has bend radius of 8 mm, 8.5 mm, 9 mm, 9.5 mm, 10 mm, 10.5 mm, 11 mm, 11.5 mm, 12 mm, 12.5 mm, 13 mm, 13.5 mm, 14 mm, 14.5 mm, 15 mm, 15.5 mm, 16 mm, 16.5 mm, 17 mm, or ranges incorporating any of the foregoing values, between 10-15 mm, about 12.5 mm, etc. The delivery catheter & suture management catheter 906 can detangle from each other. The delivery catheter & suture management catheter 906 can function to detangle or prevent tangles of the suture 654 or any suture described herein. The delivery catheter & suture management catheter 906 can function to be pushable. The delivery catheter & suture management catheter 906 can push the clips as described herein. FIG. 90B illustrates the distal end of the delivery catheter & suture management catheter 906. The delivery catheter & suture management catheter 906 can include four ports 914. The number of ports 914 can correspond to the number of apertures 508 of the transvalvular bridge 500. The number 914 of ports can correspond to the number of pushers 622.

Figure 91:
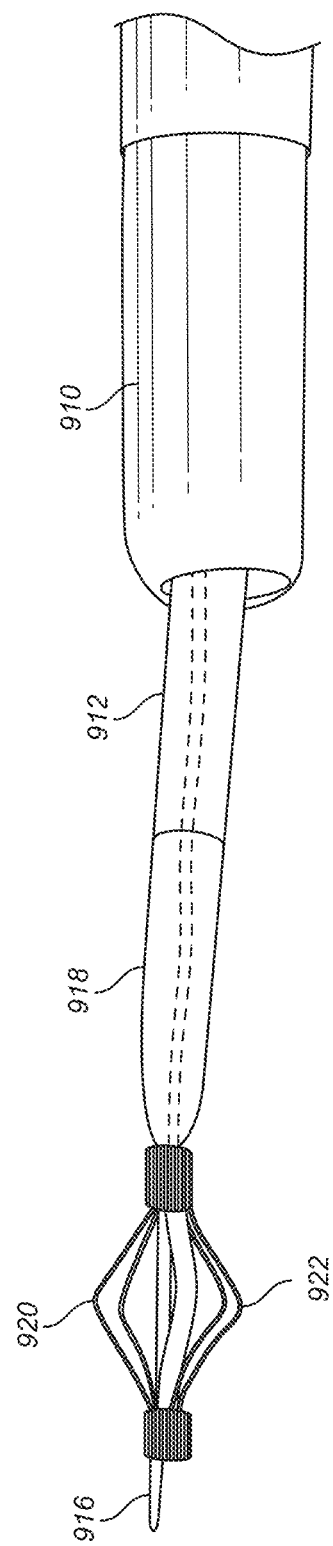

FIG. 91 illustrates the sheath & needle catheter 904 with the sheath 910 and the needle 912. The needle 912 can include a needle 916 and a needle sheath 918. The needle 916 can be deliver thermal energy, such as RF energy. The needle 916 can burn a hole through the annulus, as described herein. The needle 916 can carry a subannular anchor 920. The subannular anchor 920 can anchor the transvalvular bridge 500 or any implant described herein. The subannular anchor 920 can have a star design. The subannular anchor 920 can have a holding strength of 10 N, 12 N, 14 N, 16 N, 18 N, 20 N, 22 N, 24 N, 26 N, 28 N, 30 N, 32 N, 34 N, 36 N, 38 N, 40 N, or ranges incorporating any of the foregoing values, between 15-30 N, between 20-26 N, etc. The subannular anchor 920 flattens with tension. The subannular anchor 920 can have a compressed outer diameter. The subannular anchor 920 compressed outer diameter can be 0.2 mm, 0.4 mm, 0.6 mm, 0.8 mm, 1.0 mm, 1.2 mm, 1.4 mm, 1.6 mm, 1.8 mm, 2.0 mm. 2.1 mm, 2.2 mm, or ranges incorporating any of the foregoing values, between 1 mm and 1.5 mm, about 1.2 mm, etc. The subannular anchor 920 can have an expanded diameter. The subannular anchor 920 expanded outer diameter can be 4.5 mm, 5 mm, 5.5 mm, 6 mm, 6.5 mm, 7 mm, 7.5 mm, 8 mm, 8.5 mm, 9 mm, or ranges incorporating any of the foregoing values, between 6 mm and 7 mm, about 6.5 mm, etc.

In some embodiments, the subannular anchor 920 can be cylindrical or substantially cylindrical when compressed. In some embodiments, the subannular anchor 920 can have a longer length when compressed or under tension. In some embodiments, the subannular anchor 920 can have a pre-formed shaped. In some embodiments, the subannular anchor 920 can assume the pre-formed shaped when the tension is released. In some embodiments, the subannular anchor 920 can assume the pre-formed shaped when a constraint is removed. In some embodiments, the subannular anchor 920 comprises a shape memory material. In some embodiments, the subannular anchor 920 comprises Nitinol. In some embodiments, the subannular anchor 920 can comprise a plurality of struts 922. In some embodiments, the subannular anchor 920 can comprise four struts 922. In some embodiments, the subannular anchor 920 can comprise equally spaced or unequally spaced struts 922. In some embodiments, the struts 922 can bend outward during expansion.

In some embodiments, the subannular anchor 920 is reversible. The subannular anchor 920 can be compressed. The subannular anchor 920 can be deployed such that the subannular anchor 920 has the expanded outer diameter. If desired by the surgeon, tension can be applied to the subannular anchor 920. The subannular anchor 920 can be compressed to a smaller outer diameter. The subannular anchor 920 can be repositioned and redeployed. The subannular anchor 920 facilitates reversibility. The subannular anchor 920 can be reversible (e.g., removable) even after placement of the transvalvular band 500.

Figure 92:
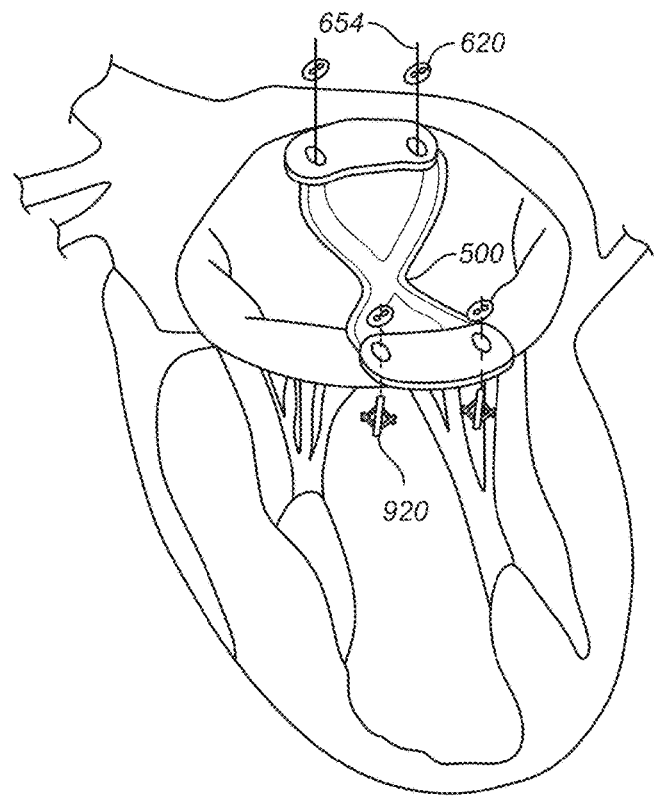
FIGS. 92-93 are views of subannular anchoring, according to some embodiments.

FIG. 92 illustrates deployment of the subannular anchor 920. The needle 916 can create holes within tissue. In some methods of use, the needle 916 can pass through the apertures 508 of the transvalvular band 500. The needle 916 punctures the underlying tissue. In some methods of use, the needle 916 applies RF energy as described herein. The subannular anchor 920 is passed through the apertures 508 of the transvalvular band 500 and the underlying tissue. The subannular anchor 920 can be in a compressed configuration during delivery such that the outer diameter of the subannular anchor 920 is reduced. The subannular anchor 920 can be carried by the needle 916 through the annulus. The subannular anchor 920 can be deployed. In some methods of use, the subannular anchor 920 is released from tension. The struts 922 of the subannular anchor 920 expand. The subannular anchor 920 can be positioned on the ventricular side of the annulus. The subannular anchor 920 can be positioned in the left ventricle. The deployed subannular anchor 920 are shown in FIG. 92.

Figure 93:
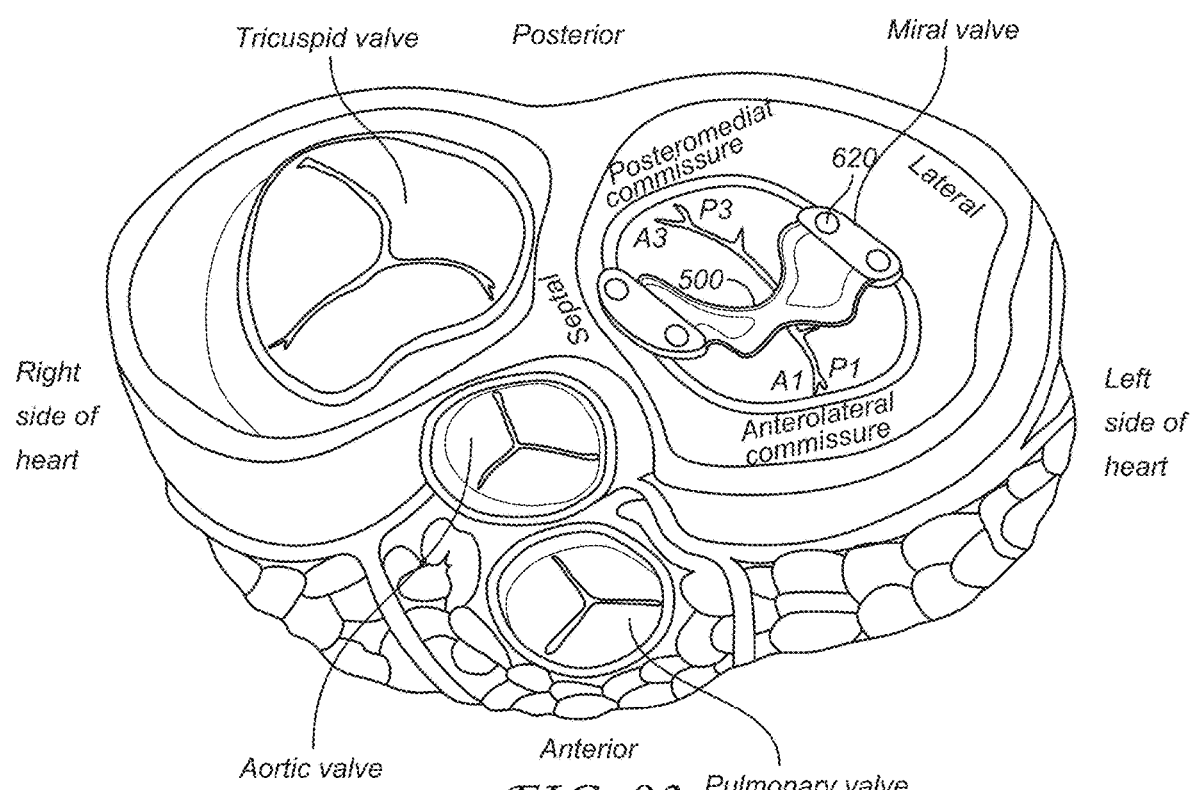

The subannular anchor 920 can be connected to the suture 654 or other sutures described herein. The clips 620 can be delivered via the delivery catheter & suture management catheter 906. The clips 620 can be pushed along the suture 654. In some embodiments, the clip 620 can be pushed against the transvalvular band 500. In some embodiments, the suture 654 can be pulled as the clip 620 is pushed against the transvalvular band 500. In some embodiments, the suture 654 can be pulled to position the subannular anchor 920 against the tissue. In some embodiments, as the subannular anchor 920 is pulled against the tissue the subannular anchor 920 flattens horizontally against the tissue. In some embodiments, as the subannular anchor 920 is pulled against the tissue the subannular anchor 920 embeds in the tissue. FIG. 93 illustrates the position of the transvalvular band 500 and the clips 620.

Figure 94:
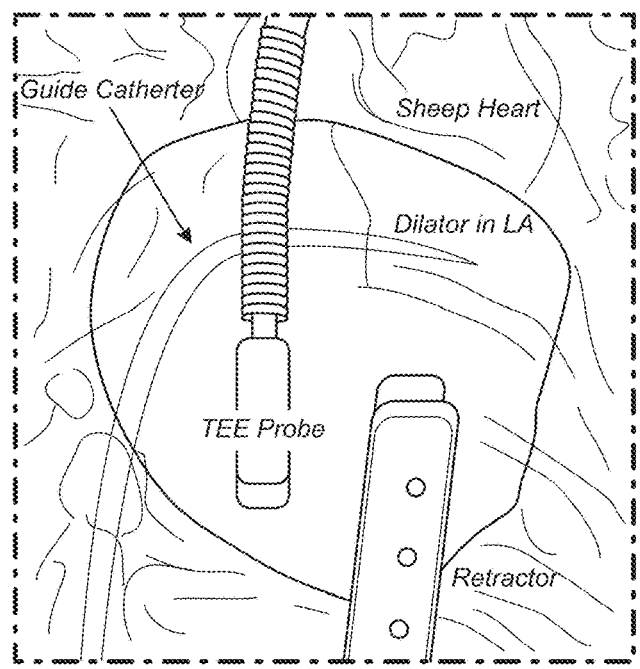
FIGS. 94-96 are views of transcatheter surgery, according to some embodiments.
Figure 95:
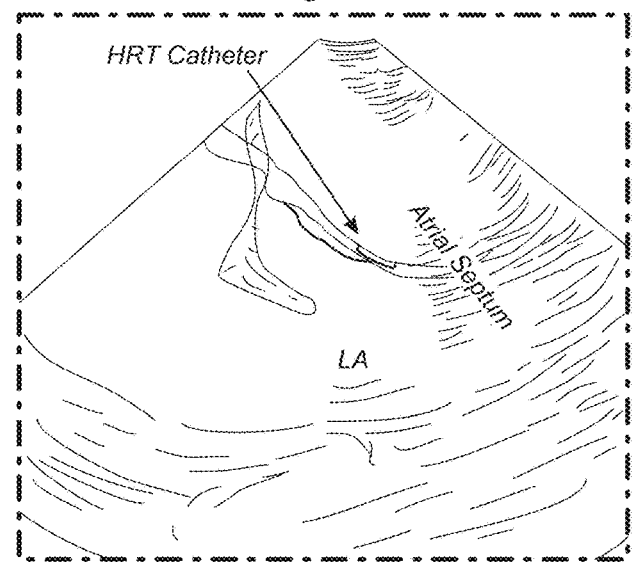
Figure 96:
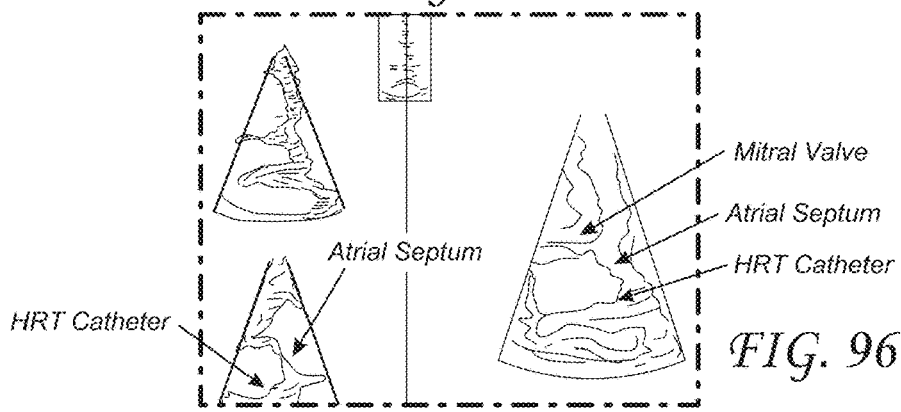

FIGS. 94-96 illustrate the transcatheter system 900. FIG. 94 illustrates a fluoroscopic image of the heart. The pipeline catheter 902 or other guide catheter is through the septal wall. The dilator is across the left atrium. The Transesophageal Echo (TEE) probe is also shown. FIG. 94-96 shows successful deployment of the transvalvular band 500.

Figure 97A:
FIGS. 97A-97E are views of a transcatheter system, according to some embodiments.
Figure 97B:
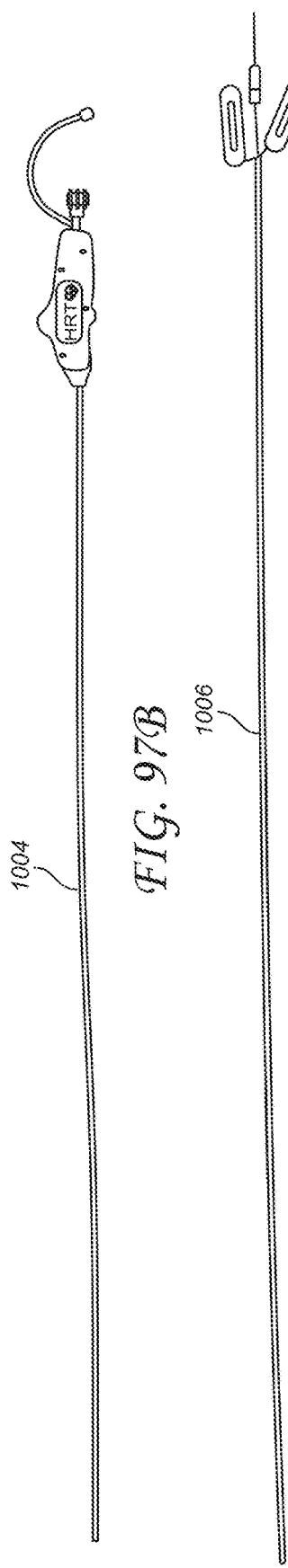
Figure 97C:
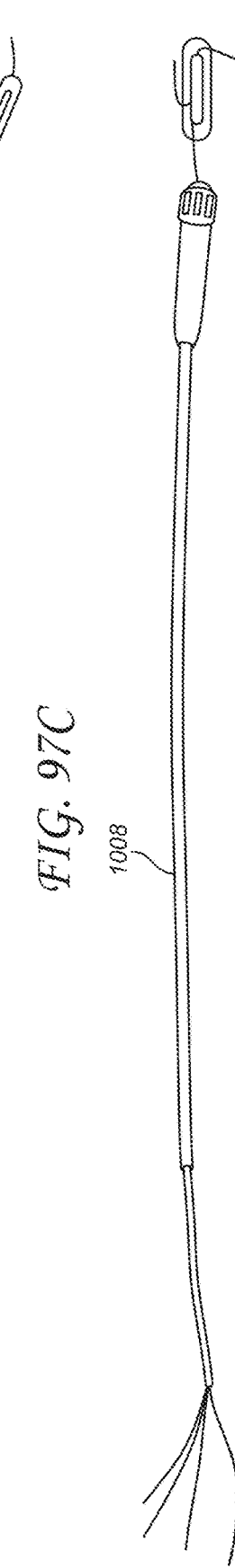
Figure 97D:
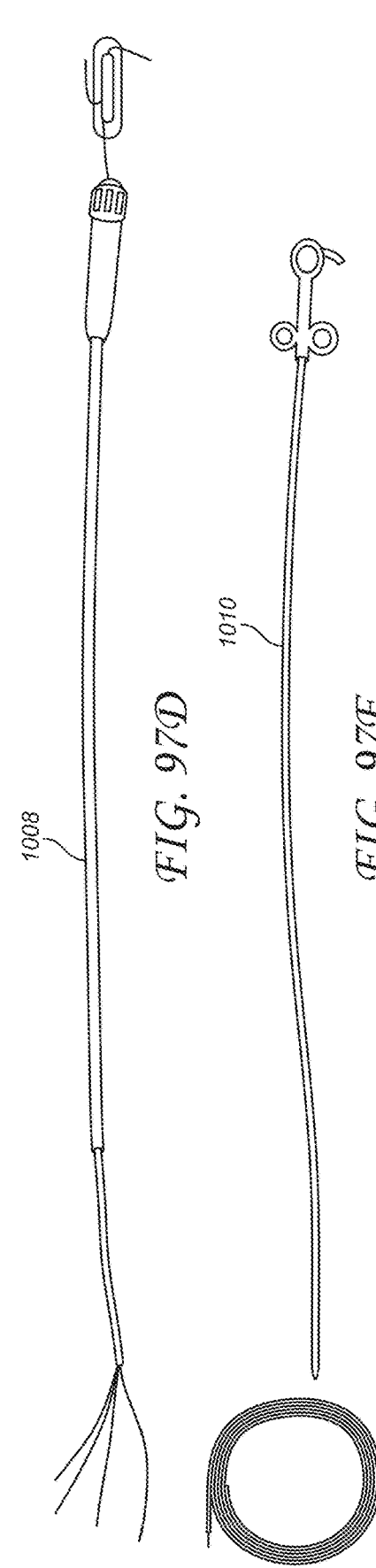
Figure 97E:
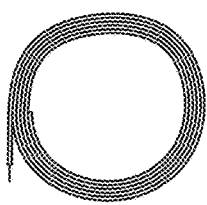

FIGS. 97A-97E are views of an embodiment of a transcatheter system 1000. The catheters of transcatheter system 1000 can include any of the features of catheters described herein. FIG. 97A illustrates a guide catheter 1002. The guide catheter 1002 can provide a transseptal conduit to the left atrium. FIG. 97B illustrates a steering catheter 1004. In some embodiments, the steering catheter 1004 can be steerable to the annulus. In some embodiments, the steering catheter 1004 can be steerable to the mitral annulus. FIG. 97C illustrates an anchor catheter 1006. The anchor catheter 1006 can deliver one or more of the subannular anchor. FIGS. 97A-97C illustrate the three catheters to place the anchors in some embodiments. The three catheters are the guide catheter 1002, the steering catheter 1004, and the anchor catheter 1006. FIG. 97D illustrates a delivery catheter 1008. The delivery catheter 1008 can deliver and secure the transvalvular band 500. The transvalvular band 500 can be considered a mitral bridge. FIG. 97E illustrates a trimming catheter 1010. The trimming catheter 1010 can cut and secure the sutures. FIGS. 97D-97E illustrates the two catheters to deliver and secure the transvalvular band 500 in some embodiments. The transcatheter system 1000 can have the advantage of replicating an open procedure. The transcatheter system 1000 can allow for delivery of the transvalvular band 500 to a beating heart. The transcatheter system 1000 can be proven to have beating heart delivery success.

The catheters of the transcatheter system 1000 can be utilized in one or more methods. In some embodiments, the five catheters can be utilized in any number of the following steps. The steps can include 1) transseptally place guide catheter 1002, 2) insert steering catheter 1004 with anchor catheter 1006 inside, 3) position the steering catheter 1004 and deliver anchors, 4) insert delivery catheter 1008, deploy transvalvular band 500, and cinch, and 5) insert trimming catheter 1010 and cut sutures. The method can include transseptal puncture with transseptal needles. After puncture, the user can transseptally place the guide catheter 1002. The guide catheter 1002 can provide a conduit to the left atrium. In some embodiments, the user can insert the steering catheter 1004 through the guide catheter 1002. The steering catheter 1004 can be steerable to the annulus. In some embodiments, the anchor catheter 1006 can be disposed inside the steering catheter 1004 during positioning of the steering catheter 1004. The user can position the steering catheter 1004 and thereby position the anchor catheter 1006. The user can deliver four anchors via the anchor catheter 1006. The user can deliver a plurality of anchors sequentially. The user can deliver a plurality of anchors simultaneously. The anchor catheter 1006 can deliver the anchors subannularly. The anchor catheter 1006 can puncture the annulus to deliver the anchor. The user can insert the delivery catheter 1008. The delivery catheter 1008 can deliver the transvalvular band 500. The user can deploy the transvalvular band 500, for instance, by unrolling the transvalvular band 500. The transvalvular band 500 can be guided by the sutures extending from the subannular anchors. The delivery catheter 1008 can secure the transvalvular band 500. The user can cinch the sutures to position the transvalvular band 500. The user can insert the trimming catheter 1010. The user can cut the sutures via the trimming catheter 1010. The catheters of the transcatheter system 1000 can be withdrawn.

Figure 98:
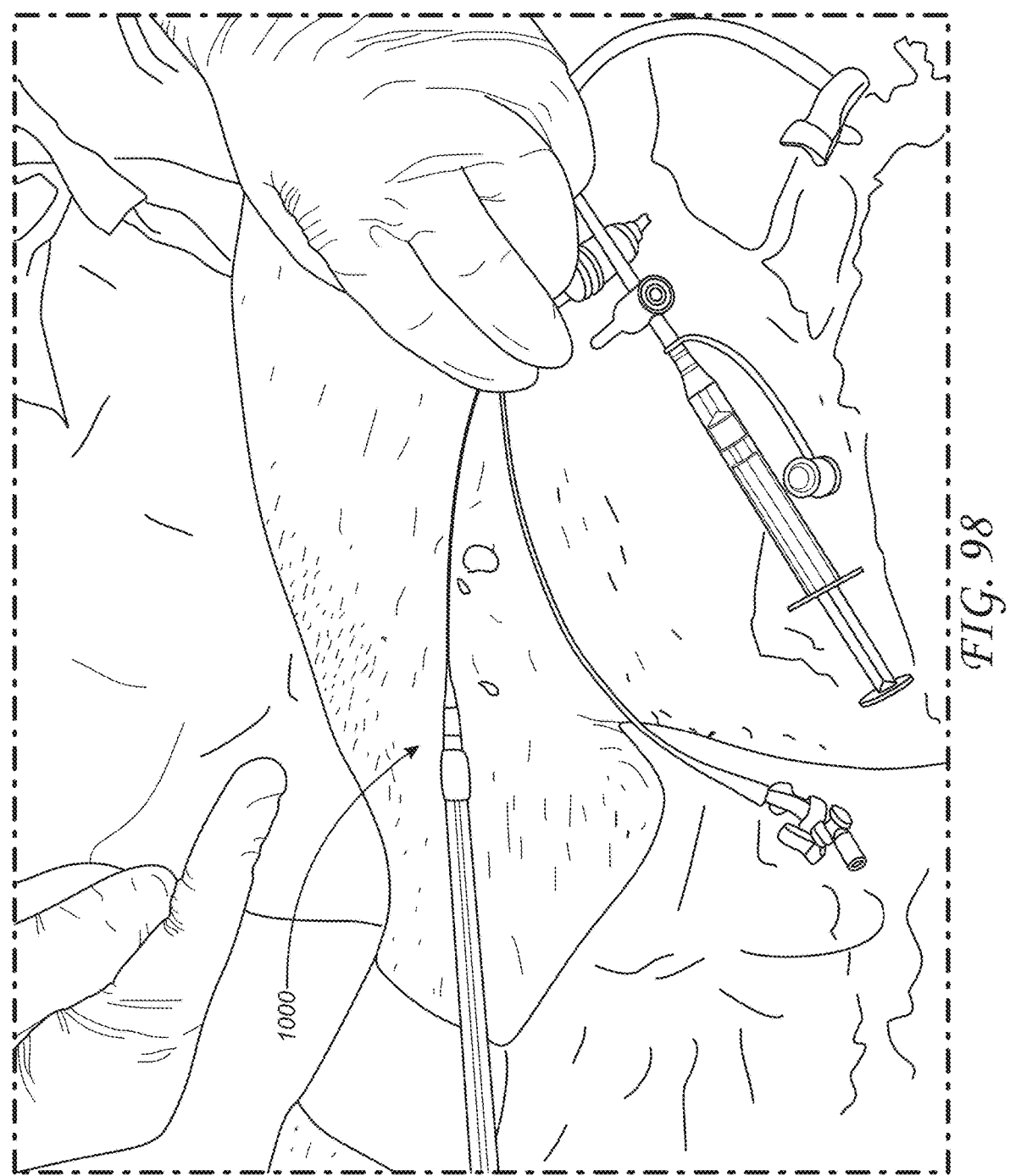
FIG. 98 is a view of the percutaneous insertion of the transcatheter system of FIGS. 97A-97E.

FIG. 98 illustrates the percutaneous delivery of the transcatheter system 1000. The transcatheter system 1000 can be inserted in a sequence for anchor and implant placement. The general transseptal steps can include placing an introducer in the right femoral vein. The introducer can be 26 Fr, or any other size to permit access (e.g., 10 Fr, 12 Fr, 14 Fr, 16 Fr, 18 Fr, 20 Fr, 22 Fr, 24 Fr, 28 Fr, 30 Fr, 32 Fr, or ranges incorporating any of the foregoing values, between 20-30 Fr, between 25-27 Fr, etc.). The general transseptal steps can include transseptal puncture with a transseptal needle system via right atrium. The general transseptal steps can include placing a guidewire through the mitral valve into the left ventricle. The general transseptal steps can include removing transseptal needle system. The general transseptal steps can include leaving the guidewire in place.

The method can include anchor placement. The guide catheter 1002, the steering catheter 1004, and/or the anchor catheter 1006 can be utilized for anchor placement. The method can include transseptally placing the guide catheter 1002 over the guidewire. This step can include angling to an appropriate angle such as about 90°. This step can include removing a dilator. This step can include removing the guidewire. The method can include inserting the steering catheter 1004 into the guide catheter 1002. The steering catheter 1004 can include the anchor catheter 1006 disposed within the steering catheter 1004. The steering catheter 1004 can be advanced through the guide catheter 1002 until the tip of the steering catheter 1004 can be visualized, such as through transesophageal echocardiography (TEE) and/or fluoroscopy. The steering catheter 1004 can be advanced beyond the guide catheter 1002. In some embodiments, the steering catheter 1004 can be advanced about 5 cm beyond the guide catheter 1002. The method can include positioning the steering catheter 1004 to deliver the anchor catheter 1006. In some embodiments, the anchors are delivered separately. In some embodiments, the steering catheter 1004 can be moved to deliver each anchor. In some embodiments, the anchor catheter 1006 can be moved to deliver each anchor. The anchor can include features of any anchor described herein.

Figure 99A:
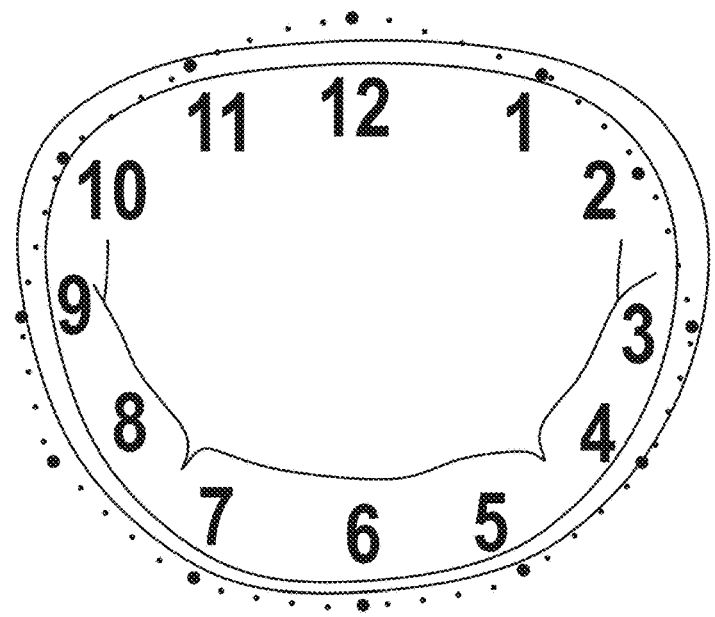
FIGS. 99A-100B are views of subannular anchoring and anchor placement, according to some embodiments.
Figure 99B:
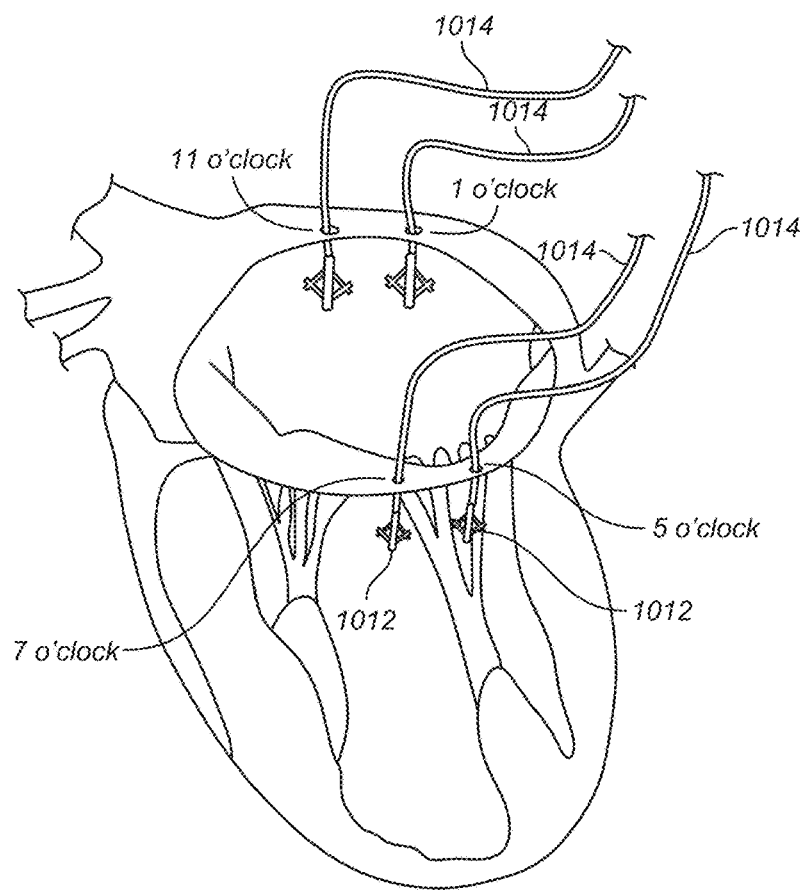

FIGS. 99-100 are views of subannular anchoring and anchor placement according to some embodiments. FIG. 99A illustrates the positions of the annulus. The steering catheter 1004 can be positioned at a desired location, e.g., the 5 o'clock position on annulus. The anchor catheter 1006 can be pushed against the annulus. The anchor catheter 1006 can include a RF needle, microwave tip, ultrasonic tool, or the like to ablate a tissue pathway through the annulus. The anchor catheter 1006 can create a passage through the annulus. The anchor catheter 1006 can advance an anchor subannularly. In some embodiments, the anchor catheter 1006 can advance an anchor subannularly about 5-10 mm. Referring to FIG. 99B, the anchor catheter 1006 can deploy the anchor 1012. The anchor 1012 can be deployed by linearly advancing a pusher. After the anchor is deployed, the pusher and the RF needle can be withdrawn. The anchor catheter 1006 can be withdrawn. The anchor catheter 1006 can be repositioned. The steering catheter 1004 can be positioned at the 7 o'clock position on annulus. The anchor catheter 1006 can be positioned against the annulus and the RF needle can burn through the annulus. The anchor catheter 1006 can advance an anchor 1012 subannularly and deploy the anchor 1012. The pusher, the RF needle can be withdrawn from the 7 o'clock position. The steering catheter 1004 can positioned at the 11 o'clock position on annulus. The anchor catheter 1006 can positioned against the annulus and the RF needle can create a hole through the annulus. The anchor catheter 1006 can advance an anchor 1012 subannularly and deploy the anchor 1012. The pusher, the RF needle can be withdrawn from the 11 o'clock position. The steering catheter 1004 can positioned at the 1 o'clock position on annulus. The anchor catheter 1006 can be positioned against the annulus and the RF needle burns through the annulus. The anchor catheter 1006 can advance an anchor 1012 subannularly and deploy the anchor 1012. The pusher, the RF needle can be withdrawn from the 1 o'clock position. The anchors can be deployed in any order. The anchors can be deployed at the 5 o'clock, 7 o'clock, 11 o'clock, and 1 o'clock position on the annulus, or other clock positions. In some embodiments, a first anchor is spaced apart about 180 degrees circumferentially on the annulus with respect to a second anchor, and a third anchor is spaced apart about 180 degrees circumferentially on the annulus with respect to a fourth anchor, each anchor spaced apart from each other. In some embodiments, a first anchor and a third anchor (and/or a second anchor and a fourth anchor) can be spaced circumferentially about 60 degrees apart, such as between about 45 degrees and about 75 degrees apart. Two anchors can be deployed on the anterior annulus. Two anchors can be deployed on the posterior annulus. The anchor deployment can be symmetrical. The anchor deployment can enable the transvalvular band 500 to span the valve. Other positions are contemplated, as well as more or less than four anchors.

Figure 100A:
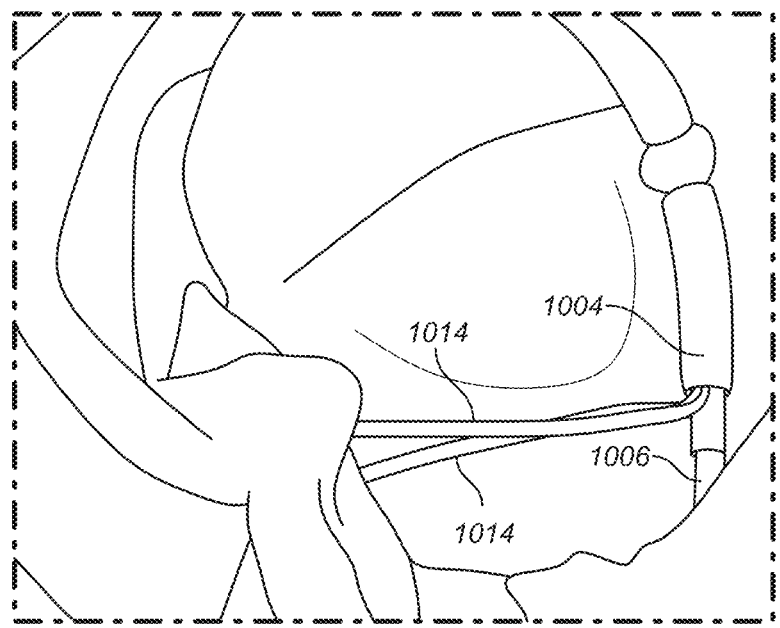
Figure 100B:
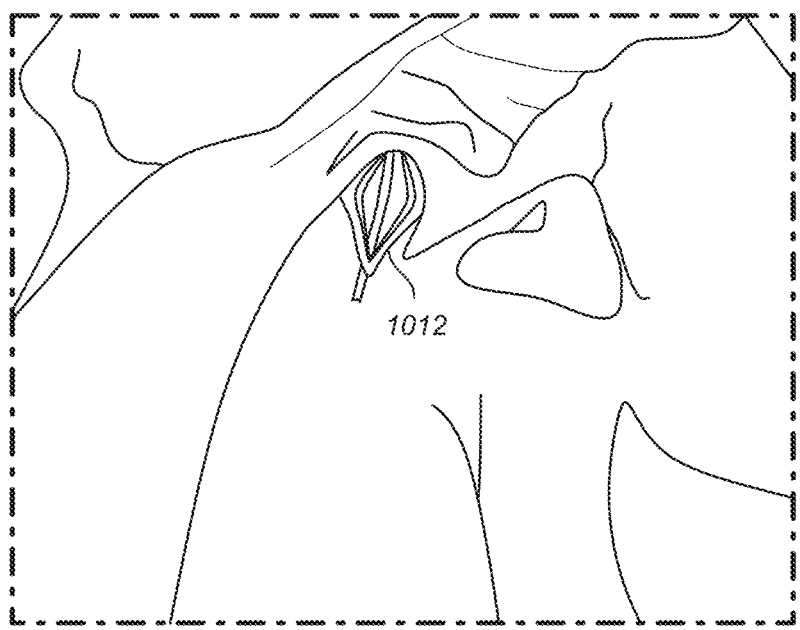

FIG. 99B illustrates the anchors deployed at the 5 o'clock, 7 o'clock, 11 o'clock, and 1 o'clock positions, according to some embodiments. The 5 o'clock and 7 o'clock positions can include the posterior anchors under the annulus. The 11 o'clock and 1 o'clock positions can include the anterior anchors under the annulus. In some embodiments, two or more anchors are delivered simultaneously. In some embodiments, two or more anchors are delivered sequentially. In some embodiments, four anchors are delivered. Each anchor 1012 can include a suture 1014, such that four anchors 1012 include four sutures 1014. In some methods of use, the four sutures 1014 can pass outside the body, extracorporeal, through the guide catheter 1002. The sutures 1014 can extend from the anchors 1012 and through the transcatheter system 1000. The sutures 1014 can remain outside of the body of the patient during the procedure. After the anchors 1012 are delivered, the sutures 1014 can be preliminary cinched for sizing of the transvalvular band 500. FIGS. 100A-100B illustrate anchor placement according to some embodiments. FIG. 100A illustrates two deployed sutures 1014 connected to deployed anchors, the steering catheter 1004, and the anchor catheter 1006. The deployed sutures 1014 can extend through the steering catheter 1004 and outside the body of the patient. The anchor catheter 1006 can be in position to deliver another anchor 1012. FIG. 100B illustrates a deployed anchor 1012, according to some embodiments.

Figure 101:
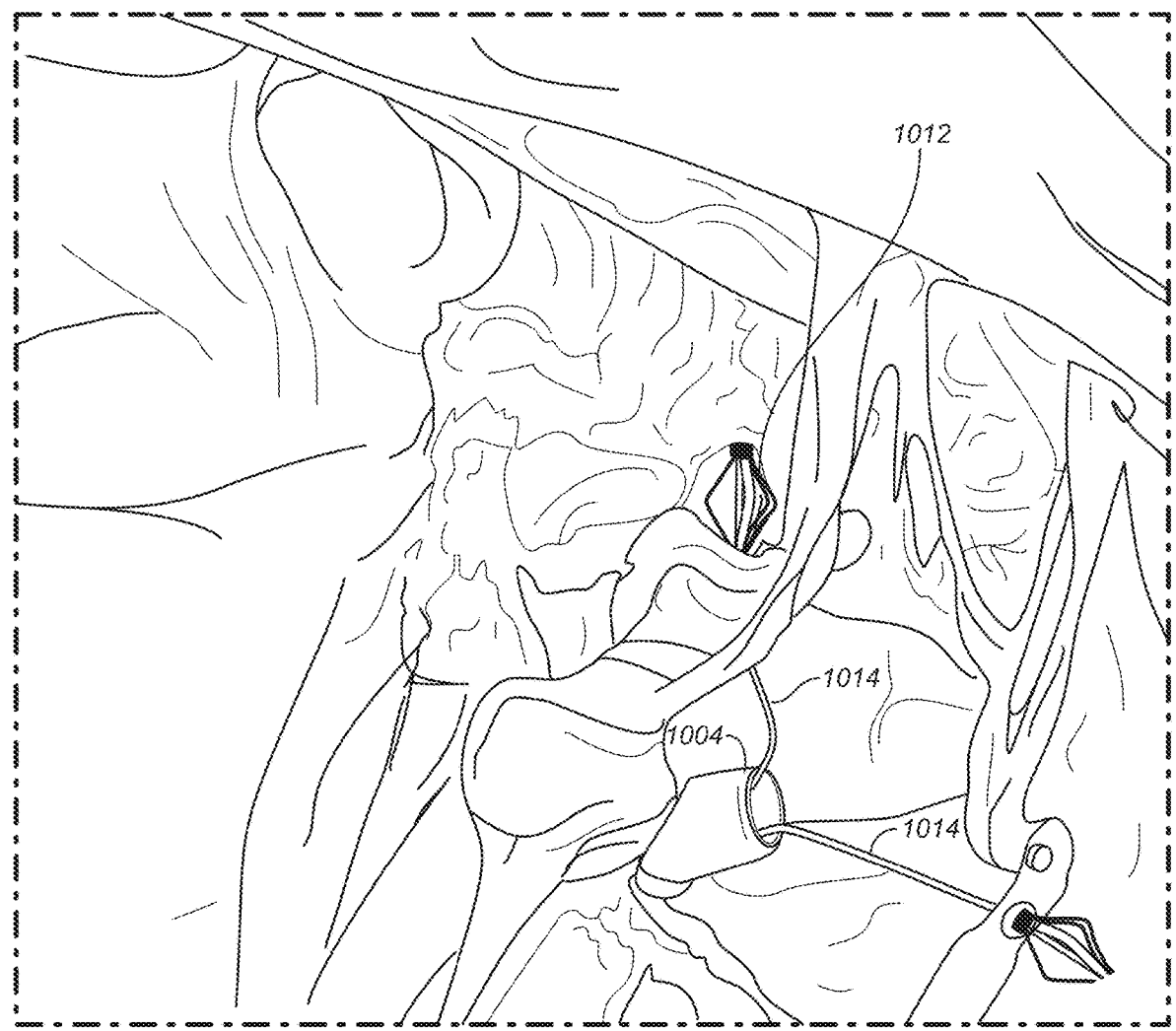
FIG. 101 is a view of preliminary cinching, according to some embodiments.

FIG. 101 is a view of preliminary cinching according to some embodiments. The four anchors 1012 can be deployed such that the four corresponding sutures extend through the annulus. The sutures can extend from the anchor to the steering catheter 1004. According to some embodiments, the sutures 1014 can be cinched together before delivery of the transvalvular band 500. In some embodiments, the preliminary cinching can allow for sizing of the transvalvular band 500. FIG. 101 is a view of the left ventricle. In some embodiments, the steering catheter 1004 can cinch the sutures 1014 by movement of the steering catheter 1004, such as movement toward the annulus.

The method can include delivery of the transvalvular band 500 or any other implant described herein, according to some embodiments. The delivery catheter 1008 and/or the trimming catheter 1010 can be utilized for delivery and securing of the transvalvular band 500. The method can include any of the following: inserting the delivery catheter 1008, deploying the transvalvular band 500, and cinching. The transvalvular band 500 can be threaded onto the four extracorporeal sutures 1014. Each suture 1014 can be threaded through an aperture 508 on the transvalvular band 500. As described herein, the four extracorporeal sutures 1014 can be coupled to the deployed subannular anchors 1012. Each suture can have a free end which can be threaded through the transvalvular band 500. In some methods of use, locking clips 1016 can be threaded onto the sutures 1014 after the transvalvular band 500 is threaded, such that a locking clip 1016 can be threaded onto each suture 1014. In some methods of use, the four sutures 1014 can be threaded through the distal end of the delivery catheter 1008 after the four sutures are threaded through the transvalvular band 500. The free ends of the four sutures 1014 can be pulled out the proximal end of the delivery catheter 1008. The transvalvular band 500 can be loaded into the guide catheter 1002 after being threaded onto the sutures 1014. In some embodiments, the transvalvular band 500 can be rolled or compressed to fit within the guide catheter 1002. The delivery catheter 1008 can be configured to push the transvalvular band 500 down the lumen of the guide catheter 1002. The delivery catheter 1008 can be configured to push the transvalvular band 500 along the sutures 1014. The delivery catheter 1008 can be configured to push the transvalvular band 500 through the distal end of guide catheter 1002. The delivery catheter 1008 can deliver the transvalvular band 500. In some embodiments, the transvalvular band 500 can unroll or expand within the heart of the patient. The transvalvular band 500 can be deployed into the left atrium. The delivery catheter 1008 can be configured to push the transvalvular band 500 along the sutures and toward the annulus. The transvalvular band 500 can be cinched into position on the annulus. The transvalvular band 500 can span the valve from the anterior leaflet to the posterior leaflet. Each locking clip 1016 can be advanced along the corresponding suture 1014 by a clip pusher. The locking clips 1016 can be secured to the transvalvular band 500 by advancing the clip pushers. The transvalvular band 500 can be pushed against the annulus and secured by the locking clips 1016. The delivery catheter 1008 can be removed after the transvalvular band 500 is secured.

The method can include trimming the sutures 1014 according to some embodiments. The suture 1014 can be fed into the trimming catheter 1010. The trimming catheter 1010 can be inserted into the guide catheter 1002. The trimming catheter 1010 can be advanced to the surface of the transvalvular band 500 and the locking clip 1016. The trimming catheter 1010 can be configured to cut the suture 1014. In some embodiments, the trimming catheter 1010 can be removed after trimming a suture 1014. Another suture can be fed into the trimming catheter 1010, and the trimming catheter 1010 can be inserted into the guide catheter 1002. The trimming catheter can be advanced toward the transvalvular band 500 and cut the corresponding suture 1014. The sequence can be repeated for all four sutures 1014. In some embodiments, after the sutures 1014 are trimmed, the guide catheter 1002 can be removed. The transvalvular band 500 can be implanted and secured. FIG. 71 illustrates the transvalvular band 500 with the locking clips securing the transvalvular band 500 according to some embodiments.

Figure 102A:
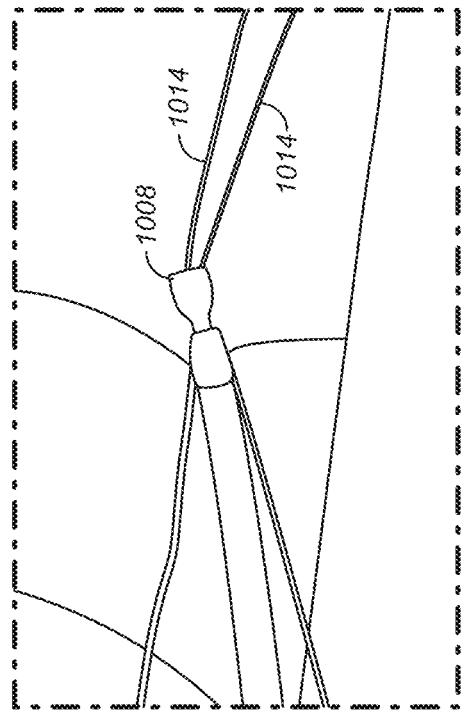
FIGS. 102A-102D are views of suture threading and insertion of the transvalvular bridge, according to some embodiments.
Figure 102B:
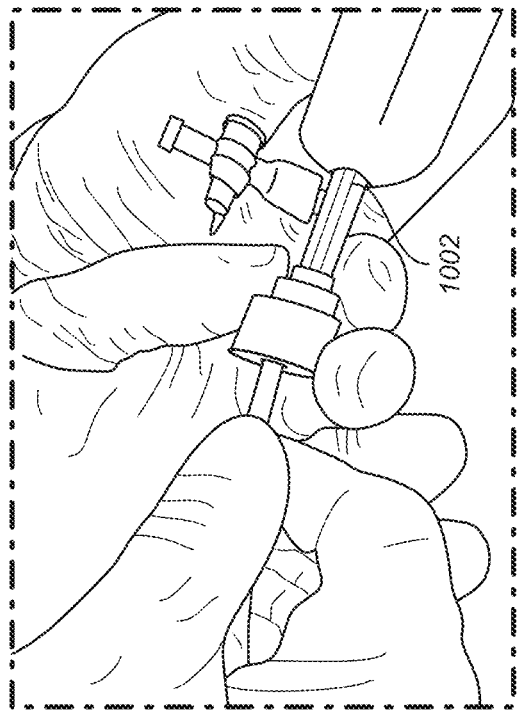
Figure 102C:
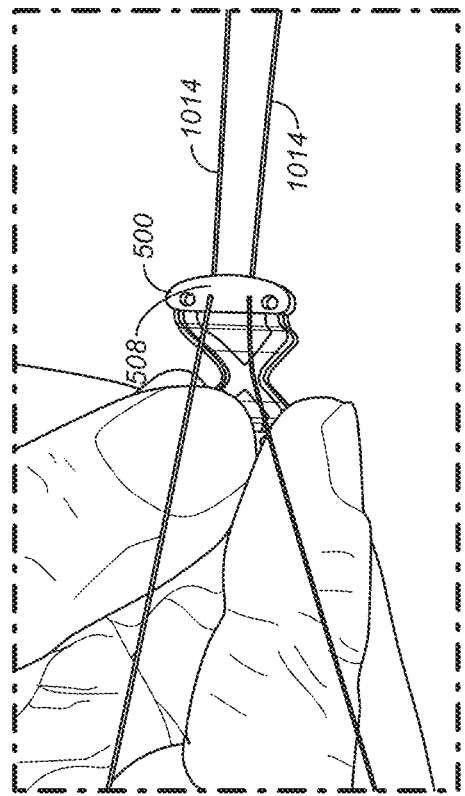
Figure 102D:
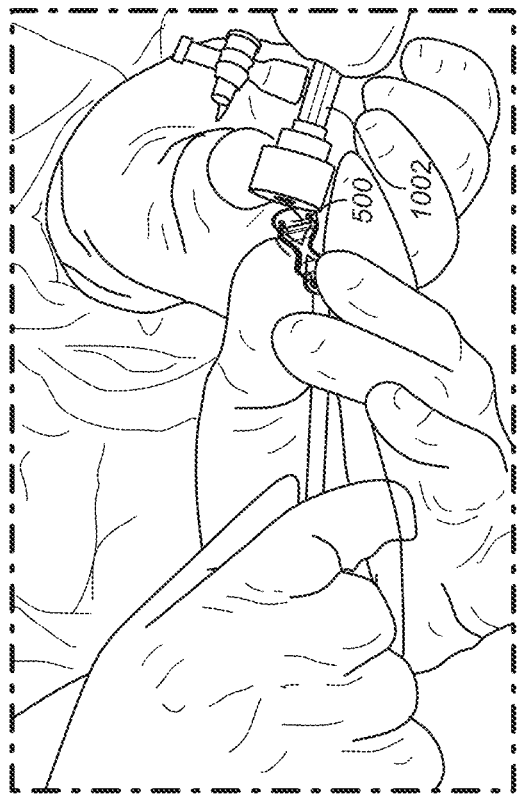

FIGS. 102A-102D are views of suture threading and insertion of the transvalvular bridge 500 according to some embodiments. FIG. 102A illustrates sutures 1014 threaded through the transvalvular band 500 according to some embodiments. Each suture 1014 can be threaded through an aperture 508 of the transvalvular band 500. FIG. 102B illustrates the sutures 1014 threaded into the delivery catheter 1008 according to some embodiments. FIG. 102C illustrates the transvalvular band 500 prior to loading in the guide catheter 1002 according to some embodiments. FIG. 102D illustrates pushing the transvalvular band 500 down the guide catheter 1002 according to some embodiments.

Figure 103A:
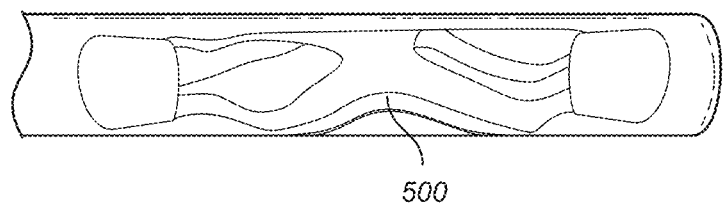
FIGS. 103A-103D are views of an embodiment of a transvalvular bridge.
Figure 103B:
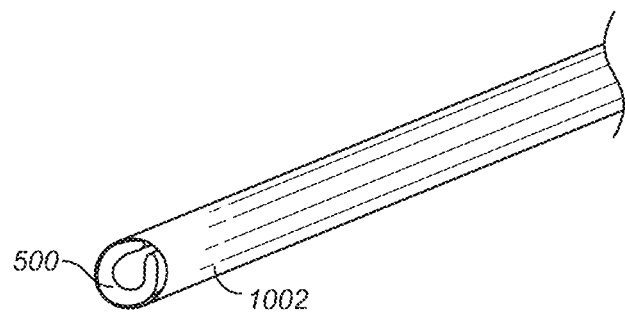
Figure 103C:
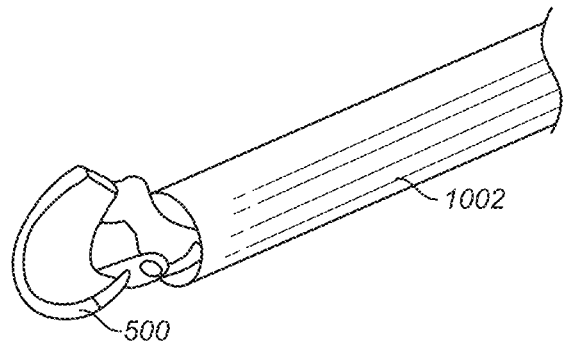
Figure 103D:
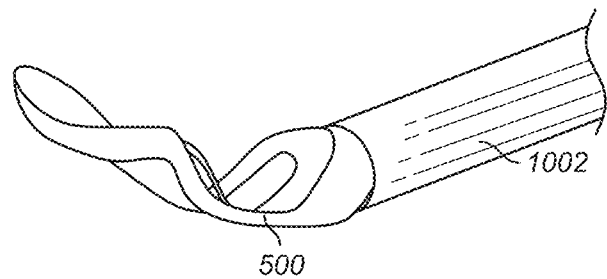

FIGS. 103A-103D are views of the transvalvular band 500 according to some embodiments. The transvalvular band 500 can be considered a bridge. In some embodiments, the transvalvular band 500 can be rolled to fit within the guide catheter 1002. The transvalvular band 500 can be rolled as shown in FIG. 103A. The transvalvular band 500 can be deployed by being pushed from the guide catheter 1002 as shown in FIG. 103B-103D. The transvalvular band 500 can fit within the inner diameter of the guide catheter 1002. In some embodiments, the transvalvular band 500 can fit within a 16 Fr inner diameter catheter. Other configurations are completed (e.g., fits within catheters of about, less than about, or more than about 10 Fr inner diameter, 12 Fr inner diameter, 14 Fr inner diameter, 18 Fr inner diameter, 20 Fr inner diameter, 22 Fr inner diameter, or ranges incorporating any of the foregoing values etc.). The transvalvular band 500 can be resilient to being rolled. In some embodiments, the transvalvular band 500 was tested after deployment, including 5 roll ups and deployment, and 750 million cycles. The transvalvular band 500 can be considered durable and showed no signs of damage or wear during the aforementioned test.

Figure 104:
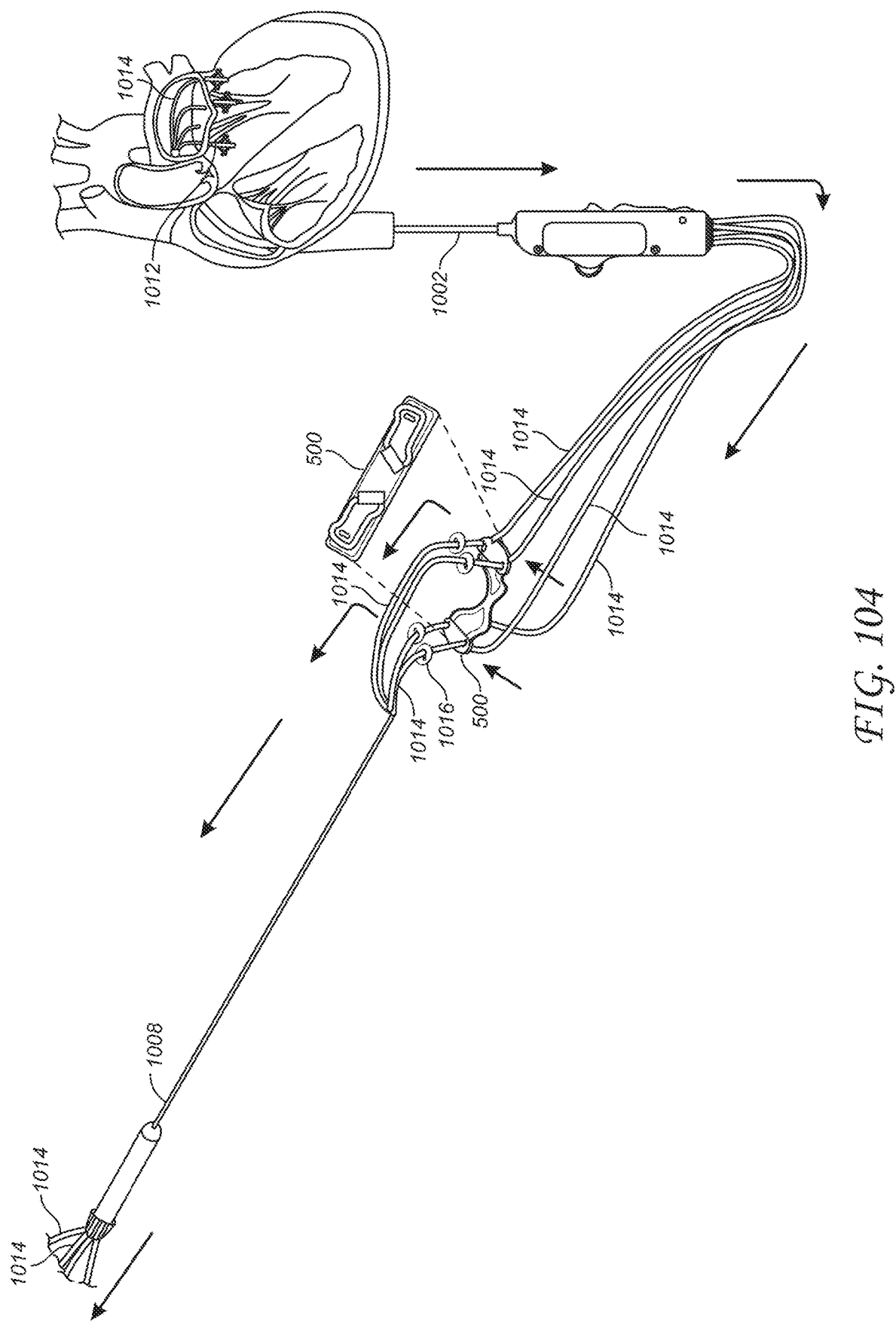
FIG. 104 is a schematic view of the threading of sutures, according to some embodiments.

FIG. 104 is a schematic view of the threading of sutures 1014 according to some embodiments. The anchors 1012 can be deployed in situ. Each anchor 1012 can be connected to a suture 1014. The anchors can be placed subannularly. In some embodiments, the sutures 1014 can extend through the annulus. The sutures 1014 can extend from the anchors 1012 in situ and through the guide catheter 1002. The sutures 1014 can extend from the guide catheter 1002 and through the transvalvular band 500. The sutures 1014 can extend from the transvalvular band 500 through the locking clips 1016. The sutures 1014 can be threaded through the transvalvular band 500 and the locking clips 1016. The threaded and crimped transvalvular band 500 can pass through the guide catheter 1002 as described herein. The sutures 1014 can extend from the locking clips 1016 through the delivery catheter 1008. The sutures 1014 can have free ends extending from the delivery catheter 1008. The sutures 1014 can extend out of the proximal end of the delivery catheter 1008. The sutures ends can be extracorporeal. The arrows show an example of the suture threading direction. The suture 1014 can be attached to an anchor 1012 which is subannularly placed. The suture 1014 can be passed through the guide catheter 1002. The suture 1014 can be threaded through the transvalvular band 500 and locking clips 1016. The threaded and crimped transvalvular band 500 according to some embodiments is shown in FIG. 104. The threaded and crimped transvalvular band 500 is sized to fit within the guide catheter 1002. The suture 1014 can pass through the delivery catheter 1008 and out the proximal end of the delivery catheter 1008.

Figure 105:
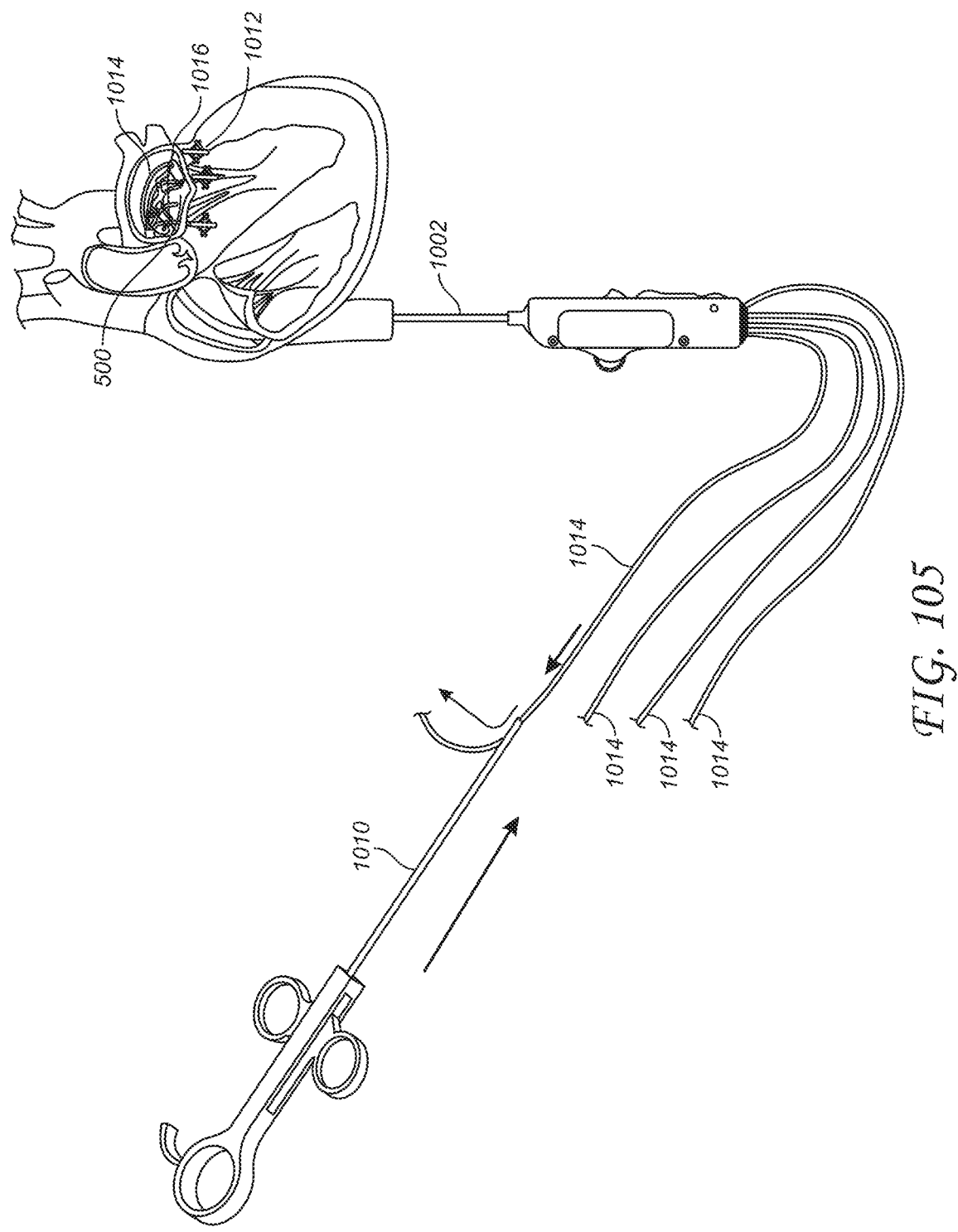
FIG. 105 is a schematic view of the trimming of sutures, according to some embodiments.

FIG. 105 is a schematic view of the trimming of sutures 1014, according to some embodiments. The anchors 1012 can be deployed in situ. Each anchor 1012 can be connected to a suture 1014. The sutures 1014 can extend from anchors 1012, through the transvalvular band 500, and through the locking clips 1016. The sutures 1014 can be threaded through the transvalvular band 500 and the locking clips 1016. The transvalvular band 500 can be positioned adjacent to the annulus and the locking clips 1016 can be secured. The sutures 1014 can extend from the locking clips 1016 and through the guide catheter 1002. The sutures 1014 can extend from the guide catheter 1002 to the trimming catheter 1010. The trimming catheter 1010 can be threaded onto each suture 1014. The suture 1014 is fed into the trimming catheter 1010. The trimming catheter 1010 can be advanced through the guide catheter 1002. The trimming catheter 1010 can be moved toward the transvalvular band 500 and locking clips 1016. The trimming catheter 1010 can be designed to stop at the surface of the transvalvular band 500 and locking clips 1016. The trimming catheter 1010 can cut the suture 1014. The sequence can be repeated three more times until each suture 1014 is trimmed. The red arrows show an example of the suture threading direction. The suture 1014 can be attached to an anchor 1012 which is subannularly placed. The suture 1014 can be threaded through the transvalvular band 500 and locking clips 1016. The suture 1014 can be passed through the guide catheter 1002. The suture 1014 passes through the trimming catheter 1010. The green arrows show the direction of the trimming catheter 1010. The suture 1014 is fed into the trimming catheter 1010. The trimming catheter 1010 can be advanced through the guide catheter 1002. The trimming catheter 1010 can stop at the surface of the transvalvular band 500 and the locking clip 1016. The trimming catheter 1010 can cut the suture 1014. The sequence can be repeated.

Figure 106A:
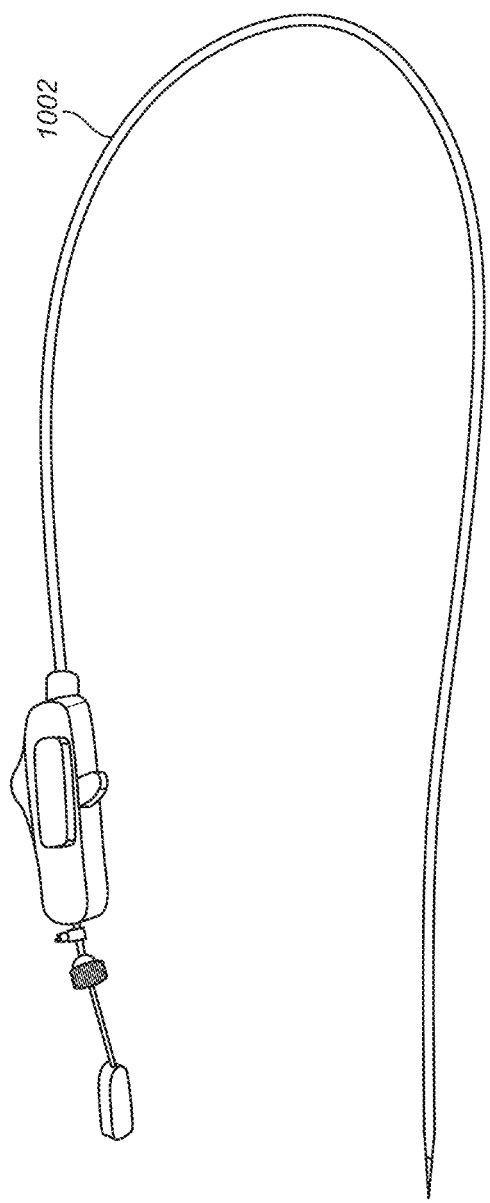
FIGS. 106A-106E are views of a transcatheter system, according to some embodiments.

FIGS. 106A-106E are views of a transcatheter system according to some embodiments. FIG. 106A illustrates the guide catheter 1002 according to some embodiments. The guide catheter 1002 can have any size outer diameter and length. The guide catheter 1002 can have a 24 Fr outer diameter. The guide catheter 1002 can have a 100 cm length. In some embodiments, the guide catheter 1002 has an outer diameter of 14 Fr, 16 Fr, 18 Fr, 20 Fr, 22 Fr, 24 Fr, 26 Fr, 28 Fr, 30 Fr, 32 Fr, 34 Fr, or ranges incorporating any of the foregoing values, between 20-30 Fr, about 24 Fr, etc. In some embodiments, the guide catheter 1002 has a length of 70 cm, 80 cm, 90 cm, 100 cm, 110 cm, 120 cm, 130 cm, or ranges incorporating any of the foregoing values, between 90-110 cm, about 100 cm, etc. The guide catheter 1002 can have a single lumen. The guide catheter 1002 can be steerable. For instance, a handle of the guide catheter 1002 can control a flexible tip. The guide catheter 1002 can be a 90° Bi-directional catheter.

Figure 106B:
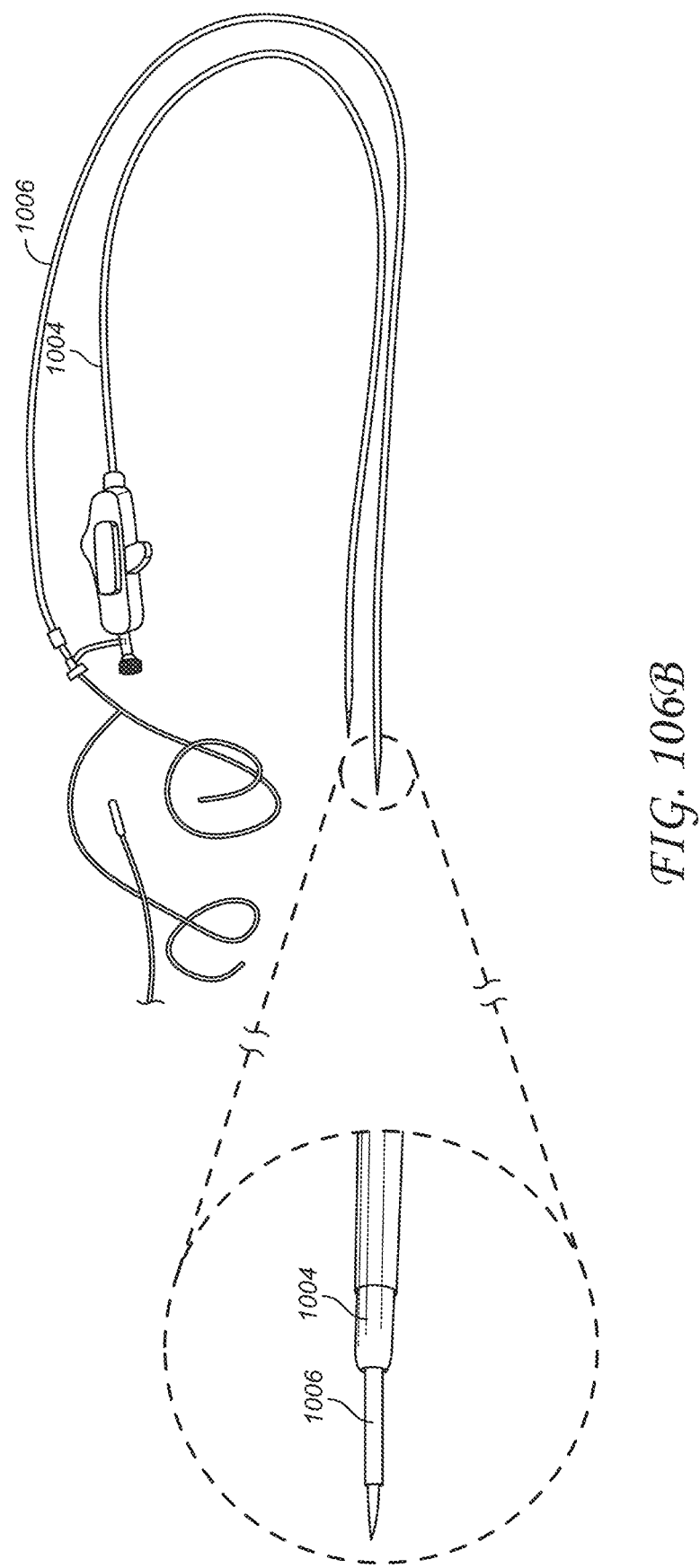
Figure 106C:
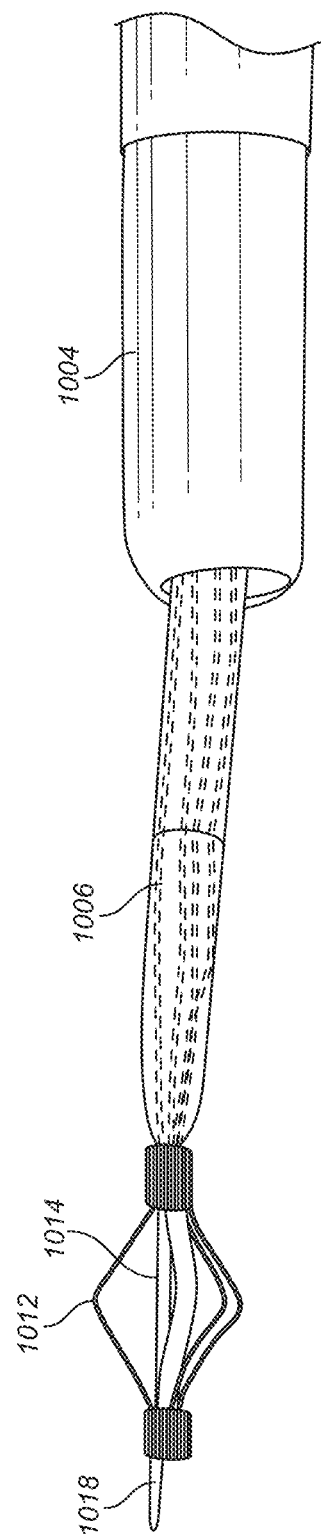

FIGS. 106B-106C illustrates the steering catheter 1004 according to some embodiments. The steering catheter 1004 can provide left atrium steering. The steering catheter 1004 can have any size outer diameter and length. The steering catheter 1004 can have a 12 Fr outer diameter. The steering catheter 1004 can have a 110 cm length. In some embodiments, the steering catheter 1004 has an outer diameter of 2 Fr, 4 Fr, 6 Fr, 8 Fr, 10 Fr, 12 Fr, 14 Fr, 16 Fr, 18 Fr, 20 Fr, 22 Fr, 24 Fr, or ranges incorporating any of the foregoing values, between 10-20 Fr, about 8 Fr, etc. In some embodiments, the steering catheter 1004 has a length of 70 cm, 80 cm, 90 cm, 100 cm, 110 cm, 120 cm, 130 cm, or ranges incorporating any of the foregoing values, between 100-120 cm, about 110 cm, etc. The steering catheter 1004 can be a 180° Bi-directional catheter. The steering catheter 1004 can have any bend radius. The steering catheter 1004 can have a 12.5 bend radius. In some embodiments, the steering catheter 1004 can have a bend radius of 8 mm, 8.5 mm, 9 mm, 9.5 mm, 10 mm, 10.5 mm, 11 mm, 11.5 mm, 12 mm, 12.5 mm, 13 mm, 13.5 mm, 14 mm, 14.5 mm, 15 mm, 15.5 mm, 16 mm, 16.5 mm, 17 mm, or ranges incorporating any of the foregoing values, between 10-15 mm, about 12.5 mm, etc.

FIGS. 106B-106C illustrates the anchor catheter 1006 according to some embodiments. The anchor catheter 1006 can be sized to be disposed within the steering catheter 1004. The anchor catheter 1006 can have any size outer diameter and length. The anchor catheter 1006 can have a 5.3 Fr outer diameter. The anchor catheter 1006 can have a 120 cm length. In some embodiments, the anchor catheter 1006 can have an outer diameter of 1 Fr, 2 Fr, 3 Fr, 4 Fr, 5 Fr, 6 Fr, 7 Fr, 8 Fr, 9 Fr, 10 Fr, 12 Fr, 14 Fr, 16 Fr, 18 Fr, 20 Fr, 22 Fr, 24 Fr, or ranges incorporating any of the foregoing values, between 1-10 Fr, about 5 Fr, etc. In some embodiments, the anchor catheter 1006 can have a length of 70 cm, 80 cm, 90 cm, 100 cm, 110 cm, 120 cm, 130 cm, 140 cm, 150 cm, or ranges incorporating any of the foregoing values, between 110-130 cm, about 120 cm, etc. The anchor catheter 1006 can be designed to provide a passage in the annulus. The anchor catheter 1006 can be designed to deliver RF energy to burn a hole in the annulus. The anchor catheter 1006 can be designed for anchor delivery through the annulus. The anchor catheter 1006 can provide pusher deployment of the anchor. FIG. 106C illustrates the distal end of the steering catheter 1004 and the anchor catheter 1006 according to some embodiments. The anchor 1012 can include a star design. The anchor 1012 can include, e.g., between about 10N and about 26 N of holding strength. The anchor 1012 can flatten with tension. The anchor 1012 can be inserted through the annulus in the flattened configuration. The anchor 1012 can be deployed by releasing the tension. FIG. 106C illustrates the steering catheter 1008 with the anchor catheter 1006 disposed within according to some embodiments. The anchor 1012 is shown in the illustrated embodiment in the deployed state according to some embodiments. In the compressed or flattened state, the anchor can have a 1 mm outer diameter. In the expanded or deployed state, the anchor can have a 6 mm outer diameter. Other configurations are completed, such as a flattened or compressed state having 0.5 mm outer diameter, 1.5 mm outer diameter, 2 mm outer diameter, 2.5 mm outer diameter, 3 mm outer diameter, 3.5 mm outer diameter, etc. Other configurations are completed, such as an expanded or deployed state having 4.5 mm outer diameter, 5 mm outer diameter, 5.5 mm outer diameter, 6.5 mm outer diameter, 7 mm outer diameter, 7.5 mm outer diameter, or ranges incorporating any of the foregoing values, etc. The anchor catheter 1006 can include an RF needle 1018. The RF needle 1018 can be disposed in the center of the anchor 1012. The anchor 1012 can deploy relative to the RF needle 1018. The RF needle 1018 can slide or be withdrawn relative to the anchor 1012. In some embodiments, the anchor catheter 1006 can include a pusher configured to push the anchor 1012 relative to the RF needle 1018. The anchor 1012 can be reversible. The anchor 1012 can transition from the compressed to expanded state, and vice versa. The anchor 1012 can be compressed after placement of the transvalvular bridge 500. The anchor 1012 can be compressed to remove the anchor 1012. The anchor 1012 can be compressed to remove the transvalvular bridge 500.

Figure 106D:
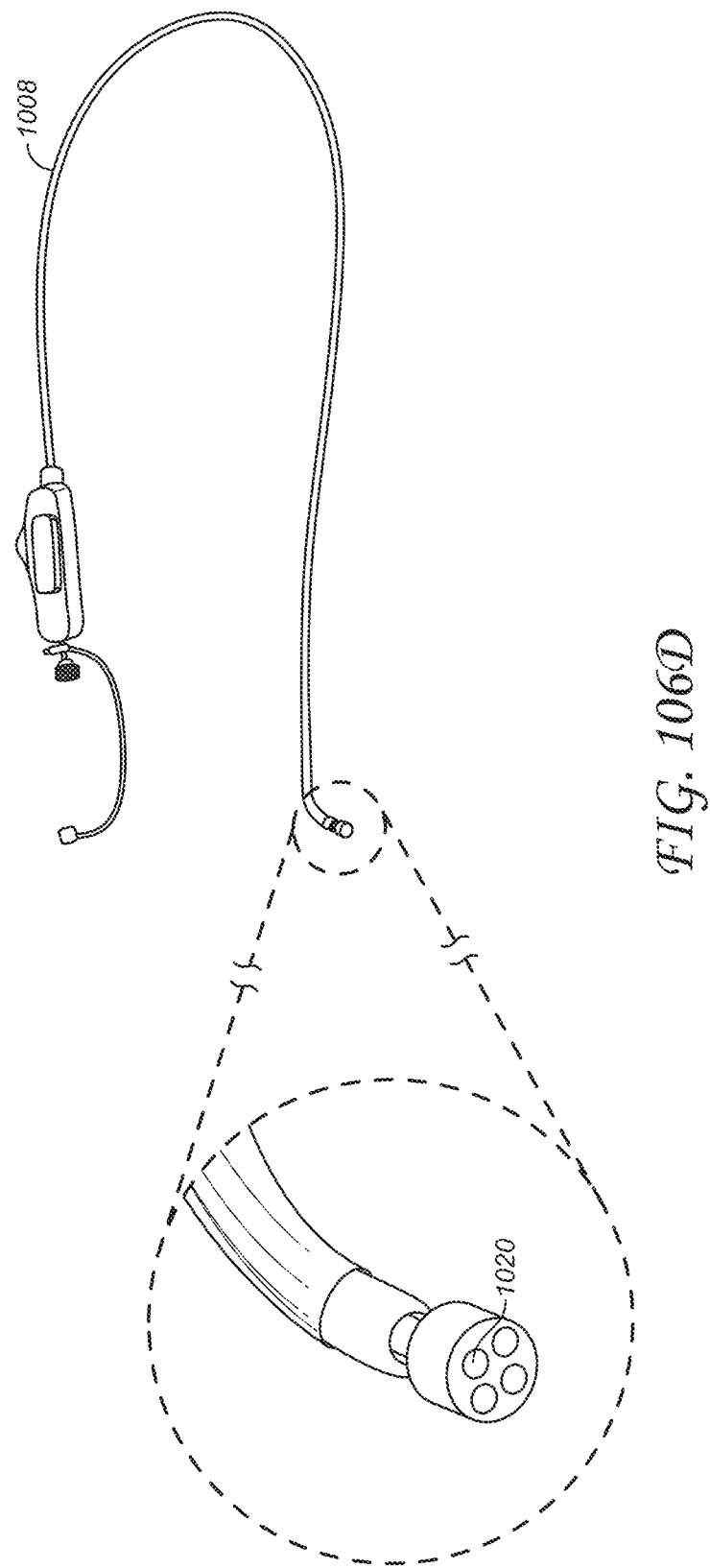

FIG. 106D illustrates a delivery catheter 1008 according to some embodiments. The delivery catheter 1008 can function for deployment of the transvalvular bridge 500 or any implant described herein. The delivery catheter 1008 can function for suture management and/or cinching. The delivery catheter 1008 can have any size outer diameter and length. The delivery catheter 1008 can have a 12 Fr outer diameter. The delivery catheter 1008 can have a 120 cm length. In some embodiments, the delivery catheter 1008 has an outer diameter of 1 Fr, 2 Fr, 3 Fr, 4 Fr, 5 Fr, 6 Fr, 7 Fr, 8 Fr, 9 Fr, 10 Fr, 12 Fr, 14 Fr, 16 Fr, 18 Fr, 20 Fr, 22 Fr, 24 Fr, or ranges incorporating any of the foregoing values, between 1-10 Fr, about 8 Fr, etc. In some embodiments, the delivery catheter 1008 has a length of 70 cm, 80 cm, 90 cm, 100 cm, 110 cm, 120 cm, 130 cm, 140 cm, 150 cm, or ranges incorporating any of the foregoing values, between 110-130 cm, about 120 cm, etc. The delivery catheter 1008 can be steerable. The delivery catheter 1008 can be a 180° Bi-directional catheter. The delivery catheter 1008 can have any bend radius. The delivery catheter 1008 can have a 12.5 bend radius. In some embodiments, the delivery catheter 1008 can have a bend radius of 8 mm, 8.5 mm, 9 mm, 9.5 mm, 10 mm, 10.5 mm, 11 mm, 11.5 mm, 12 mm, 12.5 mm, 13 mm, 13.5 mm, 14 mm, 14.5 mm, 15 mm, 15.5 mm, 16 mm, 16.5 mm, 17 mm, or ranges incorporating any of the foregoing values, between 10-15 mm, about 12.5 mm, etc. The delivery catheter 1008 can function detangle the sutures. The delivery catheter 1008 can function to detangle or prevent tangles of any suture described herein. The delivery catheter 1008 can include four ports 1020 to manage the sutures 1014, e.g., one port per suture. Each suture 1014 can be threaded through a port 1020 of the delivery catheter 1008. The number of ports 1020 can correspond to the number of apertures 508 of the transvalvular bridge 500. The number of ports 1020 can correspond to the number of sutures 1014. The delivery catheter 1008 can function to push or move one or more components. The delivery catheter 1008 can push the locking clips 1016 toward the transvalvular band 500. The delivery catheter 1008 can include one or more pushers to advance the locking clips 1016 toward the transvalvular band 500 as described herein.

Figure 106E:
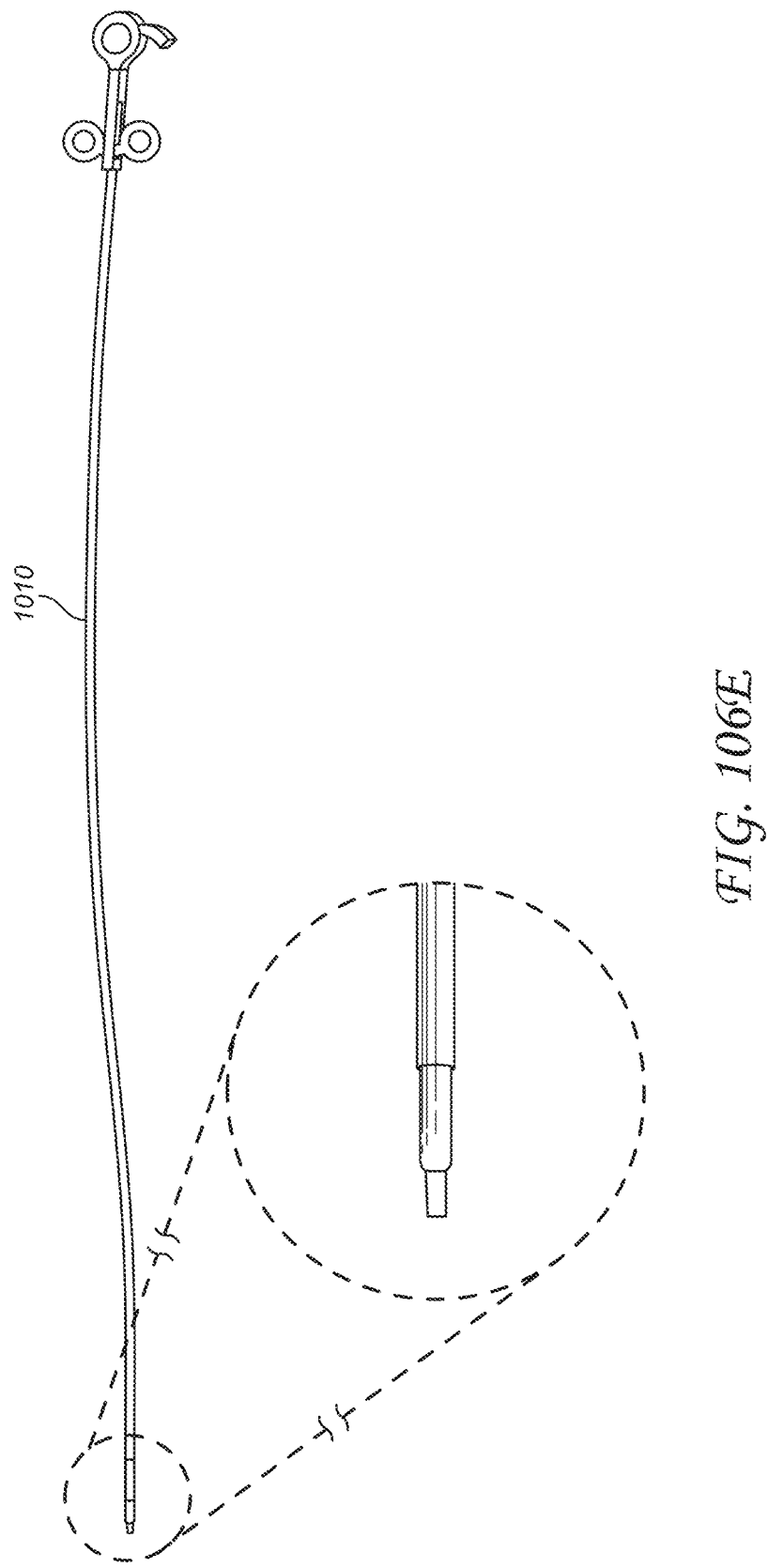

FIG. 106E illustrates the trimming catheter 1010 according to some embodiments. The trimming catheter 1010 can function to cut the sutures 1014 to a desired length. The trimming catheter 1010 can have any size outer diameter and length. The trimming catheter 1010 can have a 12 Fr outer diameter. The trimming catheter 1010 can have a 120 cm length. In some embodiments, the trimming catheter 1010 has an outer diameter of 1 Fr, 2 Fr, 3 Fr, 4 Fr, 5 Fr, 6 Fr, 7 Fr, 8 Fr, 9 Fr, 10 Fr, 12 Fr, 14 Fr, 16 Fr, 18 Fr, 20 Fr, 22 Fr, 24 Fr, or ranges incorporating any of the foregoing values, between 1-10 Fr, about 8 Fr, etc. In some embodiments, the trimming catheter 1010 has a length of 70 cm, 80 cm, 90 cm, 100 cm, 110 cm, 120 cm, 130 cm, 140 cm, 150 cm, or ranges incorporating any of the foregoing values, between 110-130 cm, about 120 cm, etc. The trimming catheter 1010 can be guided over a suture 1014. The trimming catheter 1010 can pass through the guide catheter 1002. The trimming catheter 1010 can provide a repeatable post-cut length of the suture. The trimming catheter 1010 can cut the suture to be approximately 5 to 7 mm. Other lengths are contemplated, e.g., 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, or ranges incorporating any of the foregoing values, etc. The trimming catheter 1010 can include a single cutting port for suture. The trimming catheter 1010 can be designed to cut one suture at a time, or a plurality of sutures simultaneously.

Figure 107A:
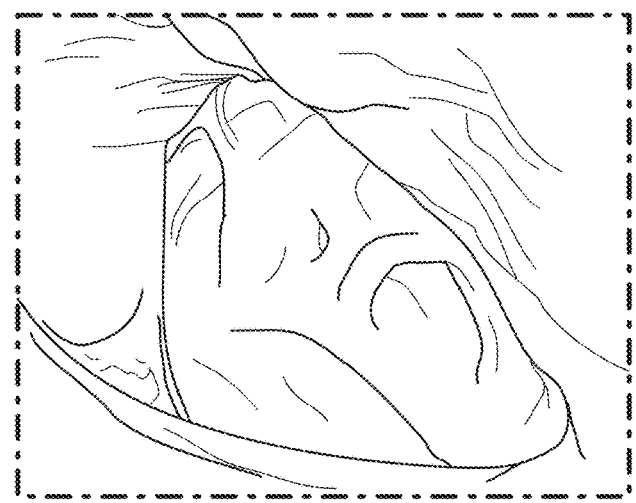
FIGS. 107A-107C are views of transseptal access, according to some embodiments.
Figure 107B:
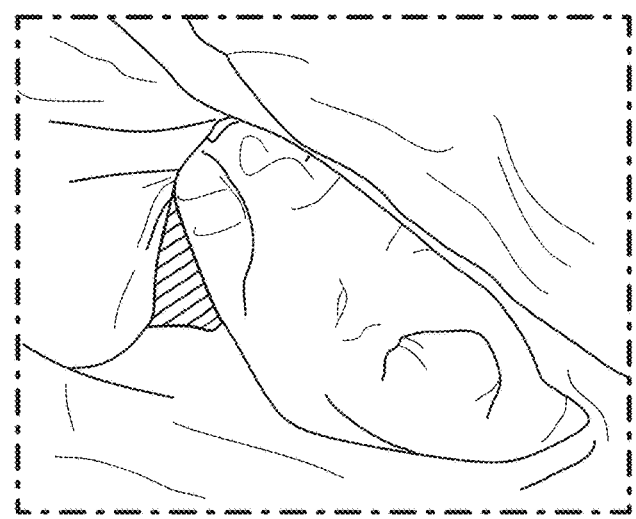
Figure 107C:
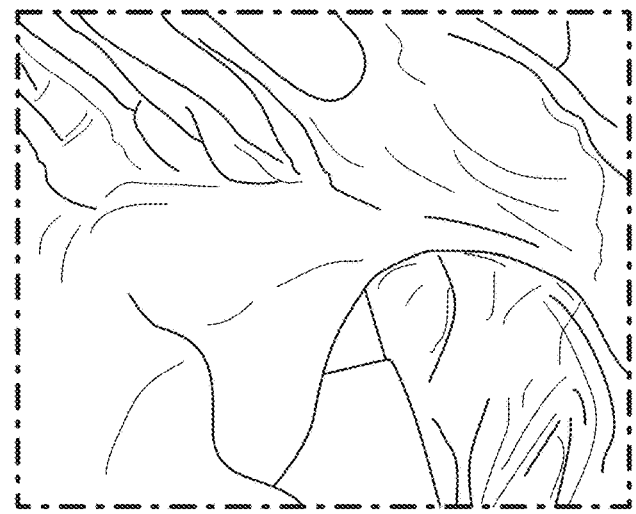

FIGS. 107A-107C are views of transseptal access according to some embodiments. FIG. 107A illustrates the general steps of transseptal access according to some embodiments. The introducer can be placed in the right femoral vein or another access point. FIG. 107B illustrates transseptal puncture with a dilator inserted through the atrial septum according to some embodiments. FIG. 107C is a view of the posterior leaflet after transseptal access according to some embodiments.

Figure 108A:
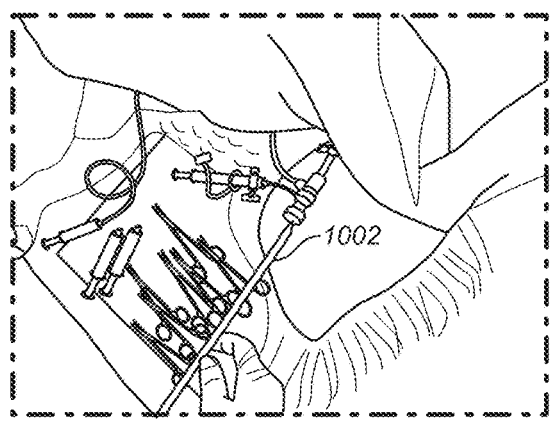
FIGS. 108A-108C are views of introduction of the transcatheter system, according to some embodiments.
Figure 108B:
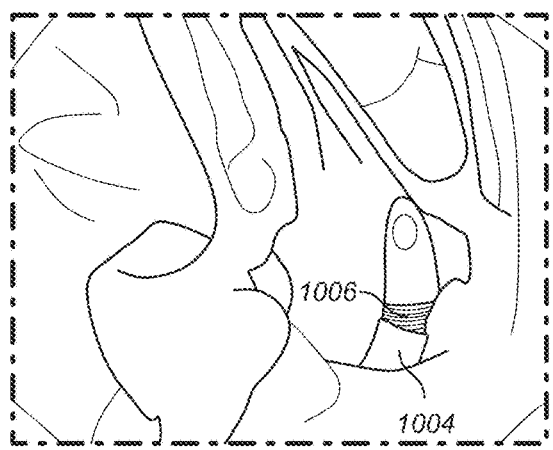
Figure 108C:
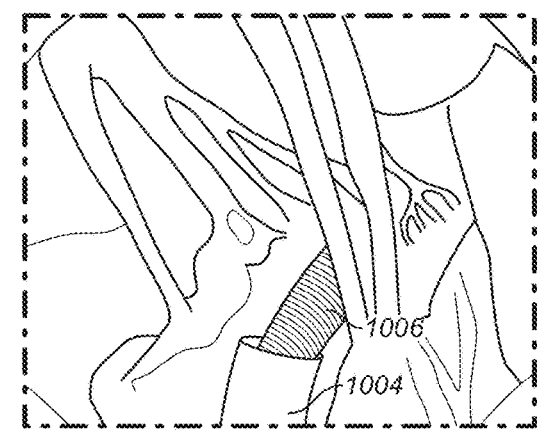

FIGS. 108A-108C are views of introduction of the transcatheter system 1000 according to some embodiments. FIG. 108A illustrate an introducer according to some embodiments. As described herein, the introducer can be a 24 Fr introducer catheter. The guide catheter 1002 can be inserted into the introducer. FIGS. 108B-108C illustrate the steering catheter 1004 and the anchor catheter 1006 according to some embodiments. The posterior leaflet and the anterior leaflet are also identified.

Figure 109A:
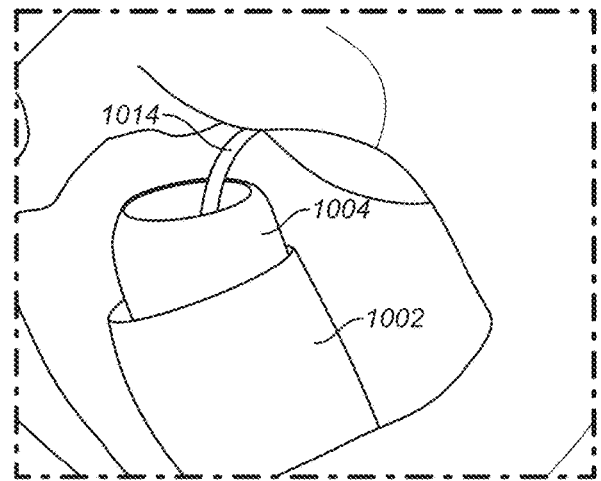
FIGS. 109A-110B are views of anchor deployment, according to some embodiments.
Figure 109B:
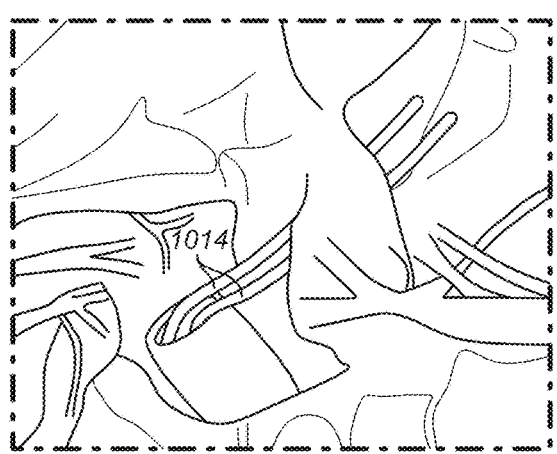
Figure 109C:
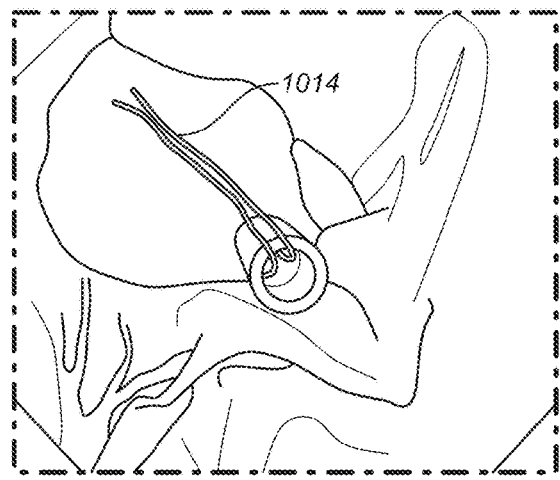
Figure 109D:
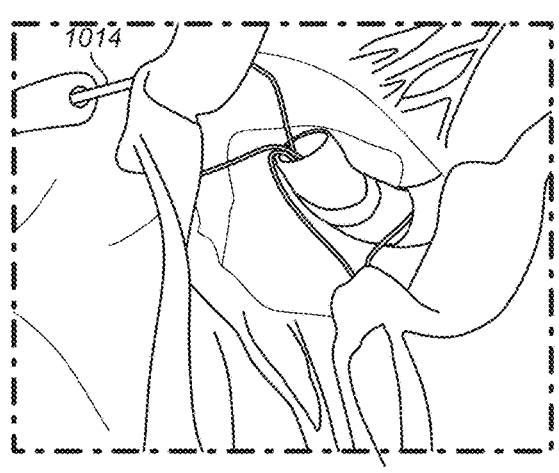
Figure 110A:
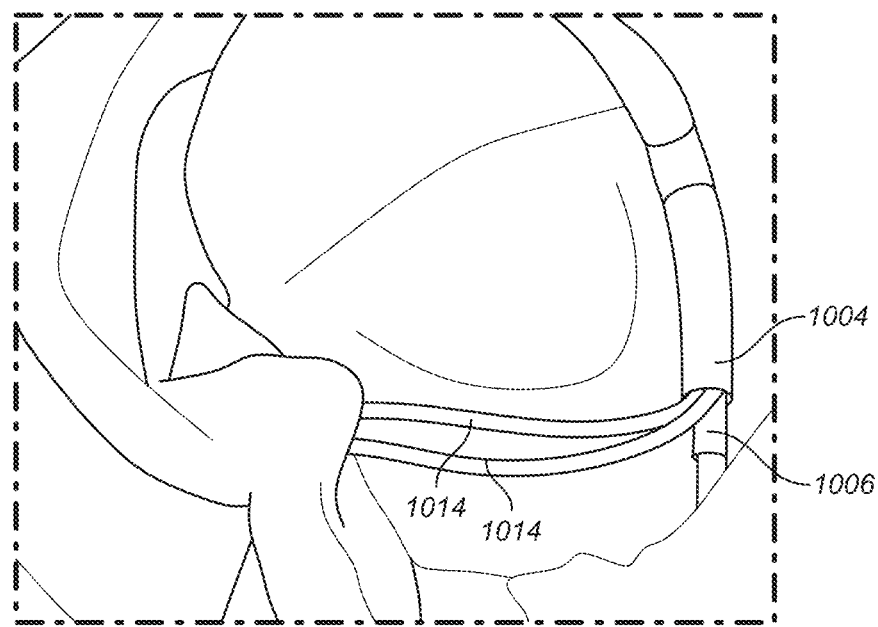
Figure 110B:
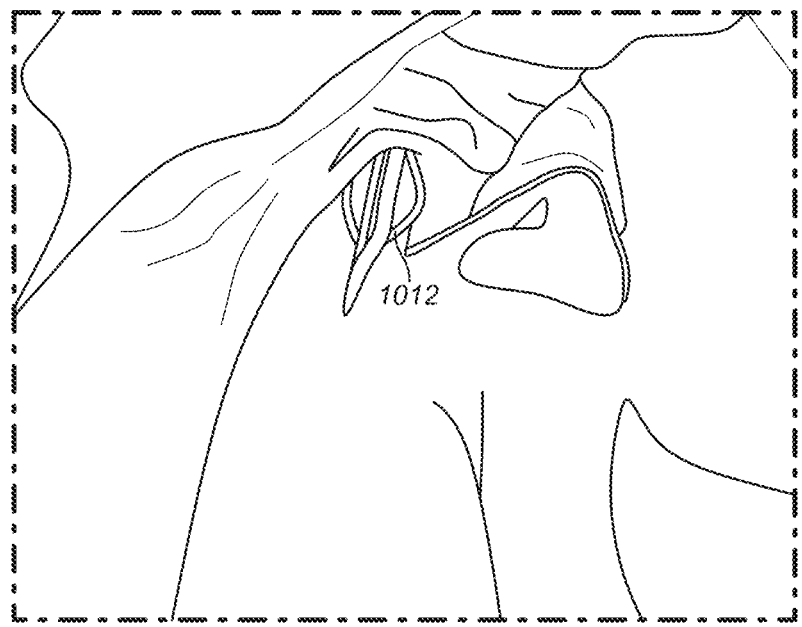

FIGS. 109A-110B are views of anchor deployment according to some embodiments. FIG. 109A illustrates the guide catheter 1002 and the steering catheter 1004 according to some embodiments. FIG. 109B illustrates two sutures 1014 deployed according to some embodiments. FIG. 109C illustrates another view of the two deployed sutures 1014, which are coupled to subannular anchors 1012. FIG. 109D illustrates a view of three deployed sutures 1014. The posterior leaflet and the anterior leaflet are also identified. FIG. 110A illustrate the steering catheter 1004 and the anchor catheter 1006 according to some embodiments. The deployed sutures 1014 are shown. The anchor catheter 1006 is illustrated deploying the last of the four anchors according to some embodiments. FIG. 110B illustrates another view of the anchor 1012. The aortic valve is shown. The anchor 1012 can be pushed through the annulus after the RF needle creates a passage. The anchor 1012 can be in a compressed state when the anchor 1012 is passed through the annulus. The anchor 1012 can be deployed by releasing the tension on the anchor 1012. Other configurations are contemplated such as a shape memory material to deploy the anchor or a mechanical force to deploy the anchor. The enlarged outer diameter of the deployed anchor 1012 can prevent or limit the anchor 1012 from passing back through the annulus.

Figure 111A:
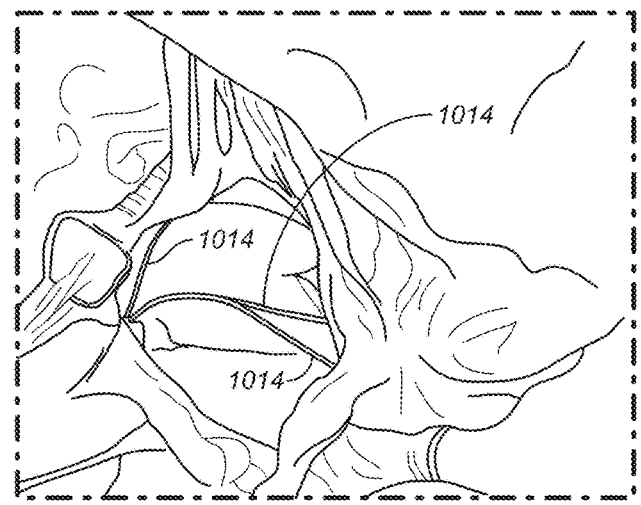
FIGS. 111A-111C are views of cinching, according to some embodiments.
Figure 111B:
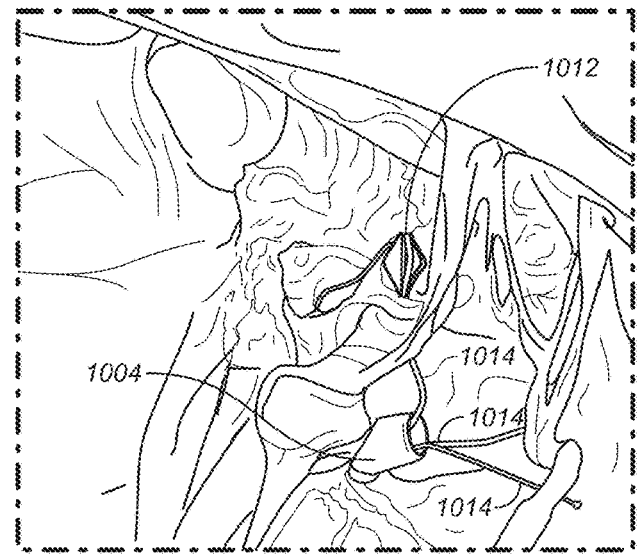
Figure 111C:
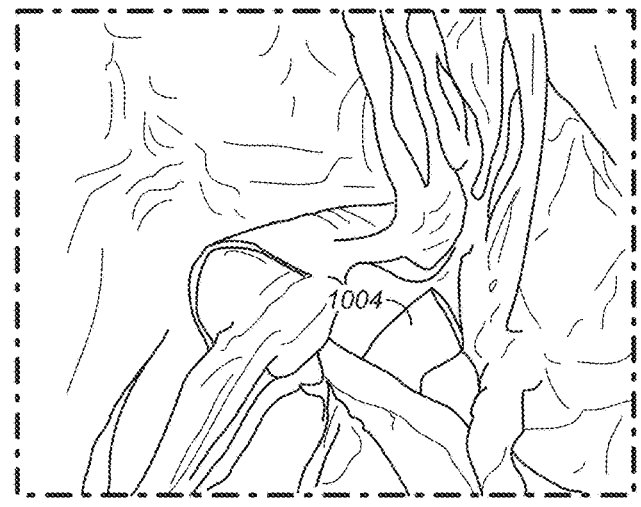

FIGS. 111A-111C are views of cinching according to some embodiments. FIG. 111A illustrates four deployed sutures 1014 according to some embodiments. The sutures 1014 can be coupled to subannular anchors 1012. FIG. 111B illustrates the steering catheter 1004, the sutures 1014, and the anchor 1012 connected to one of the sutures 1014. FIG. 111C illustrates the fully cinched sutures 1014 according to some embodiments. The posterior leaflet and the anterior leaflet are also identified. The aortic valve is shown.

Figure 112A:
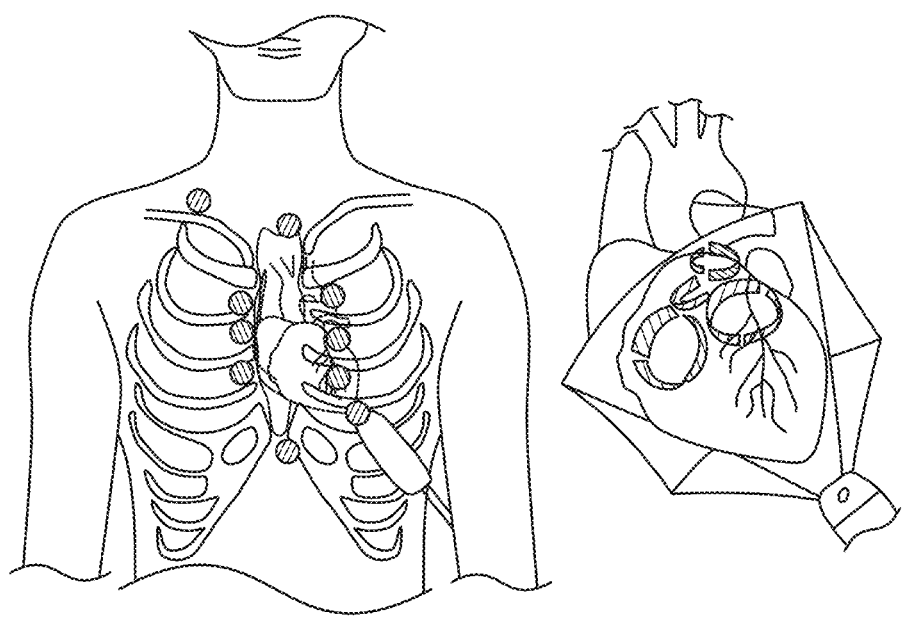
FIGS. 112A-112B are schematic views of transducer positions and planes of the heart, according to some embodiments.
Figure 112B:
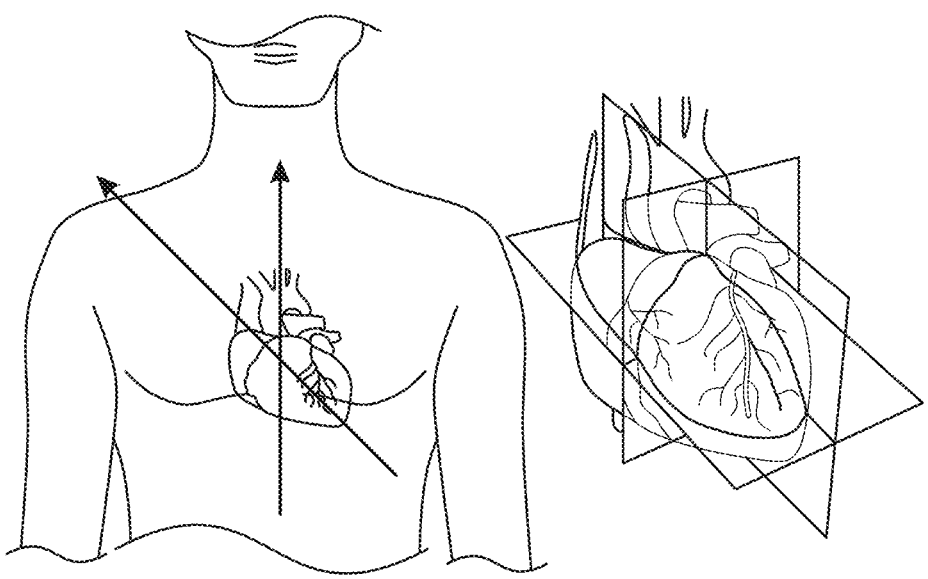

FIG. 112A is a schematic view of transducer positions according to some embodiments. FIG. 112B shows the 3D echo full volume image at one transducer position. The heart has three planes: the long axis or sagittal plane, the short axis or transverse plane, and the four-chamber or oblique coronal plane. The transducer positions can provide various views of the heart.

Advantages can include any of the following related to the placement and coaxial nature of the one or more catheters. The transcatheter system 1000 can provide catheters configured to be disposed within one another. As described herein, the guide catheter 1002 can provide a transseptal conduit to the left atrium. The guide catheter 1002 can have an inner diameter sized to accept one or more other catheters. For instance, the guide catheter 1002 can accept the steering catheter 1004 therethrough. The guide catheter 1002 can accept the anchor catheter 1006 therethrough. In some embodiments, the guide catheter 1002 can accept the steering catheter 1004 therethrough, and the steering catheter 1004 can accept the anchor catheter 1006 therethrough. In some embodiments, the steering catheter 1004 and the anchor catheter 1006 can be removed after one or more anchors are installed. In some methods of use, the steering catheter 1004 and the anchor catheter 1006 can be removed after four anchors are installed. The guide catheter 1002 can remain in place as a transseptal conduit to the left atrium after the steering catheter 1004 and the anchor catheter 1006 are removed. The guide catheter 1002 can accept the delivery catheter 1008 therethrough. In some embodiments, the delivery catheter 1008 can be removed after the transvalvular band 500 is positioned. In some embodiments, the delivery catheter 1008 can be removed after the transvalvular band 500 is secured by the locking clips 1016. The guide catheter 1002 can remain in place as a transseptal conduit to the left atrium after the delivery catheter 1008 is removed. The guide catheter 1002 can accept the trimming catheter 1010 therethrough. In some embodiments, the trimming catheter 1010 can be removed after cutting each suture 1014. In some embodiments, the trimming catheter 1010 can be removed after cutting a plurality of sutures 1014. The guide catheter 1002 can be removed after the sutures 1014 are cut.

Also, advantages can include any of the following related to the function of the one or more catheters. The transcatheter system 1000 can provide the following functions or purposes related to anchor delivery. The guide catheter 1002 can be designed to provide a conduit to the left atrium. In some embodiments, an introducer and/or dilator can puncture the atrial septum. The guide catheter 1002 can be positioned to provide access to the valve. The steering catheter 1004 can be designed to be steerable to the annulus. The steering catheter 1004 can include a bend radius allowing the tip to position near the annulus. The steering catheter 1004 can guide the anchor catheter 1006 to various locations on the annulus. The steering catheter 1004 can position the anchor catheter 1006 at the 5 o'clock position to deliver an anchor 1012. The steering catheter 1004 can position the anchor catheter 1006 at the 7 o'clock position to deliver an anchor 1012. The steering catheter 1004 can position the anchor catheter 1006 at the 11 o'clock position to deliver an anchor 1012. The steering catheter 1004 can position the anchor catheter 1006 at the 1 o'clock position to deliver an anchor 1012. The steering catheter 1004 can position the anchor catheter 1006 at any position on the annulus to deliver an anchor 1012. The steering catheter 1004 can position the anchor catheter 1006 at two positions on the posterior leaflet or posterior annulus to deliver two anchors 1012. The steering catheter 1004 can position the anchor catheter 1006 at two positions on the anterior leaflet or anterior annulus to deliver two anchors 1012. The steering catheter 1004 can position the anchor catheter 1006 at four positions on the annulus to deliver four anchors 1012.

Furthermore, advantages can include any of the following related to the function of one or more catheters. The transcatheter system 1000 can provide the following functions or purposes related to implant delivery. The delivery catheter 1008 can deliver the transvalvular band 500. The delivery catheter 1008 can slide the transvalvular band 500 along the sutures 1014 which are attached to the subannular anchors 1012. The guide catheter 1002 can be sized to accept the transvalvular band 500 in a collapsed configuration. The delivery catheter 1008 can be designed to separate the four sutures 1014. The delivery catheter 1008 can be designed to limit or prevent tangles of the sutures 1014 within the guide catheter 1002. The delivery catheter 1008 can be designed to facilitate sliding of the transvalvular band 500 along the sutures 1014. The delivery catheter 1008 can be designed to facilitate sliding of the transvalvular band 500 along the sutures 1014 and toward the annulus. The delivery catheter 1008 can be designed to facilitate sliding of the locking clips 1016 toward the transvalvular band 500 along the sutures 1014. The delivery catheter 1008 can be designed to accommodate a clip pusher on each suture 1014 to push the locking clip 1016 along the suture 1014. The delivery catheter 1008 can be designed to position the transvalvular band 500 relative to the annulus. The delivery catheter 1008 can be designed to secure the transvalvular band 500 relative to the annulus. The trimming catheter 1010 can be designed to trim the sutures 1014 after the transvalvular band 500 is secured. The trimming catheter 1010 can be designed to trim one suture 1014 at a time. The trimming catheter 1010 can be designed to slide along the suture toward the locking clip 1016 and the transvalvular band 500. The trimming catheter 1010 can be designed to cut the suture close or substantially close to the locking clip 1016.

Moreover, advantages can include any of the following related to surgical technique and procedure management. The transcatheter system 1000 can provide an intuitive and easy system to deliver the transvalvular band 500. Each catheter can be utilized in a step of a method. In some methods of use, the heart can be accessed via a transseptal puncture with one or more transseptal needles. The first step, according to some embodiments, can include transseptally placing the guide catheter 1002. The second step according to some embodiments, can include inserting the steering catheter 1004 with the anchor catheter 1006 inside. The third step according to some embodiments, can include positioning the steering catheter 1004 and delivering the anchors 1012. The fourth step according to some embodiments, can include inserting the delivery catheter to deploy the transvalvular band 500 and cinch. The fifth step according to some embodiments, can include inserting the trimming catheter 1010 to cut the sutures 1014.

In some embodiments, advantages can include any of the following related to anchor delivery. Each anchor 1012 can be attached to a suture 1014. Each anchor 1012 can be attached to a suture 1014 prior to delivery to the annulus. The sutures 1014 can be firmly and rigidly attached to the anchors 1012. In some embodiments, the suture 1014 can extend from the distal end of the anchor 1012 to the proximal end of the anchor 1012. In some embodiments, the suture 1014 can extend from the distal end of the anchor 1012 and through the anchor catheter 1006. In some embodiments, the anchor catheter 1006 can be designed to deliver a single anchor 1012. The anchor catheter 1006 can be designed to manage the suture 1014 attached to the single anchor 1012. The suture 1014 can extend from the anchor 1012 to the proximal end of the transcatheter system 1000. The suture 1014 can extend from the anchor 1012 to outside the body of the patient. In some embodiments, the anchor catheter 1006 can be steerable. In some embodiments, the steering catheter 1004 can be designed to steer and position the anchor catheter 1006. In some embodiments, the anchor catheter 1006 can deliver a second anchor 1012. In some embodiments, the anchor catheter 1006 can deliver all four anchors 1012. In some embodiments, the anchor catheter 1006 can be removed after delivery of an anchor 1012. In some embodiments, the anchor catheter 1006 can be reloaded with another anchor 1012 after delivery of an anchor 1012. In some embodiments, a second anchor catheter 1006 can be inserted into the steering catheter 1004 to deliver the second anchor 1012. The anchor catheter 1006 can be designed to manage one or more sutures 1014 extending therethrough. In some embodiments, the anchor catheter 1006 can include one or more channels or grooves to accommodate the suture 1014.

Still further, advantages can include any of the following related to the one or more anchors. The anchor 1012 can have a compressed configuration in which the anchor 1012 has a smaller outer diameter. In some embodiments, the anchor catheter 1006 can apply tension to the anchor 1012 to collapse the anchor 1012. The anchor 1012 can have an expanded configuration in which the anchor 1012 has a larger outer diameter. In some embodiments, the anchor catheter 1006 can release tension to the anchor 1012 to expand the anchor 1012. In some embodiments, the anchor catheter 1006 can remove a constraint on the anchor 1012 to expand the anchor 1012. In some embodiments, the anchor catheter 1006 is configured to push the anchor 1012 from the distal end of the anchor catheter 1006 to expand the anchor 1012. In some embodiments, the anchor catheter 1006 can include a mechanism to expand the anchor 1012. The mechanism can move the distal end and the proximal end of the anchor 1012 toward each other. In some embodiments, the anchor 1012 can be reversible. The anchor 1012 can expand and compress and expand again. In some embodiments, the anchor 1012 can be irreversible. The anchor 1012 cannot compresses again after expansion. The transcatheter system 1000 can provide a compact system combining a suture 1014 and an anchor 1012. The suture 1014 and the anchor 1012 can be rigidly coupled. The suture 1014 and the anchor 1012 can be rigidly coupled prior to subannular delivery. The suture 1014 and the anchor 1012 can be rigidly coupled to withstand anchor deployment. The suture 1014 and the anchor 1012 can be rigidly coupled during the life cycle of the transvalvular band 500.

Advantages can additionally include any of the following related to subannular anchoring. In some embodiments, the anchor catheter 1006 can include a mechanism to create a passageway in the annulus. In some embodiments, the mechanism can be the RF needle 1018. The RF needle 1018 can apply energy to the annulus to burn a hole through the annulus. The RF needle 1018 can extend through the anchor 1012. The RF needle 1018 can be centrally placed. The RF needle 1018 can create a passageway having a diameter equal to the outer diameter of the compressed anchor 1012. The RF needle 1018 can create a passageway having a diameter larger than the outer diameter of the compressed anchor 1012. The RF needle 1018 can create a passageway having a diameter smaller than the outer diameter of the expanded anchor 1012. Other mechanisms are contemplated. The mechanism can include a punch. The punch can create the passageway. The punch can be sharpened or blunt. The mechanism can include the application of heat, light, or energy. The number of anchors 1012 can correspond to the transvalvular band 500. The transvalvular band 500 can be secured by any number of anchors. In some embodiments, the transvalvular band 500 can be designed to be secured with four anchors 1012. The user therefore can know the suture count prior to surgery based on the selected transvalvular band 500.

Also, advantages can include any of the following related to securing the implant. In some embodiments, the transcatheter system 1000 can provide knotless securement. The locking clips 1016 can be designed to slide along the suture 1014. The locking clips 1016 can slide after subannular anchoring. The locking clips 1016 can slide after the transvalvular band 500 is deployed. In some embodiments, the locking clips 1016 can be pushed by clip pushers along the sutures 1014. The clip pushers can be designed to manage the sutures 1014. Each clip pusher can surround a suture 1014 to prevent or limit tangles of the suture 1014. The transcatheter system 1000 can provide implant delivery that is reversible. In some embodiments, the transvalvular band 500 can be removable until the locking clips 1014 are secured. In some embodiments, the anchors 1012 can be removable until the locking clips 1014 are secured.

Advantages can further include any of the following related to suture management. The anchor catheter 1006 can be designed to manage the attached suture 1014 during delivery of the anchor 1012. The four sutures 1014 can extend outside of the body after subannular deployment of the anchors 1012. The transvalvular band 500 can include one or more apertures 508. The number of apertures 508 can correspond to the number of sutures 1014. The sutures 1014 can be threaded through the apertures 508 as shown in FIG. 102A. In some embodiments, the sutures 1014 can be threaded through the apertures 508 after subannular anchoring. In some embodiments, the sutures 1014 can be threaded through the apertures 508 outside the body of the patient. The sutures 1014 can be threaded through the ports 1020 in the delivery catheter 1008. The ports 1020 can be channels or grooves to facilitate separation of the sutures 1014. In some embodiments, the sutures 1014 can be threaded through the ports 1020 in the delivery catheter 1008 after threading the sutures 1014 through the transvalvular band 500. In some embodiments, the sutures 1014 can be threaded through the ports 1020 in the delivery catheter 1008 after subannular anchoring. In some embodiments, the sutures 1014 can be threaded through the ports 1020 in the delivery catheter 1008 outside the body of the patient. The delivery catheter 1008 can prevent or reduce tangles of the sutures during delivery of the transvalvular band 500. The transvalvular band 500 can slide along the sutures 1014 within the guide catheter 1002. The locking clips 1016 can slide along the sutures 1014 within the guide catheter 1002. The trimming catheter 1010 can slide along each suture 1014 after the transvalvular band 500 is positioned and secured. The trimming catheter 1010 can include one port designed to accept one suture 1014. The trimming catheter 1010 can be designed to manage the suture 1014 as the trimming catheter 1010 slides along the suture 1014. In some embodiments, suture management relates to the sutures themselves. In some embodiments, two or more sutures 1014 can be the same or similar. In some embodiments, two or sutures 1014 can be different. The sutures 1014 can include an identifier (e.g., color, label, markings, etc.) For instance, the suture 1014 can include an identifier related to the annular position of the associated anchor 1012.

In addition, advantages can include any of the following related to implant delivery including, but not limited to, implant delivery to a beating heart. The transcatheter system 1000 can replicate an open procedure. The transcatheter system 1000 can be delivered percutaneously. The transcatheter system 1000 can be delivered in a minimally invasive manner. The transcatheter system 1000 can be inserted through transseptal access. The transcatheter system 1000 can allow for processes to be completed outside of the body of the patient. The sutures 1014 can extend outside of the body of the patient after subannular anchoring of the anchors 1012. The transcatheter system 1000 can allow for the sutures 1014 to be threaded through the transvalvular band 500 outside of the body of the patient after subannular anchoring. The transcatheter system 1000 can allow for the sutures 1014 to be threaded through the delivery catheter 1008 outside of the body of the patient after subannular anchoring. The transcatheter system 1000 can allow for the sutures 1014 to be threaded through the trimming catheter 1010 outside of the body of the patient after subannular anchoring. The transcatheter system 1000 can allow retrieval of the sutures tails outside of the body of the patient after subannular anchoring. The heart valve can be, for example, a mitral, aortic, tricuspid, or pulmonary valve. The heart valve annulus can be, for example, a mitral, aortic, tricuspid, or pulmonary valve annulus. The transcatheter system 1000 can be utilized in any valve of the human body.

The transcatheter systems and methods include many distinguishing features over the prior art, including but not limited to those disclosed herein. In some embodiments, the transvalvular bridge is not or does not include an annuloplasty ring. In some embodiments, the transvalvular bridge does not comprise an enclosed or ring-like shape. As known in the art, the annuloplasty ring may not be optimal for anatomy. The annuloplasty ring can flatten the annulus from its natural saddle shape. Further, for an annuloplasty ring, the procedure, and subsequent outcome, can be dependent on surgical technique.

In some embodiments, the transvalvular bridge can be an elongate structure. In some embodiments, the transvalvular bridge can be shaped to span across the valve instead of encircle or partially encircle the valve. In some embodiments, the transvalvular bridge can be shaped to cinch the valve together. In some embodiments, the transvalvular bridge can cinch the leaflets toward each other to close the valve. In some embodiments, the transvalvular bridge can be designed to span across the leaflets. The transvalvular bridge can include an elongate body having a first end, a second end, and a central portion connected to the first end and the second end. In some embodiments, the central portion can have a convex arcuate shape which is configured to be displaced downward from the first end and the second end.

In some embodiments, the valve is not replaced. In some embodiments, the leaflets are not replaced or rendered non-functional. In some embodiments, the transvalvular bridge can be considered a leaflet support, rather than a valve replacement. In some embodiments, the transvalvular bridge is not designed to keep the valve open. In some embodiments, the transvalvular bridge is not designed to keep the leaflets separated. In some embodiments, the transvalvular bridge can allow for normal coaptation of the leaflets which are supported by the transvalvular bridge. In some embodiments, the transvalvular bridge can at least partially close or cinch the valve together to increase the contact between the leaflets.

In some embodiments, the delivery systems and methods can allow optimal placement of the transvalvular bridge based on guided sutures which are anchored subannularly. In some embodiments, the first end and the second end can be delivered along sutures to the mitral valve annulus. In some embodiments, the delivery systems and methods can include templates for optimal spacing between two sutures. In some embodiments, the delivery systems and methods can include templates for optimal spacing between four sutures. In some embodiments, two anchors can be positioned on the posterior annulus. In some embodiments, the spacing between the two anchors on the posterior annulus can correspond with the spacing of two apertures on the first end of the transvalvular bridge. In some embodiments, two anchors can be positioned on the anterior annulus. In some embodiments, the spacing between the two anchors on the anterior annulus can correspond with the spacing of two apertures on the second of the transvalvular bridge. In some embodiments, the systems and methods can include a guide to position the anchor catheter. In some embodiments, the anchors are delivered sequentially such that the single anchor catheter is repeatedly positioned at the anchor location. In some embodiments, two or more anchors are delivered simultaneously.

In some embodiments, the suture can extend linearly or substantially linearly from the anchor. In some embodiments, the suture can extend linearly or substantially linearly through the hole or other opening in tissue, such as the annulus. In some embodiments, the suture can extend linearly or substantially linearly through the transvalvular bridge. In some embodiments, the suture can form a linear path from the anchor positioned under the annulus and through the transvalvular bridge positioned over the annulus.

In some embodiments, the transvalvular bridge can be anchored to the annulus. In some embodiments, the transvalvular bridge is not anchored to the commissures, but rather a non-commissure part of the annulus. However, the implant can be anchored to the commissures in some embodiments. In some embodiments, the transvalvular bridge is not anchored to a natural orifice. In some embodiments, the transvalvular bridge can be anchored via an artificially created orifice in the annulus. In some embodiments, the annulus provides a robust tissue for anchoring. The annulus can be described as a fibrous ring attached to the posterior and anterior leaflet. The annulus can provide sufficient strength to prevent the anchors from backing out or tearing through the annulus when tension is applied to the sutures. The annulus can be described as saddle shaped and the annulus can be described as changing shape during the cardiac cycle. In some embodiments, the transvalvular bridge can be shaped to match the saddle shape of the annulus and provide support during the cardiac cycle.

In some embodiments, the transvalvular bridge can be designed to cinch the posterior annulus and the anterior annulus. In some embodiments, the transvalvular bridge can bring the leaflets toward each other. In some embodiments, the transvalvular bridge can cinch the leaflets to provide support. In some embodiments, the transvalvular bridge can cinch the leaflets to change the shape of the leaflets. In some embodiments, the transvalvular bridge can cinch the leaflets to encourage more contact at coaptation points or a larger coaptation zone.

In some embodiments, the transvalvular bridge can be reversibly anchored. In some embodiments, the subannular anchors can be adapted to be compressed to be delivered through the hole. In some embodiments, the subannular anchors can assume a larger diameter shape on the underside of the annulus. In some embodiments, the subannular anchors can change configuration with the application of tension to the subannular anchors. In some embodiments, each subannular anchor can be retrieved through the hole in the annulus. In some embodiments, each subannular anchor can be retrieved after the sutures are cinched. In some embodiments, each subannular anchor can be retrieved after the transvalvular bridge is deployed. In some embodiments, each subannular anchor can be retrieved after the locking clips are advanced. In some embodiments, each subannular anchor can be retrieved until the sutures are trimmed. In some embodiments, each subannular anchor can be retrieved after complete implantation of the transvalvular bridge.

In some embodiments, the sutures connected to subannular anchors can function as a guide member for the transvalvular bridge. In some embodiments, the system can include a plurality of guide members, including at least one guide member for each end of the transvalvular bridge. In some embodiments, the system can include two guide members for each end of the transvalvular bridge. In some embodiments, the sutures described herein are distinct sutures. In some embodiments, each subannular anchor can include only one suture. In some embodiments, the suture can be threaded through the transvalvular bridge. In some embodiments, the suture can form a straight path through the transvalvular bridge. In some embodiments, the suture is not woven through the transvalvular bridge.

In some embodiments, the suture does not form a U-shaped configuration. In some embodiments, the suture does not include two free ends. In some embodiments, one end of the suture can be fixed to the anchor and one end of the suture can be free. In some embodiments, the suture does not form a loop. In some embodiments, the suture does not form a looped portion. In some embodiments, the suture is not stitched through the annulus. In some embodiments, the suture has only one free end. In some embodiments, the suture is connected to the subannular anchor at a fixed end. In some embodiments, the suture can form a single path from the anchor through the body of the patient. In some embodiments, the suture can form a straight path through the annulus. In some embodiments, the suture can form a straight path through the hole in the annulus. In some embodiments, the suture has a diameter between about 0.02 mm and about 0.8 mm (e.g., 0.02 mm, 0.03 mm, 0.05 mm, 0.07 mm, 0.1 mm, 0.15 mm. 0.2 mm, 0.3 mm, 0.35 mm, 0.4 mm, 0.5 mm, 0.6 mm, 0.7 mm, 0.8 mm, or ranges incorporating any of the foregoing values).

In some embodiments, the procedure can begin with anchoring. In some embodiments, the subannular anchors can be advanced toward the annulus of the valve. In some embodiments, the subannular anchors are not positioned near the first and second commissures of the valve. In some embodiments, the anchors can be advanced into the left atrium toward the annulus. In some embodiments, the anchors can be advanced from the left atrium to the left ventricle, through the annulus. In some embodiments, the anchors are not advanced from the left ventricle toward the left atrium.

In some embodiments, a hole can be created in the annulus to pass the compressed anchor therethrough. In some embodiments, the hole can be created with the application of energy to ablate the annulus. In some embodiments, the hole can include smooth edges. In some embodiments, the hole can be stretched/dilated to accept a larger diameter catheter therethrough. In some embodiments, the method of creating the hole can prevent tearing of the annulus. In some embodiments, the hole can be a smaller diameter than the anchor catheter. In some embodiments, the anchor catheter can include features such as a tapper or dilator which increases the diameter of the hole, or is not configured to dilate the aperture. In some embodiments, the anchor catheter can reversibly stretch the hole to allow delivery of the anchor. In some embodiments, the hole can retain its original diameter when the anchor catheter is removed. In some embodiments, the deployed anchor can have a larger diameter than the hole. In some embodiments, the deployed anchor can have a cross-section which is larger than the hole (e.g., twice the diameter, three times the diameter, four times the diameter, five times the diameter, or ranges incorporating any of the foregoing values).

In some embodiments, the subannular anchor, or a surface thereof can rest against the underside of the annulus. In some embodiments, the subannular anchor can maintain its position against the underside of the annulus while the suture is cinched. In some embodiments, the system can include four anchors. In some embodiments, the system can include two anchors on the posterior annulus and two anchors on the anterior annulus. In some embodiments, the suture can pass through the annulus only once. In some embodiments, the suture is not looped through the annulus in a sewing pattern. In some embodiments, the subannular anchor can be expanded on the ventricular side of the annulus. In some embodiments, the suture can extend from the ventricular side of annulus and through the hole in the annulus. In some embodiments, the holes and sutures can be in a one-to-one correspondence. In some embodiments, each suture can have a separate hole through the annulus. In some embodiments, the suture can extend to the atrial side of the annulus. In some embodiments, the sutures can be flexible. In some embodiments, the sutures can be pulled taut to be semi-rigid. In some embodiments, the semi-rigid sutures can provide a guide for the advancement of the delivery catheter along the sutures. In some embodiments, the semi-rigid sutures can provide a guide for advancement of the transvalvular bridge. In some embodiments, the semi-rigid sutures can provide a guide for advancement of the locking clips.

In some embodiments, the transvalvular bridge does not include ventricular attachment. In some embodiments, the transvalvular bridge can extend along the plane of the annulus. In some embodiments, the transvalvular bridge can be similar to the saddle shape of the valve. In some embodiments, the convex central portion does not extend beyond the point of coaptation or coapatation zone of the leaflets. In some embodiments, the convex central portion does not interfere with natural coaptation.

Access to the annulus can be provided in various ways according to some embodiments. In some embodiments, the systems can be advanced through the vasculature toward the annulus using any known point of enter to the left atrium. In some embodiments, the catheters described herein can be introduced via the femoral vein, to an inferior vena cava, to the right atrium, and then to the left atrium. The catheters can be delivered transseptally. The catheters can be delivered through the fossa ovalis. In some embodiments, the catheters can be introduced via the basilic vein, to the subclavian vein, to the superior vena cava, to the right atrium, and to the left atrium. In some embodiments, the catheters can be introduced via the external jugular vein, to the subclavian vein, to the superior vena cava, to the right atrium, and to the left atrium. Access can be provided by dilators, if needed, according to some embodiments. Access can be provided by one or more sheaths, according to some embodiments. Access can be provided by one or more steerable catheters, according to some embodiments. Access can be provided by one or more catheters or needles configured to puncture the septum to create access, according to some embodiments.

In some embodiments, the anchors can be guided into position by the anchor catheter. In some embodiments, the anchor catheter can be guided into position by the template catheter. In some embodiments, the template catheter can ensure spacing between the anchors appropriate for the corresponding band. In some embodiments, the surgeon can position the anchor catheter at spaced locations along the annulus. In some embodiments, two anchors can be positioned on the posterior annulus and two anchors can be positioned on the anterior annulus. In some embodiments, two anchors can be positioned adjacent to the posterior leaflet and two anchors can be positioned adjacent to the anterior leaflet. In some methods, one set of anchors is parallel to another set of anchors.

In some embodiments, the anchors can comprise a shape memory material such as Nitinol or other springy metals. In some embodiments, the anchors can comprise a flexible material allowing the anchors to assume a compressed and expanded shape. In some embodiments, the anchors can comprise one or more radially expandable prongs that can be reversibly expanded and compressed. In some embodiments, the anchors can be coupled and carried by the anchor catheter through the hole in the annulus. The anchors can be held under tension to assume a compressed shape. Other configurations are contemplated such as a sheath or other constraining structure.

In some embodiments, the anchors can be advanced through the hole and pushed distally to the ventricle. In some embodiments, once on the ventricular side of the annulus, the anchor catheter can release tension on the subannular anchor allowing the anchor to expand such that the anchor cannot fit through the hole. In some embodiments, as the tension is released from the anchors, the anchors can expand. In some embodiments, the struts of the anchors can radially expand and longitudinally compress. In some embodiments, the anchor can expand to a star shape. The expanded subannular anchor can create a larger cross-sectional shape than the hole. The expanded subannular anchor can create a larger surface area than the anchors when compressed. In some embodiments, the anchor catheter can retract after placement of the anchor. In some embodiments, the anchors can be reversible. The anchor can be compressed and pulled back through the hole. In some embodiments, the anchor can compress under the influence of tension and can be extracted through the hole. In some embodiments, the anchor catheter can apply tension to the anchor to compress the anchor.

In some embodiments, the suture can be anchored to the ventricular side of the annulus. The suture can extend from the subannular anchor and through the catheter system. The free end of the suture can be external to the patient. The extracorporeal sutures can be easily managed. Once trimmed, the extracorporeal sutures can be pulled to retrieve the sutures from the left atrium. In some embodiments, the surgeon can retrieve all four sutures and maintain the suture count.

The annulus can provide a robust tissue for anchoring the suture. The tissue in the area of the annulus can be thicker than other tissues of the heart. The tissue can be continuous, without any natural orifices or weaknesses. The anchor can be passed through an artificial hole created in the annulus. In some embodiments, the hole can be perfectly circular, oval, or other geometries. In some embodiments, the hole can be cauterized such as by the application of heat or energy. In some embodiments, the hole can be punched. In some embodiments, the hole can be created in a way to prevent any areas for stress cracks or tears.

In some embodiments, after placement of the anchors, the transvalvular bridge can advanced toward the annulus. The transvalvular bridge can be advanced along the sutures after the subannular anchors are expanded. The transvalvular bridge can be pushed distally by one or more guides or by the delivery catheter itself. The transvalvular bridge can be advanced in a compressed configuration. The transvalvular bridge can be rolled to a compressed configuration but still be able to slide along the suture. The transvalvular bridge can be expanded within the left atrium of the heart. The transvalvular bridge can be expanded when approaching the annulus. In some embodiments, as the transvalvular bridge is expanded from the delivery catheter, the transvalvular bridge can assume a pre-set shape. The central portion can curve downward from the first end and the second end. The transvalvular bridge can assume a convex shape. In some embodiments, the transvalvular bridge can be expanded by removal of a constraint. In some embodiments, the transvalvular bridge can be expanded by removal of a tubular covering or sheath. In some embodiments, the transvalvular bridge can be expanded by being pushed distally.

In some embodiments, the transvalvular bridge can include two or more apertures for slidable delivery along the sutures. In some embodiments, the transvalvular bridge can be preloaded on the sutures. The manufacturer can thread the sutures through the transvalvular bridge. In some embodiments, the surgeon can thread the sutures through the apertures of the transvalvular bridge. The sutures can be threaded through the transvalvular bridge outside the body of the patient. In some embodiments, each suture can correspond to a single aperture in the transvalvular bridge. In some embodiments, prior to delivery of the transvalvular bridge, the sutures can be threaded through the transvalvular bridge such that the transvalvular bridge can slide along the sutures toward the annulus. The transvalvular bridge can provide support to the valve. The transvalvular bridge can be positioned to allow natural coaptation. In some embodiments, the transvalvular bridge does not force the valve open. In some embodiments, the transvalvular bridge does not extend into the ventricle. In some embodiments, the transvalvular bridge does not comprise a stent.

In some embodiments, the locking clips can slide along the sutures. The locking clips can be pushed distally toward the annulus. The locking clips can be designed to be positioned against the transvalvular bridge. In some embodiments, the sutures can allow the surgeon to accurately position the locking clips relative to the transvalvular bridge. In some embodiments, the surgeon can be provided with tactile feedback when the locking clip is secured by abutting the locking clips against the transvalvular bridge. The locking clips can be unidirectional to allow distal movement but prevent proximal movement of the locking clip.

Figure 113F:
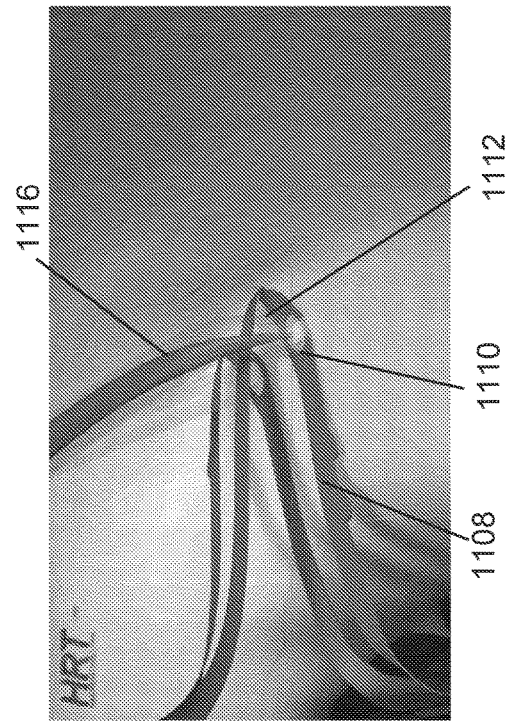
FIGS. 113A-113T are schematic views of methods of use of a transcatheter system, according to some embodiments.
Figure 113H:
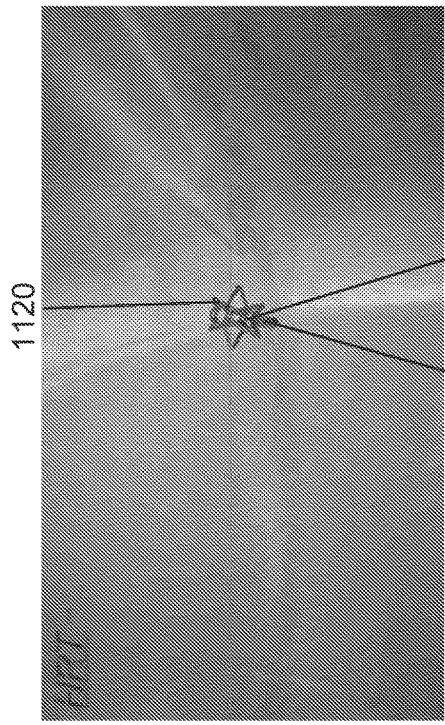
Figure 113E:
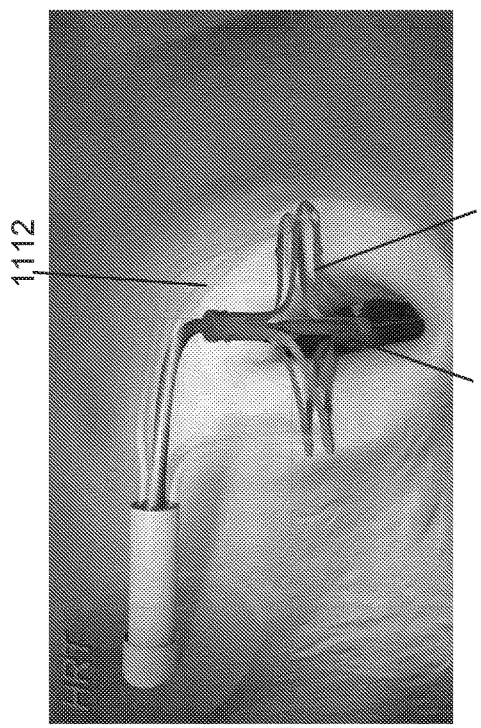
Figure 113G:
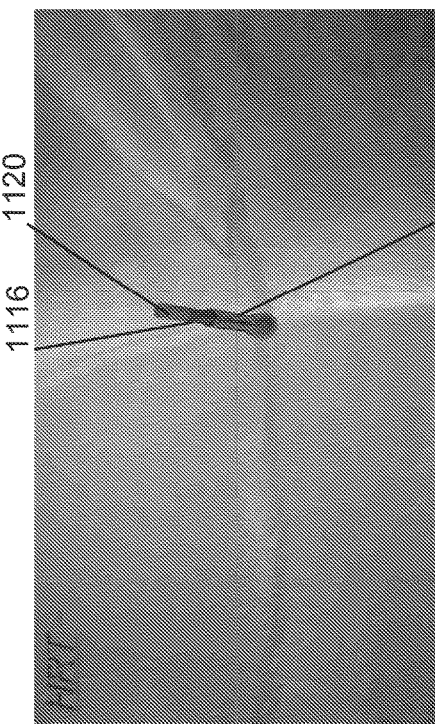
Figure 113J:
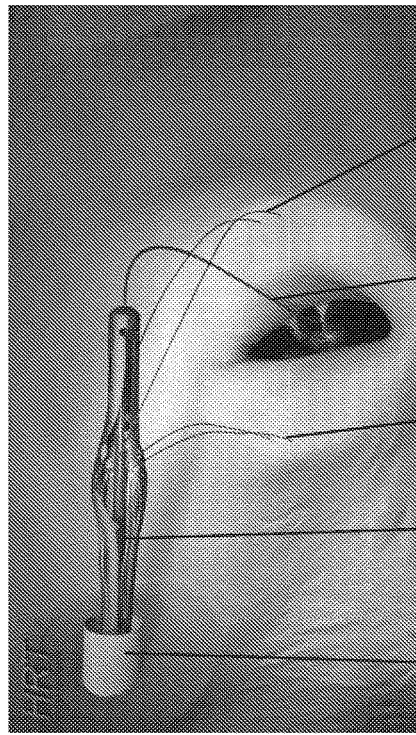
Figure 113L:
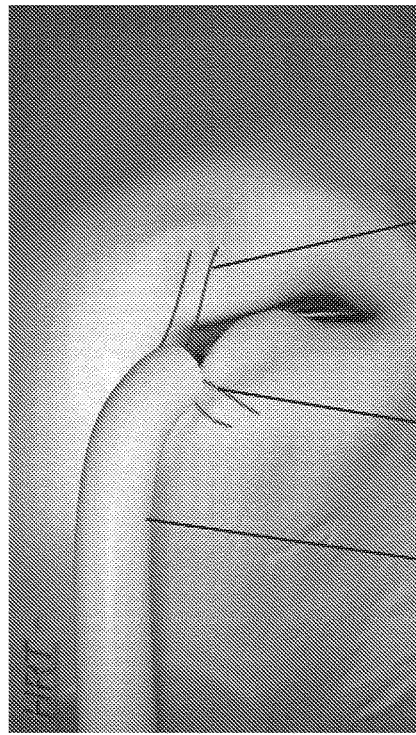
Figure 113I:
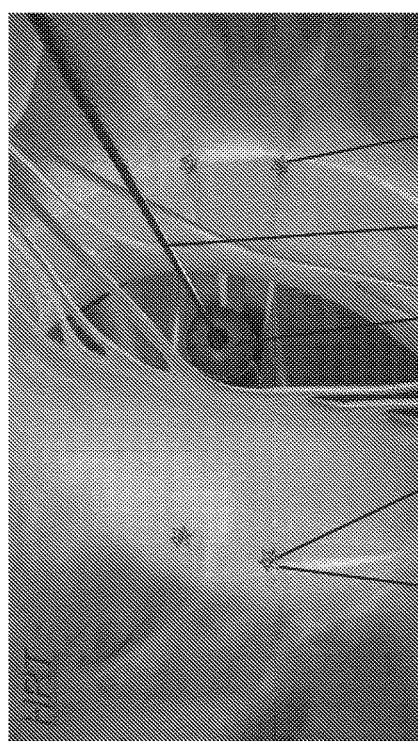
Figure 113K:
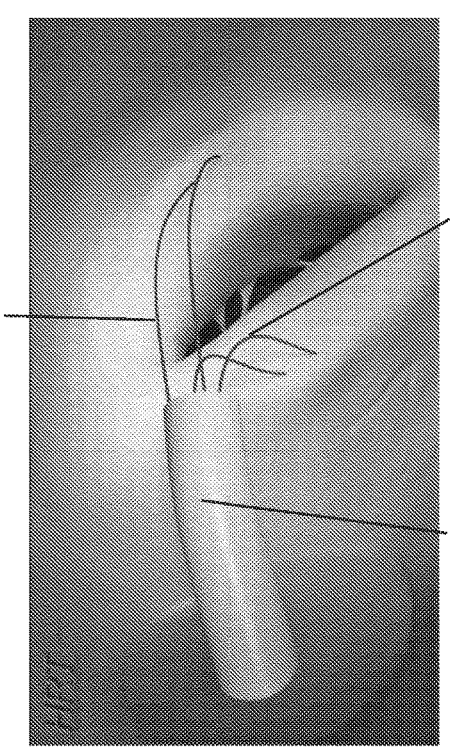
Figure 113M:
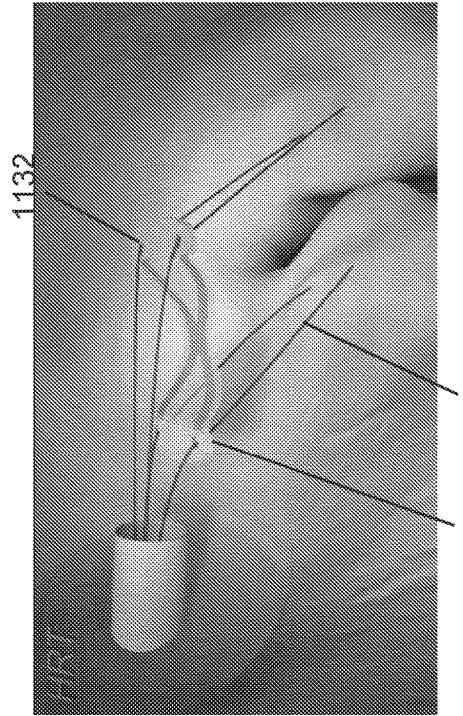
Figure 113N:
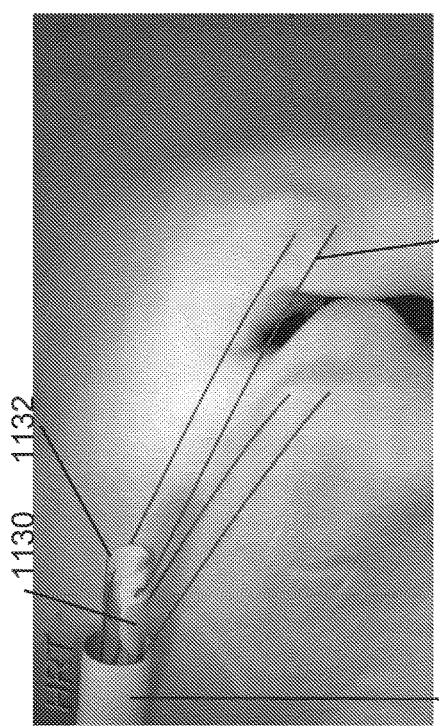
Figure 113O:
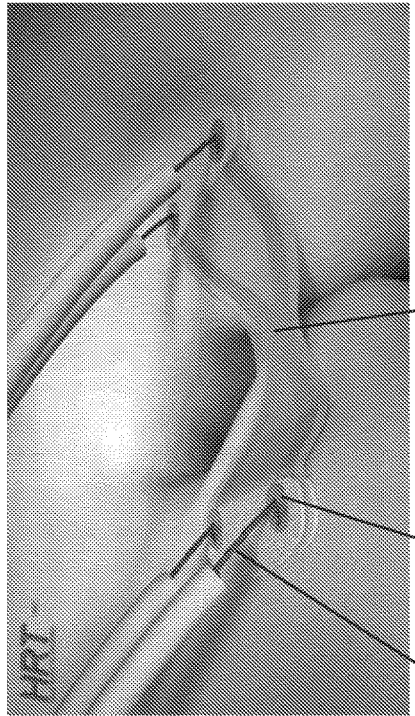
Figure 113P:
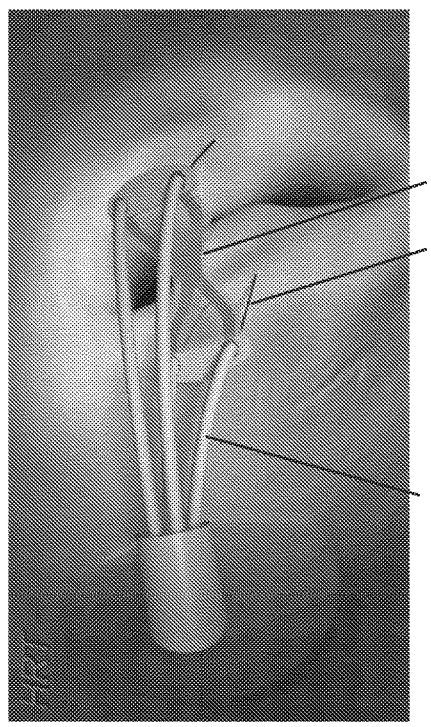
Figure 113Q:
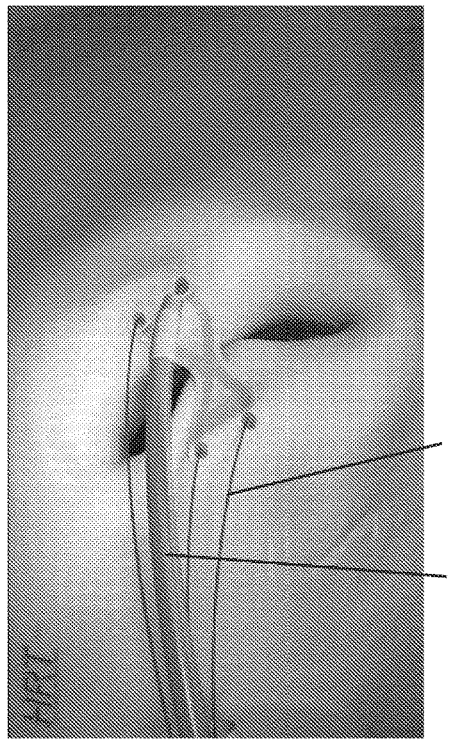
Figure 113R:
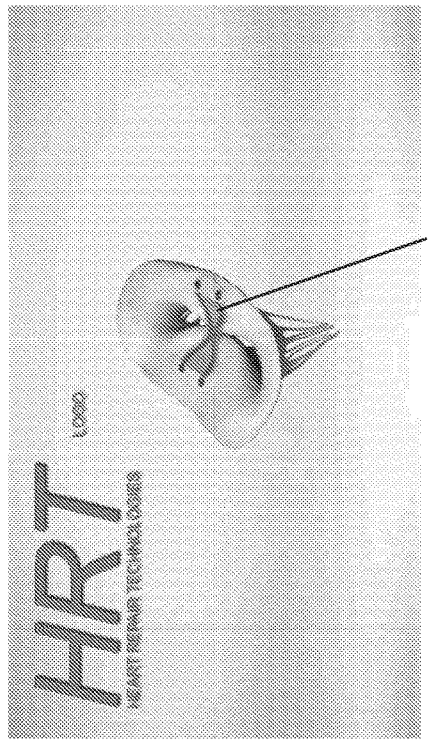
Figure 113S:
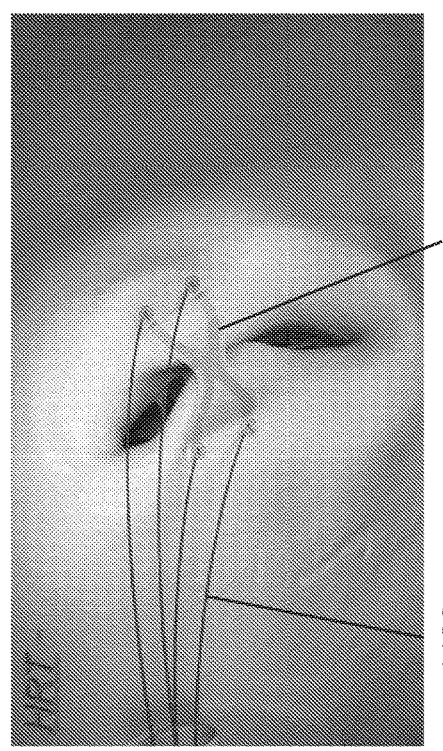
Figure 113T:
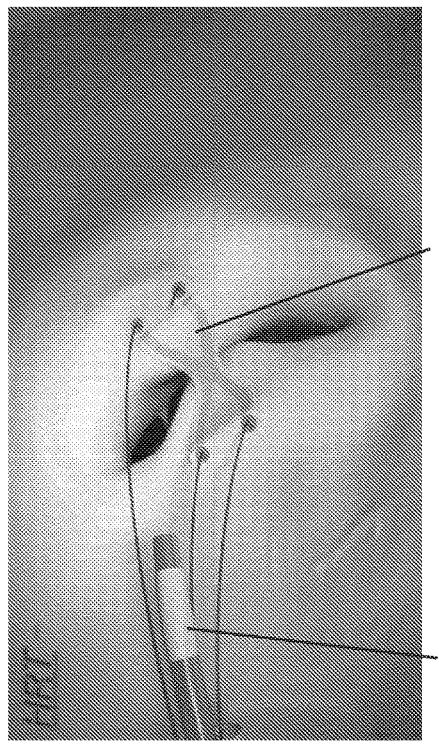

FIGS. 113A-113T are schematic views of methods of use of a transcatheter system according to some embodiments. The systems and methods can revolutionize the treatment of mitral or other valve regurgitation. In a simple procedure, surgeons can treat mitral valve regurgitation in vivo, as an alternative to open heart surgery. The catheter system can be introduced via the femoral vein or other access point and delivered to the heart. The catheter system can be delivered using a transseptal puncture. In some embodiments, a guide wire can be positioned to the left atrium. The guide catheter can be navigated into the heart along the guide wire. The guide catheter can gain access to the mitral valve.

FIGS. 113A-113T are views of a transcatheter system 1100 and methods of use according to some embodiments. The catheters of transcatheter system 1100 can include any of the features of catheters described herein. FIG. 113A illustrates a guide catheter 1102. The guide catheter 1102 can provide a transseptal conduit to, for example, the left atrium. The transcatheter system 1100 can include a guide wire 1104. The guide wire 1104 can span between the right atrium and the left atrium. The guide wire 1104 can extend from the left atrium, through the valve annulus and toward the left ventricle. While some embodiments are described in the context of a mitral bridge, other implants that span the annulus can be utilized, and the method adapted to other valve annuli including the tricuspid, aortic, and/or pulmonic valve annuli depending on the desired clinical result.

The guide catheter 1102 can be placed in the left atrium through the transseptal access. In some embodiments, a template catheter 1106 can be utilized after the guide catheter 1102 is placed. The template catheter 1106 can be delivered in a compressed configuration in FIG. 113A. The template catheter 1106 can be deployed in the left atrium to direct the system appropriately to the mitral valve.

FIG. 113B illustrates the template catheter 1106 being deployed according to some embodiments. The template catheter 1106 can slide along the guide wire 1104 toward the mitral valve. The template catheter 1106 can include one or more struts 1008. In some embodiments, the number of struts 1108 can correspond to the number of anchors, as described herein. The template catheter 1106 can be steered toward the mitral valve along the guide wire 1104.

FIG. 113C illustrates the deployed template catheter 1106 according to some embodiments. The struts 1108 can assume an enlarged cross-section. The struts 1108 can radially expand. The struts 1108 can axially shorten. The struts 1108 can fold outward as shown. In some embodiments, each strut can comprise a pair of apertures 1110 through which an anchor catheter conduit 1112 passes. In the illustrated embodiment, the template catheter 1106 can include four struts 1108 with four corresponding anchor catheter conduits 1112. In some embodiments, each strut 1108 can support one, two, or more anchor catheter conduit 1112. Other configurations are contemplated (e.g., one strut 1108 supports two anchor catheter conduits 1112, one strut 1108 supports three anchor catheter conduits 1112, one strut 1108 supports four anchor catheter conduits 1112, etc.). The anchor catheter conduit 1112 can be a flexible tube. The anchor catheter conduit 1112 can be an enclosed channel or partially enclosed channel.

FIG. 113D illustrates the deployed template catheter 1106 being moved toward the mitral valve according to some embodiments. The template catheter 1106 can be positioned across the anterior and posterior leaflets. The template catheter 1106 can provide the appropriate spacing for the anchors via anchor catheter conduits 1112. The template catheter 1106 can be rotated relative to the guide wire 1104 to position the anchor catheter conduits 1112. The anchor catheter conduits 1112 can be positioned at or near the 5 o'clock, 7 o'clock, 11 o'clock, and 1 o'clock positions. In some embodiments, two anchors can be spaced apart from another two anchors along an axis of symmetry. The 5 o'clock and 7 o'clock positions can be the locations of the anchors on the posterior annulus. The 11 o'clock and 1 o'clock positions can be the locations of the anchors on the anterior annulus. Other positions are contemplated (e.g., 1 o'clock, 2 o'clock, 3 o'clock, 4 o'clock, 5 o'clock, 6 o'clock, 7 o'clock, 8 o'clock, 9 o'clock, 10 o'clock, 11 o'clock, 12 o'clock, or any range including two or more values). FIG. 113E illustrates the position of the template catheter 1106 against the leaflets and the annulus, according to some embodiments. A portion of the template catheter 1106 can extend toward the left ventricle and between the leaflets. The struts 1108, or a portion thereof, can be positioned against the annulus. The anchor catheter conduits 1112 can extend in an appropriate direction such as downward toward the annulus.

FIG. 113F illustrates an anchor catheter 1116 according to some embodiments. The anchor catheter 1116 can be sized to pass through the anchor catheter conduit 1112 toward the annulus. As described herein, the strut 1108 can include the pair of apertures 1110. The pair of apertures 1110 can provide a passageway to the annulus. The pair of apertures 1110 can allow the anchor catheter 1116 to create a hole in the annulus. The anchor catheter 1116 can be passed through the anchor catheter conduit 1112 to deliver an anchor subannularly. The anchor catheter 1116 can use a radio frequency wire system or other electromagnetic, mechanical, or other source of energy to ablate a small pilot hole in the annulus. The anchor catheter 1116 can apply energy to the annulus as shown in FIG. 113F. In some embodiments, the hole created by the anchor catheter 116 can be smaller in diameter than the anchor catheter 1116. In some embodiments, the hole can reversibly stretch to allow passage of the anchor catheter 1116.

FIG. 113G illustrates an anchor catheter 1116 extending through the pilot hole on the ventricular side of the annulus according to some embodiments. The anchor catheter 1116 can carry the anchor 1118 through the pilot hole in a compressed configuration. The anchor 1118 can be axially elongated in the compressed state. The distal tip of the anchor catheter 1116 can include a wire 1120 used to create the hole. In some embodiments, the anchor catheter 1116 can include a punch to create a hole. FIG. 113H illustrates the deployed anchor 1118 on the ventricular side of the annulus according to some embodiments. The anchor catheter 1116 can be retracted through the pilot hole. The anchor 1118 can include a tether, such as a suture extending from the anchor 1118. The suture 1122 can extend through the anchor catheter 1116. In some embodiments, as the anchor catheter 1116 is retracted, the suture 1122 can remain extending from the anchor 1118, through the pilot hole, and to the left atrium as described herein. The suture 1122 can extend through the catheter system and extend external to the patient.

FIG. 113I illustrates the plurality of anchors 1118 deployed in a similar manner according to some embodiments. Four or a different number of anchors 1118 can be used to secure the mitral bridge. The plurality of anchors, e.g., four anchors, can be delivered subannularly. In some embodiments, the subannular anchors 1118 can be placed through the pilot holes under the annulus with minimal pressure. In some embodiments, the anchors 1118 can be delivered sequentially such that the anchor catheter 1116 can be removed from one anchor catheter conduit 1112 after anchor delivery, and can be inserted into a second anchor catheter conduit 1112 for delivery of a second anchor, until all four anchors 1118 are sequentially delivered. In other embodiments, two or more of the anchors can be delivered simultaneously. FIG. 113I illustrates a portion of the template catheter 1106 extending between the leaflets and along the guide wire 1104 according to some embodiments. In some embodiments, the anchors can be removed after being deployed. The anchors 1118 can be compressed and retrieved from the annulus. The template catheter 1106 can be redeployed. The anchor catheter 1116 can create one or more additional holes for the subannular anchors.

FIG. 113J shows the four sutures 1122 extending from the four anchors 1118 according to some embodiments. In some embodiments, after all four anchors 1118 are delivered, the template catheter 1106 can be removed. FIG. 113J shows the removal of the template catheter 1106 according to some embodiments. The template catheter 1106 can be compressed for passage through the guide catheter 1102. In some embodiments, the template catheter 1106 including the anchor catheter conduit 1112 can provide suture management. Each suture 1122 can extend through the anchor catheter conduit 1112 such that the sutures 1122 are prevented from tangling or tangling is reduced. In some embodiments, the sutures 1122 can extend through separate lumens. In some embodiments, the template catheter 1106 can be retracted by sliding along the guide wire 1104. In some embodiments, the guide wire 1104 can remain in position after the template catheter 1106 is removed.

FIG. 113K illustrates the cinching of the annulus according to some embodiments. FIG. 113L illustrates further cinching of the annulus according to some embodiments. In some embodiments, with the anchors 1118 in place subannularly and the sutures extending through the annulus, the annulus can be cinched, in other words, the opposing sides of the annulus can be brought closer together along part of the annulus. The cinching can confirm securement of the subannular anchors 1118. The cinching can position the anchors 1118 against the annulus. The cinching can reduce any slack in the sutures 1122. The cinching can confirm the correct mitral bridge size. The cinching can confirm the desired spacing or length between the pair of sutures associated with the posterior leaflet and the pair of sutures associated with the anterior leaflet. The length of the implant, e.g., mitral bridge, can be selected to maintain the cinched position of the annulus. In some embodiments, the guide catheter 1102 can be brought toward the annulus to cinch the sutures 1122. In some embodiments, as the guide catheter 1102 moves toward the annulus, the sutures 1122 can be moved toward each other. In some embodiments, tension is applied to the sutures 1122 to cinch the sutures 1122. The sutures 1122 can be connected to the annulus via the subannular anchors 1118 in order to move the annulus. The cinching can increase the engagement between the posterior and anterior leaflet to enhance coaptation, as described herein.

FIG. 113M illustrates the mitral bridge 1130 which can be as described elsewhere herein and can include any of the features of any implant described herein including a transvalvular band 500. The mitral bridge 1130 can be deployed after the anchors are deployed. The mitral bridge 1130 can be guided into place through the guide catheter 1102 via the sutures 1122 which are permanently attached to the subannular anchors. The mitral bridge 1130 can include apertures 1132 through which the sutures 1122 can pass. In some embodiments, each aperture 1132 can be designed to accept one suture 1122. The first end of the mitral bridge 1130 can include two apertures 1132 designed to accept two sutures 1122. The mitral bridge 1130 can be compressed for delivery through the guide catheter 1102. FIG. 113N illustrates the mitral bridge 1130 deployed in the left atrium according to some embodiments. The mitral bridge 1130 can slide along the anchored sutures 1122 toward the annulus. The second end of the mitral bridge 1130 can include two apertures 1132 designed to accept two sutures 1122. The four apertures 1132 can correspond to the four sutures 1122. The four apertures 1132 can provide suture management to prevent the sutures 1122 from being tangled during delivery.

FIG. 113O illustrates a delivery catheter 1134 according to some embodiments. The delivery catheter 1134 can move the mitral bridge 1132 toward the annulus. Once positioned, the mitral bridge 1130 can be used in conjunction with the anchored sutures 1122 to cinch the posterior annulus toward the anterior annulus to facilitate proper leaflet coaptation. The delivery catheter 1134 can move locking clips 1136 toward the annulus. Each locking clip 1136 can slide along the corresponding suture 1122 during delivery. The locking clips 1136 can secure the mitral bridge 1130. The suture 1122 can be threaded through the locking clip 1136 to allow for unidirectional movement. The locking clip 1136 can allow movement of the locking clip 1136 toward the annulus but prevent or limit movement of the locking clip 1136 away from the annulus. In some embodiments, the mitral bridge 1130 and the locking clips 1136 can be simultaneously delivered. In some embodiments, the mitral bridge 1130 can be delivered first and the locking clips 1136 can be delivered after. In some embodiments, the locking clips 1136 can be sequentially delivered. The delivery catheter 1134 can be removed as shown in FIG. 113P according to some embodiments.

FIG. 113Q illustrates the deployed mitral bridge 1130 according to some embodiments. The mitral bridge 1130 can be sized to maintain the position of the sutures 1122. The mitral bridge 1130 can be sized to cinch the sutures 1122 and therefore the annulus. FIG. 113R illustrates a trimming catheter 1138 according to some embodiments. The trimming catheter 1138 can slide along the suture 1122 toward the annulus. FIG. 113R illustrates a trimming catheter 1138 trimming the suture 1122 according to some embodiments. FIG. 113R illustrates the deployed mitral bridge 1130 according to some embodiments. In some embodiments, all four sutures 1122 can be sequentially trimmed by the trimming catheter 1138. The trimming catheter 1138 can allow the suture 1128 to be retrieved by pulling the suture from the body of the patient.

In some embodiments, the systems and methods can allow deployment of a mitral bridge without open heart surgery. In some embodiments, the systems and methods can facilitate septal-lateral annular cinching. In some embodiments, the systems and methods can be used to close dilated valves. In some embodiments, the systems and methods can promote coapation early in the systolic phase. In some embodiments, the systems and methods can restore the natural biomechanics of the mitral or other valve. In some embodiments, the systems and methods can promote a healthy valve saddle shape. In some embodiments, the systems and methods can promote cardiac muscle alignment.

Any of a wide variety of specific tissue anchor constructions may be utilized in combination with the transvalvular band of the present invention. In addition, a variety of features have been described as illustrative in connection with a variety of implementations of the invention. Any of the features described above, may be recombined with any other of the embodiments disclosed herein, without departing from the present invention, as should be apparent to those of skill in the art. In some embodiments, the transvalvular band does not include a complete or partial annuloplasty ring, stent-valve, or partial or complete replacement valve or replacement valve leaflets and/or does not affect or substantially affect the size and/or shape of the valve annulus when operably attached to the valve annulus.

While the foregoing detailed description has set forth several exemplary embodiments of the apparatus and methods of the present invention, it should be understood that the above description is illustrative only and is not limiting of the disclosed invention. It will be appreciated that the specific dimensions and configurations disclosed can differ from those described above, and that the methods described can be used within any biological conduit within the body.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "attaching a transvalvular bridge to the mitral valve annulus" includes "instructing the attaching of a transvalvular bridge to the mitral valve annulus." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A system comprising:
   a plurality of tissue anchors;
   a template catheter comprising a first configuration in which the template catheter has a low profile and a second configuration in which the template catheter is expanded to be positioned relative to a valve annulus, the template catheter comprising a plurality of pathways;
   an anchor catheter configured to move along a pathway of the plurality of pathways of the template catheter to deliver a tissue anchor of the plurality of tissue anchors to the valve annulus; and
   a transvalvular band configured to move along a suture toward the tissue anchor, wherein the transvalvular band comprises an eyelet configured to receive the suture.

2. The system of claim 1, wherein the template catheter comprises two pathways.

3. The system of claim 1, wherein the template catheter comprises four pathways.

4. The system of claim 1, further comprising a locking clip configured to move along the suture.

5. The system of claim 1, wherein the transvalvular band comprises two eyelets.

6. The system of claim 1, wherein the transvalvular band comprises crossing struts.

7. The system of claim 1, further comprising a plurality of locking clips.

8. The system of claim 1, wherein at least two tissue anchors of the plurality of tissue anchors are configured to be delivered sequentially.

9. The system of claim 1, wherein at least two tissue anchors of the plurality of tissue anchors are configured to be delivered simultaneously.

10. The system of claim 1, further comprising a guide catheter configured to cinch the valve annulus.

11. The system of claim 1, wherein the transvalvular band is configured to treat a mitral valve.

12. The system of claim 1, wherein the transvalvular band is configured to treat a tricuspid valve.

13. The system of claim 1, further comprising a guide wire.

14. The system of claim 1, wherein the template catheter is configured to be positioned across an anterior leaflet and a posterior leaflet.

15. The system of claim 1, wherein the template catheter is configured to provide an appropriate spacing for the plurality of tissue anchors.

16. The system of claim 1, wherein a tissue anchor of the plurality of tissue anchors is configured to be spaced apart from another tissue anchor of the plurality of tissue anchors along an axis of symmetry.

17. The system of claim 1, wherein the template catheter is configured to provide suture management.

18. The system of claim 1, further comprising a locking clip, wherein the locking clip configured to allow movement of the locking clip toward the valve annulus but limit movement of the locking clip away from the valve annulus.

19. The system of claim 1, further comprising a locking clip, wherein the transvalvular band and the locking clip are configured to be simultaneously delivered.

20. The system of claim 1, further comprising a locking clip, wherein the transvalvular band is configured to be delivered first and the locking clip is configured to be delivered after the transvalvular band.

* * * * *